(12) United States Patent
van Rijn et al.

(10) Patent No.: US 8,394,789 B2
(45) Date of Patent: Mar. 12, 2013

(54) (DIHYDRO)PYRROLO[2,1-α]ISOQUINOLINES

(75) Inventors: Rachel Deborah van Rijn, Oss (NL);
Hubert Jan Josef Loozen, Oss (NL);
Cornelis Marius Timmers, Oss (NL);
Lars Anders van der Veen, Oss (NL);
Willem Frederik Johan Karstens, Oss (NL)

(73) Assignee: MSD Oss B.V., Oss (NL)

( * ) Notice: Subject to any disclaimer, the term of this patent is extended or adjusted under 35 U.S.C. 154(b) by 134 days.

(21) Appl. No.: 12/866,468

(22) PCT Filed: Feb. 6, 2009

(86) PCT No.: PCT/EP2009/051366
§ 371 (c)(1),
(2), (4) Date: Oct. 26, 2010

(87) PCT Pub. No.: WO2009/098283
PCT Pub. Date: Aug. 13, 2009

(65) Prior Publication Data
US 2011/0039832 A1    Feb. 17, 2011

Related U.S. Application Data

(60) Provisional application No. 61/027,062, filed on Feb. 8, 2008.

(30) Foreign Application Priority Data

Feb. 8, 2008   (EP) ...................... 08151199

(51) Int. Cl.
*C07D 471/04* (2006.01)
*C07D 471/18* (2006.01)
*A61K 31/551* (2006.01)
*A61P 15/08* (2006.01)

(52) U.S. Cl. ............. 514/218; 514/233.2; 514/253.03; 514/269; 514/294; 540/470; 540/492; 540/553; 544/126; 544/318; 544/361; 546/94

(58) Field of Classification Search ............ 514/218, 514/233.2, 253.03, 269, 294; 540/470, 492, 540/553; 544/126, 318, 361; 546/94
See application file for complete search history.

(56) References Cited

U.S. PATENT DOCUMENTS
2006/0223813 A1  10/2006  Magar et al.

FOREIGN PATENT DOCUMENTS

| WO | 00/08015 A2 | 2/2000 |
|---|---|---|
| WO | 00/08015 A3 | 2/2000 |
| WO | 00/48144 A1 | 8/2000 |
| WO | 02/09706 A1 | 2/2002 |
| WO | 03/004028 A1 | 1/2003 |
| WO | 03/014115 A1 | 2/2003 |
| WO | 03/014116 A1 | 2/2003 |
| WO | 03/014117 A1 | 2/2003 |
| WO | 03/051877 A1 | 6/2003 |
| WO | 2004/031182 A1 | 4/2004 |
| WO | 2005/002579 A1 | 1/2005 |
| WO | 2005/003129 A1 | 1/2005 |
| WO | 2005/003130 A1 | 1/2005 |
| WO | 2005/087765 A1 | 9/2005 |
| WO | 2006/075012 A2 | 7/2006 |
| WO | 2006/089815 A1 | 8/2006 |
| WO | 2006/117023 A1 | 11/2006 |
| WO | 2006/117368 A1 | 11/2006 |
| WO | 2006/117370 A1 | 11/2006 |
| WO | 2006/117371 A1 | 11/2006 |

OTHER PUBLICATIONS

C. Bailey, Curr. Med. Chem.—Anti-Cancer Agents, (2004), vol. 4, p. 363-378.
P. Devroey, et al., The Lancet, (1992), vol. 339, p. 1170-1171.
J. H. Dorrington, et al., Recent Progress in Hormone Research, (1979), vol. 35, p. 301-343.
H. Fan, et al., Chem. Rev., (2008), vol. 108, p. 264-287.
V. Insler, Int/Fertil, (1988), vol. 33, p. 85-97.
J. Morse, et al., American Journal of Reproductive Immunology and Microbiology (1988), vol. 17, p. 134-140.
D. Navot, et al., Journal of in Vitro Fertilization and Embryo Transfer, (1988), vol. 5, No. 1, p. 3-13.
W. Olijve, et al., Molecular Human Reproduction, (1996), vol. 2, No. 5, p. 371-382.
D. Pla, et al., Journal of Med. Chem., (2006), vol. 49, p. 3257-3268.
R. M. Sharpe, Clinical Endocrinology, (1990), vol. 33, p. 787-807.
C. Zhu, et al., Chemical Abstract Service, XP002486104, (1994).
International Search Report for U.S. Appl. No. 12/866,468, PCT/EP2009/051366 (2009).

*Primary Examiner* — Bruck Kifle
(74) *Attorney, Agent, or Firm* — Kenrick L. Vidale; John C. Todaro

(57) ABSTRACT

The invention relates to 5,6-dihydropyrrolo[2,1-α]isoquinoline and pyrrolo[2,1-α]isoquinoline derivatives according to general formula (I) or a pharmaceutically acceptable salt thereof. The compounds can be used for the treatment of infertility.

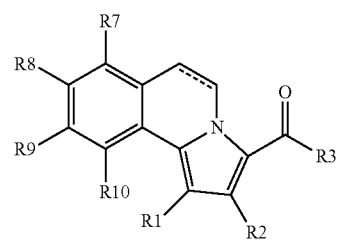

I

20 Claims, No Drawings

(DIHYDRO)PYRROLO[2,1-α]ISOQUINOLINES

CROSS REFERENCE TO RELATED APPLICATIONS

This application is a U.S. National Phase application under 35 U.S.C. §371 of International Patent Application No. PCT/EP2009/051366, filed Feb. 6, 2009 which claims priority under 35 U.S.C. 119(a) from EP08151199.0 filed Feb. 8, 2008 and under 35 U.S.C. §119(e) from U.S. Provisional Application Ser. No. 61/027,062, filed Feb. 8, 2008.

The present invention relates to 5,6-dihydropyrrolo[2,1-α]isoquinoline and pyrrolo[2,1-α]isoquinoline derivatives, to pharmaceutical compositions comprising the same and to the use of said compounds for the manufacture of medicaments for the treatment of infertility.

Gonadotropins serve important functions in a variety of bodily functions including metabolism, temperature regulation and the reproductive process. Gonadotropins act on specific gonadal cell types to initiate ovarian and testicular differentiation and steroidogenesis. The pituitary gonadotropin FSH (follicle stimulating hormone) for example plays a pivotal role in the stimulation of follicle development and maturation whereas LH (luteinizing hormone) induces ovulation [Sharp, R. M. Clin Endocrinol. 33, 787-807 (1990); Dorrington and Armstrong, Recent Prog. Horm. Res. 35, 301-342 (1979)]. Currently, FSH is applied clinically for ovarian stimulation i.e. ovarian hyperstimulation for in vitro fertilisation (IVF) and induction of ovulation in infertile anovulatory women [Insler, V., Int. J. Fertility 33, 85-97 (1988), Navot and Rosenwaks, J. Vitro Fert. Embryo Transfer 5, 3-13 (1988)], as well as for male hypogonadism and male infertility.

The gonadotropin FSH is released from the anterior pituitary under the influence of gonadotropin-releasing hormone and estrogens, and from the placenta during pregnancy. In the female, FSH acts on the ovaries promoting development of follicles and is the major hormone regulating secretion of estrogens. In the male, FSH is responsible for the integrity of the seminiferous tubules and acts on Sertoli cells to support gametogenesis. Purified FSH is used clinically to treat infertility in females and for some types of failure of spermatogenesis in males. Gonadotropins destined for therapeutic purposes can be isolated from human urine sources and are of low purity [Morse et al, Amer. J. Reproduct. Immunol. and Microbiology 17, 143 (1988)]. Alternatively, they can be prepared as recombinant gonadotropins. Recombinant human FSH is available commercially and is being used in assisted reproduction [Olijve et al. Mol. Hum. Reprod. 2, 371-381 (1996); Devroey et al. Lancet 339, 1170-1171 (1992)].

The actions of the FSH hormone are mediated by a specific membrane receptor that is a member of the large family of G-protein coupled receptors. These receptors consist of a single polypeptide with seven transmembrane domains and are able to interact with the Gs protein, leading to the activation of adenylate cyclase.

The FSH receptor (FSHR) is a highly specific target in the ovarian follicle growth process and is exclusively expressed in the ovary. Low molecular weight FSHR agonists can be used for the same clinical purposes as native FSH, i.e. for the treatment of infertility and for ovarian hyperstimulation on preceeding in vitro fertilisation.

Certain tetrahydroquinoline derivatives have recently been disclosed in the International Application WO 2003/004028 (AKZO NOBEL N.V.) as FSHR modulating substances, either having agonistic or antagonistic properties.

Low molecular weight FSH mimetics with agonistic properties were disclosed in the International Application WO 2000/08015 (Applied Research Systems ARS Holding N.V.); WO 2004/031182 (Applied Research Systems ARS Holding N.V.); WO 2002/09706 (Affymax Research Institute); WO 2005/087765 (Arena Pharmaceuticals, Inc); WO 2006/117368 (AKZO NOBEL N.V.); WO 2006/117370 (AKZO NOBEL N.V.); WO 2006/117371 (AKZO NOBEL N.V.) and in WO 2006/117023 (AKZO NOBEL N.V.).

There clearly is a need for low molecular weight hormone mimetics that selectively activate the FSH receptor.

To that aim the present invention provides 5,6-dihydropyrrolo[2,1-α]isoquinoline and pyrrolo[2,1-α]isoquinoline derivatives.

Certain 5,6-dihydropyrrolo[2,1-α]isoquinolines, as well as their unsaturated analogs pyrrolo[2,1-α]isoquinolines are known in literature.

The lamellarins, a family of polyaromatic pyrrole alkaloids, some of which contain the 5,6-dihydropyrrolo[2,1-α]isoquinoline or the pyrrolo[2,1-α]isoquinoline scaffold (see structures A and B), are reviewed in C. Bailly, Curr. Med. Chem. Anti-Cancer Agents, 4, 363-387 (2004) and Fan, H. et al Chem. Rev., 108, 264-287 (2008). Some of these compounds exhibit potent cytotoxic activities against tumor cells in vitro.

Open-chain Lamellarin D analogues, described in D. Pla et al., J. Med. Chem., 49, 3257 (2006), contain general formula (C) and exhibit cytotoxicity in the low micrmolar range.

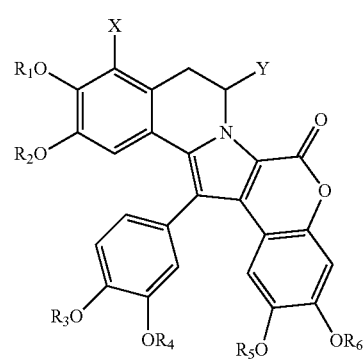

A

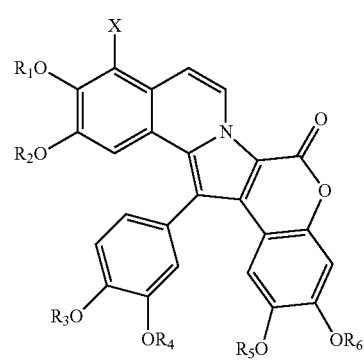

B

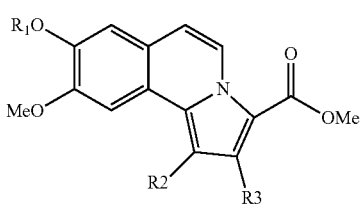

5,6-Dihydropyrrolo[2,1-α]isoquinolines and pyrrolo[2,1-α]isoquinolines of the formula (D) and formula (E) are described in WO 2006/089815; WO 2006/075012; WO 2005/002579; WO 2005/003129; WO 2005/003130; WO 2003/051877; WO 2003/014115; WO 2003/014116; WO 2003/014117 and WO 2002/48144. These compounds are reported to inhibit phoshodiesterase 10A (PDE10A).

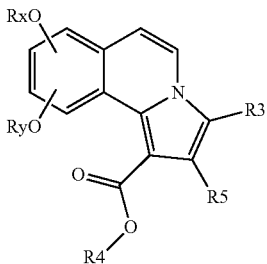

D

R3 = H, formyl, (substituted) alkyl, alkoxycarbonyl, alkyl carbonyl or amine

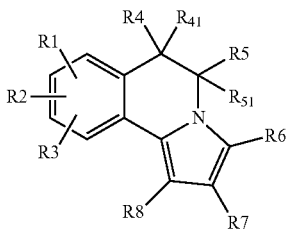

E

R6 = H, formyl, amino, or (substituted) alkyl

The present invention provides related compounds according to general formula I or a pharmaceutically acceptable salt thereof

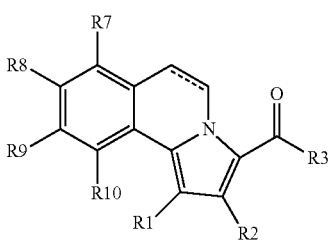

Formula I

In this formula $R^1$ through $R^{10}$ have the following definitions:

The bond at the C5-C6 position (dotted line in Formula I) can either be saturated or unsaturated.

$R^1$ is halogen, cyano, (1-6C)alkyl, (2-6C)alkenyl, (2-6C)alkynyl, (3-6C)cycloalkyl, (5-6C)cycloalkenyl, or phenyl or (1-5C)heteroaryl, each of said phenyl and heteroaryl moieties being independently optionally substituted with one or more substituents selected from $R^{13}$.

$R^2$ is H, cyano, halogen, (1-4C)alkyl, (1-4C)alkoxy(1-4C)alkyl, hydroxy(1-4C)alkyl, formyl, (1-4C)alkylcarbonyl or C=N—OH, C=N—OCH$_3$.

$R^3$ is $R^{15}$,$R^{16}$-amino or $R^3$ is (1-6C)alkyl, (3-6C)cycloalkyl, (di)[(1-4C)alkyl]amino(1-4C)alkyl or $R^3$ is (2-6C)heterocycloalkyl(1-4C)alkyl, the (2-6C)heterocycloalkyl moiety of which optionally may be substituted with (1-4C)alkylcarbonyl or (3-6C)cycloalkylcarbonyl, or $R^3$ is a group selected from

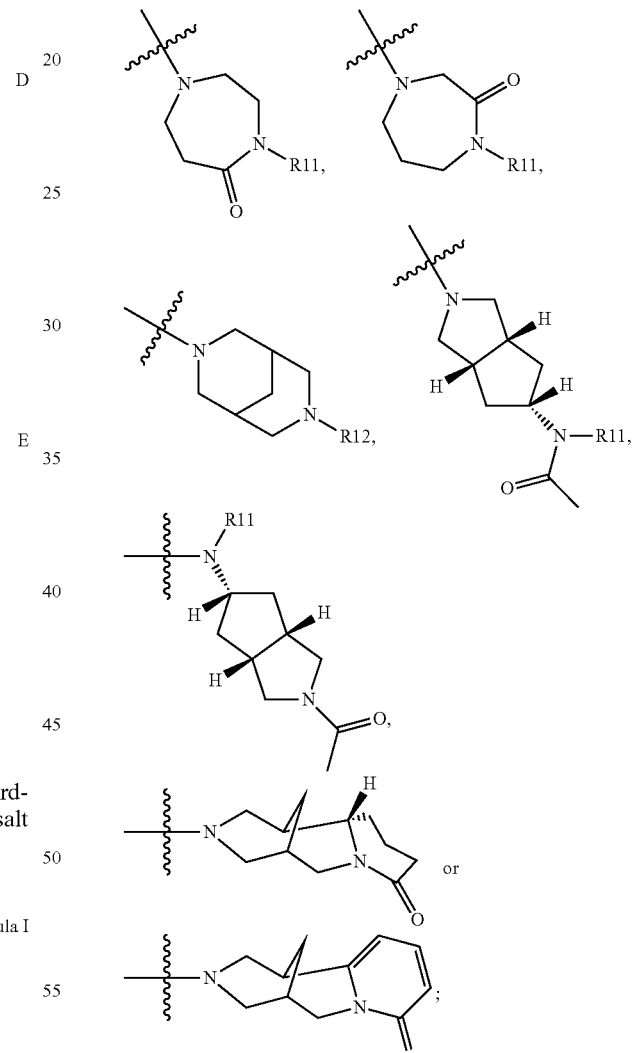

$R^7$ is H, halogen, or methyl.

$R^8$ is H, halogen, (1-4C)alkyl, (1-4C)alkoxy, (1-4C)alkoxy(1-4C)alkyl or hydroxy.

$R^9$ is H, formyl, halogen, hydroxy, amino, cyano, nitro, (2-6C)alkynyl, (3-6C)cycloalkoxy, (2-6C)heterocycloalkoxy, (2-5C)heteroaryloxy, (di)[(1-4C)alkyl]aminocarboxy, (1-6C)alkylcarbonyl, (1-4C)alkoxycarbonyl, (di)[(1-4C)alkyl]aminocarbonyl, (2-6C)heterocycloalkylcarbonyl, (di)[(1-4C)alkyl]amino, (2-6C)heterocycloalkylcarbonylamino, (2-5C)heteroarylcarbonylamino, (di)[(1-4C)alkyl]aminocarbonylamino, (1-4C)alkoxycarbonylamino, (di)[(1-4C)alkyl]aminosulfonylamino, (1-4C)alkylsulfonylamino, 1-imidazolidinyl-2-one, 3-oxazolidinyl-2-one or 1-pyrrolidinyl-2-one, or $R^9$ is (1-6C)alkyl, (1-6C)alkoxy, (2-6C)alkenyl, (1-6C)alkylcarbonylamino or (2-6C)heterocycloalkyl, (2-5C)heteroarylaminocarbonyl, each of said alkyl, alkoxy, alkenyl, heterocycloalkyl and heteroaryl being independently optionally substituted with one or more substituents selected from $R^{14}$, or $R^9$ is (1-5C)heteroaryl, phenyl or phenoxy, each of said heteroaryl, phenyl and phenoxy being independently optionally substituted with one or more substituents selected from $R^{13}$.

$R^{10}$ is H, methoxy, halogen or methyl.

$R^{11}$ through $R^{18}$ as mentioned in one of the other R groups are defined below:

$R^{11}$ is H, (1-6C)alkyl or (3-4C)alkenyl.

$R^{12}$ is (1-4C)alkylcarbonyl or (3-6C)cycloalkylcarbonyl, both optionally substituted with one or more substituents selected from $R^{13}$.

$R^{13}$ is hydroxy, amino, halogen, nitro, trifluoromethyl, cyano, (1-4C)alkyl, (1-4C)alkoxy, (1-4C)alkylthio or (di)[(1-4C)alkyl]amino. In each of the occurrences of $R^{13}$ each definition for a certain group can be chosen independently.

$R^{14}$ is hydroxy, amino, halogen, azido, cyano, (1-4C)alkyl, (1-4C)alkoxy, (1-4C)alkylthio, (di)[(1-4C)alkyl]amino, (3-6C)cycloalkyl, (2-6C)heterocycloalkyl, (1-4C)alkylcarbonylamino, (di)[(1-4C)alkyl]aminocarbonylamino, (1-4C)alkylsulfonylamino, (1-4C)alkoxycarbonylamino, (1-4C)alkylcarbonyl, (1-4C)alkoxycarbonyl, (1-4C)alkylsulfoxy, (2-6C)heterocycloalkoxy, (di)[(1-4C)alkyl]aminocarbonyl, (1-4C)alkylsulfonyl, (3-6C)cycloalkylcarbonylamino and [(1-4C)alkyl][(1-4C)alkylcarbonyl]amino.

$R^{15}$ and $R^{16}$ in $R^3$ is independently selected from H, or (1-6C)alkyl, (3-6C)cycloalkyl, (2-6C)heterocycloalkyl or (di)[(1-4C)alkyl]amino, all optionally substituted with hydroxy, (1-4C)alkyl, (1-4C)alkoxy, (1-4C)alkylcarbonyl, (1-4C)alkoxycarbonyl, (3-6C)cycloalkylcarbonyl, (di)[(1-4C)alkyl]amino, (di)[(1-4C)alkyl]aminocarbonyl or (di)[(1-4C)alkoxy(1-4C)alkyl]amino.

Alternately, $R^{15},R^{16}$-amino in $R^3$ can be joined to form a (3-8C)heterocycloalkyl ring wherein said ring can optionally be substituted with $R^{18}$.

Still alternately, $R^{15},R^{16}$-amino in $R^3$ can also be joined to form a (4-8C)heterocycloalkyl ring or (4-6C)heterocycloalkenyl ring, which rings both contain one nitrogen and which are each said ring being independently optionally substituted with one or more substituents selected from $R^{17}$.

$R^{17}$ and $R^{18}$ as mentioned in one of the other R groups are defined below:

$R^{17}$ is hydroxy, amino, halogen, (1-4C)alkyl, (1-4C)alkoxy, (di)[(1-4C)alkyl]amino, (1-4C)alkylcarbonylamino, (di)[(1-4C)alkyl]aminocarbonylamino, (1-4C)alkylsulfonylamino, (1-4C)alkoxycarbonylamino, (1-4C)alkylsulfoxy, (3-6C)cycloalkylcarbonylamino, [(1-4C)alkyl][(1-4C)alkylcarbonyl]amino, or $R^{17}$ is phenyl and (2-5C)heteroaryl, both optionally substituted with one or more substituents selected from $R^{13}$.

$R^{18}$ is (1-4C)alkyl, (3-6C)cycloalkyl, (4-6C)cyclo alkenylcarbonyl, (di)[(1-4C)alkyl]aminocarbonyl, (1-4C)alkylsulfonyl, (di)[(1-4C)alkyl]aminosulfonyl, (2-6C)hetero cycloalkylsulfonyl, (2-5C)hetero aryl, phenylcarbonyl, (1-4C)alkylcarbonyl, (3-6C)cyclo alkylcarbonyl, (2-5C)hetero arylcarbonyl, phenyl, phenylsulfonyl, (2-5C)heteroarylsulfonyl and (2-6C)heterocycloalkylcarbonyl, of which the (cyclo)alkyl and (hetero)aryl moieties can be substituted with one or more substituents selected from $R^{13}$.

The 5,6-dihydropyrrolo[2,1-α]isoquinoline and pyrrolo[2,1-α]isoquinoline derivatives according to the present invention are potent FSH receptor activators and can be used for the same clinical purposes as native FSH since they behave like agonists, with the advantage that they may be prepared synthetically, may display altered stability properties and may be administered differently.

Thus, the FSH-receptor agonists of the present invention may be used for the treatment of fertility disorders e.g. controlled ovarian stimulation and IVF procedures.

The term (1-4C)alkyl as used in the definition means a branched or unbranched alkyl group having 1-4 carbon atoms, being methyl, ethyl, propyl, isopropyl, butyl, isobutyl, sec-butyl and tert-butyl.

The term (1-6C)alkyl means a branched or unbranched alkyl group having 1-6 carbon atoms, for example methyl, ethyl, propyl, isopropyl, butyl, tert-butyl, n-pentyl and n-hexyl. (1-5C)Alkyl groups are preferred, (1-4C)alkyl being the most preferred.

The term (1-4C)alkylcarbonyl means an alkylcarbonyl group, the alkyl group of which contains 1-4 carbon atoms with the same meaning as previously defined.

The term (1-4C)alkylsulfonyl means an alkylsulfonyl group, the alkyl group of which contains 1-4 carbon atoms with the same meaning as previously defined.

The term (1-4C)alkylthio means an alkylthio group having 1-4 carbon atoms, the alkyl group of which contains 1-4 carbon atoms with the same meaning as previously defined.

The term (1-4C)alkylsulfoxy means an alkylsulfoxy group, the alkyl group of which contains 1-4 carbon atoms with the same meaning as previously defined.

The term (1-4C)alkylsulfonylamino means a alkylsulfonylamino group, the alkyl group of which contains 1-4 carbon atoms with the same meaning as previously defined.

The term (1-6C)alkylcarbonylamino means an alkylcarbonyl group, the alkyl group of which contains 1-6 carbon atoms with the same meaning as previously defined.

The term (2-6C)alkenyl means a branched or unbranched alkenyl group having 2-6 carbon atoms, such as ethenyl, 2-butenyl, and n-pentenyl.

The term (2-6C)alkynyl means a branched or unbranched alkynyl group having 2-6 carbon atoms, such as ethynyl, propynyl and n-pentynyl.

The term (3-6C)cycloalkyl means a cycloalkyl group having 3-6 carbon atoms, such as cyclopropyl, ethylcyclopropyl, cyclobutyl, methylcyclobutyl, cyclopentyl and cyclohexyl.

The term (3-6C)cycloalkylcarbonyl means a cycloalkylcarbonyl group, the cycloalkyl group of which contains 3-6 carbon atoms with the same meaning as previously defined.

The term (5-6C)cycloalkenyl means a cycloalkenyl group having 5-6 carbon atoms, being cyclopentenyl, methylcyclopentyl and cyclohexenyl.

The term (5-6C)cycloalkenylcarbonyl means a cycloalkenylcarbonyl group, the cycloalkenyl group of which contains 5-6 carbon atoms with the same meaning as previously defined.

The term (2-6C)heterocycloalkyl means a heterocycloalkyl group having 2-6 carbon atoms, preferably 3-5 carbon atoms, including 1-3 heteroatom s selected from N, O and/or S, which may be attached via a nitrogen if feasible, or a carbon atom. Preferred heteroatoms are N or O. Preferred number of heteroatoms is one or two. Most preferred are piperidin-1-yl, morpholin-4-yl, pyrrolidin-1-yl and piperazin-1-yl.

The term (4-8C)heterocycloalkyl in R³ means a heterocycloalkyl group having 4-8 carbon atoms, preferably 4-5 carbon atoms, including one nitrogen, which is attached via a nitrogen. Most preferred are piperidin-1-yl and pyrrolidin-1-yl.

The term (3-8C)heterocycloalkyl in R³ means a heterocycloalkyl group having 3-8 carbon atoms, preferably 4-5 carbon atoms, including 2-3 heteroatoms selected from N, O and/or S, which may be attached via a nitrogen if feasible, or a carbon atom. Preferred heteroatoms are N or O. Preferred number of heteroatoms is two, such as N,N or N,O. More preferred is [1,4]diazacycloheptanyl.

The term (2-6C)heterocycloalkoxy means a heterocycloalkyl group which contains 2-6 carbon atoms with the same meaning as previously defined, attached via a carbon atom to an exocyclic oxygen atom.

The term (2-6C)heterocycloalkyl(1-4C)alkyl means a heterocycloalkylalkyl group, the heterocycloalkyl group of which contains 2-6 carbon atoms, preferably 3-5 carbon atoms, with the same meaning as previously defined and the alkyl group of which contains 1-4 carbon atoms with the same meaning as previously defined.

The term (2-6C)heterocycloalkylcarbonyl means a heterocycloalkylcarbonyl group, the heterocycloalkyl group of which contains 2-6 carbon atoms, preferably 3-5 carbon atoms, with the same meaning as defined previously.

The term (2-6C)heterocycloalkylsulfonyl means a heterocycloalkylsulfonyl group, the heterocycloalkyl group of which contains 2-6 carbon atoms, preferably 3-5 carbon atoms, with the same meaning as defined previously.

The term (2-6C)heterocycloalkylcarbonylamino means a heterocycloalkylcarbonylamino group, the heterocycloalkyl group of which contains 2-6 carbon atoms, preferably 3-5 carbon atoms, with the same meaning as defined previously.

The term (4-6C)heterocycloalkenyl means a heterocycloalkenyl group having 4-6 carbon atoms, preferably 3-5 carbon atoms, and including 1-3 heteroatoms selected from N, O and/or S, which may be attached via a nitrogen if feasible, or a carbon atom. Preferred heteroatoms are N or O. Preferred number of heteroatoms is one or two.

The term (1-5C)heteroaryl means an aromatic group having 1-5 carbon atoms and 1-4 heteroatoms selected from N, O and S, like imidazolyl, thiadiazolyl, pyridinyl, thienyl, tetrazolyl, oxazolyl, imidazolyl, pyrazolyl or furyl. Preferred number of heteroatoms is one or two. Preferred heteroaryl groups are thienyl, oxazolyl, imidazolyl, pyrazolyl, pyrimidinyl, pyrazinyl, furyl and pyridinyl. Most preferred are thienyl, furyl and pyridinyl. The (1-5C)heteroaryl group may be attached via a carbon atom or a nitrogen, if feasible.

The term (2-5C)heteroaryl means an aromatic group having 2-5 carbon atoms and 1-3 heteroatoms selected from N, O and S, like imidazolyl, thiadiazolyl, pyridinyl, thienyl or furyl. Preferred heteroaryl groups are thienyl, pyrimidinyl, pyrazinyl, furyl and pyridinyl. The (2-5C)heteroaryl group may be attached via a carbon atom or a nitrogen, if feasible.

The term (2-5C)heteroarylcarbonyl means a heteroarylcarbonyl group, the heteroaryl group of which contains 2-5 carbon atoms with the same meaning and preferences as previously defined.

The term (2-5C)heteroarylaminocarbonyl means a heteroarylaminocarbonyl group, the heteroaryl group of which contains 2-5 carbon atoms with the same meaning and preferences as previously defined.

The term (2-5C)heteroarylsulfonyl means a heteroarylsulfonyl group, the heteroaryl group of which contains 2-5 carbon atoms with the same meaning and preferences as previously defined.

The term (2-5C)heteroaryloxy means a heteroaryloxy group, the heteroaryl group of which contains 2-5 carbon atoms with the same meaning and preferences as previously defined, attached via a carbon atom to an exocyclic oxygen atom.

The term (1-4C)alkoxy means an alkoxy group having 1-4 carbon atoms, the alkyl moiety having the same meaning as previously defined. (1-3C)Alkoxy groups are preferred.

The term (1-4C)alkoxycarbonyl means an alkoxycarbonyl group, the alkoxy group of which contains 1-4 carbon atoms with the same meaning as previously defined. (1-2C)Alkoxycarbonyl groups are preferred.

The term (1-4C)alkoxy(1-4C)alkyl means an alkoxyalkyl group, the alkoxy group of which contains 1-4 carbon atoms with the same meaning as previously defined, which is attached to an alkyl group containing 1-4 carbon atoms with the same meaning as previously defined.

The term (1-4C)alkoxycarbonylamino means an alkoxycarbonylamino group, the alkoxy group of which contains 1-4 carbon atoms with the same meaning as previously defined.

The term hydroxy(1-4C)alkyl as used herein means an hydroxyalkyl group, the alkyl group of which contains 1-4 carbon atoms with the same meaning as previously defined.

The term (di)[(1-4C)alkyl]amino as used herein means an amino group, monosubstituted or disubstituted with alkyl group(s), each containing 1-4 carbon atoms and having the same meaning as previously defined.

The term (di)[(1-4C)alkyl]aminocarbonyl means a (di)alkylaminocarbonyl group, the alkyl group (s) of which each contain(s) 1-4 carbon atoms with the same meaning as previously defined.

The term (di)[(1-4C)alkyl]aminosulfonyl means a (di)alkylaminosulfonyl group, the alkyl group (s) of which each contain(s) 1-4 carbon atoms with the same meaning as previously defined.

The term (di)[(1-4C)alkyl]aminocarbonyloxy means a (di)alkylaminocarbonyloxy group, the alkyl group (s) of which each contain(s) 1-4 carbon atoms with the same meaning as previously defined.

The term (di)[(1-4C)alkyl]aminocarbonylamino means a (di)alkylaminocarbonylamino group, the alkyl group (s) of which each contain(s) 1-4 carbon atoms with the same meaning as previously defined.

The term (di)(1-4C)alkylamino(1-4C)alkyl as used herein means a (di)alkylamino group, the alkyl group (s) of which each contain(s) 1-4 carbon atoms with the same meaning as previously defined, connected via the amino group to an alkyl group which contains 1-4 carbon atoms with the same meaning as previously defined.

The term (di)[(1-4C)alkyl]aminosulfonylamino means a (di)alkylaminosulfonylamino group, the alkyl group (s) of which each contain(s) 1-4 carbon atoms with the same meaning as previously defined.

The term halogen means fluorine, chlorine, bromine or iodine.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

In the above definitions with multifunctional groups the attachment point is at the last group.

The term pharmaceutically acceptable salt represents those salts which are, within the scope of medical judgement, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

In one aspect the invention relates to compounds of formula I wherein the C5-C6 bond is saturated.

The invention also relates to compounds of formula I, wherein $R^1$ is (1-5C)heteroaryl, optionally substituted with one or more substituents selected from $R^{13}$.

In another aspect the invention relates to compounds of formula I wherein $R^2$ is H, cyano, halogen, (1-4C)alkoxy(1-4C)alkyl or hydroxy(1-4C)alkyl.

In yet another aspect the invention concerns compounds of formula I wherein $R^2$ is H.

Another aspect concerns compounds wherein $R^3$ is $R^{15}$, $R^{16}$-amino or

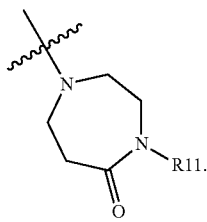

In another aspect the invention concerns compounds wherein $R^3$ is $R^{15}$,$R^{16}$-amino.

In still another aspect the invention concerns compounds of formula I wherein $R^7$ is H. The invention also relates to compounds wherein $R^8$ is (1-4C)alkoxy or hydroxy.

In another aspect the invention relates to compounds of formula I wherein $R^9$ is halogen, cyano, nitro, (2-6C)alkynyl, (3-6C)cycloalkoxy, (2-5C)heterocycloalkoxy, (2-5C)heteroaryloxy, (di)[(1-4C)alkyl]aminocarbonyl, (2-6C)heterocycloalkylcarbonyl or (di)[(1-4C)alkyl]amino. $R^9$ might also be (1-6C)alkyl, (1-6C)alkoxy, (2-6C)alkenyl, (1-6C)alkylcarbonylamino or (2-5C)heteroarylaminocarbonyl. These latter groups all may be independently optionally substituted with one or more substituents selected from $R^{14}$. Alternatively, $R^9$ may be (1-5C)heteroaryl or phenoxy, optionally substituted with one or more substituents selected from $R^{13}$.

In yet another aspect the invention relates to compounds of formula I wherein $R^9$ is halogen, cyano, nitro, (2-6C)alkynyl or (di)[(1-4C)alkyl]amino, or $R^9$ is (1-6C)alkyl, (1-6C)alkoxy, (2-6C)alkenyl or (1-6C)alkylcarbonylamino, each of said groups independently optionally substituted with one or more substituents selected from $R^{14}$, or $R^9$ is (1-5C)heteroaryl, optionally substituted with one or more substituents selected from $R^{13}$.

In another aspect the invention concerns compounds of formula I wherein $R^9$ is (2-6C)alkynyl, or wherein $R^9$ is (1-6C)alkyl, (1-6C)alkoxy, (2-6C)alkenyl, or (1-6C)alkylcarbonylamino, each of said groups independently optionally substituted with one or more substituents selected from $R^{14}$, or wherein $R^9$ is (1-5C)heteroaryl optionally substituted with one or more substituents selected from $R^{13}$.

In another aspect the invention relates to compounds of formula I wherein $R^{10}$ is H.

In a further aspect the invention relates to compounds of formula I wherein $R^1$ is (1-5C)heteroaryl, optionally substituted with one or more substituents selected from $R^{13}$, $R^2$ is H, $R^3$ is $R^{15}$,$R^{16}$-amino, $R^7$ is H, $R^8$ is (1-4C)alkoxy and $R^{10}$ is H.

In yet another aspect the invention relates to compounds of formula I wherein $R^{14}$ is (2-6C)heterocycloalkyl, hydroxy, (1-4C)alkoxy or (di)[(1-4C)alkyl]amino.

In yet another aspect the invention relates to compounds of formula I wherein $R^{15}$ and $R^{16}$ may be independently selected from (1-6C)alkyl.

In another aspect the invention relates to compounds of formula I wherein $R^3$ is 1,4 diazacycloheptan-1-yl, optionally substituted with (1-4C)alkylcarbonyl or (3-6C)cycloalkylcarbonyl.

In yet another aspect the invention relates to compounds of formula I wherein $R^{15}$ is methyl and $R^{16}$ is tert-butyl.

In another aspect the invention relates to compounds of formula I wherein $R^3$ is 2,2-dimethylpyrrolidin-1-yl.

The invention also relates to those compounds wherein all specific definitions for $R^1$ through $R^{18}$ in the various aspects of the invention as defined hereabove occur in any combination within the definition of the (dihydro)pyrrolo[2,1-α]isoquinoline compound of formula I.

All compounds of the invention have an $EC_{50}$ of less than 10 μM.

In another aspect the invention relates to compounds of formula I which have an $EC_{50}$ of less than 100 nM. In yet another aspect the invention relates to compounds of formula I which have an $EC_{50}$ of 10 nM or less The invention also relates to the compounds described in examples 1-4, 7c, 7d, 8, 10, 11, 12a, 12b, 14a, 14d, 16, 20, 21, 36, 39-43, 51, 55, 58b, 58c, 59, 61-62, 64, 65d, 65f, 69, 70d, 81-84, 85b, 91a, 91d, 92-94, 96-98, 100, 101, 104, 111a, 111b, 121a, 121b, 122 and 123.

In yet another aspect the invention relates to the compounds described in examples 1, 2, 7d, 14a, 58b, 91d, 100 and 123.

The term $EC_{50}$ means the concentration of the test compound that elicits half-maximal (50%) stimulation compared to the compound's maximally attainable effect. The values can be determined e.g. in a cell line transfected with a FSH receptor gene and cotransfected with a cAMP responsive element/promoter directing the expression of a reporter gene. Values can be determined using the software program such as MathIQ (version 2.0, ID Business Solutions Limited).

Excluded from the invention is the compound 3-acetyl-pyrrolo[2,1-α]isoquinoline-1-carbonitrile.

The disclaimer relates to the disclosures in Database CA, accession no 1994:655585.

Suitable methods to prepare 5,6-dihydropyrrolo[2,1-α] isoquinoline and pyrrolo[2,1-α]isoquinoline compounds are outlined below.

5,6-Dihydro-pyrrolo[2,1-α]isoquinolines are known in literature. Chemical approaches to specific analogs involve total synthesis starting from pyrrole esters, followed by sequential bromination/organometal-mediated arylation reactions.

Other synthetic procedures are based on Pictet-Spengler type chemistry, leading to substituted 1-methylene-tetrahydroisoquinolines, followed by Michael-type condensation to the required dihydro-pyrroloisoquinoline derivatives, or entail 1,3-dipolar cycloaddition reactions. One report describes the synthesis of several dihydro-pyrroloisoquinolines via cycloaddition of acetylenes to 3,4-dihydro-isoquinoline N-oxides, followed by thermal rearrangement of intermediately formed Δ4-isoxazolines, to give as the most related (vide infra) compound I-phenyl-8,9-dimethoxy-5,6-dihydro-pyrrolo[2,1-α]isoquinoline-3-carboxylic acid ethyl ester.

For relevant literature see: M. Alvarez et al., *Tetrahedron Lett.*, 46, 2041 (2005); M. Alvarez et al., *J. Org. Chem.*, 70, 8231 (2005); S. Handy, *J. Org. Chem.*, 69, 2362 (2004); M. Vennemann et al., (Altana Pharma A.G) WO 05/003130; Niewoehner et al. (Bayer AG), WO 02/48144; Banwell et al. WO 99/67250. W. Anderson et al., *J. Med. Chem.*, 27, 1321 (1984); S. Eguchi et al., *Tetrahedron* 52, 12049 (1996).

Here we describe hitherto unknown compounds of general formula I and, more specifically, 5,6-dihydro-pyrrolo[2,1-α]isoquinoline-3-carbonamides, 1-(5,6-dihydro-pyrrolo[2,1-α]isoquinolin-3-yl)-alkyl-1-ones, cycloalkyl-(5,6-dihydro-pyrrolo[2,1-α]iso-quinolin-3-yl)-methanones and related 2-amino-1-(5,6-dihydro-pyrrolo[2,1-α]isoquinolin-3-yl)-ethanones, as well as their unsaturated analogs pyrrolo[2,1-α]isoquinoline-3-carbonamides, 1-(pyrrolo[2,1-α]isoquinolin-3-yl)-alkyl-1-ones, cycloalkyl-(pyrrolo[2,1-α]isoquinolin-3-yl)-methanones and 2-amino-1-(pyrrolo[2,1-α]isoquinolin-3-yl)-ethanones (formula I with R3=alkyl or cycloalkyl, I-a and I-b).

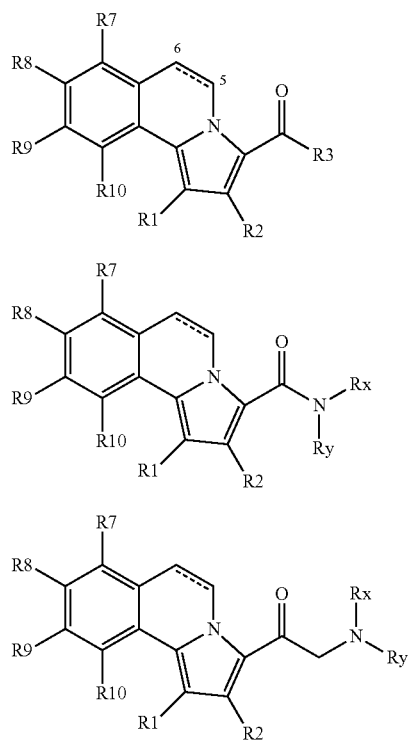

The new specifically substituted 5,6-dihydro-pyrrolo[2,1-α]isoquinolines we aim at, are made accessible via 1,3-dipolar cycloaddition reactions of acetylenes with reactive muchnone intermediates derived from tetrahydroisoquinolino-1-carboxylic acids (III). Fundamentals of this chemistry have been described by R. Huisgen et al., *Chem. Ber.*, 103, 2611 (1970), and are further exemplified by F. Hershenson, *J. Org. Chem.*, 40, 740 (1975).

For our purpose (i.e. introduction of a carbonyl group at C-3) this methodology was modified by performing the 1,3-dipolar cycloaddition reactions with oxalates (IV), rendering directly the required 3-carboxylic esters (V), as precursors for e.g. amides (1-a). The intermediate tetrahydroisoquinolino-1-carboxylic acids of general formula III (needed for the preparation of oxalates IV) were synthesized in a Bishler-Napieralski-type closure from appropriately substituted phenethyl amines (II) with glyoxylic acid, according to a published procedure (S. Bajusz et al., WO 93/12091).

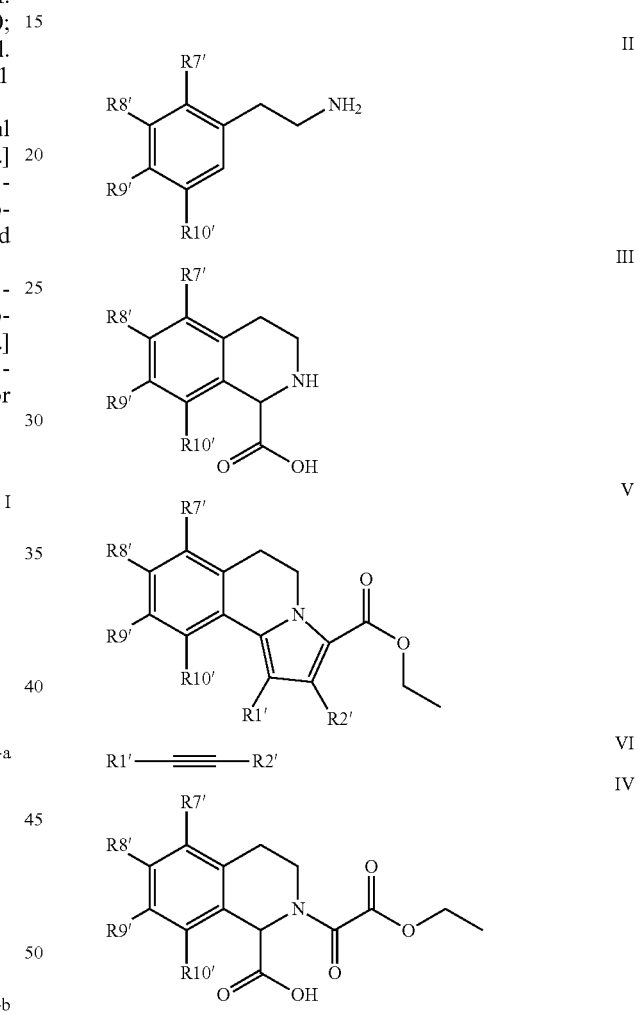

For the synthesis of specific compounds I-a and I-b (vide infra), the overall approach indicated above was employed, making use of tailor-made functionalized intermediates. This means that, depending on the required substituents R1-R10 (where R-numbering refers to the atom numeration in the scaffold), either the required substituents are brought in place at the beginning of the synthesis (i.e. R1=R1', R2=R2', etc.), or are introduced at any stage judged to be convenient in the course of the synthesis of the products of general formula I. In that case suitable alternative functionalities are introduced first, indicated as R1'-R10', which allow for the conversion into the desired R1-R10 in one or more additional manipulations, with R1-R10 having the same meaning as previously defined.

Substituents on the aromatic ring (R7-R10) can often be introduced already in the phenethyl amine precursors (II), carrying them unchanged throughout the further synthetic process. The appropriate phenethyl amines of general structure II are either commercially available or are prepared readily via chloromethylation of appropriately substituted benzenes, followed by conversion into cyanomethyl derivatives and reduction of the nitrile functionality, yielding the required phenethyl amines. Phenethyl amines (II) are also accessible via Henry reaction of suitably substituted aromatic aldehydes with nitroalkanes, followed by reduction by hydride reagents, (LiAlH$_4$, boranes etc.), according to procedures well documented in literature. Alternatively, the required R7-R10 can be introduced via latent functional groups (as said before), to be manipulated further on in the synthetic procedure (vide infra).

The subsequent conversion of said phenethyl amines (II) into the intermediate 1,2,3,4-tetrahydroisoquinoline carboxylic acids (III) was efficiently accomplished in a three-step procedure by first converting the phenethyl amines (II) to carbamate derivatives (VII) and subsequent reaction with glyoxylic acid (leading to VIII), followed by deprotection of the carbamate protective group. An alloxycarbonyl (Alloc) group (see VII-a→VIII-a→III) was preferentially used here, because of its ease of removal. Alloc-protection and removal methods are well-known to those skilled in the art. In cases where final deprotection under reductive conditions was detrimental, alternative carbamate protective groups like 9-fluorenyl-methoxycarbonyl (Fmoc) were effective as well.

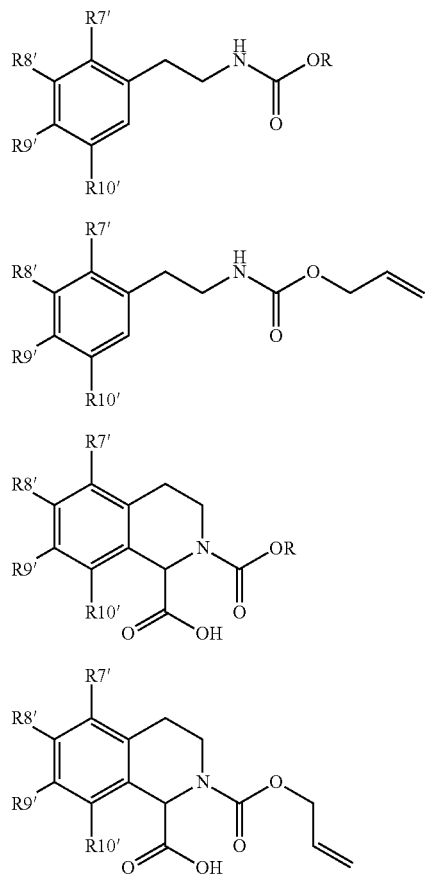

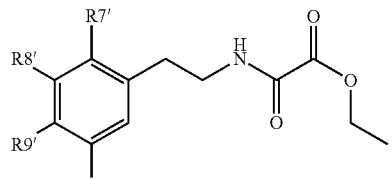

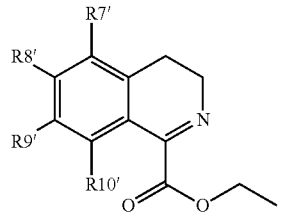

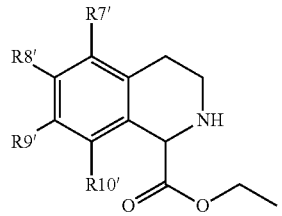

An alternative approach to generate the tetrahydroisoquinoline system present in compounds of general formula III comprises reaction of phenethyl amines (II) with ethyl oxalyl chloride to obtain oxalamides IX, which may undergo cyclisation to the dihydroisoquinolines (X) upon treatment with strong acids under dehydrating conditions, e.g. methanesulphonic acid and phosphorous pentoxide. Derivatives of general formula X may subsequently be reduced to the corresponding tetrahydroisoquinolines (XI), e.g. by reduction with sodium cyanoborohydride under acidic conditions. Saponification of tetrahydroquinolines (XI) under standard conditions well known to those skilled in the art can provide derivatives of general formula III.

In order to diversify the substituents R7-R10 on the phenyl moiety of derivatives of general formula I (or V) halogen atoms (preferentially bromine and iodine) may serve as masked functionalities (R7'-R10') to be converted in later stages of the synthesis to various target substituents (R7-R10), e.g. via lithiation followed by reaction with electrophilic reagents into carboxylates, carboxaldehydes (serving as precursors for olefins via subsequent Wittig reaction, or for amines via reductive amination) or hydroxymethyl groups (and derived ethers and esters).

Alternatively, aryl halogens (R7'-R10') can be employed as reactive substrates for well known organometallic reactions like Ullmann, Suzuki-, Stille-, Sonogashira-, Heck- and Buchwald protocols, to create new carbon-carbon single, double and triple bonds, carbon nitrogen bonds (aniline derivatives) and nitriles. These, in turn, may serve as substrates for further functionalization, like mono- and dihydroxylation (from alkenes), or conversion into triazoles (from acetylenes; "click chemistry") and into tetrazoles (from nitriles).

Demasking phenolic OH groups by e.g. selective cleavage of isopropoxy ethers (R7'-R10') with electrophilic reagents like BCl$_3$, followed by conversion into reactive sulphonate esters (e.g. triflates) allows for connection of heterocyclic structures via heteroaryl boronic acids or organotin derivatives, analogous to the above mentioned protocols starting from halogenated aryl groups. Conversion of aryl halogens (R7'-R10') into boronic acids (either via lithiation or transition metal-mediated boronation), followed by oxidation, provides a means of introducing alternative oxygen functionalities, well known to those skilled in the art. The phenolic functions arising from the deprotected alkoxy ethers can also be used for formation of aryl-aryl and aryl-heteroaryl ethers via Cu-mediated coupling with boronic acids and (hetero)aryl halides. Meaning and application of these reactions is amply explained in some selected literature sources outlined below.

For recent references see for example: A. Suzuki, *Chem. Comm.*, 4759 (2005); Bach et al., *Tetrahedron*, 61, 2245 (2005); R. Rossi et al., *Synthesis*, 2419 (2004).

Phenolic triflates (R7'-R10') can be (similarly as described for aryl bromides, vide supra) employed for the introduction of amine and amide functionalities (R7-R10) on the benzene ring by palladium-mediated coupling of either carbamates, carbonamides, imines, and silyl amides in processes known as Buchwald-Hartwig amination reactions. Alternatively, nitro groups introduced in an early stage of the synthesis (R7'-R10') enable the preparation of target molecules of general structure I incorporating amine and amide functionalities.

The assembly of the 5,6-dihydro-pyrrolo[2,1-α]isoquinoline skeleton via the 1,3-dipolar cycloadditon reaction (IV→V) requires acetylenes (VI) as reactants. This step offers the possibility of introducing the desired C-1 and C-2 substituents.

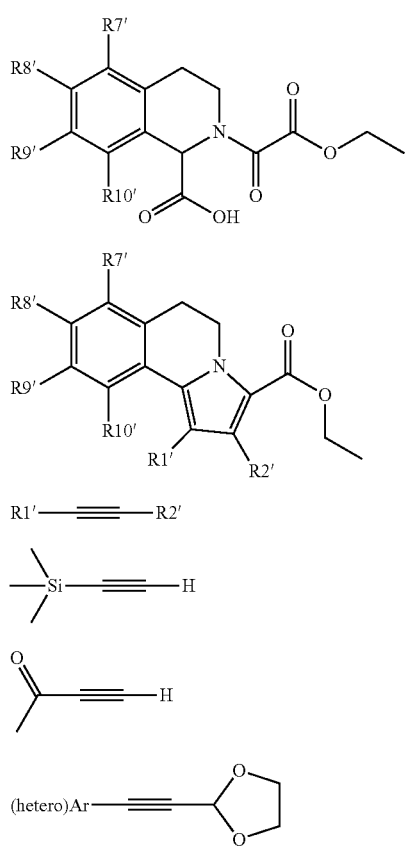

Generally, these reactions can be carried out with good regioselectivity, in which the most bulky substituent has a preference for position-1 of the final scaffold, if R1'/R2' are sufficiently different. Consequently, a range of products of general structure V are accessible with R1'=(hetero)aryl (like 2-thienyl, 3-thienyl, 3-pyridyl, etc) and R2'=H. If R2'=H, subsequent reaction with electrophilic reagents, like N-chlorosuccinimide (NCS) or chlorosulphonyl isocyanate, allows Cl or CN substituents to be introduced at the C2-position of the skeleton (V, R2'=CN or Cl).

The use of silylated acetylene (VI-a) provides C1-silylated 5,6-dihydro-pyrrolo[2,1-α]isoquinolines (V, R1'= trimethylsilyl), which upon acid treatment and bromination give the 1-bromo derivatives (V, R1'=Br). This allows for the synthesis of a variety of 1-substituted analogs of general formula V which are not accessible using the previously described 1,3-dipolar cycloaddition; e.g. due to poor availability of appropriate acetylenes VI or incompatibility of some substrates with the reaction conditions, for example in the preparation of dihydro-pyrroloisoquinolines V with R1'=cyano, ethynyl or ethenyl. In a similar manner as described for processing substituents R7'-R10' to R7-R10 (vide supra), treatment of 1-bromo-5,6-dihydro-pyrrolo[2,1-α]isoquinolines with either (hetero)aryl boron or (hetero)aryl tin derivatives provides 1-(hetero)arylated 5,6-dihydro-pyrrolo[2,1-α]isoquinolines (like 1-oxazolyl, 1-thiazolyl and 1-pyridyl derivatives.

Heterocyclic substituents at R1 which are difficult to obtain by methods described above can be also introduced by construction of the desired heterocycle from a suitable functionality at C-1. For example, 1-cyano-5,6-dihydro-pyrrolo[2,1-α]isoquinolines (V, R1'=CN), obtained by cyanide substitution of the corresponding 1-bromides (V, R1'=Br), may be used as an entry to e.g. 1-tetrazolyl-5,6-dihydro-pyrrolo[2,1-α]isoquinolines by condensation with silyl azides. Similarly, 1-ethinyl-5,6-dihydro-pyrrolo[2,1-α]isoquinolines (V, R1'=ethynyl) can be converted to 1-triazolo-5,6-dihydro-pyrrolo[2,1-α]isoquinolines by reaction with trimethylsilyl azide. 1-Acetyl-5,6-dihydro-pyrrolo[2,1-α] isoquinolines (V-b), obtained by reaction of IV with acetylenes VI-b, can subsequently be modified into e.g. 1-thiadiazolo-pyrrolo[2,1-α]isoquinolines (V, R1'=5-thiadiazolyl) by reaction with thionyl chloride and hydrazone.

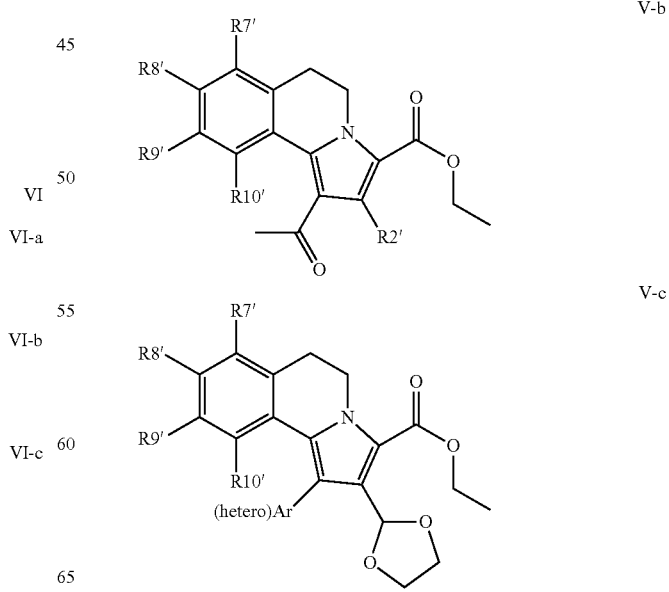

If acetylenes are used, equipped with a protected aldehyde functionality (e.g. VI-c), the corresponding 5,6-dihydro-pyrrolo[2,1-α]isoquinolines (V-c) are obtained, which can be further processed to derivatives of general structure I, bearing substituents at C-2 like oxime, aldehyde, aminoalkyl, alkenyl, (alkoxy, hydroxy)alkyl, and alkynyl groups.

Conversion of the carboxylate ester at C-3 in 5,6-dihydro-pyrrolo[2,1-α]isoquinolines (V) into the corresponding amides I-a may be achieved by a standard two-step procedure, well known to those skilled in the art, comprising saponification with e.g. aqueous NaOH in a suitable solvent such as dioxane or THF to obtain the respective 3-carboxylic acids, followed by reaction with the desired amine in the presence of a (commercially available) peptide coupling agent, like DCC, TBTU, HATU, EEDC, etc. Alternatively, the ethyl esters of general structure V can by converted directly into the corresponding amides I-a via metal derivatives of the amines (reaction known in literature as the Bodroux reaction), but variants may be applied as well; see for example Bassett et al., *J. Chem. Soc.*, 1188 (1954; Singh et al., *Tetrahedron Lett.*, 321 (1971)). The stage at which ester to amide transformations at C-3 are brought about is not necessarily the ultimate stage of synthesis, but may well be any moment deemed to be practical during the transformations outlined.

Alternatively, the amide functionality at C-3 in compounds of general formula I-a can be introduced already in the tetrahydroisoquinoline intermediate stage. For example, reaction of compounds of general formula XI with appropriately functionalized mono-amidated oxalic acid derivatives (XIII) under standard peptide coupling conditions well-known to those of skill in the art (vide supra), followed by saponification of the remaining ethyl ester moiety, may provide oxalamides of general structure XII. The required oxalic acid amides of general formula XIII can be obtained by reaction of the appropriate amines with ethyl oxalyl chloride and ensuing saponification of the ethyl ester under standard conditions. Subsequent 1,3-dipolar cycloaddition of oxalamides XII in the presence of suitably functionalized acetylenes of general formula VI, as described above, may give access to the desired derivatives of general formula I-a.

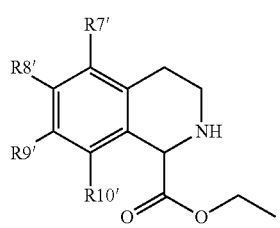

XI

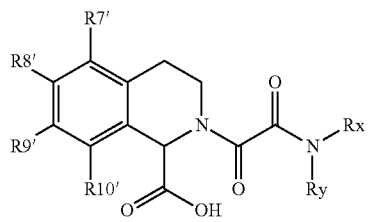

XII

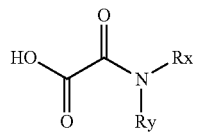

XIII

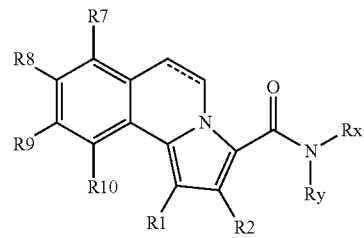

I-a

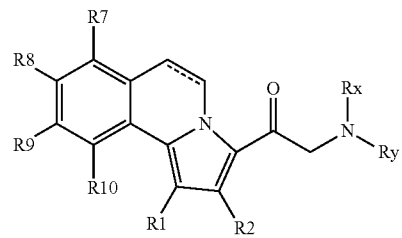

I-b

The construction of an additional double bond between C-5 and C-6 (cf. conversion of 5,6-dihydro-pyrrolo[2,1-α] isoquinolines to their aromatic analogs pyrrolo[2,1-α]isoquinolines) can generally be achieved by means of reagents which effect dehydrogenation/aromatization and are known to those skilled in the art. 2,3-Dichloro-5,6-dicyano-1,4-benzoquinone (DDQ) was preferentially used for that purpose.

In order to synthesize the 3-aminomethyl ketones of general structure I-b, in fact C1 homologs of previously mentioned amides 1-a, the overall approach used was rather similar. The 5,6-dihydro-pyrrolo[2,1-α]isoquinoline skeleton present in compounds of general formula XV (in this case R3=H instead of a carboxylate), is accessible by reaction of N-formyl substituted tetrahydroisoquinoline-1-carboxylic acids (XIV) with acetic anhydride and appropriately protected acetylenes of general formula VI. For introduction of the required functionality at C-3 a Friedel-Crafts-type acylation with appropriately functionalized carboxylic acid derivatives was performed first, leading to compounds of general formula XVI (X=reactive group, like halogen) or to compounds of general formula XVII (R3=alkyl or cycloalkyl). Examples of such reactions on pyrroles are amply documented in literature; see e.g. M. Kakushima, et al., *J. Org. Chem.*, 48, 3214 (1983); R. M. Silverstein, et al., *J. Org. Chem.*, 20, 668 (1955). Subsequent reactions of ethanones XVI with suitable amines may provide derivatives of general structure I-b.

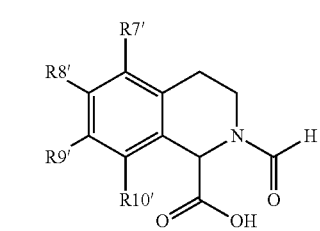

XIV

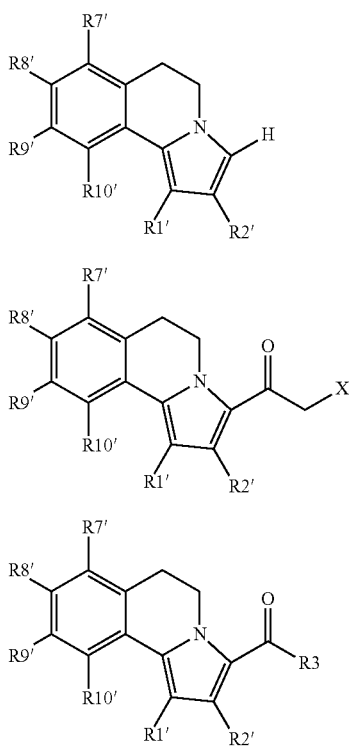

The compounds of the invention may form hydrates or solvates. It is known to those of skill in the art that charged compounds form hydrated species when lyophilized with water, or form solvated species when concentrated in a solution with an appropriate organic solvent. The compounds of this invention include the prodrugs, hydrates or solvates of the compounds listed.

A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates.

Non-limiting examples of suitable solvates include ethanolates, methanolates, and the like. "Hydrate" is a solvate wherein the solvent molecule is $H_2O$.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The (dihydro)pyrrolo[2,1-α]isoquinoline compounds of the invention were found to stimulate the FSH receptor. Methods to determine receptor binding, as well as in vitro and in vivo assays to determine biological activity, of gonadotropins are well known. In general, expressed receptor is incubated with the compound to be tested and binding or stimulation or inhibition of a functional response is measured.

To measure a functional response, isolated DNA encoding the FSH receptor gene, preferably the human receptor, is expressed in suitable host cells. Such a cell might be the Chinese Hamster Ovary cell, but other cells are also suitable. Preferably the cells are of mammalian origin (Jia et al, *Mol. Endocrin.*, 5, 759-776, (1991)).

Methods to construct recombinant FSH receptor expressing cell lines are well known in the art (Sambrook et al., Molecular Cloning: a Laboratory Manual, Cold Spring Harbor Laboratory Press, Cold Spring Harbor). Expression of receptor is attained by expression of the DNA encoding the desired protein. Techniques for site directed mutagenesis, ligation of additional sequences, PCR, and construction of suitable expression systems are all, by now, well known in the art. Portions, or all, of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available which are compatible with a wide variety of hosts, including prokaryotic hosts such as bacteria and eukaryotic hosts such as yeast, plant cells, insect cells, mammalian cells, avian cells and the like.

Cells expressing the receptor are then incubated with the test compound to observe binding of the test compound, or stimulation of a functional response.

Alternatively, isolated cell membranes containing the expressed receptor may be used to measure binding of the test compound.

For measurement of binding, radioactive or fluorescent compounds may be used. Such compounds are also part of the invention.

In the alternative also competition binding assays may be performed.

Another assay involves screening for FSH receptor agonistic compounds by determining stimulation of receptor mediated cAMP accumulation. Thus, such a method involves expression of the receptor in a host cell and exposing the cell to the test compound. The amount of cAMP is then measured. The level of cAMP will be increased, by the stimulating effect of the test compound upon binding to the receptor.

For the measurement of intrinsic activity human recombinant FSH can be used as a reference compound.

In addition to direct measurement of e.g. cAMP levels in the exposed cell, cells lines can be used which in addition to transfection of DNA encoding the FSH receptor are also transfected with a second DNA encoding a reporter gene the expression of which responds to the level of cAMP. Such reporter genes might be cAMP inducible or might be constructed in such a way that they are connected to novel cAMP responsive elements. In general, reporter gene expression might be controlled by any response element reacting to changing levels of cAMP. Suitable reporter genes are e.g. LacZ, alkaline phosphatase, firefly luciferase and green fluorescence protein. The principles of such transactivation assays are well known in the art and are described e.g. in Stratowa, Ch., Himmler, A. and Czernilofsky, A. P., *Curr. Opin. Biotechnol.*, 6, 574-581 (1995).

To investigate whether the LMW FSH-receptor agonist has a direct effect on the ovary, immature rats can be treated orally twice daily for 3 days, with ovarian weight augmentation as end parameter (determined on the fourth day). By co-administering a fixed amount of hCG for maximizing androgen production (also in the placebo animals) this test is very selective for the FSH-activity of the tested compound. If any LH-activity would be present, this is overruled by hCG activity. This test is an adaptation from the Steelman Pohley assay used for release of recombinant FSH (Steelman and Pohley, 1953).

The effect of the LMW FSH-receptor agonists on follicular growth can be further investigated in a model using GnRH-antagonist treated cyclic rats. Ovarian stimulation can be determined by increased ovarian weight and the number of ovulated ova (following ovulation induction by hCG). Also, clinically relevant biomarkers like estradiol and Inhibin B can be determined. In this model, stimulation with FSH (agonists) will lead to super ovulation (more than 15 ova).

For investigation of oocyte quality the animals can also be mated after ovulation induction and fertility can be determined.

The present invention also relates to a pharmaceutical composition comprising a (dihydro)pyrrolo[2,1-α]isoquinoline derivative or pharmaceutically acceptable salts thereof having the general formula I in admixture with pharmaceutically acceptable auxiliaries and optionally other therapeutic agents. The auxiliaries must be "acceptable" in the sense of being compatible with the other ingredients of the composition and not deleterious to the recipients thereof.

Compositions include e.g. those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general, parenteral administration requires lower dosages than other methods of administration which are more dependent upon absorption. However, a suitable dosage for humans may be 0.05-25 mg per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient.

The compounds according to the invention can be used in therapy. They can be used for the same clinical purposes as the native FSH.

A further aspect of the invention resides in the use of (dihydro)pyrrolo[2,1-α]isoquinoline compounds having the general formula I for the manufacture of a medicament to be used for the treatment of disorders responsive to FSH receptor mediated pathways, preferably for the treatment of fertility disorders. Thus, patients in need thereof can be administered with suitable amounts of the compounds according to the invention.

In yet another aspect the invention resides in the use of (dihydro)pyrrolo[2,1-α]isoquinoline compounds having the general formula I for the manufacture of a medicament to be used for the treatment of infertility. In particular the compounds can be used to induce ovulation (OI) or in controlled ovarian stimulation (COS) protocols.

The invention is illustrated by the following examples.

EXAMPLES

General Comments:

The following abbreviations are used in the examples: DIPEA=N,N-diisopropylethylamine, TFA=trifluoroacetic acid, HATU=O-(7-azabenzotriazole-1-yl)-N,N,N',N'-tetramethyl-uronium hexafluorophosphate, Fmoc=9-fluorenyl-methoxy-carbonyl, Fmoc-Cl=9-fluorenylmethoxycarbonyl chloride, Alloc=allyloxycarbonyl, DMF=N,N-dimethyl-formamide, DME=1,2-dimethoxyethane, THF= etrahydrofuran, Boc=t-butoxycarbonyl, NMP=N-methylpyrrolidone, TBTU=O-benzotriazol-1-yl-N,N,N,N'-tetrabutyluronium tetrafluoro-borate, BOP=(benzotriazol-1-yloxy)tris(dimethylamino)-phosphonium hexafluorophosphate, HOBt=1-hydroxybenzotriazole hydrate, DMAP=4-(dimethylamino) pyridine.

Unless stated otherwise, all final products of the examples below were lyophilized from water/1,4-dioxane, water/tent-butanol or water/acetonitrile mixtures. If the compound was prepared as a TFA salt, the acid was added in an appropriate amount to the solvent mixture before lyophilization.

The names of the final products described in the examples were generated using the Beilstein Autonom program (version: 2.02.304).

The following analytical HPLC methods were used for determination of retention times:

Method 1: Column: 5 μm Luna C-18(2) 150×4.6 mm; flow: 1 ml/min; detection: 210 nm; column temperature: 40° C.; solvent A: $CH_3CN/H_2O=1/9$ (v/v); solvent B: $CH_3CN$; solvent C, 0.1 M aqueous trifluoroacetic acid; gradient: solvent A/B/C=65/30/5 to 10/85/5 (v/v/v) in 30.00 min, then constant for an additional 10.00 min at A/B/C=10/85/5 (v/v/v).

Method 2: Identical to method 1, except for the gradient used: Gradient: solvent A/B/C=75/20/5 to 15/80/5 (v/v/v) in 30.00 min, then constant for an additional 10.00 min at A/B/C=15/80/5 (v/v/v).

Method 3: Identical to method 1, except for the gradient used: Gradient: solvent A/B/C=35/60/5 to 10/85/5 (v/v/v) in 30.00 min, then constant for an additional 10.00 min at A/B/C=10/85/5 (v/v/v).

Method 4: Identical to method 1, except for the gradient used: Gradient: solvent A/B/C=95/0/5 to 15/80/5 (v/v/v) in 30.00 min, then constant for an additional 10.00 min at A/B/C=15/80/5 (v/v/v).

Method 5: Identical to method 1, except for the gradient used: Gradient: solvent A/B/C=75/25/0 to 0/100/0 (v/v/v) in 30.00 min, then constant for an additional 10.00 min at A/B/C=0/100/0 (v/v/v).

Method 6: Identical to method 1, except for the gradient used: Gradient: solvent A/B/C=60/40/0 to 0/100/0 (v/v/v) in 30.00 min, then constant for an additional 10.00 min at A/B/C=0/100/0 (v/v/v).

Method 7: Column: 3 μm Luna C-18(2) 100×2 mm (Phenomenex); flow: 0.25 ml/min; detection: 210 nm; column temperature: 40° C.; solvent A: $CH_3CN/H_2O=1/9$ (v/v); solvent B: $CH_3CN$; gradient: solvent A/B=65/35 to 10/90 (v/v) in 30.00 min, in 2.00 minutes to A/B=0/100 (v/v), then constant for an additional 8.00 min at A/B=0/100 (v/v), then in 1.00 minute to A/B=65/35 (v/v) and finally constant for an additional 15.00 min at A/B=65/35 (v/v).

Method 8: Identical to method 7, except for the gradient used: Gradient: Solvent A/B=40/60 to 0/100 (v/v) in 30.00 min, in 2.00 minutes to A/B=0/100 (v/v), then constant for an additional 8.00 min at A/B=0/100 (v/v), then in 1.00 minute to A/B=40/60 (v/v) and finally constant for an additional 15.00 min at A/B=40/60 (v/v).

Method 9: Identical to method 7, except for the gradient used: Gradient: Solvent A/B=100/0 to 50/50 (v/v) in 30.00 min, in 2.00 minutes to A/B=0/100 (v/v), then constant for an additional 8.00 min at A/B=0/100 (v/v), then in 1.00 minute to A/B=100/0 (v/v) and finally constant for an additional 15.00 min at A/B=100/0 (v/v).

Method 10: Column: 3 μm an Luna C-18(2) 100×2 mm (Phenomenex); flow: 0.25 ml/min; detection: 210 nm; column temperature: 40° C.; solvent A: $CH_3CN/H_2O/TFA=1/9/0.0035$ (v/v); solvent B: $CH_3CN/TFA=1/0.0035$ (v/v); gradient: solvent A/B=65/35 to 10/90 (v/v) in 30.00 min, in 2.00 minutes to A/B=0/100 (v/v), then constant for an additional 8.00 min at A/B=0/100 (v/v), then in 1.00 minute to A/B=65/35 (v/v) and finally constant for an additional 15.00 min at A/B=65/35 (v/v).

Method 11: Identical to method 10, except for the gradient used: Gradient: Solvent A/B=40/60 to 0/100 (v/v) in 30.00 min, in 2.00 minutes to A/B=0/100 (v/v), then constant for an additional 8.00 min at A/B=0/100 (v/v), then in 1.00 minute to A/B=40/60 (v/v) and finally constant for an additional 15.00 min at A/B=40/60 (v/v).

Method 12: Identical to method 10, except for the gradient used: Gradient: Solvent A/B=100/0 to 50/50 (v/v) in 30.00 min, in 2.00 minutes to A/B=0/100 (v/v), then constant for an additional 8.00 min at A/B=0/100 (v/v), then in 1.00 minute to A/B=100/0 (v/v) and finally constant for an additional 15.00 min at A/B=100/0 (v/v).

Method 13: HPLC/MS (Acquity Ultra Performance LC; Waters): Column: Acquity HPLC BEH C18 2.1×100 mm 1.7 μl); flow: 0.65 ml/min; detection: 210 nm; MS: 100-1000 AMU; column temperature: 40° C.; solvent A: $CH_3CN/H_2O=1/9$ (v/v); solvent B: $CH_3CN$; gradient: solvent A/B=60/40 to 20/80 (v/v) in 3.0 min, in 0.2 min to A/B=0/100 (v/v), then for 0.49 min A/B=0/100 (v/v), then in 0.1 min A/B=60/40 (v/v) and finally A/B=60/40 (v/v) for 1.3 min.

The following preparative HPLC systems were used for purification:

System 1: 5 μm Luna C18(2) 150×21.2 mm column with water/acetonitrile mixtures, optionally in the presence of 0.1% aqueous TFA, using the indicated gradient: Flow: 20 ml/min: Detection: 210 nm: Runtime: 30 minutes.

System 2: 10 μm Luna C18(2) 250×50.00 mm column with water/acetonitrile mixtures, optionally in the presence of 0.1% aqueous TFA, using the indicated gradient: Flow: 50 ml/min: Detection: 210 nm: Runtime: 60 minutes.

Microwave reactions were carried out on a Biotage (model: Initiator) microwave oven with autosampler.

Thin Layer Chromatograpy (TLC) was conducted on Merck TLC plates (5×10 cm) silica gel 60 $F_{254}$.

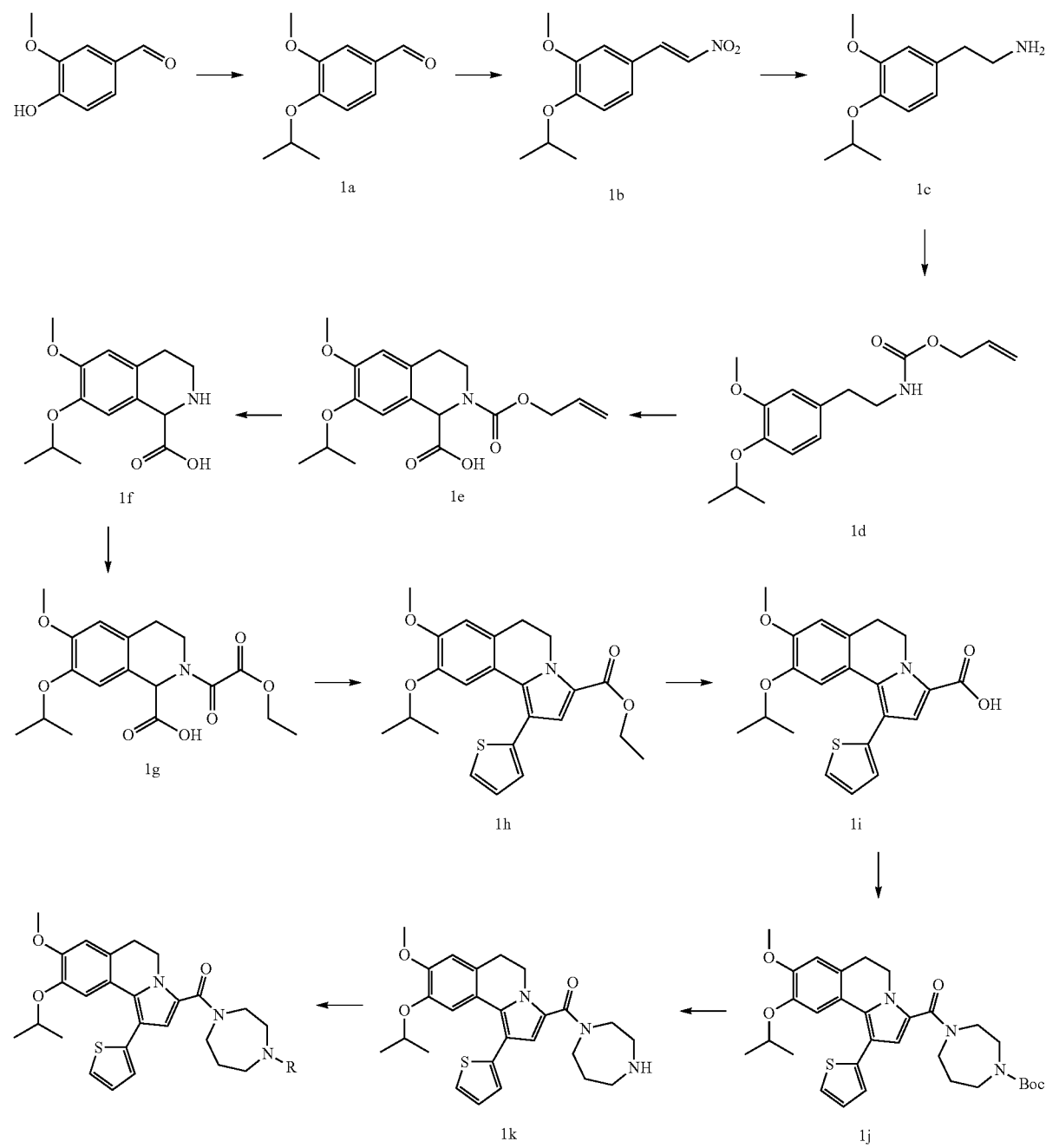

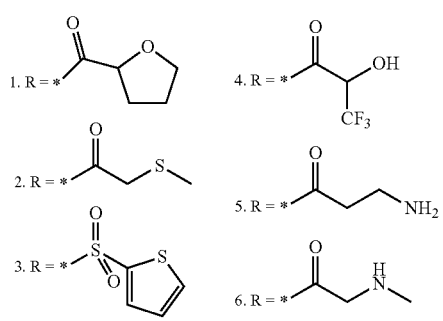

Example 1

(9-Isopropoxy-8-methoxy-1-thiophen-2-yl-5,6-dihydro-pyrrolo[2,1-α]isoquinolin-3-yl)-[4-(tetrahydrofuran-2-carbonyl)-[1,4]diazepan-1-yl]-methanone

(a). 4-Isopropoxy-3-methoxy-benzaldehyde

A mixture of 4-hydroxy-3-methoxybenzaldehyde (100 g), potassium carbonate (182 g) and 2-bromopropane (81 ml) in DMF (500 ml) was stirred at 65° C. for 2 h. The reaction mixture was poured into water and extracted with ethyl acetate. The organic layer was washed with water and brine. The organic layer was dried (MgSO$_4$), filtered and concentrated in vacuo.

Yield: 124 g. $^1$H NMR (CDCl$_3$): δ 1.40 (s, 6H), 3.95 (s, 3H), 4.7 (m, 1H), 6.98 (d, 1H), 7.43 (m, 2H), 9.85 (s, 1H)

(b). 1-Isopropoxy-2-methoxy-4-((E)-2-nitro-vinyl)-benzene

A mixture of the product of example 1a (16.1 g), nitromethane (120 ml) and ammonium acetate (6.1 g) was stirred at 70° C. for 18 h (Caution: reaction can be performed at higher temperature but this is not recommended because an explosion can occur). At room temperature the precipitate was filtered. The precipitate was washed with water and cold ethanol. The precipitate was taken up in dichloromethane and washed with brine. The organic layer was dried (MgSO$_4$), filtered and concentrated in vacuo.

Yield: 13.54 g. $^1$H NMR (CDCl$_3$): δ 1.40 (s, 6H), 3.9 (s, 3H), 4.65 (m, 1H), 6.9 (d, 1H), 7.0 (d, 1H), 7.15 (dd, 1H), 7.52 (d, 1H), 7.95 (d, 1H)

(c). 2-(4-Isopropoxy-3-methoxy-phenyl)-ethylamine

The product of example 1b (20 g) was dissolved in THF (80 ml) and was added drop-wise to a mixture of lithium aluminium hydride (12.8 gram) in dry ether (70 ml) and dry THF (70 ml). After the addition was complete, the reaction mixture was heated under reflux for 2 h. The reaction mixture was quenched by the addition of water (15 ml) in THF (50 ml). Then an aqueous NaOH solution (30 ml 2 N) and H$_2$O (4 ml) were added. The resulting mixture was filtered and the filtrate was concentrated in vacuo. The residue was taken up in ethyl acetate and washed with an aqueous HCl solution (2 N). Solid NaOH was added to the water layer until pH=10. The water layer was extracted with ethyl acetate. The organic layer was washed with brine, dried (MgSO$_4$), filtered and concentrated in vacuo.

Yield: 13.8 g. LC/MS-ESI: [M+H]$^+$=210.1

(d). [2-(4-Isopropoxy-3-methoxy-phenyl)-ethyl]-ceramic acid ally ester

Allyl chloroformate (25 ml) in dichloromethane (100 ml) was added to a mixture of the product of example 1c (44.9 g) and DIPEA (75 ml) in dichloromethane (400 ml) at 0° C. After stirring at room temperature for 1 h, the reaction mixture was washed with an aqueous HCl solution (2 N), water, a sat. aqueous NaHCO$_3$ solution and brine. The organic layer was dried (MgSO$_4$), filtered and concentrated in vacuo. The residue was purified by chromatography on silica gel in heptane/ethyl acetate [3/2 (v/v)] as eluent.

Yield: 9.7 g. LC/MS-ESI: [M+H]$^+$=294.1

(e). 7-Isopropoxy-6-methoxy-3,4-dihydro-1H-isoquinoline-1,2-dicarboxylic acid 2-allyl ester Sulfuric acid (120 ml) was added to a solution of the product of example 1d (45.6 g), glyoxylic acid (21.5 g) and acetic acid (350 ml) at 0° C. After stirring at room temperature for 1 h, the reaction mixture was poured into water and extracted with dichloromethane. The organic layer was washed with brine, dried (MgSO$_4$), filtered and concentrated in vacuo. The residue was purified by chromatography on silica gel in dichloromethane/methanol [95/5 (v/v)] as eluent.

Yield: 43.5 g. LC/MS-ESI: [M+H]$^+$=350.2

(f). 7-Isopropoxy-6-methoxy-1,2,3,4-tetrahydro-isoquinoline-1-carboxylic acid A mixture of the product of example 1e (43.5 g), dimedone (26.2 g) and Pd(PPh$_3$)$_4$ (500 mg) was stirred in THF at reflux for 1 h. Ether (300 ml) and water (20 ml) were added to the reaction mixture at room temperature. The reaction mixture was cooled to 0° C. and the precipitate was filtered and dried in vacuo (50° C.).

Yield: 27 g. LC/MS-ESI: [M+H]$^+$=266.2

(g). 2-Ethoxyoxalyl-7-isopropoxy-6-methoxy-1,2,3,4-tetrahydro-isoquinoline-1-carboxylic acid Ethyl oxalyl chloride (1.85 ml) was added to a suspension of the product of example 1f (2.2 g) in refluxing THF (200 ml). After stirring at reflux for 30 min, the reaction mixture was concentrated in vacuo. The residue was purified by chromatography on silica gel in methanol/dichloromethane [1/9 (v/v)] as eluent.

Yield: 2.75 g. LC/MS-ESI: [M+H]$^+$=366.2

(h). 9-Isopropoxy-8-methoxy-1-thiophen-2-yl-5,6-dihydro-pyrrolo[2,1-α]isoquinoline-3-carboxylic acid ethyl ester A mixture of the product of example 1g (601 mg), acetic anhydride (5 ml) and 2-ethynylthiophene (178 mg) in THF (5 ml) was stirred at 140° C. using microwave irradiation for 15 min. The reaction mixture was diluted with ethyl acetate and washed with water, a sat. aqueous $NaHCO_3$ solution and brine. The organic layer was dried ($MgSO_4$) and concentrated in vacuo. The residue was suspended in ethanol and the precipitate was filtered and dried in vacuo (50° C.).
Yield: 1.34 g. LC/MS-ESI: $[M+H]^+$=412.2

(i). 9-Isopropoxy-8-methoxy-1-thiophen-2-yl-5,6-dihydro-pyrrolo[2,1-α]isoquinoline-3-carboxylic acid KOH (1.2 g) was added to a suspension of the product of example 1h (2.8 g) in EtOH/$H_2O$ 1/1 (v/v) (80 ml). The reaction mixture was stirred at 78° C. for 1 h. The reaction mixture was diluted with ethyl acetate and extracted with an aqueous NaOH solution (2 N). The aqueous layer was acidified with an aqueous HCl solution (2 N) and extracted with ethyl acetate. The organic layer was dried ($MgSO_4$), filtered and concentrated in vacuo.
Yield: 2.6 g. LC/MS-ESI: $[M+H]^+$=384.2

(j). 4-(9-Isopropoxy-8-methoxy-1-thiophen-2-yl-5,6-dihydro-pyrrolo[2,1-α]isoquinoline-3-carbonyl)-[1,4]diazepane-1-carboxylic acid tert-butyl ester A mixture of the product of example 1i (1 gram), HATU (1.47 gram) and tert-butyl 1,4-diazepane-1-carboxylate (564 μl) in dichloromethane (100 ml) was stirred at room temperature for 1 h. The reaction mixture was diluted with dichloromethane and washed with an aqueous HCl solution (1 N). The organic layer was dried ($MgSO_4$), filtered and concentrated in vacuo. The residue was purified by chromatography on silica gel in heptane/ethyl acetate [2/3 (v/v)] as eluent.
Yield: 1.4 g. LC/MS-ESI: $[M+H]^+$=566.2

(k). [1,4]Diazepan-1-yl-(9-isopropoxy-8-methoxy-1-thiophen-2-yl-5,6-dihydro-pyrrolo[2,1-α]isoquinolin-3-yl)-methanone TFA (3 ml) was added to a solution of the product of example 1j (1.4 g) in dichloromethane (10 ml). After stirring at room temperature for 18 h, the reaction mixture was diluted with dichloromethane and washed with an aqueous NaOH solution (2 N). The organic layer was dried ($MgSO_4$), filtered and concentrated in vacuo.
Yield: 1.3 g. LC/MS-ESI: $[M+H]^+$=466.2

(l). (9-Isopropoxy-8-methoxy-1-thiophen-2-yl-5,6-dihydro-pyrrolo[2,1-α]isoquinolin-3-yl)-[4-(tetrahydro-furan-2-carbonyl)-[1,4]diazepan-1-yl]-methanone A mixture of the product of example 1k (100 mg), 2-tetrahydrofuran carboxylic acid (31 μl), HATU (160 mg) and DIPEA (110 μl) in dichloromethane (2 ml) was stirred at room temperature for 4 h. The reaction mixture was concentrated in vacuo and the residue was purified by preparative HPLC (0→90% acetonitrile; system 1).

Yield: 120 mg. LC/MS-ESI: $[M+H]^+$=564.2; anal. HPLC: $R_t$=18.71 min (method 2); hFSHRago (CHO luc) $EC_{50}$=0.9 nM.

Example 2

1-[4-(9-Isopropoxy-8-methoxy-1-thiophen-2-yl-5,6-dihydro-pyrrolo[2,1-α]isoquinoline-3-carbonyl)-[1,4]diazepan-1-yl]-2-methylsulfanyl-ethanone Amide formation of the product of example 1k (100 mg) with (methylthio)acetic acid (33 mg) was performed according to the method described in example 1l.
Yield: 50 mg. LC/MS-ESI: $[M+H]^+$=554.2; anal. HPLC: $R_t$=20.36 min (method 2); hFSHRago (CHO luc) $EC_{50}$=0.5 nM Example 3

(9-Isopropoxy-8-methoxy-1-thiophen-2-yl-5,6-dihydro-pyrrolo[2,1-α]isoquinolin-3-yl)-[4-(thiophene-2-sulfonyl)-[1,4]diazepan-1-yl]-methanone A mixture of the product of example 1k (60 mg), triethylamine (54 μl) and 2-thiophenesulfonyl chloride (29 mg) in dichloromethane (2 ml) was stirred for 1 h at room temperature. The reaction mixture was diluted with dichloromethane and washed with $H_2O$ and an aqueous HCl solution (1N). The organic layer was dried ($MgSO_4$), filtered and concentrated in vacuo. The residue was purified by preparative HPLC (0→90% acetonitrile; system 1).
Yield: 35 mg LC/MS-ESI: $[M+H]^+$=612.2; anal. HPLC: $R_t$=26.14 min (method 2); hFSHRago (CHO luc) $EC_{50}$=4.6 nM Example 4

3,3,3-Trifluoro-2-hydroxy-1-[4-(9-isopropoxy-8-methoxy-1-thiophen-2-yl-5,6-dihydro-pyrrolo[2,1-α]isoquinoline-3-carbonyl)-[1,4]diazepan-1-yl]-propan-1-one A mixture of the product of example 1k (50 mg), 3,3,3-trifluorolactic acid (32 mg), DIPEA (90 μl) and BOP (114 mg) in dichloromethane (2.5 ml) was stirred for 18 h at room temperature. The reaction mixture was concentrated in vacuo and the residue was purified by preparative HPLC (10→90% acetonitrile; system 1).
Yield: 17 mg. LC/MS-ESI: $[M+H]^+$=592.3; anal. HPLC: $R_t$=21.77 min (method 2); hFSHRago (CHO luc) $EC_{50}$=1.3 nM Example 5

3-Amino-1-[4-(9-isopropoxy-8-methoxy-1-thiophen-2-yl-5,6-dihydro-pyrrolo[2,1-α]isoquinoline-3-carbonyl)-[1,4]diazepan-1-yl]-propan-1-one (a). {3-[4-(9-Isopropoxy-8-methoxy-1-thiophen-2-yl-5,6-dihydro-pyrrolo[2,1-α]iso-quinoline-3-carbonyl)-[1,4]diazepan-1-yl]-3-oxo-propyl}-carbamic acid tert-butyl ester Coupling of the product of example 1k (100 mg) with 3-tert-Butoxycarbonylamino-propionic acid (60 mg) was performed according to the method described in example 1l.

Yield: 53 mg. LC/MS-ESI: [M+H]$^+$=637.2; HPLC: $R_t$=21.63 min (method 2)

(b). 3-Amino-1-[4-(9-isopropoxy-8-methoxy-1-thiophen-2-yl-5,6-dihydro-pyrrolo[2,1-α]isoquinoline-3-carbonyl)-[1,4]diazepan-1-yl]-propan-1-one A mixture of the product of example 5a (40 mg) and TFA (100 μl) in dichloromethane was stirred for 2 h at room temperature. The reaction mixture was concentrated in vacuo and the residue was purified by preparative HPLC (0→90% acetonitrile, 0.1% TFA; system 1)

Yield: 34 mg. LC/MS-ESI: [M+H]$^+$=537.2; HPLC: $R_t$=9.97 min (method 2); hFSHRago (CHO luc) EC$_{50}$=1400 nM Example 6

1-[4-(9-Isopropoxy-8-methoxy-1-thiophen-2-yl-5,6-dihydro-pyrrolo[2,1-α]isoquinoline-3-carbonyl)-[1,4]diazepan-1-yl]-2-methylamino-ethanone (a) {2-[4-(9-Isopropoxy-8-methoxy-1-thiophen-2-yl-5,6-dihydro-pyrrolo[2,1-α]isoquinoline-3-carbonyl)-[1,4]diazepan-1-yl]-2-oxo-ethyl}-methyl-carbamic acid tert-butyl ester Coupling of the product of example 1k (100 mg) with N-tert-butoxycarbonyl-sarcosine (64 mg) was performed according to the method described in example 11.

Yield: 64 mg. LC/MS-ESI: [M+H]$^+$=637.2; anal. HPLC: $R_t$=23.69 min (method 2)

(b) 1-[4-(9-Isopropoxy-8-methoxy-1-thiophen-2-yl-5,6-dihydro-pyrrolo[2,1-α]isoquinoline-3-carbonyl)-[1,4]diazepan-1-yl]-2-methylamino-ethanone Boc-deprotection of the product of example 6a (40 mg) was performed according to the method described in example 5b.

Yield: 32.7 mg. LC/MS-ESI: [M+H]$^+$=537.2; anal. HPLC: $R_t$=10.11 min (method 2); hFSHRago (CHO luc) EC$_{50}$=264.0 nM

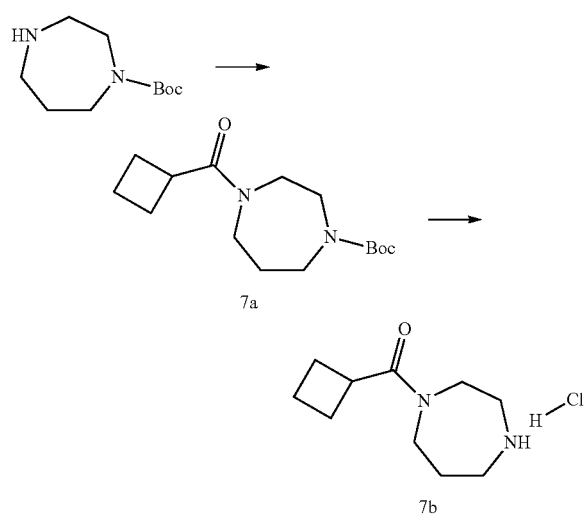

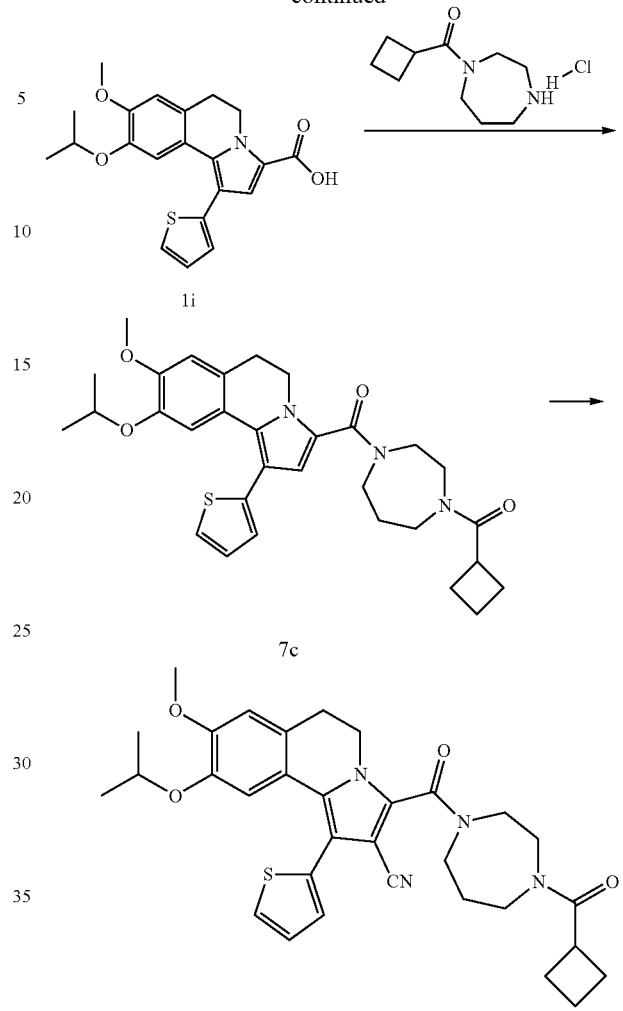

Example 7

3-(4-Cyclobutanecarbonyl-[1,4]diazepane-1-carbonyl)-9-isopropoxy-8-methoxy-1-thiophen-2-yl-5,6-dihydro-pyrrolo[2,1-α]isoquinoline-2-carbonitrile and (4-cyclobutanecarbonyl-[1,4]diazepan-1-yl)-(9-isopropoxy-8-methoxy-1-thiophen-2-yl-5,6-dihydro-pyrrolo[2,1-α]isoquinolin-3-yl)-methanone (a). 4-Cyclobutanecarbonyl-[1,4]diazepane-1-carboxylic acid tert-butyl ester Cyclobutanecarbonyl chloride (3.7 ml) and triethylamine (14 ml) were added to a solution of [1,4]diazepane-1-carboxylic acid tert-butyl ester (4.9 ml) in dichloromethane (175 ml). After stirring for 1 h at room temperature, the reaction mixture was washed with water, an aqueous HCl solution (1 N), water and brine. The organic layer was dried (MgSO$_4$), filtered and concentrated in vacuo.

Yield: 7 g. LC/MS-ESI: [M+H]$^+$=283.4

(b). Cyclobutyl-[1,4]diazepan-1-yl-methanone, hydrochloride

A mixture of the product of example 7a (7 g) and a HCl solution (33 ml, 4 N in dioxane) in dichloromethane (166 ml) was stirred for 4 h at room temperature. The reaction mixture was concentrated in vacuo. The residue was treated with diethyl ether and the precipitate was filtered and dried in vacuo (50° C.).

Yield: 4.76 g (as HCl-salt)

(c). (4-Cyclobutanecarbonyl-[1,4]diazepan-1-yl)-(9-isopropoxy-8-methoxy-1-thiophen-2-yl-5,6-dihydro-pyrrolo[2,1-α]isoquinolin-3-yl)-methanone A mixture of the product of example 1i (250 mg), cyclobutyl-[1,4]diazepan-1-yl-methanone, hydrochloride (214 mg), HATU (373 mg) and DIPEA (0.25 ml) in DMF (3 ml) was stirred for 18 h at 50° C. The reaction mixture was diluted with ethyl acetate and washed with water and brine. The organic layer was dried (MgSO$_4$), filtered and concentrated in vacuo. The residue was purified by chromatography on silica gel in dichloromethane/methanol [100/0→95/5 (v/v)] as eluent.

Yield: 355 mg. LC/MS-ESI: [M+H]$^+$=548.1; hFSHRago (CHO luc) EC$_{50}$=1.7 nM

(d). 3-(4-Cyclobutanecarbonyl-[1,4]diazepane-1-carbonyl)-9-isopropoxy-8-methoxy-1-thiophen-2-yl-5,6-dihydro-pyrrolo[2,1-α]isoquinoline-2-carbonitrile At −78° C., chlorosulfonylisocyanate (0.112 ml) was added to a solution of the product of example 7c (350 mg) in THF (3 ml). After stirring for 1 h at −78° C., DMF (3 ml) was added. After stirring for 2.5 h at room temperature, the reaction mixture was poured into water and extracted with ethyl acetate. The organic layer was washed with brine, dried (MgSO$_4$), filtered and concentrated in vacuo. The residue was purified by preparative HPLC (40%→60% acetonitrile; system 2).

Yield: 74 mg. MS-ESI: [M+H]$^+$=573.5; anal. HPLC: R$_t$=14.18 min 1 (method 10); hFSHRago (CHO luc) EC$_{50}$=0.3 nM

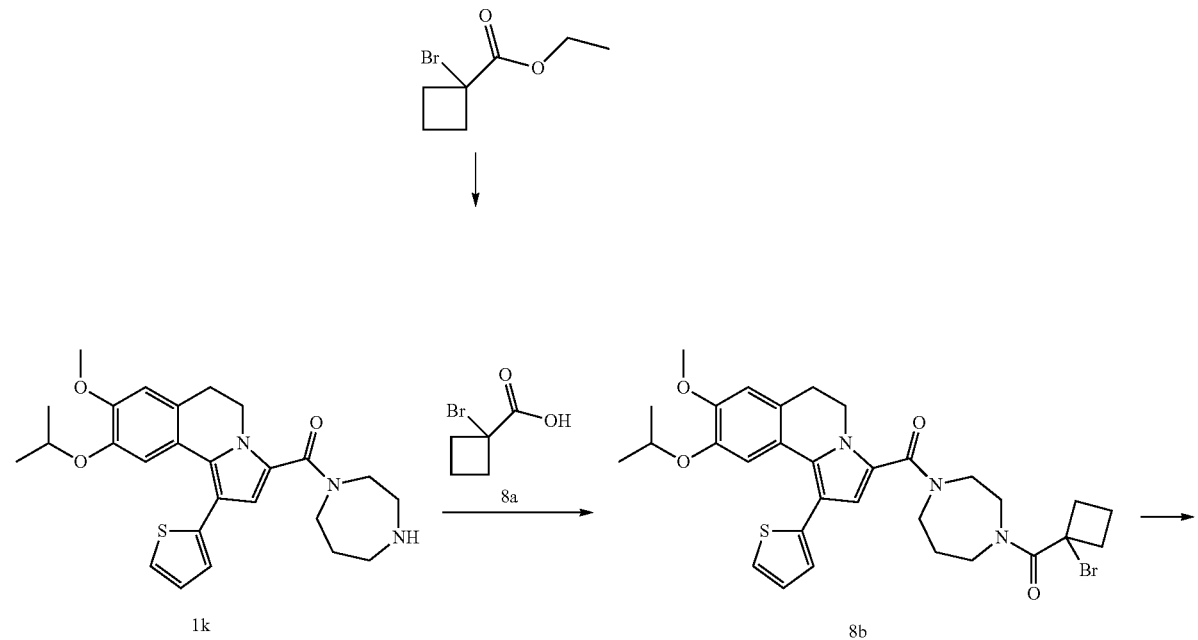

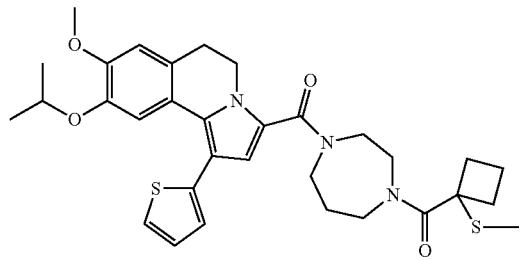

Example 8

[4-(1-Bromo-cyclobutanecarbonyl)-[1,4]diazepan-1-yl]-(9-isopropoxy-8-methoxy-1-thiophen-2-yl-5,6-dihydro-pyrrolo[2,1-α]isoquinolin-3-yl)-methanone (a). 1-Bromo-cyclobutanecarboxylic acid A mixture of 1-bromo-cyclobutanecarboxylic acid ethyl ester (1.0 ml) in an aqueous NaOH solution (10 ml, 2 N) was stirred vigorously for 3 h at room temperature. The reaction mixture was washed with diethyl ether. The aqueous layer was acidified with an aqueous HCl solution (2 N) and extracted with ethyl acetate. The organic layer was dried (MgSO$_4$), filtered and concentrated in vacuo.

Yield: 952 mg (b). [4-(1-Bromo-cyclobutanecarbonyl)-[1,4]diazepan-1-yl]-(9-isopropoxy-8-methoxy-1-thiophen-2-yl-5,6-dihydro-pyrrolo[2,1-α]isoquinolin-3-yl)-methanone A mixture of BOP (580 mg), DIPEA (540 μl) and the product of example 8a (280 μl) in dichloromethane (3 ml) was added to a solution of the product of example 1k (330 mg) in dichloromethane (12 ml). After stirring at room temperature for 2 h, the reaction mixture was poured into an aqueous citric acid solution (5%) and extracted with dichloromethane. The organic layer was dried (MgSO$_4$), filtered and concentrated in vacuo. The residue was purified by chromatography on silica gel in dichloromethane/acetone [1/0→9/1 (v/v)] as eluent.

Yield: 329 mg. LC/MS-ESI: [M+H]$^+$=626.3/628.3 (1:1); anal. HPLC: R$_t$=26.32 min (method 2); hFSHRago (CHO luc) EC$_{50}$=6.8 nM

Example 9

(9-Isopropoxy-8-methoxy-1-thiophen-2-yl-5,6-dihydro-pyrrolo[2,1-α]isoquinolin-3-yl)-[4-(1-methylsulfanyl-cyclobutanecarbonyl)-[1,4]diazepan-1-yl]-methanone A mixture of the product of example 8b (42 mg) and sodium thiomethoxide (35 mg) in ethanol (5 ml) was stirred for 4 h at 40° C., 2 days at room temperature and finally 2 h at 50° C. The reaction mixture was concentrated in vacuo, taken up in an aqueous NaOH solution (0.5 N) and extracted with ethyl acetate. The organic layer was washed with brine, dried (MgSO$_4$), filtered and concentrated in vacuo. The residue was purified by chromatography on silica gel in dichloromethane/acetone [1/0→9/1 (v/v)] as eluent.

Yield: 20 mg. LC/MS-ESI: [M+H]$^+$=594.3; anal. HPLC: R$_t$=26.36 min (method 2); hFSHRago (CHO luc) EC$_{50}$=16.4 nM

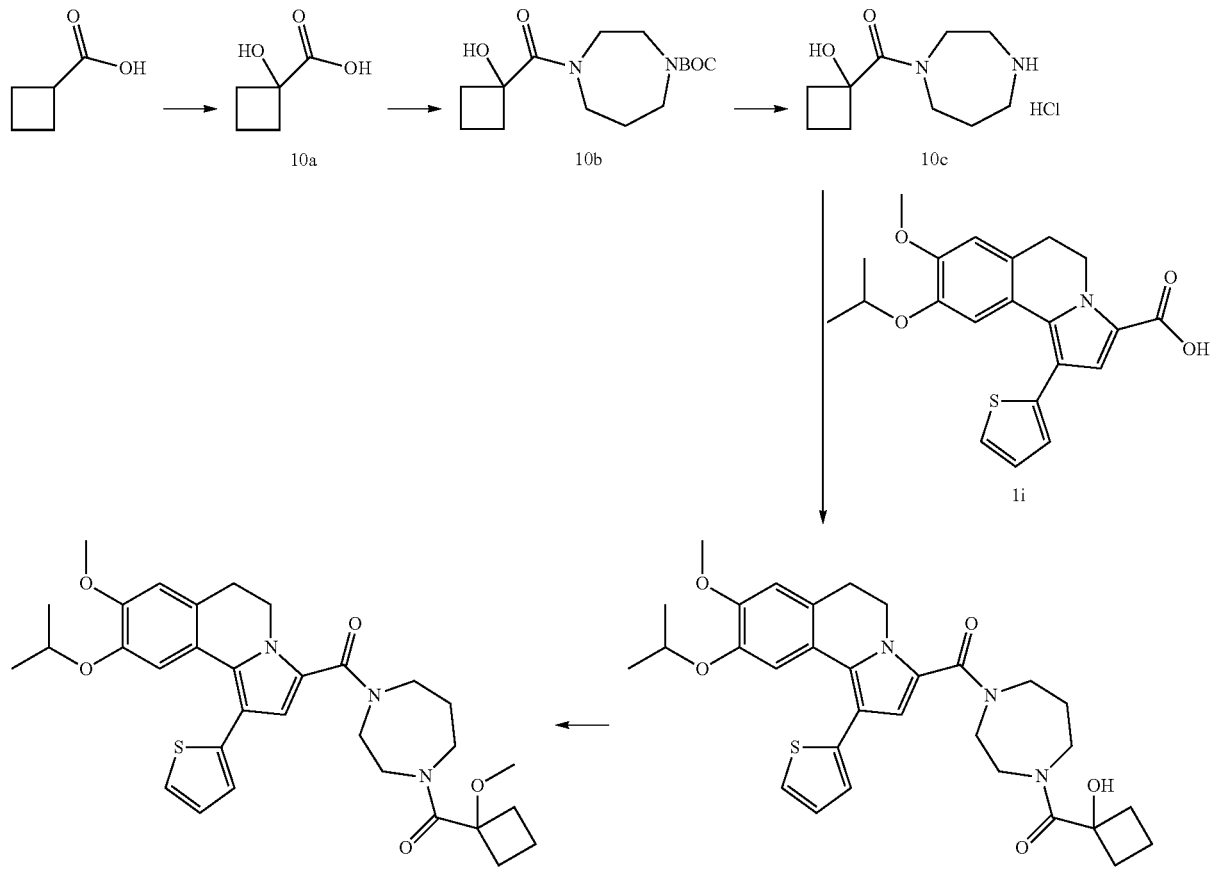

Example 10

[4-(1-Hydroxy-cyclobutanecarbonyl)-[1,4]diazepan-1-yl]-(9-isopropoxy-8-methoxy-1-thiophen-2-yl-5,6-dihydro-pyrrolo[2,1-α]isoquinolin-3-yl)-methanone

(a). 1-Hydroxy-cyclobutanecarboxylic acid n-Butyllithium (14 ml, 1.6 M in heptane) was added at 0° C. to a solution of diisopropyl amine in THF (30 ml). After 30 min the reaction mixture was cooled to −20° C. and cyclobutane carboxylic acid (960 μl) in THF (10 ml) was added. After stirring at room temperature for 30 min, oxygen was passed through for 1 h and the reaction mixture was stirred for 18 h under an atmosphere of oxygen. The reaction mixture was poured into water and washed with ethyl acetate. The aqueous layer was acidified with an aqueous HCl solution (2 N) and extracted with ethyl acetate (2×). The organic layer was dried (MgSO$_4$), filtered and concentrated in vacuo.

Yield: 690 mg

(b). 4-(1-Hydroxy-cyclobutanecarbonyl)-[1,4]diazepane-1-carboxylic acid tert-butyl ester A mixture of the product of example 10a (340 mg), tert-butyl 1,4-diazepane-1-carboxylate (694 μl), DIPEA (2.4 ml) and BOP (1.9 g) in dichloromethane (15 ml) was stirred for 18 h at room temperature. The reaction mixture was poured into an aqueous citric acid solution (5%) and extracted with ethyl acetate. The organic layer was dried (MgSO$_4$), filtered and concentrated in vacuo. The residue was purified by chromatography on silica gel in toluene/acetone [1/0→7/3 (v/v)] as eluent.

Yield: 732 mg

(c). [1,4]Diazepan-1-yl-(1-hydroxy-cyclobutyl)-methanone, hydrochloride

A mixture of a HCl solution (2 ml, 2.0 M in ether) and the product of example 10b (420 mg) in dichloromethane (18 ml) was stirred for 4 h at room temperature and concentrated in vacuo.

Yield: 330 mg

(d). [4-(1-Hydroxy-cyclobutanecarbonyl)-[1,4]diazepan-1-yl]-(9-isopropoxy-8-methoxy-1-thiophen-2-yl-5,6-dihydro-pyrrolo[2,1-α]isoquinolin-3-yl)-methanone A mixture of the product of example 10c (330 mg), DIPEA (830 μl), BOP (530 mg) and the product of example 1k (383 mg) in dichloromethane (15 ml) was stirred for 18 h at room temperature. The reaction mixture was poured into an aqueous citric acid solution (5%) and extracted with dichloromethane (2×). The organic layer was dried (MgSO$_4$), filtered and concentrated in vacuo. The residue was purified by chromatography on silica gel in dichloromethane/acetone [1/0→1/1 (v/v)] as eluent.

Yield: 538 mg. LC-MS: [M+H]$^+$=564.4; hFSHRago (CHO luc) EC$_{50}$=1.4 nM

Example 11

(9-Isopropoxy-8-methoxy-1-thiophen-2-yl-5,6-dihydro-pyrrolo[2,1-α]isoquinolin-3-yl)-[4-(1-methoxy-cyclobutanecarbonyl)-[1,4]diazepan-1-yl]-methanone A mixture of the product of example 10d (82 mg), sodium hydride (14 mg, 60% dispersion in oil) and iodomethane (70 μl) in DMF (3 ml) was stirred at room temperature for 1 h. The reaction mixture was poured into a sat. aqueous NH$_4$Cl solution and extracted with ethyl acetate. The organic layer was dried (MgSO$_4$), filtered and concentrated in vacuo. The residue was purified by chromatography on silica gel in dichloromethane/acetone [1/0→9/1 (v/v)] as eluent.

Yield: 46 mg. LC-MS: [M+H]$^+$=578.4; anal HPLC 24.57 min (method 2); hFSHRago (CHO luc) EC$_{50}$=5.4 nM

Example 12

1-[4-(2-Chloro-9-isopropoxy-8-methoxy-1-thiophen-2-yl-5,6-dihydro-pyrrolo[2,1-α]isoquinoline-3-carbonyl)-[1,4]diazepan-1-yl]-ethanone and 2-acetyl-9-ethoxy-8-methoxy-1-thiophen-2-yl-5,6-dihydro-pyrrolo[2,1-α]isoquinoline-3-carboxylic acid ethyl ester (a). 2-Acetyl-9-ethoxy-8-methoxy-1-thiophen-2-yl-5,6-dihydro-pyrrolo[2,1-α]isoquinoline-3-carboxylic acid ethyl ester A mixture of the product of example 1i (160 mg), N-acetyl-homopiperazine (89 mg), DIPEA (370 μL) and HATU (192 mg) in dichloromethane (5 ml) was stirred at 40° C. for 1 h. The reaction mixture was diluted with ethyl acetate and washed with an aqueous HCl solution (0.2 M), water and brine. The organic layer was dried (MgSO$_4$), filtered and concentrated in vacuo. The residue was purified by chromatography on silica gel in heptane/ethyl acetate [10/0→8/2 (v/v)] as eluent.

Yield: 230 mg; hFSHRago (CHO luc) EC$_{50}$=5.2 nM (b). 1-[4-(2-Chloro-9-isopropoxy-8-methoxy-1-thiophen-2-yl-5,6-dihydro-pyrrolo[2,1-α]isoquinoline-3-carbonyl)-[1,4]diazepan-1-yl]-ethanone A mixture of the product of example 12a (230 mg) and N-chlorosuccinimide (64 mg) in DMF (3 ml) was stirred and heated using microwave irradiation at 120° C. for 5 min. The reaction mixture was diluted with ethyl acetate and washed with water and brine. The organic layer was dried (MgSO$_4$), filtered and concentrated in vacuo. The residue was purified by chromatography on silica gel in ethyl acetate [0→10% isopropylamine (v/v)] as eluent.

Yield: 150 mg. MS-ESI: [M+H]$^+$=542.2; anal. HPLC R$_t$=10.98 (method 7); hFSHRago (CHO luc) EC$_{50}$=1.9 nM

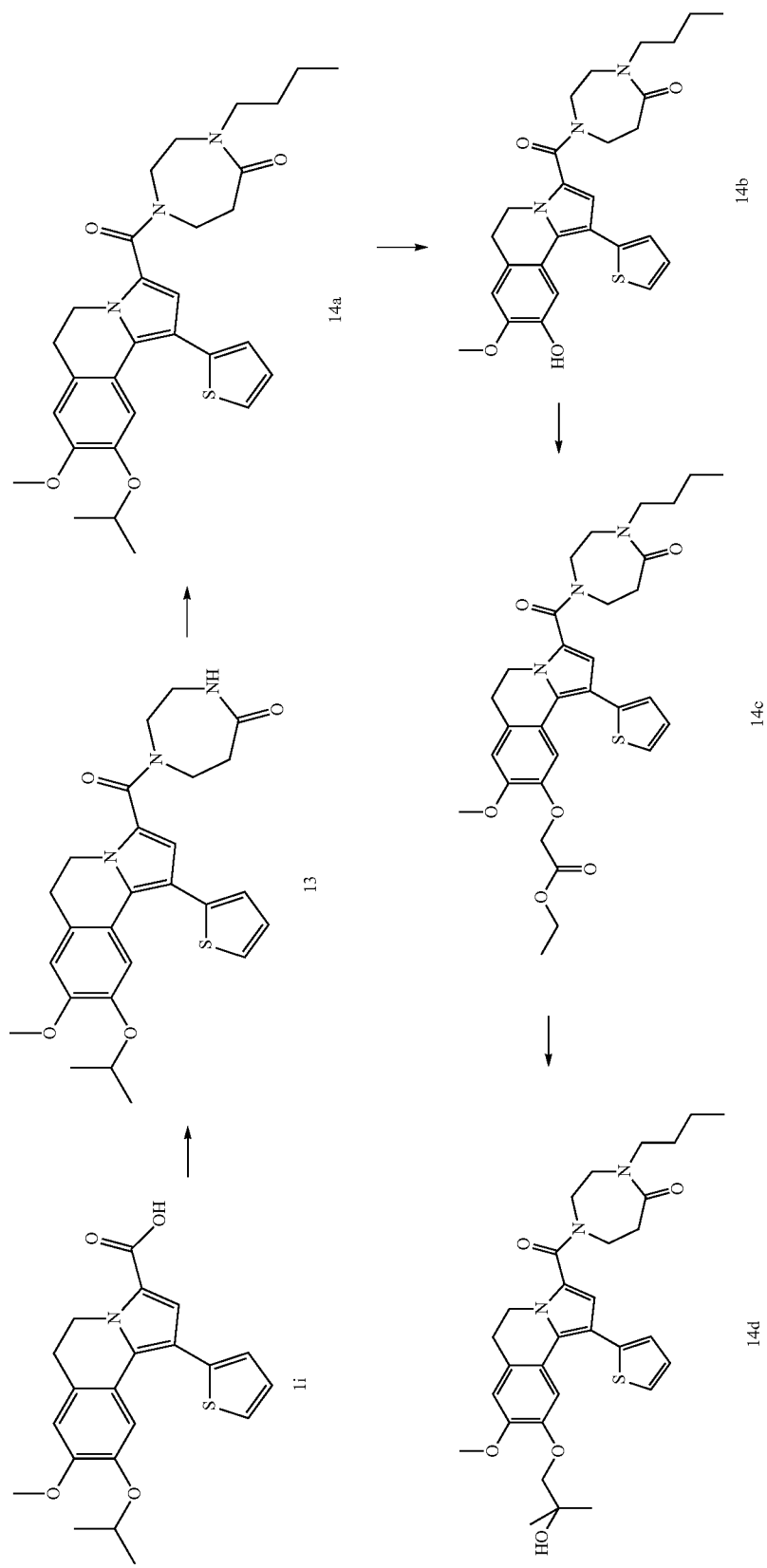

Example 13

1-(9-Isopropoxy-8-methoxy-1-thiophen-2-yl-5,6-dihydro-pyrrolo[2,1-α]isoquinoline-3-carbonyl)-[1,4]diazepan-5-one BOP (111 mg), 2,3,6,7-tetrahydro-(1H)-1,4-diazepin-5(4H)-one (50 mg) and DIPEA (0.2 ml) were added to a solution of the product of example 1i (80 mg) in dichloromethane (4 ml). After stirring for 2 h at room temperature, the reaction mixture was diluted with dichloromethane and washed with an aqueous HCl solution (0.5 N) and brine. The organic layer was dried (MgSO$_4$), filtered and concentrated in vacuo. The residue was purified by preparative HPLC (10%→90% acetonitrile; system 1).

Yield: 38 mg. LC/MS-ESI: [M+H]$^+$=480.2; anal. HPLC: R$_t$=15.51 min (method 2); hFSHRago (CHO luc) EC$_{50}$=106.0 nM

Example 14

4-Butyl-1-[9-(2-hydroxy-2-methyl-propoxy)-8-methoxy-1-thiophen-2-yl-5,6-dihydro-pyrrolo[2,1-α]isoquinoline-3-carbonyl]-[1,4]diazepan-5-one, 4-butyl-1-(9-isopropoxy-8-methoxy-1-thiophen-2-yl-5,6-dihydro-pyrrolo[2,1-α]iso-quinoline-3-carbonyl)-[1,4]diazepan-5-one and [3-(4-butyl-5-oxo-[1,4]diazepane-1-carbonyl)-8-methoxy-1-thiophen-2-yl-5,6-dihydro-pyrrolo[2,1-α]isoquinolin-9-yloxy]-acetic acid ethyl ester

(a). 4-Butyl-1-(9-isopropoxy-8-methoxy-1-thiophen-2-yl-5,6-dihydro-pyrrolo[2,1-α]iso-quinoline-3-carbonyl)-[1,4]diazepan-5-one Sodium hydride (160 mg, 60% dispersion in oil) was added to a solution of the product of example 13 (767 mg) in DMF (24 ml). After stirring for 5 min at room temperature, 1-iodobutane (1.46 ml) was added and stirring was continued for 18 h at 60° C. The reaction mixture was poured in a sat. aqueous NH$_4$Cl solution and extracted with ethyl acetate. The organic layer was washed with brine, dried (MgSO$_4$), filtered and concentrated in vacuo. The residue was purified by chromatography on silica gel in dichloromethane/methanol [100/0→90/0 (v/v)] as eluent.

Yield: 1.26 g. LC/MS-ESI: [M+H]$^+$=536.4; hFSHRago (CHO luc) EC$_{50}$=0.8 nM

(b). 4-Butyl-1-(9-hydroxy-8-methoxy-1-thiophen-2-yl-5,6-dihydro-pyrrolo[2,1-α]isoquinoline-3-carbonyl)-[1,4]diazepan-5-one At 0° C., trichloroborane (3.2 ml) was added dropwise to a solution of the product of example 14a (857 mg) in dichloromethane (10 ml). After stirring for 18 h at room temperature, the reaction mixture was quenched with water and extracted with dichloromethane. The organic layer was washed with brine, dried (MgSO$_4$), filtered and concentrated in vacuo. The residue was purified by chromatography on silica gel in dichloromethane/methanol [100/0→90/0 (v/v)] as eluent.

Yield: 318 mg. LC/MS-ESI: [M+H]$^+$=494.3.

(c). [3-(4-Butyl-5-oxo-[1,4]diazepane-1-carbonyl)-8-methoxy-1-thiophen-2-yl-5,6-dihydro-pyrrolo[2,1-α]isoquinolin-9-yloxy]-acetic acid ethyl ester A mixture of the product of example 14b (100 mg), cesium carbonate (198 mg) and ethyl bromoacetate (27 μl) in DMF (6 ml) was stirred for 2 h at 90° C. The reaction mixture was poured into water and extracted with dichloromethane. The organic layer was washed with water and brine, dried (MgSO$_4$), filtered and concentrated in vacuo. The residue was purified by preparative HPLC (0%→100% acetonitrile; system 1).

Yield: 43 mg. LC/MS-ESI: [M+H]$^+$=580.3; anal. HPLC: R$_t$=11.76 min (method 10); hFSHRago (CHO luc) EC$_{50}$=11 nM.

(d). 4-Butyl-1-[9-(2-hydroxy-2-methyl-propoxy)-8-methoxy-1-thiophen-2-yl-5,6-dihydro-pyrrolo[2,1-α]isoquinoline-3-carbonyl]-[1,4]diazepan-5-one At 0° C., methylmagnesium chloride (61 μl) was added dropwise to a solution of the product of example 14c (36 mg) in THF (2 ml). The reaction mixture was stirred for 2 h at room temperature, After dilution with ethyl acetate, the reaction mixture was treated with a sat. aqueous NH$_4$Cl solution. The organic layer was washed with water and brine, dried (MgSO$_4$), filtered and concentrated in vacuo. The residue was purified by preparative HPLC (0%→100% acetonitrile; system 1).

Yield: 15.8 mg. LC/MS-ESI: [M+H]$^+$=566.3; anal. HPLC: R$_t$=9.15 min (method 10); hFSHRago (CHO luc) EC$_{50}$=1.5 nM

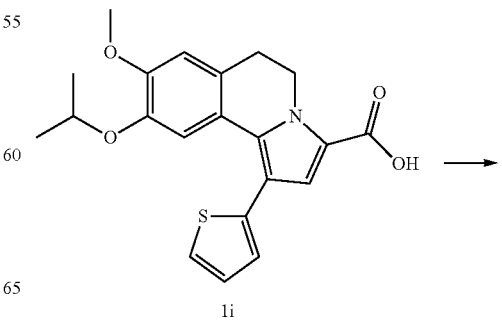

1i

-continued

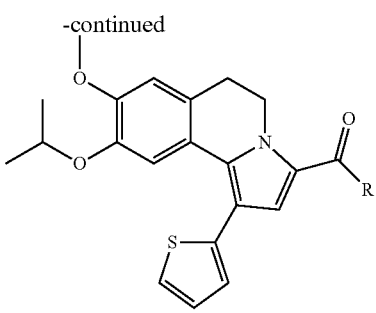

15. R = 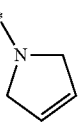

16. R = 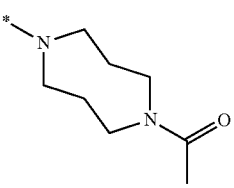

17. R = 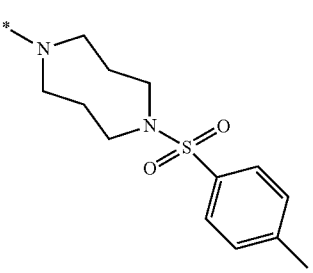

18. R =

19. R =

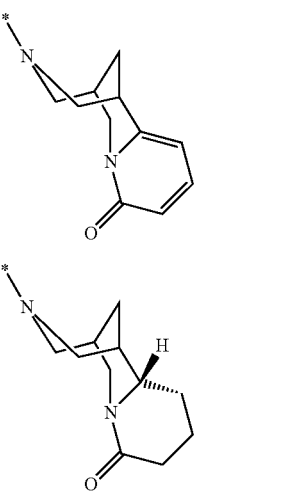

Example 15

(2,5-Dihydro-pyrrol-1-yl)-(9-isopropoxy-8-methoxy-1-thiophen-2-yl-5,6-dihydro-pyrrolo[2,1-α]isoquinolin-3-yl)-methanone HATU (74.5 g), 2,5-dihydro-1H-pyrrole (30 μl) and DIPEA (0.114 ml) were added to a solution of the product of example 1i (50 mg) in DMF (2 ml). After stirring for 18 h at 50° C., the reaction mixture was diluted with ethyl acetate and washed with a sat. aqueous NH₄Cl solution, water and brine. The organic layer was dried (MgSO₄), filtered and concentrated in vacuo. The residue was purified by preparative HPLC (20%→100% acetonitrile; system 1).

Yield: 16.5 mg. MS-ESI: $[M+H]^+$=435.3; anal. HPLC: $R_t$=20.78 min (method 1); hFSHRago (CHO luc) $EC_{50}$=249.0 nM Example 16

1-[5-(9-Isopropoxy-8-methoxy-1-thiophen-2-yl-5,6-dihydro-pyrrolo[2,1-α]isoquinoline-3-carbonyl)-[1,5]diazocan-1-yl]-ethanone (a). [1,5]Diazocan-1-yl-(9-isopropoxy-8-methoxy-1-thiophen-2-yl-5,6-dihydro-pyrrolo[2,1-α]isoquinolin-3-yl)-methanone 1,5-Diazacyclooctane was prepared according to well documented macrocyclization methods described in literature based on the Richman and Atkins protocols: J. E. Richman, T. J. Atkins, *J. Am. Chem. Soc.* 96, 2268, (1974); R. C. Hoye, J. E. Richman, G. A. Dantas, M. F. Lightbourne, L. Scott Shinneman, *J. Org. Chem.* 66, 2722 (2001); G. Ewin, J. O. Hill., *J. Chem. Res* (M), 3501 (1985); J. A. Halfen, H. L. Moore, D. C. Fox, *Inorg. Chem.* 41, 3935 (2002).

A mixture of the product of example 1i (170 mg) and [1,5]diazocane.HBr (140 mg), N-ethylmorpholine (200 μl) and HATU (250 mg) in DMF (2 ml) was stirred for 16 h at room temperature. The reaction was diluted with water and extracted with ethyl acetate. The organic layer was dried (MgSO₄), filtered and concentrated in vacuo. The residue was purified by chromatography on silica gel in dichloromethane/methanol [8/1→1/1 (v/v)] as eluent Yield: 75 mg. LC/MS-ESI: $[M+H]^+$=480.5; TLC $R_f$=0.45 (dichloromethane/methanol 8/2).

(b). 1-[5-(9-Isopropoxy-8-methoxy-1-thiophen-2-yl-5,6-dihydro-pyrrolo[2,1-α]isoquinoline-3-carbonyl)-[1,5]diazocan-1-yl]-ethanone To a solution of the product of example 16a (75 mg) in pyridine (0.3 ml) was added acetic anhydride (75 mg) and DMAP (10 mg) and the mixture was stirred for 1 h at 60° C. The reaction mixture was diluted with water, acidified to pH4 with an aqueous HCl solution (2 N) and extracted with ethyl acetate. The organic layer was dried (MgSO₄), filtered and concentrated in vacuo. The residue was purified by chromatography on silica gel in dichloromethane/acetone [9/1→1/1 (v/v)] as eluent.

Yield: 50 mg. Mp 153-155° C.; LC/MS-ESI: $[M+H]^+$=522.5; TLC $R_f$=0.35 (dichloromethane/acetone 8/2); hFSHRago (CHO luc) $EC_{50}$=5.0 nM Example 17

(9-Isopropoxy-8-methoxy-1-thiophen-2-yl-5,6-dihydro-pyrrolo[2,1-α]isoquinolin-3-yl)-[5-(toluene-4-sulfonyl)-perhydro-1,5-diazocin-1-yl]-methanone To a mixture of 1-(toluene-4-sulfonyl)-perhydro-1,5-diazocine.hydrobromide (60 mg) and the product of example 1i (50 mg) in DMF (1.5 ml) was added N-ethylmorpholine (50 μl) and TBTU (100 mg). The reaction was stirred at room temperature for 16 h and poured into an aqueous NH₄Cl solution (5%). The mixture was extracted with ethyl acetate and the organic layer was dried (MgSO$_4$), filtered and concentrated in vacuo. The residue was purified on silica gel in dichloromethane/ethyl acetate as eluent to yield a white solid.

Yield: 45 mg. TLC R$_f$=0.60 (dichloromethane/ethyl acetate 1/1) LC/MS-ESI: [M+H]$^+$=634.5. $^1$H NMR (DMSO-d6) 6.40 (s, 1H, H2-pyrrole), 6.85, 6.72 (2xs, 2H, H7 and H10 7.40, 7.64 (2x dd, 4, tosyl), 2.38 (s, 3, CH3-tosyl), 4.13 (t, 2, H5), 2.95 (t, 2, H6), 3.75 (s, 3, CH$_3$O), 1.08 (d, 6, iPr); hFSHRago (CHO luc) EC$_{50}$=914.0 nM

Example 18

3-(9-Isopropoxy-8-methoxy-1-thiophen-2-yl-5,6-dihydro-pyrrolo[2,1-α]isoquinoline-3-carbonyl)-1,2,3,4,5,6-hexahydro-1,5-methano-pyrido[1,2-α][1,5]diazocin-8-one A mixture of the product of example 1i (125 mg) and racemic cytisine (80 mg), N-ethylmorpholine (50 μl) and TBTU (200 mg) in DMF (2 ml) was stirred at room temperature for 3 h. The reaction mixture was diluted with water and extracted with ethyl acetate. The organic layer was dried (MgSO$_4$), filtered and concentrated in vacuo. The residue was purified by chromatography on silica gel in dichloromethane/acetone as eluent.

Yield: 130 mg. Mp 260° C.; Tlc: TLC R$_f$=0.50 (dichloromethane/acetone 1/1). LC/MS-ESI: [M+H]$^+$=556.

$^1$H NMR (DMSO-d6) signals of pyridone ring at 6.16 (bd, 1H), 6.25 (dd, 1H), 7.35 (dd, 1H); hFSHRago (CHO luc) EC$_{50}$=37.3 nM

Example 19

3-(9-Iso propoxy-8-methoxy-1-thiophen-2-yl-5,6-dihydro-pyrrolo[2,1-α]isoquinoline-3-carbonyl)-decahydro-1,5-methano-pyrido[1,2-α][1,5]diazocin-8-one Cytisine was hydrogenated according to a procedure described; M. J. Johansson, L. Schwartz, S. Mamedjkouh, N. Kann, *Tetrahedron Asymmetry*, 15, 3531 (2004). Mp 98-102° C.

A mixture of the product of example 1i (125 mg) and 85 mg of tetrahydrocytisine (85 mg), N-ethyl-morpholine (50 μl) and TBTU (225 mg) in DMF (2 ml) was stirred at room temperature for 16 h. The reaction mixture was diluted with water and extracted with ethyl acetate. The organic layer was dried (MgSO$_4$), filtered and concentrated in vacuo. The residue was purified by chromatography on silica gel in dichloromethane/acetone, followed by trituration in diethyl ether.

Yield: 130 mg. Mp 207-208° C.; TLC R$_f$=0.64 (dichloromethane/acetone 1/1); LC/MS-ESI: [M+H]$^+$=560; hFSHRago (CHO luc) EC$_{50}$=29.4 nM

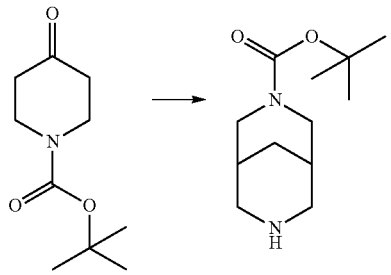

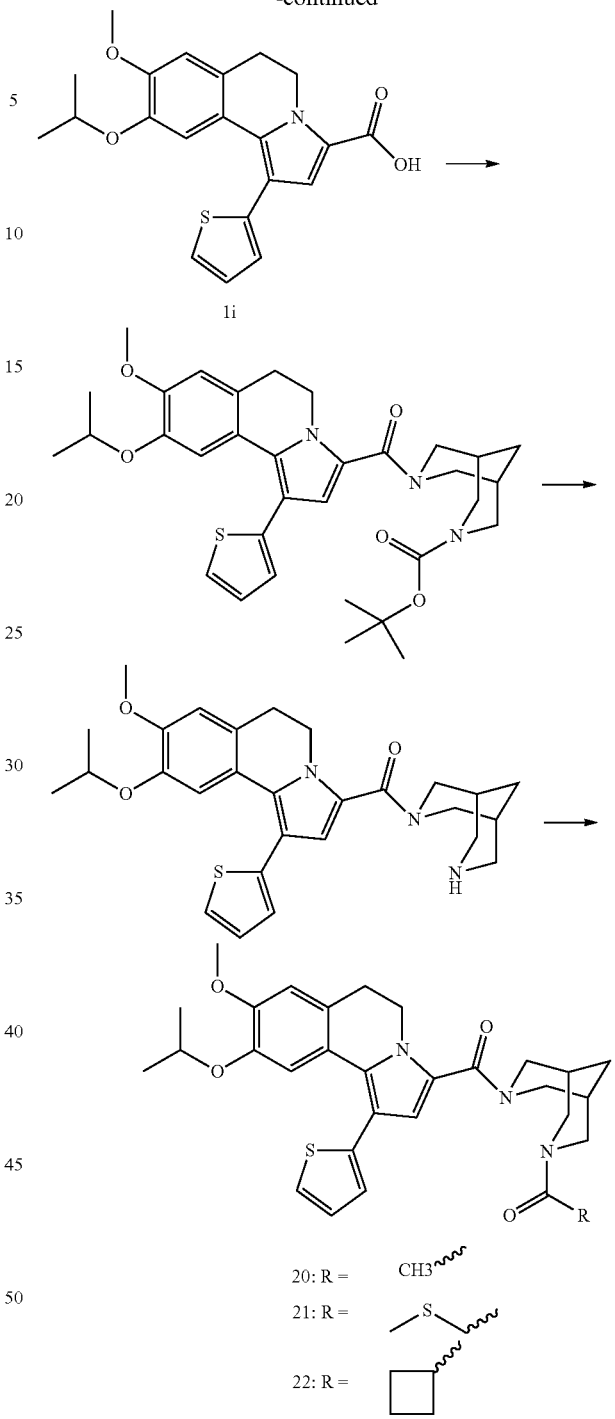

Example 20

(a). 7-(9-Isopropoxy-8-methoxy-1-thiophen-2-yl-5,6-dihydro-pyrrolo[2,1-α]iso-quinoline-3-carbonyl)-3,7-diaza-bicyclo[3.3.1]nonane-3-carboxylic acid tert-butyl ester A mixture of the product of example 1i (150 mg) and 3,7-diaza-bicyclo[3.3.1]nonane-3-carboxylic acid tert-butyl ester (177 mg) [Prepared according to O. Huttenloch, E.

Laxman, H. Waldmann, *Chem. Eur. J.*, 8(20), 4767 (2002)] in dichloromethane (2 ml) was treated with TBTU (188 mg) and diisopropylamine (350 µl). The reaction mixture was stirred at room temperature for 16 h. The reaction was worked up by addition of an aqueous NH$_4$Cl solution (5%) and extracted with ethyl acetate. The organic layer was dried (MgSO$_4$), filtered and concentrated in vacuo. The residue was purified by chromatography on silica gel in toluene/acetone as eluent.

Yield: 153 mg. $^1$H NMR (CDCl$_3$) δ 1.18 (d, 6H, isopropoxy), 1.4 (bs, 9H, tert.-Bu), 6.45 (s, 1H, H-2, pyrrole), 6.69 (s, 1H, H7-Ar), 6.93 (s, 1H, H-9 Ar), 7.04, 7.27 (m, 3H, thienyl). TLC R$_f$=0.62 (toluene/acetone 3/2). LC/MS-ESI: [M+H]$^+$=592

(b). 3,7-diaza-bicyclo[3.3.1]non-3-yl)-(9-isopropoxy-8-methoxy-1-thiophen-2-yl-5,6-dihydro-pyrrolo[2,1-α]isoquinolin-3-yl)-methanone.hydrochloride To a solution of the product of example 20b (150 mg) in dichloromethane (10 ml) was added a HCl solution (3 ml, 2.0 M in ether). The mixture was stirred for 4 h and concentrated in vacuo.

Yield: 110 mg (crude). TLC R$_f$=0.23 (dichloromethane/methanol 9/1).

(c). 1-[7-(9-isopopoxy-8-methoxy-1-thiophen-2-yl-5,6-dihydro-pyrrolo[2,1-α]isoquinoline-3-carbonyl)-3,7-diaza-bicyclo[3.3.1]non-3-yl]-ethanone A solution of the crude product of example 20b (66 mg) in dichloromethane (2 ml) was treated with diisopropylamine (100 µl) and acetyl chloride (12 µl). Reaction was stirred at room temperature for 2 h and diluted with an aqueous citric acid solution (10%) and extracted with dichloromethane. The organic layer was dried (MgSO$_4$), filtered and concentrated in vacuo. The residue was purified with preparative HPLC (0 →100% acetonitrile; system 1).

Yield: 29 mg. TLC R$_f$=0.70 (dichloromethane/methanol 9/1); LC/MS-ESI: [M+H]$^+$=534. $^1$H NMR (CDCl$_3$) δ 1.18 (m, 6H, isopropyl), 2.18 (s, 3H, acetyl), 3.85 (s, 3H, MeO), 3.0 (t, 2H, C$_6$H2 4.04 (t, 2H, C$_5$H2), 6.33 (s, 1H, pyrrole H), 6.69 (3, 1H, Ar H7), 6.92 (s, 1H, Ar H10); hFSHRago (CHO luc) EC$_{50}$=8.2 nM.

Example 21

1-[7-(9-Isopropoxy-8-methoxy-1-thiophen-2-yl-5,6-dihydro-pyrrolo[2,1-α]isoquinoline-3-carbonyl)-3,7-diaza-bicyclo[3.3.1]non-3-yl]-2-methylsulfanyl-ethanone Reaction of the product of example 20b (55 mg) with methylsulfanyl-acetyl chloride was performed according to the method described in example 20c.

Yield: 36 mg. LC/MS-ESI: [M+H]$^+$=580. $^1$H NMR (CDCl$_3$) δ 1.18 (m, 6, isopropyl), 2.16 (s, 3, SCH$_3$), 3.85 (s, 3, MeO), 3.0 (t, 2, C(6)H2) 4.04 (t, 2, C(5)H2), 6.35 (s, 1, pyrrole H), 6.70 (3, 1H, Ar H7), 6.92 (s, 1, Ar H10); hFSHRago (CHO luc) EC$_{50}$=77.8 nM Example 22

(7-Cyclobutanecarbonyl-3,7-diaza-bicyclo[3.3.1]non-3-yl)-(9-isopropoxy-8-methoxy-1-thiophen-2-yl-5,6-dihydro-pyrrolo[2,1-α]isoquinolin-3-yl)-methanone Coupling of the product of example 20b (55 mg) with cyclobutane carbonyl chloride was performed according to the method described in example 20c.

Yield: 20 mg. LC/MS-ESI: [M+H]$^+$=574. hFSHRago (CHO luc) EC$_{50}$=8.9 nM.

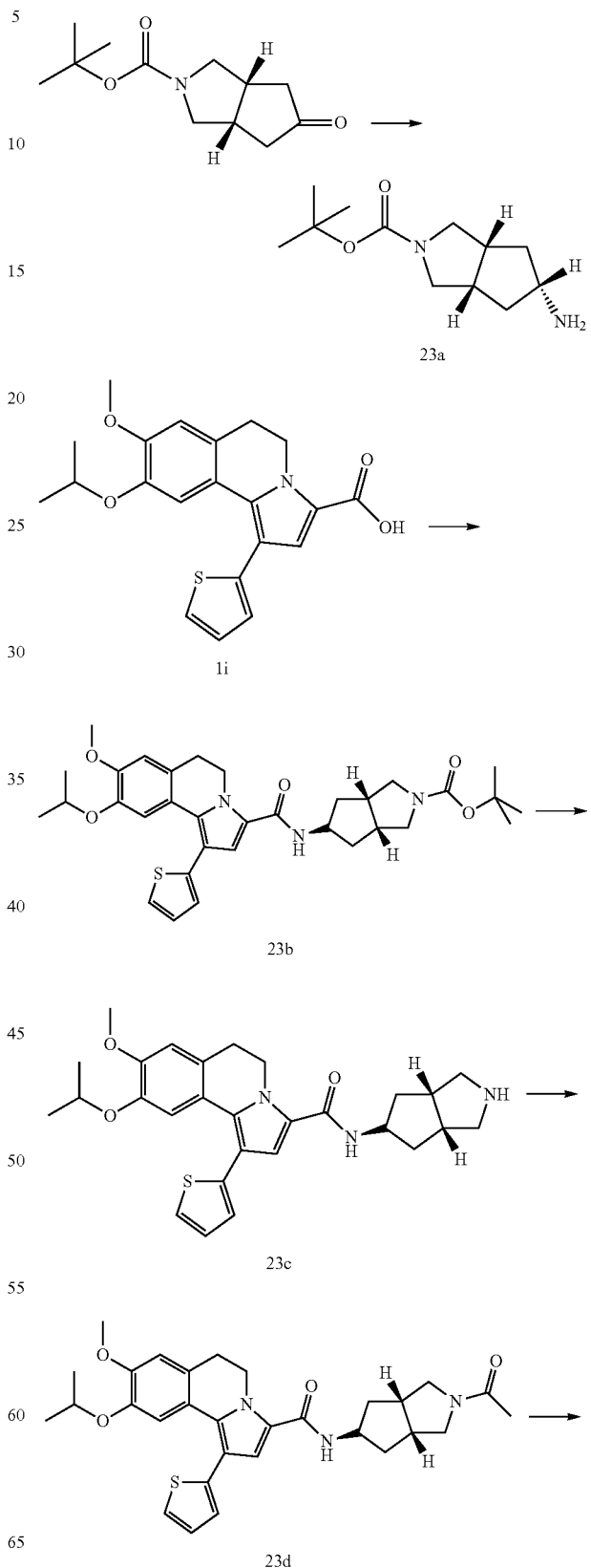

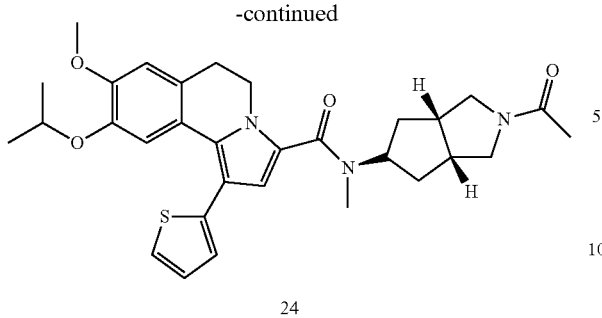

24

Example 23

9-Isopropoxy-8-methoxy-1-thiophen-2-yl-5,6-dihydro-pyrrolo[2,1-α]isoquinoline-3-carboxylic acid (2-acetyl-octahydro-cyclopenta[c]pyrrol-5(endo)-yl)-amide

(a). (3aS,5R,6aR)-5-Amino-hexahydro-cyclopenta[c]pyrrole-2-carboxylic acid tert-butyl ester For the synthesis of carboxamides derived from octahydro-cyclopenta[c]pyrrol-5-ylamine, 5-oxo-hexahydro-cyclopenta[c]pyrrole-2-carboxylic acid tert-butyl ester was prepared, making use of well documented procedures (Pauson-Khand reaction), starting from allyl-propargylamine; see: S. W. Brown, P. L. Pauson, *J. Chem. Soc. Perkin Trans* 11205 (1990); D. P. Becker, D. L. Flynn, *Tetrahedron Lett.*, 34(10) 2087 (1993); D. P. Decker, D. L. Flynn, *Tetrahedron*, 49(23), 5047 (1993); Y. Li, T. Marks, *J. Am. Chem. Soc.*, 120, 1757 (1998).

Next the keto function was converted into an endoamine by means of well known reductive amination procedure, via the derived benzyl imine, followed by Na(OAc)$_3$BH reduction and catalytic debenzylation (Pearlmans catalyst).

(b). 5-(Endo)[(9-isopropoxy-8-methoxy-1-thiophen-2-yl-5,6-dihydro-pyrrolo[2,1-α]iso-quinoline-3-carbonyl)-amino]-hexahydro-cyclopenta[c]pyrrole-2-carboxylic acid tert-butyl ester To a mixture of the product of example 1i (220 mg) and the product of example 23a (145 mg) in DMF (1.5 ml) was added N-ethylmorpholine (100 μl) and TBTU (200 mg). The reaction mixture was stirred at room temperature for 2 h. Water (5 ml) was added, followed by filtration and drying of the precipitate. Trituration with heptane/diisopropylether afforded the product.

Yield: 260 mg. Mp 199-200° C.; TLC R$_f$=0.35 (heptane/ethyl acetate 1/1).

(c). 9-Isopropoxy-8-methoxy-1-thiophen-2-yl-5,6-dihydro-pyrrolo[2,1-α]isoquinoline-3-carboxylic acid (octahydro-cyclopenta[c]pyrrol-5(endo)-yl)-amide, hydrochloride To a solution of the product of example 23b (250 mg) in dichloromethane (10 ml) was added a HCl solution (4 ml, 2M in ether). The reaction was stirred for 2 h and concentrated in vacuo. The residue was treated with ether to give a white solid.

Yield: 210 mg. Mp 140-142° C.

(d). 9-Isopropoxy-8-methoxy-1-thiophen-2-yl-5,6-dihydro-pyrrolo[2,1-α]isoquinoline-3-carboxylic acid (2-acetyl-octahydro-cyclopenta[c]pyrrol-5(endo)-yl)-amide A solution of the product of example 23c (210 mg) in ethyl acetate (10 ml) was treated with an aqueous sat. NaHCO$_3$ solution to liberate the amine from its HCl salt. The organic solution was concentrated in vacuo. The residue was taken up in pyridine (2 ml) and treated with acetic anhydride (150 μl) and DMAP (5 mg). The reaction mixture was stirred at 66° C. for 10 min. The reaction was poured into water and extracted with ethyl acetate. The organic layer was dried (MgSO$_4$), filtered and concentrated in vacuo. The remaining residue was treated with ether.

Yield: 170 mg. Mp 207-208° C.; LC/MS-ESI: [M+H]$^+$=534.5; TLC R$_f$=0.45 (dichloromethane/acetone 1/1); hFSHRago (CHO luc) EC$_{50}$=787.0 nM

Example 24

9-Isopropoxy-8-methoxy-1-thiophen-2-yl-5,6-dihydro-pyrrolo[2,1-α]isoquinoline-3-carboxylic acid (2-acetyl-octahydro-cyclopenta[c]pyrrol-5(endo)-yl)-methyl-amide A solution of the product of example 23d (50 mg) in dry DMF (1 ml) was treated with sodium hydride (17 mg, 60% dispersion in oil) and stirred for 15 min at 65° C. Then the mixture was cooled to room temperature and methyl iodide (35 μl) was added. After 30 min, the methylation was complete. The reaction was poured into water and extracted with ethyl acetate. The organic layer was dried (MgSO$_4$), filtered and concentrated in vacuo. The residue was purified by chromatography on silica gel in dichloromethane/acetone as eluent to yield an amorphous white solid.

Yield: 170 mg. TLC R$_f$=0.45 (dichloromethane/acetone 1/1); LC/MS-ESI: [M+H]$^+$=548.5; hFSHRago (CHO luc) EC$_{50}$=191.0 nM

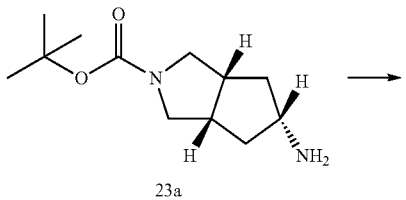

23a

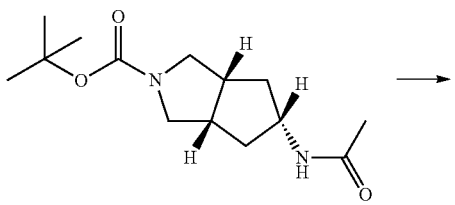

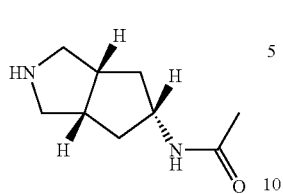

25a

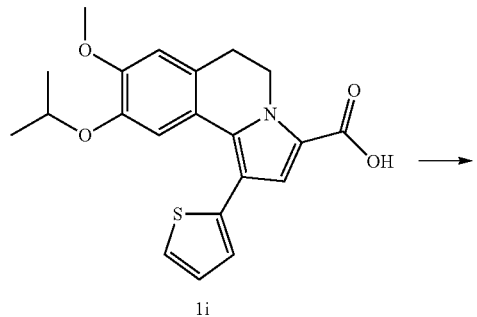

1i

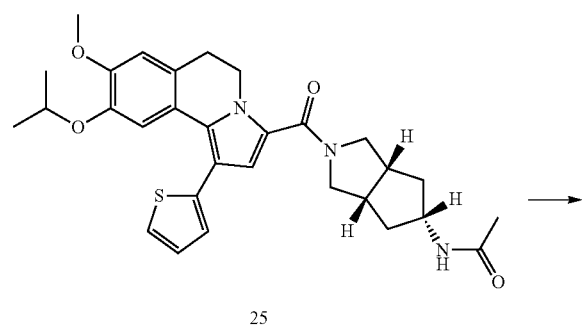

25

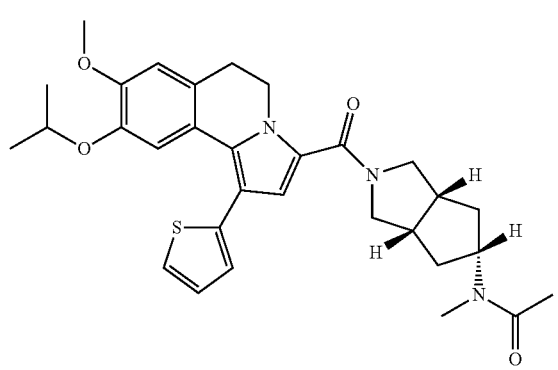

26

Example 25

N-[-2-(9-isopropoxy-8-methoxy-1-thiophen-2-yl-5,6-dihydro-pyrrolo[2,1-α]isoquinoline-3-carbonyl)-octahydro-cyclopenta[c]pyrrol-5-endo-yl]-acetamide (a). 5-Endo-N-(octahydro-cyclopenta[c]pyrrol-5-yl)-acetamide The product of example 23a (100 mg) was acetylated with acetic anhydride in pyridine, deprotected with HCl in dichloromethane to provide a hygroscopic hydrochloride salt.

Yield: 105 mg. LC/MS-ESI: [M+H]$^+$=169.3

(b). N-[-2-(9-isopropoxy-8-methoxy-1-thiophen-2-yl-5,6-dihydro-pyrrolo[2,1-α]isoquinoline-3-carbonyl)-octahydro-cyclopenta[c]pyrrol-5-endo-yl]-acetamide A mixture of the product of example 1i (153 mg) and the product of example 25a (75 mg) in dry DMF (2 ml) was treated with N-ethylmorpholine (200 μl) and TBTU (160 mg). The reaction was stirred at room temperature for 16 h, poured into water and extracted with ethyl acetate. The organic layer was dried (MgSO$_4$), filtered and concentrated in vacuo. The residue was purified by chromatography on silica gel in dichloromethane/acetone.

Yield: 130 mg. Mp 106-112° C.; LC/MS-ESI: [M+H]$^+$= 534.5; TLC R$_f$=0.52 (dichloromethane/acetone 1/1); hFSHRago (CHO luc) EC$_{50}$=45.4 nM

Example 26

N-[2-(9-Isopropoxy-8-methoxy-1-thiophen-2-yl-5,6-dihydro-pyrrolo[2,1-α]isoquinoline-3-carbonyl)-octahydro-cyclopenta[c]pyrrol-5-yl]-N-methyl-acetamide Methylation of the product of example 25b (50 mg) was performed according to the method described in example 24.

Yield: 35 mg. TLC R$_f$=0.58 (dichloromethane/acetone 1/1); LC/MS-ESI: [M+H]$^+$=548.3; hFSHRago (CHO luc) EC$_{50}$=173.0 nM

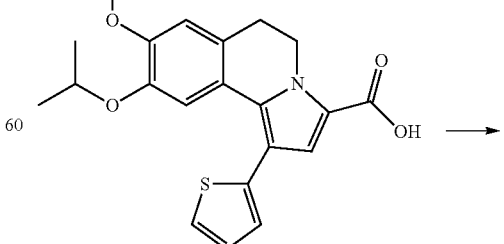

1i

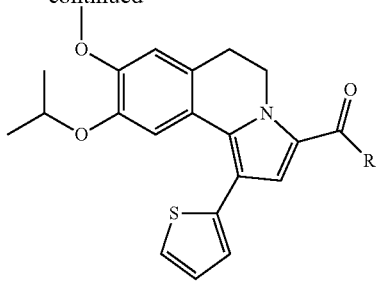

27: R = (2-ethyl-pyrrolidin-1-yl)

28: R = [2-(3-fluoro-phenyl)-pyrrolidin-1-yl]

29: R = (2-pyridin-3-yl-pyrrolidin-1-yl)

30: R = N-methyl-N-(2-hydroxy-1,1-dimethyl-ethyl)amino

Example 27

(2-Ethyl-pyrrolidin-1-yl)-(9-isopropoxy-8-methoxy-1-thiophen-2-yl-5,6-dihydro-pyrrolo[2,1-α]isoquinolin-3-yl)-methanone A mixture of the product of example 1i (168 mg), 2-ethyl-pyrrolidine (130 mg), N-ethylmorpholine (170 μl) and TBTU (260 mg) was stirred at room temperature for 18 h. The reaction was poured into water and extracted with ethyl acetate. The organic layer was dried (MgSO₄), filtered and concentrated in vacuo. The residue was purified by preparative HPLC (20%→100% acetonitrile; system 2).

Yield: 150 mg. LC/MS-ESI: [M+H]⁺=465.3; hFSHRago (CHO luc) EC₅₀=16.2 nM

Example 28

[2-(3-Fluoro-phenyl)-pyrrolidin-1-yl]-(9-isopropoxy-8-methoxy-1-thiophen-2-yl-5,6-dihydro-pyrrolo[2,1-α]isoquinolin-3-yl)-methanone This product was prepared from the product of example 1i (168 mg) amd 2-(3-fluoro-phenyl)-pyrrolidine in a similar manner as described for example 27.

Yield: 187 mg. LC/MS-ESI: [M+H]⁺=531.3; hFSHRago (CHO luc) EC₅₀=752.0 nM

Example 29

(9-Isopropoxy-8-methoxy-1-thiophen-2-yl-5,6-dihydro-pyrrolo[2,1-α]isoquinolin-3-yl)-(2-pyridin-3-yl-pyrrolidin-1-yl)-methanone, This product was prepared from the product of example 1i (168 mg) and 3-pyrrolidin-2-yl-pyridine in a similar manner as described for example 27. The residue was purified by preparative HPLC (20%→100% acetonitrile; system 2).

Yield: 174 mg. LC/MS-ESI: [M+H]⁺=514.3; hFSHRago (CHO luc) EC₅₀=624.0 nM

Example 30

9-Isopropoxy-8-methoxy-1-thiophen-2-yl-5,6-dihydro-pyrrolo[2,1-α]isoquinoline-3-carboxylic acid (2-hydroxy-1,1-dimethyl-ethyl)-methyl-amide This product was prepared from the product of example 1i (60 mg) and 2-methyl-2-methylamino-propan-1-ol [prepared according to S. G. Kuznetsov, A. V. Eltsov, *J. Gen. Chem. USSR*, 32, 502 (1962)] in a similar manner as described for example 27.

Yield: 14 mg. LC/MS-ESI: [M+H]⁺=469.5; Mp 150-152° C.; hFSHRago (CHO luc) EC₅₀=1.0 nM

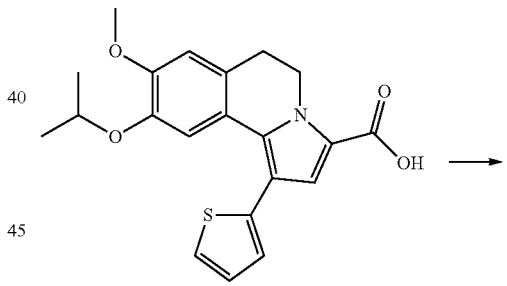

1i

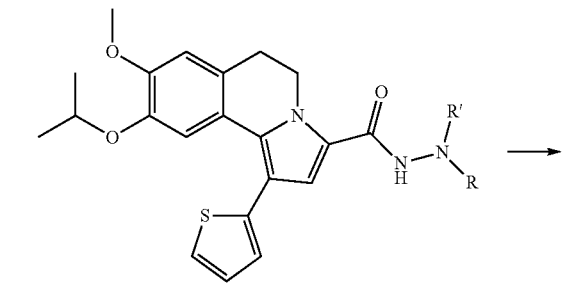

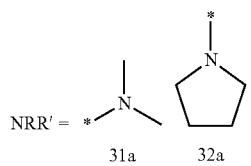

NRR' = 31a, 32a

-continued

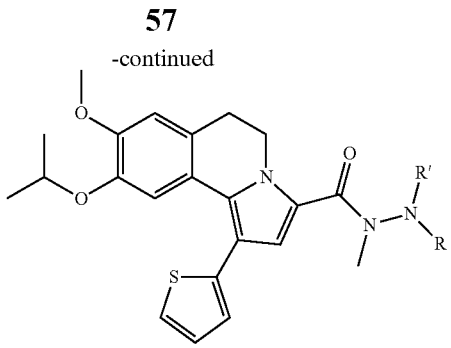

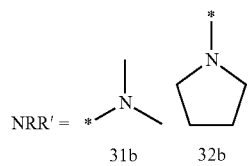

NRR' =

Example 31

9-Isopropoxy-8-methoxy-1-thiophen-2-yl-5,6-dihydro-pyrrolo[2,1-α]isoquinoline-3-carboxylic acid trimethylhydrazide (a). 9-Isopropoxy-8-methoxy-1-thiophen-2-yl-5,6-dihydro-pyrrolo[2,1-α]isoquinoline-3-carboxylic acid N',N'-dimethyl-hydrazide A mixture of the product of example 1i (75 mg), DIPEA (0.171 ml), HATU (112 mg) and 1,1-dimethylhydrazine (19.5 µl) in dichloromethane (2 ml) was stirred for 1 h at room temperature. The reaction mixture was diluted with dichloromethane and washed with a sat. aqueous NaHCO$_3$ solution and brine. The organic layer was dried (MgSO$_4$), filtered and concentrated in vacuo. The residue was purified by chromatography on silica in heptane/ethyl acetate [7/3→1/1 (v/v)] as eluent.

Yield: 75 mg. LC/MS-ESI: [M+H]$^+$=426.1

(b). 9-Isopropoxy-8-methoxy-1-thiophen-2-yl-5,6-dihydro-pyrrolo[2,1-α]isoquinoline-3-carboxylic acid trimethylhydrazide Methyl iodide (11 µl) was added to a solution of the product of example 31a (72 mg) and KOH (10 mg) in acetone (5 ml). After stirring for 1 h at room temperature, the reaction mixture was diluted with ethyl acetate and washed with a sat. aqueous NaHCO$_3$ solution and brine. The organic layer was dried (MgSO$_4$), filtered and concentrated in vacuo. The residue was purified by preparative HPLC (10→90% acetonitrile, 0.1% TFA; system 1).

Yield: 42 mg. LC/MS-ESI: [M+H]$^+$=440.1; anal. HPLC: R$_t$=17.61 min (method 4); hFSHRago (CHO luc) EC$_{50}$=241.0 nM

Example 32

9-Isopropoxy-8-methoxy-1-thiophen-2-yl-5,6-dihydro-pyrrolo[2,1-α]isoquinoline-3-carboxylic acid methyl-pyrrolidin-1-yl-amide (a). 9-Isopropoxy-8-methoxy-1-thiophen-2-yl-5,6-dihydro-pyrrolo[2,1-α]isoquinoline-3-carboxylic acid pyrrolidin-1-ylamide Hydrazide formation of the product of example 1i (75 mg) with pyrrolidin-1-ylamine. hydrochloride (31 mg) was performed according to the method described in example 31a.

Yield: 94 mg. LC/MS-ESI: [M+H]$^+$=452.1

(b). 9-Isopropoxy-8-methoxy-1-thiophen-2-yl-5,6-dihydro-pyrrolo[2,1-α]isoquinoline-3-carboxylic acid methyl-pyrrolidin-1-yl-amide Methylation of the product of example 32a (94 mg) was performed according to the method described in example 31b.

Yield: 51 mg. LC/MS-ESI: [M+H]$^+$=466.1; anal. HPLC: R$_t$=18.92 min (method 4); hFSHRago (CHO luc) EC$_{50}$=55.2 nM

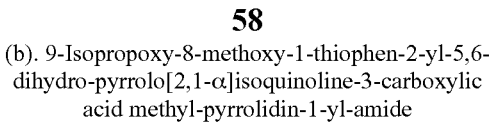

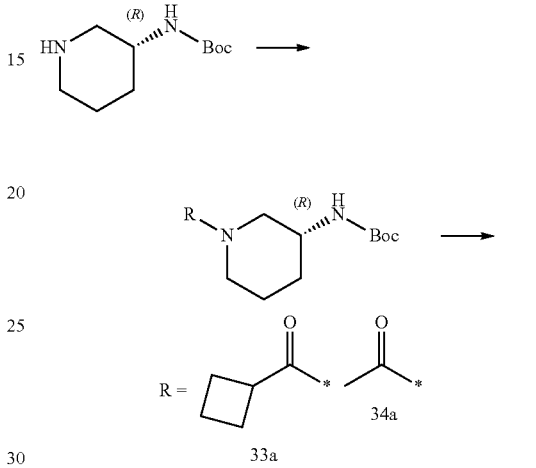

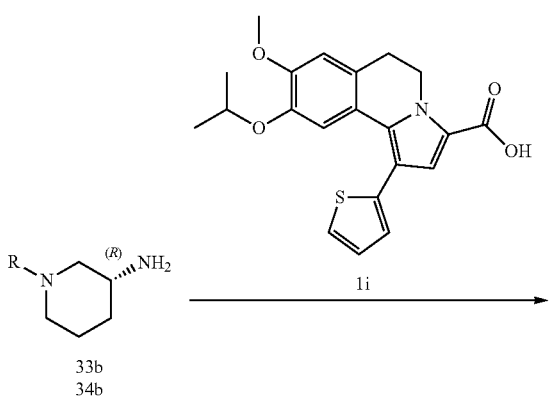

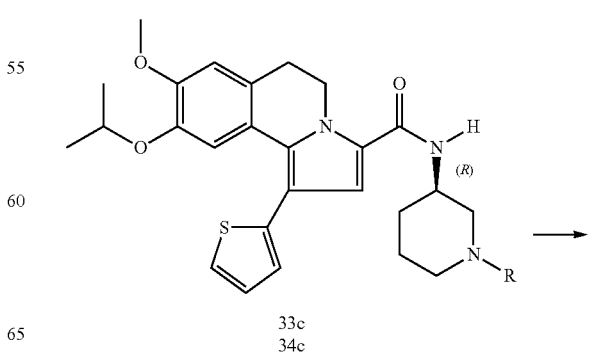

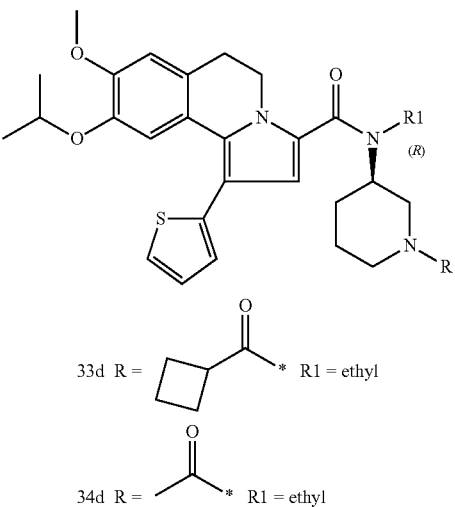

33d R = cyclobutanecarbonyl, R1 = ethyl
34d R = acetyl, R1 = ethyl

Example 33

9-Isopropoxy-8-methoxy-1-thiophen-2-yl-5,6-dihydro-pyrrolo[2,1-α]isoquinoline-3-carboxylic acid ((R)-1-cyclobutanecarbonyl-piperidin-3-yl)-ethyl-amide and 9-isopropoxy-8-methoxy-1-thiophen-2-yl-5,6-dihydro-pyrrolo[2,1-α]isoquinoline-3-carboxylic acid ((R)-1-cyclobutanecarbonyl-piperidin-3-yl)-amide

(a). ((R)-1-Cyclobutanecarbonyl-piperidin-3-yl)-carbamic acid tert-butyl ester Acylation of (R)-piperidin-3-yl-carbamic acid tert-butyl ester (300 mg) with cyclobutyl carbonylchloride (0.342 ml) was performed according to the method described for example 20c. The residue was concentrated in vacuo and used in the next step without purification.

Yield: 423 mg.

(b). ((R)-3-Amino-piperidin-1-yl)-cyclobutyl-methanone

Deprotection of the product of example 33a (423 mg) was performed according to the method described for example 7b.

Yield: 327 mg (as HCl-salt).

(c). 9-Isopropoxy-8-methoxy-1-thiophen-2-yl-5,6-dihydro-pyrrolo[2,1-α]isoquinoline-3-carboxylic acid ((R)-1-cyclobutanecarbonyl-piperidin-3-yl)-amide Amide formation of the product of example 33b (214 mg) with the product of example 11 (250 mg) was performed according to the method described for example 13. The residue was purified by chromatography on silica in toluene/acetone [100/0→6/4 (v/v)] as eluent.

Yield: 316 mg. MS-ESI: $[M+H]^+=548.5$; anal. HPLC: $R_t=25.16$ min (method 2); hFSHRago (CHO luc) $EC_{50}=252$ nM.

(d). 9-Isopropoxy-8-methoxy-1-thiophen-2-yl-5,6-dihydro-pyrrolo[2,1-α]isoquinoline-3-carboxylic acid ((R)-1-cyclobutanecarbonyl-piperidin-3-yl)-ethyl-amide Ethyl iodide (80 μl) and sodium hydride (12.6 mg, 60% dispersion in oil) were added to a solution of the product of example 33c (69 mg) in DMF (1 ml). After stirring for 3 h at 50° C., the reaction mixture was diluted with dichloromethane and washed with water. The organic layer was dried (MgSO₄), filtered and concentrated in vacuo. The residue was purified by preparative HPLC (10%→100% acetonitrile; system 1).

Yield: 26.4 mg. MS-ESI: $[M+H]^+=576.5$; anal. HPLC: $R_t=26.46$ min (method 2); hFSHRago (CHO luc) $EC_{50}=279$ nM

Example 34

9-Isopropoxy-8-methoxy-1-thiophen-2-yl-5,6-dihydro-pyrrolo[2,1-α]isoquinoline-3-carboxylic acid ((R)-1-acetyl-piperidin-3-yl)-methyl-amide and 9-isopropoxy-8-methoxy-1-thiophen-2-yl-5,6-dihydro-pyrrolo[2,1-α]isoquinoline-3-carboxylic acid ((R)-1-acetyl-piperidin-3-yl)-amide

(a). ((R)-1-Acetyl-piperidin-3-yl)-carbamic acid tert-butyl ester

Acylation of ((R)-1-acetyl-piperidin-3-yl)-carbamic acid tert-butyl ester (300 mg) with acetyl chloride (0.214 ml) was performed according to the method described for example 20c. The residue was concentrated in vacuo and used in the next step without purification.

Yield: 348 mg.

(b). 1-((R)-3-Amino-piperidin-1-yl)-ethanone

Deprotection of the product of example 34a (348 mg) was performed according to the method described for example 7b.

Yield: 256 mg (as HCl-salt).

(c). 9-Isopropoxy-8-methoxy-1-thiophen-2-yl-5,6-dihydro-pyrrolo[2,1-α]isoquinoline-3-carboxylic acid ((R)-1-acetyl-piperidin-3-yl)-amide Amide formation of the product of example 34b (175 mg) with the product of example 11 (250 mg) was performed according to the method described for example 13. The residue was purified by chromatography on silica in toluene/acetone [100/0→4/6 (v/v)] as eluent. The product was purified by preparative HPLC (10%→90% acetonitrile; system 1).

Yield: 32 mg. MS-ESI: $[M+H]^+=508.3$; anal. HPLC: $R_t=18.32$ min (method 1); hFSHRago (CHO luc) $EC_{50}=251$ nM.

(d). 9-Isopropoxy-8-methoxy-1-thiophen-2-yl-5,6-dihydro-pyrrolo[2,1-α]isoquinoline-3-carboxylic acid ((R)-1-acetyl-piperidin-3-yl)-methyl-amide Alkylation of the product of example 34c (50 mg) with methyl iodide (62.3 μl) was performed according to the method described for example 33d.

Yield: 36.6 mg. MS-ESI: $[M+H]^+=522.5$; anal. HPLC: $R_t=18.45$ min (method 1); hFSHRago (CHO luc) $EC_{50}=496.0$ nM

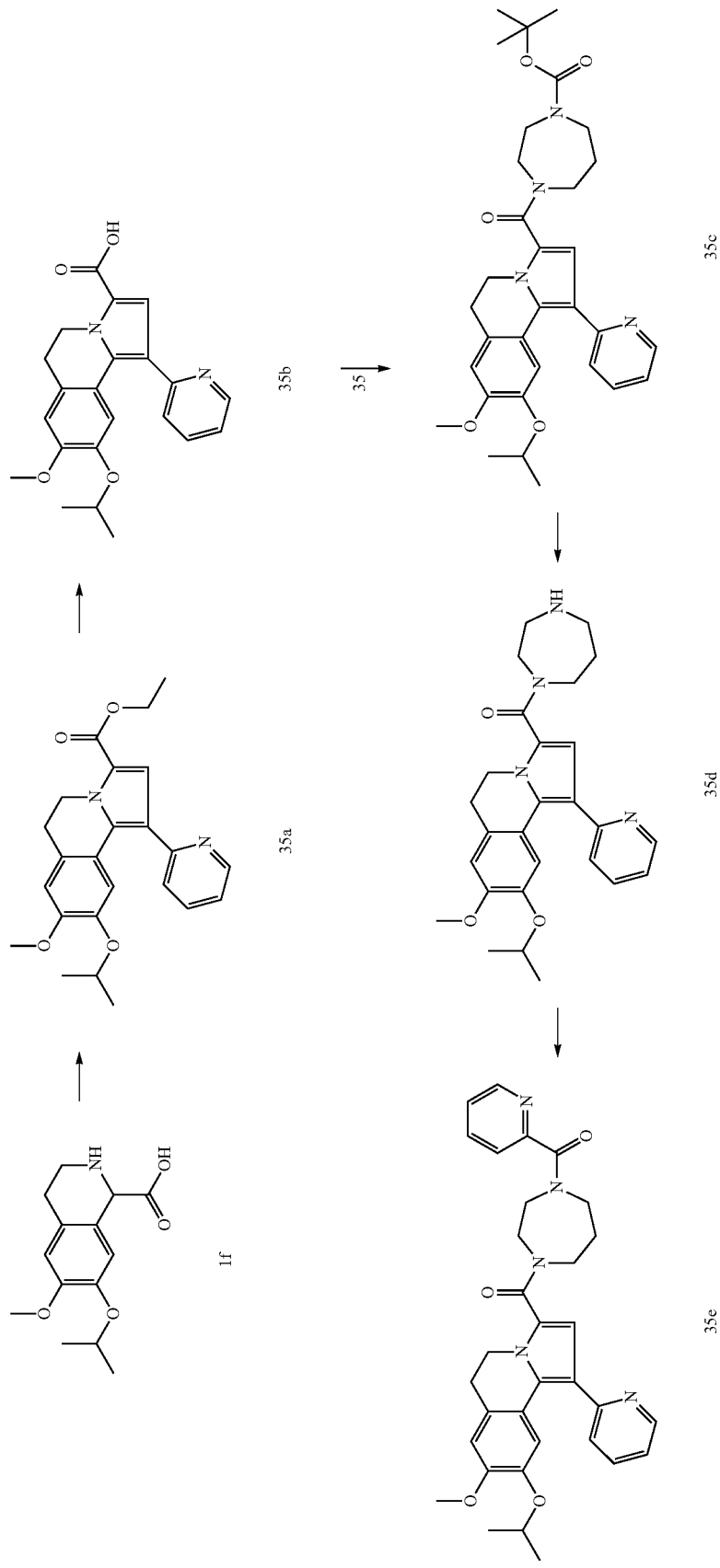

Example 35

(9-Isopropoxy-8-methoxy-1-pyridin-2-yl-5,6-dihydro-pyrrolo[2,1-α]isoquinolin-3-yl)-[4-(pyridine-2-carbonyl)-[1,4]diazepan-1-yl]-methanone; trifluoro acetic acid (a). 9-Isopropoxy-8-methoxy-1-pyridin-2-yl-5,6-dihydro-pyrrolo[2,1-α]isoquinoline-3-carboxylic acid ethyl ester A mixture of the product of example 1f (800 mg) and ethyl oxalyl chloride (0.4 ml) in THF (5 ml) was stirred and heated using microwave irradiation at 100° C. for 5 min. The reaction mixture was concentrated in vacuo. A mixture of the residue and 2-ethynyl-pyridine (340 μl) in acetic anhydride (5 ml) was stirred and heated using microwave irradiation at 140° C. for 15 min. At room temperature, the reaction mixture was diluted with ethyl acetate and extracted with a sat. aqueous NaHCO₃ solution, brine, dried (MgSO₄), filtered and concentrated in vacuo. The residue was purified by chromatography on silica gel in heptane/ethyl acetate [1:1 (v/v)] as eluent.

Yield: 960 mg. MS-ESI: $[M+H]^+=407.5$ (b). 9-Isopropoxy-8-methoxy-1-pyridin-2-yl-5,6-dihydro-pyrrolo[2,1-α]isoquinoline-3-carboxylic acid A mixture of the product of example 35a (850 mg) and solid KOH (500 mg) in ethanol (15 ml) and water (15 ml) was stirred at 80° C. for 1 h. At room temperature, the reaction mixture was neutralized with an aqueous HCl solution (1.0 M) until pH=6-7 and extracted with dichloromethane. The organic layer was washed with brine, dried (MgSO₄), filtered and concentrated in vacuo.

Yield: 673 mg. MS-ESI: $[M+H]^+=379.3$ (c). 4-(9-Isopropoxy-8-methoxy-1-pyridin-2-yl-5,6-dihydro-pyrrolo[2,1-α]isoquinoline-3-carbonyl)-[1,4]diazepane-1-carboxylic acid tert-butyl ester To a solution of the product of example 35b (473 mg), DIPEA (1.0 ml) and [1,4]diazepane-1-carboxylic acid tert-butyl ester (370 μl) in dichloromethane (5 ml) was added HATU (950 mg). After stirring at room temperature for 18 h, the reaction mixture was washed with a sat. aqueous NaHCO₃ solution, brine, dried (MgSO₄), filtered and concentrated in vacuo. The residue was purified by preparative HPLC (0→75% acetonitrile; 0.1% TFA; system 2).

Yield: 768 mg. MS-ESI: $[M+H]^+=561.5$ (d). [1,4]Diazepan-1-yl-(9-isopropoxy-8-methoxy-1-pyridin-2-yl-5,6-dihydro-pyrrolo[2,1-α]isoquinolin-3-yl)-methanone At room temperature, TFA (1 ml) was added dropwise to a solution of the product of example 35c (768 mg) in dichloromethane (9 ml). After stirring at room temperature for 18 h, the reaction mixture was concentrated in vacuo.

Yield: 630 mg. MS-ESI: $[M+H]^+=461.3$ (e). (9-Isopropoxy-8-methoxy-1-pyridin-2-yl-5,6-dihydro-pyrrolo[2,1-α]isoquinolin-3-yl)-[4-(pyridine-2-carbonyl)-[1,4]diazepan-1-yl]-methanone; trifluoro acetic acid A mixture of the product of example 35d (105 mg), DIPEA (200 μl), pyridine-2-carboxylic acid (57 mg) and HATU (350 mg) in dichloromethane (5 ml) was stirred at room temperature for 18 h. The reaction mixture was washed with a sat. aqueous NaHCO₃ solution, brine, dried (MgSO₄), filtered and concentrated in vacuo. The residue was purified by preparative HPLC (0→75% acetonitrile; 0.1% TFA; system 1).

Yield: 96 mg. MS-ESI: $[M+H]^+=566.5$; anal. HPLC $R_t=15.08$ min (method 4); hFSHRago (CHO luc) $EC_{50}=244.0$ nM.

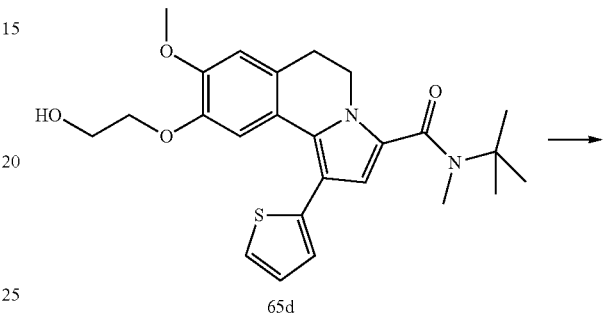

65d

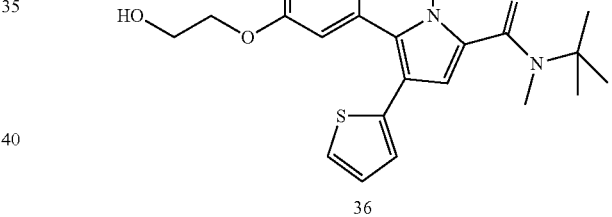

36

Example 36

9-(2-Hydroxy-ethoxy)-8-methoxy-1-thiophen-2-yl-pyrrolo[2,1-α]isoquinoline-3-carboxylic acid tert-butyl-methyl-amide 2,3-Dichloro-5,6-dicyano-1,4-benzoquinone (197 mg) was added to a solution of the product of example 65d (376 mg) in toluene (10 ml). After stirring for 7 h at room temperature, the reaction mixture was diluted with ethyl acetate and washed with brine. The organic layer was dried (MgSO₄), filtered and concentrated in vacuo. The residue was purified by preparative HPLC (10→100% acetonitrile; system 2).

Yield: 200 mg. LC/MS-ESI: $[M+H]^+=453.2$; anal. HPLC: $R_t=15.79$ min (method 11); hFSHRago (CHO luc) $EC_{50}=2.5$ nM

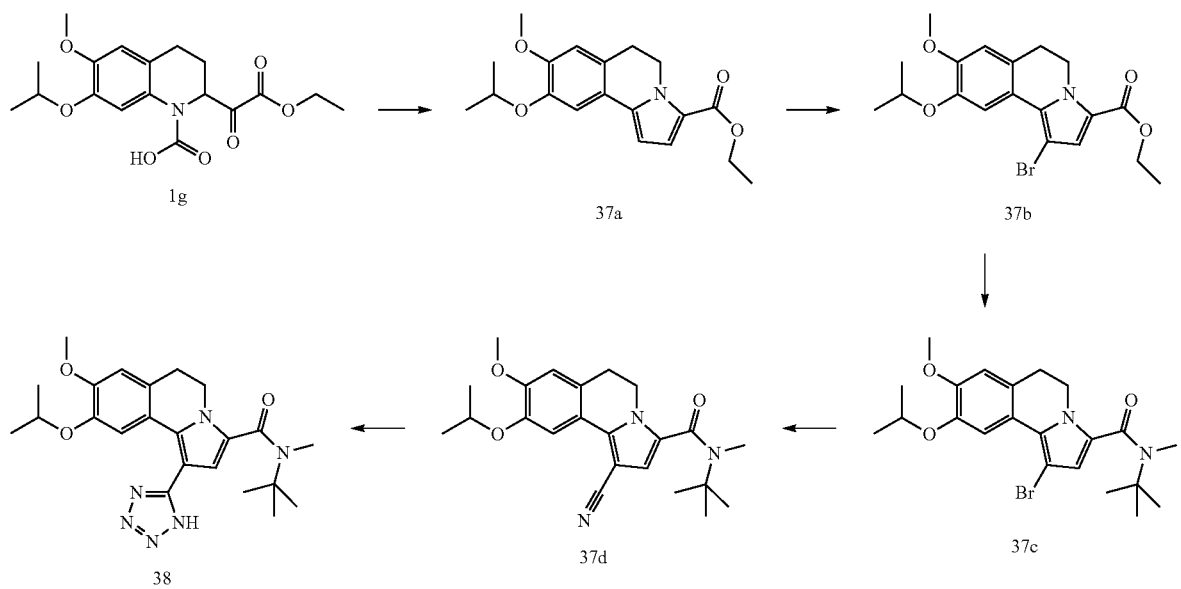 [SMILES: CCOC(=O)C(=O)C1CCc2cc(OC)c(OC(C)C)cc2N1C(=O)O ; CCOC(=O)c1ccc2n1CCc1cc(OC)c(OC(C)C)cc1-2 ; CCOC(=O)c1cc(Br)c2n1CCc1cc(OC)c(OC(C)C)cc1-2 ; COc1cc2c(cc1OC(C)C)-c1c(-c3nnn[nH]3)cc(C(=O)N(C)C(C)(C)C)n1CC2 ; COc1cc2c(cc1OC(C)C)-c1c(C#N)cc(C(=O)N(C)C(C)(C)C)n1CC2 ; COc1cc2c(cc1OC(C)C)-c1c(Br)cc(C(=O)N(C)C(C)(C)C)n1CC2]

Example 37

1-Cyano-9-isopropoxy-8-methoxy-5,6-dihydro-pyrrolo[2,1-α]isoquinoline-3-carboxylic acid tert-butyl-methyl-amide and 1-bromo-9-isopropoxy-8-methoxy-5,6-dihydro-pyrrolo[2,1-α]isoquinoline-3-carboxylic acid tert-butyl-methyl-amide (a). 9-Isopropoxy-8-methoxy-5,6-dihydro-pyrrolo[2,1-α]isoquinoline-3-carboxylic acid ethyl ester A mixture of the product of example 1g (6.5 g) and trimethylsilyl-acetylene (3.3 ml) in acetic anhydride (15 ml) was stirred and heated using microwave irradiation for 15 min at 140° C. The reaction mixture was concentrated in vacuo. The residue was purified by chromatography on silica gel in heptane/ethyl acetate [1/0→3/1 (v/v)] as eluent.
Yield: 1.8 g. LC/MS-ESI: $[M+H]^+=330.1$.

(b). 1-Bromo-9-isopropoxy-8-methoxy-5,6-dihydro-pyrrolo[2,1-α]isoquinoline-3-carboxylic acid ethyl ester N-bromosuccinimide (980 mg) was added to a solution of the product of example 37a (1.8 g) in DMF (20 ml). After stirring for 3 h at room temperature, the reaction mixture was concentrated in vacuo. The residue was purified by chromatography on silica gel in heptane/ethyl acetate [4/1→1/4 (v/v)] as eluent.
Yield: 1.65 g. LC/MS-ESI: $[M+H]^+=408.1/410.1$ (1:1).

(c). 1-Bromo-9-isopropoxy-8-methoxy-5,6-dihydro-pyrrolo[2,1-α]isoquinoline-3-carboxylic acid tert-butyl-methyl-amide An aqueous NaOH solution (8 ml, 2N) was added to a solution of the product of example 37b (1.6 g) in ethanol (50 ml). After stirring for 4 h at 70° C., the reaction mixture was concentrated to a small volume, diluted with ethyl acetate and washed with an aqueous HCl solution (2N) and brine. The organic layer was dried ($MgSO_4$), filtered and concentrated in vacuo. This residue was dissolved in DMF (10 ml) and HATU (2.1 g), N-methyl-N-tert-butyl-amine (3.4 ml) and DIPEA (3.1 ml) were added. After stirring for 18 h at room temperature, the reaction mixture was poured into sat. aqueous $NH_4Cl$ solution, the solids were collected by filtration and washed with water. The solids were taken up in ethyl acetate, dried ($MgSO_4$), filtered and concentrated in vacuo.
Yield: 1.76 g. LC/MS-ESI: $[M+H]^+=409.1/412.1$ (1:1); hFSHRago (CHO luc) $EC_{50}=234.0$ nM (d). 1-Cyano-9-isopropoxy-8-methoxy-5,6-dihydro-pyrrolo[2,1-α]isoquinoline-3-carboxylic acid tert-butyl-methyl-amide A mixture of the product of example 37c (485 mg), copper (I)iodide (21 mg), sym-dimethylethylene diamine (236 μl) and copper(I)cyanide (197 mg) in NMP (10 ml) was stirred and heated using microwave irradiation for 20 min at 200° C. The reaction mixture was diluted with water and extracted with ethyl acetate. The organic layer was washed with sat. aqueous NaCl/sat. aqueous $NH_4Cl$ (1:1), dried ($MgSO_4$), filtered and concentrated in vacuo. The residue was purified by chromatography on silica gel in heptane/ethyl acetate [1/0→1/1 (v/v)] as eluent.
Yield: 326 mg. LC/MS-ESI: $[M+H]^+=330.1$; anal. HPLC: $R_t=15.88$ min (method 7); hFSHRago (CHO luc) $EC_{50}=67.1$ nM

Example 38

9-Isopropoxy-8-methoxy-1-(1H-tetrazol-5-yl)-5,6-dihydro-pyrrolo[2,1-α]isoquinoline-3-carboxylic acid tert-butyl-methyl-amide A mixture of the product of example 37d (22.5 mg) and azidotributyltin (20 μl) in xylene (200 μl) was stirred at 110° C. for 44 h. The reaction mixture was purified by chromatography directly on silica in heptane/ethyl acetate [1/0→6/4 (v/v)] as eluent.
Yield: 9.6 mg. LC/MS-ESI: $[M+H]^+=439.3$; anal. HPLC: $R_t=11.49$ min (method 10); hFSHRago (CHO luc) $EC_{50}=1640.0$ nM

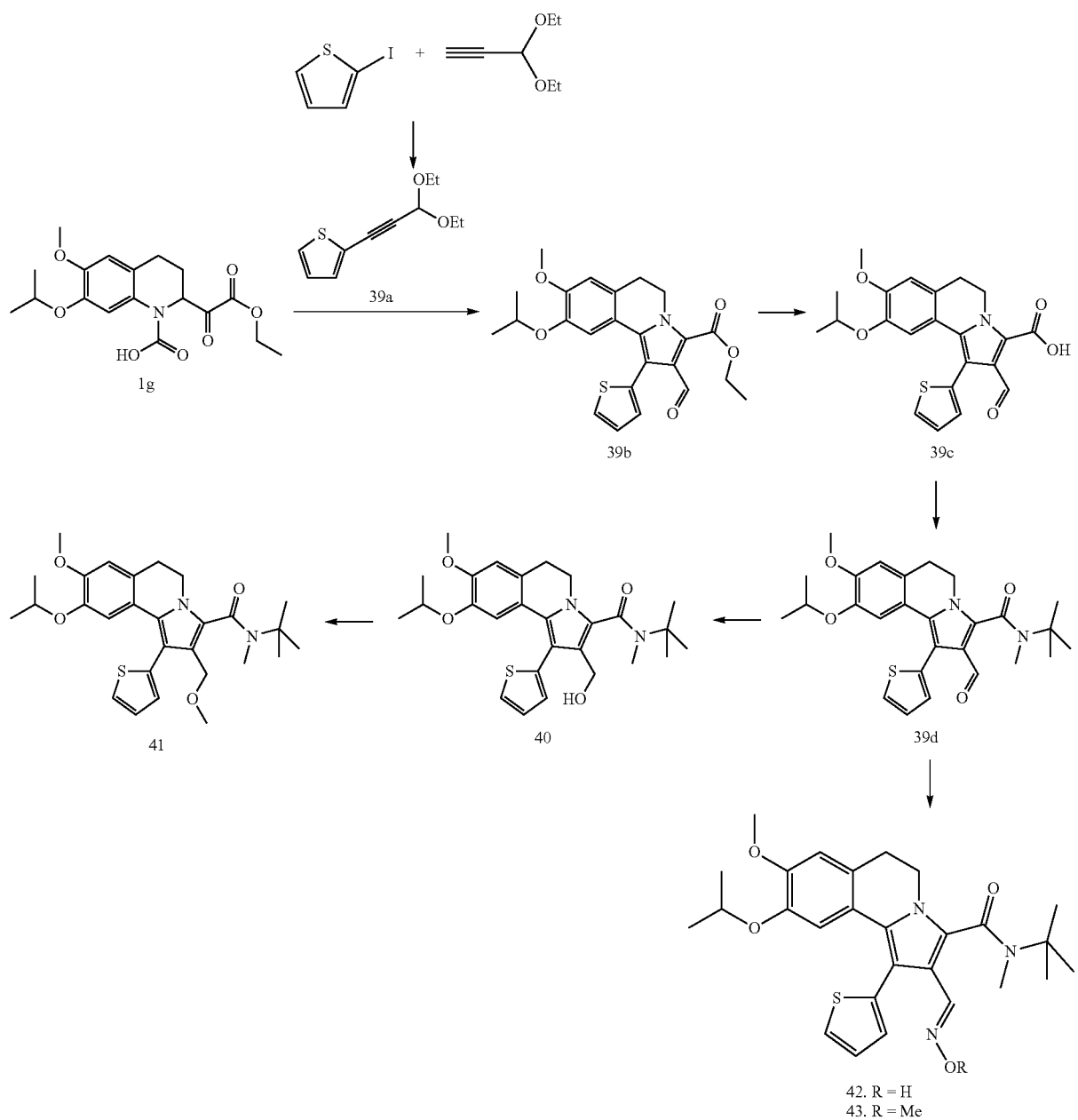

Example 39

2-Formyl-9-isopropoxy-8-methoxy-1-thiophen-2-yl-5,6-dihydro-pyrrolo[2,1-α]isoquinoline-3-carboxylic acid tert-butyl-methyl-amide (a). 2-(3,3-Diethoxy-prop-1-ynyl)-thiophene To a solution of propargylaldehyde diethyl acetal (405 mg) in diisopropylamine (8 ml) were added 2-iodothiophene (1.2 g) and copper(II) acetate monohydrate (66.4 mg). The suspension was flushed with a stream of $N_2$. Pd(PPh$_3$)$_4$ (75 mg) was added, the reaction mixture was flushed with nitrogen again. The suspension was stirred for 1 h at 55° C. A precipitate was formed and it was necessary to dilute the reaction mixture with diisopropylamine (6 ml) to keep it stirring. The reaction mixture was filtered and concentrated in vacuo. The residue was purified by chromatography on silica gel in heptane/ethyl acetate [1/0→17/3 (v/v)] as eluent.

Yield: 680 mg.

(b). 2-Formyl-9-isopropoxy-8-methoxy-1-thiophen-2-yl-5,6-dihydro-pyrrolo[2,1-α]isoquinoline-3-carboxylic acid ethyl ester A mixture of the product of example 1g (300 mg) and the product of example 39a (350 mg) in acetic anhydride (6.5 ml) was stirred and heated using microwave irradiation for 12 min at 140° C. The reaction mixture was concentrated in vacuo. The residue was purified by chromatography on silica gel in heptane/ethyl acetate [1/0→3/2 (v/v)] as eluent.

Yield: 283 mg. LC/MS-ESI: [M+H]$^+$=440.2.

(c). 2-Formyl-9-isopropoxy-8-methoxy-1-thiophen-2-yl-5,6-dihydro-pyrrolo[2,1-α]iso-quinoline-3-carboxylic acid (sodium salt)

An aqueous NaOH solution (5 ml, 2 N) was added to a solution of the product of example 39b (220 mg) in ethanol (10 ml). After stirring for 2 h at 60° C. the reaction mixture was concentrated in vacuo.

Yield: 216 mg.

(d). 2-Formyl-9-isopropoxy-8-methoxy-1-thiophen-2-yl-5,6-dihydro-pyrrolo[2,1-α]iso-quinoline-3-carboxylic acid tert-butyl-methyl-amide HATU (103 mg), N-methyl-N-tert-butyl-amine (125 µl) and DIPEA (182 µl) were added to a solution of the product of example 39c (86 mg) in NMP (5 ml). After stirring for 3 h at room temperature, the reaction mixture was poured into water and extracted with ethyl acetate (2×). The organic layers were combined, dried (MgSO$_4$), filtered and concentrated in vacuo.

Yield: 45 mg. LC/MS-ESI: [M+H]$^+$=481.2; anal. HPLC: R$_t$=16.90 min (method 7); hFSHRago (CHO luc) EC$_{50}$=2.7 nM Example 40

2-Hydroxymethyl-9-isopropoxy-8-methoxy-1-thiophen-2-yl-5,6-dihydro-pyrrolo[2,1-α]isoquinoline-3-carboxylic acid tert-butyl-methyl-amide Sodium borohydride (3.6 mg) was added to a solution of the product of example 39d (38 mg) in methanol (5 ml). After stirring for 2 h at room temperature, an additional amount of sodium borohydride (3.6 mg) was added and the reaction was stirred for 18 h at room temperature. The reaction mixture was concentrated in vacuo and purified by chromatography on silica gel in heptane/ethyl acetate [1/0→1/1 (v/v)] as eluent.

Yield: 27 mg. LC/MS-ESI: [M+H]$^+$=482.3; anal. HPLC: R$_t$=14.77 min (method 7); hFSHRago (CHO luc) EC$_{50}$=8.8 nM Example 41

9-Isopropoxy-8-methoxy-2-methoxymethyl-1-thiophen-2-yl-5,6-dihydro-pyrrolo[2,1-α]isoquinoline-3-carboxylic acid tert-butyl-methyl-amide A mixture of the product of example 40 (20 mg), sodium hydride (3.3 mg, 60% dispersion in oil) and iodomethane (13 µl) in THF (2.5 ml) was stirred for 18 h at room temperature. The reaction mixture was poured into water and extracted with ethyl acetate. The organic layers were combined, dried (MgSO$_4$), filtered and concentrated in vacuo. The residue was purified by chromatography on silica gel in heptane/ethyl acetate [1/0→1/1 (v/v)] as eluent.

Yield: 12 mg. LC-MS: [M+H]$^+$=497.3; anal HPLC 20.40 min (method 7); hFSHRago (CHO luc) EC$_{50}$=2.8 nM Example 42

2-(Hydroxyimino-methyl)-9-isopropoxy-8-methoxy-1-thiophen-2-yl-5,6-dihydro-pyrrolo[2,1-α]isoquinoline-3-carboxylic acid tert-butyl-methyl-amide A mixture of the product of example 39d (74 mg) and hydroxylamine hydrochloride (21.5 mg) in pyridine (1.5 ml) was stirred for 18 h at room temperature. The reaction mixture was diluted with ethyl acetate, washed with water and brine. The organic layers were combined, dried (MgSO$_4$), filtered and concentrated in vacuo. The residue was purified by chromatography on silica gel in heptane/ethyl acetate [1/0→3/7 (v/v)] as eluent.

Yield: 40 mg. MS: [M+H]$^+$=496.3; anal HPLC 15.33 min (method 7); hFSHRago (CHO luc) EC$_{50}$=1.2 nM Example 43

9-Isopropoxy-8-methoxy-2-(methoxyimino-methyl)-1-thiophen-2-yl-5,6-dihydro-pyrrolo[2,1-α]isoquinoline-3-carboxylic acid tert-butyl-methyl-amide Methoxime formation of the product of example 39d (76 mg) with o-methylhydroxylamine hydrochloride (26.4 mg) was performed according to the method described in example 42.

Yield: 60 mg. MS-ESI: [M+H]$^+$=452.1; anal HPLC 22.60 min (method 7); hFSHRago (CHO luc) EC$_{50}$=4.3 nM

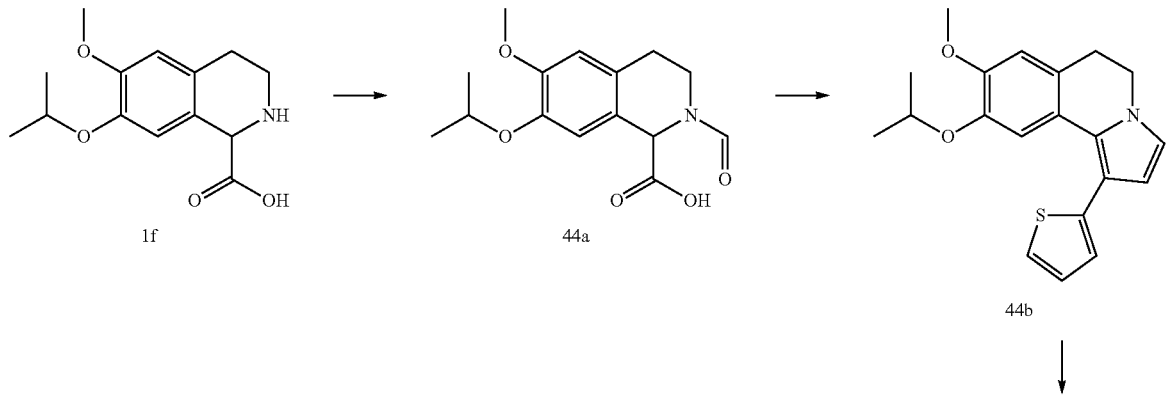

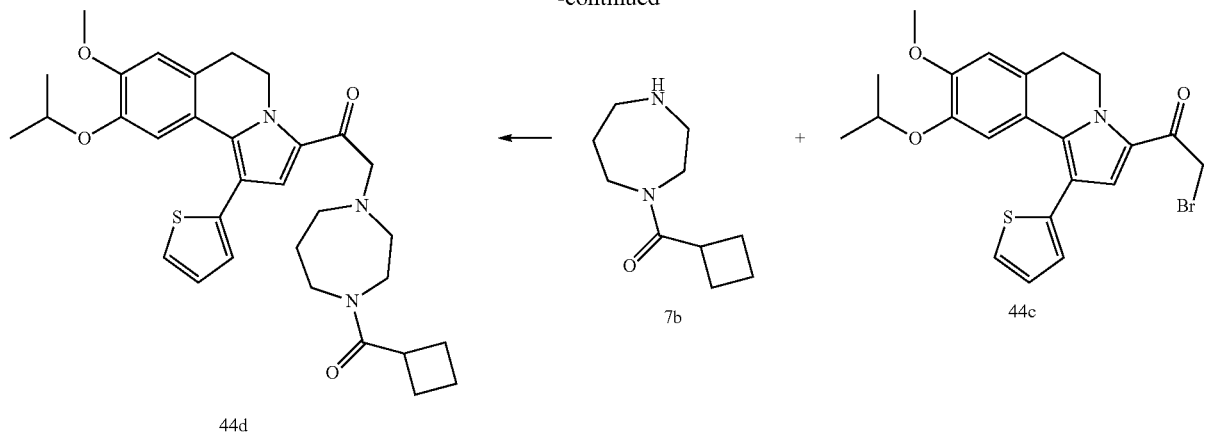

Example 44

2-(4-Cyclobutanecarbonyl-[1,4]diazepan-1-yl)-1-(9-isopropoxy-8-methoxy-1-thiophen-2-yl-5,6-dihydro-pyrrolo[2,1-α]isoquinolin-3-yl)-ethanone (a). 2-Formyl-7-isopropoxy-6-methoxy-1,2,3,4-tetrahydro-isoquinoline-1-carboxylic acid Acetic anhydride (8.9 ml) was added dropwise to a cooled solution of the product of example 1f (5 g) dissolved in formic acid (35.5 ml) at 5° C. The reaction mixture was diluted with ice-water and concentrated in vacuo. The residue was purified by chromatography on silica gel in dichloromethane/methanol [95/5 (v/v)] as eluent.
Yield: 2.28 g. LC/MS-ESI: [M+H]$^+$=294.3

(b). 9-Isopropoxy-8-methoxy-1-thiophen-2-yl-5,6-dihydro-pyrrolo[2,1-α]isoquinoline A mixture of the product of example 44a (400 mg) and 2-ethynylthiophene (134 µl) in tetrahydrofuran/acetic anhydride=1:1 (v/v) (10 ml) was stirred and heated using microwave irradiation at 140° C. for 15 min. The reaction mixture was neutralized with a sat. aqueous NaHCO$_3$ solution and extracted with dichloromethane. The organic layer was washed with brine and concentrated in vacuo. The residue was purified by chromatography on silica gel in heptane/ethyl acetate [7/3 (v/v)] as eluent.
Yield: 209 mg. LC/MS-ESI: [M+H]$^+$=340.2

(c). 2-Bromo-1-(9-isopropoxy-8-methoxy-1-thiophen-2-yl-5,6-dihydro-pyrrolo[2,1-α]iso-quinolin-3-yl)-ethanone Bromoacetyl bromide (902 µl) was added dropwise to a stirred mixture of the product of example 44b (1.17 g) in dioxane (50 ml). After 1 h, the reaction mixture was quenched with a sat. aqueous NaHCO$_3$ solution, washed with water and brine. The organic layers were combined, dried (Na$_2$SO$_4$), filtered and concentrated in vacuo.
Yield: 209 mg. LC/MS-ESI: [M+H]$^+$=460.0/462.0

(d). 2-(4-Cyclobutanecarbonyl-[1,4]diazepan-1-yl)-1-(9-isopropoxy-8-methoxy-1-thiophen-2-yl-5,6-dihydro-pyrrolo[2,1-α]isoquinolin-3-yl)-ethanone A mixture of the product of example 44c (105 mg), DIPEA (200 µl) and the product of example 7b (125 mg) in THF (4 ml) was stirred at room temperature for 18 h. The reaction mixture was washed with water and brine. The organic layers were combined, dried (Na$_2$SO$_4$), filtered and concentrated in vacuo. The residue was purified by preparative HPLC (10→100% acetonitrile, 0.1% TFA; system 1).
Yield: 15 mg (as TFA salt). LC/MS-ESI: [M+H]$^+$=562.3; anal. HPLC: R$_t$=13.47 (Method 2); hFSHRago (CHO luc) EC$_{50}$=1120.0 nM

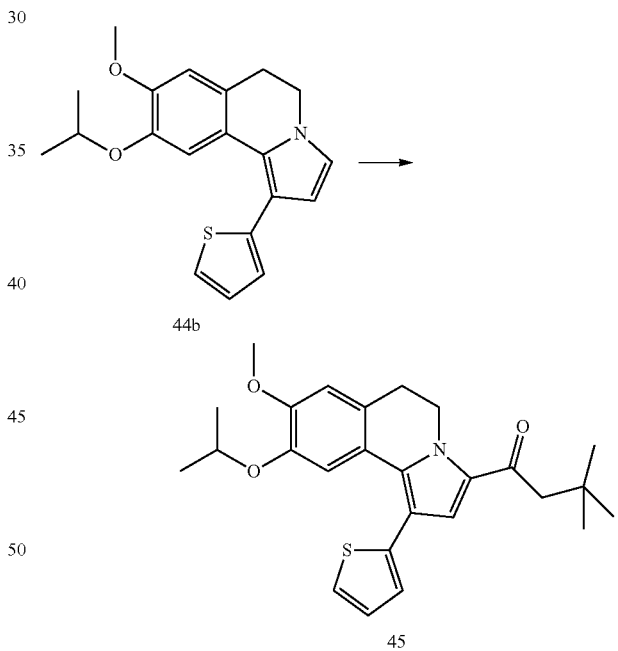

Example 45

1-(9-Isopropoxy-8-methoxy-1-thiophen-2-yl-5,6,6a,10a-tetrahydro-pyrrolo[2,1-α]isoquinolin-3-yl)-3,3-dimethyl-butan-1-one A mixture of the product of example 44b (100 mg), 3,3-dimethylbutyryl chloride (102 µl) and AlCl$_3$ (catalytic amount) in dioxane (4 ml) was stirred at room temperature for 64 h. The reaction mixture was poured into ice water and extracted with ethyl acetate. The organic layer was washed with water and brine and concentrated in vacuo. The residue was purified by preparative HPLC (30→100% acetonitrile; system 1).

Yield: 56 mg. LC/MS-ESI: [M+H]$^+$=438.1; anal. HPLC: R$_t$=27.07 (Method 3); hFSHRago (CHO luc) EC$_{50}$=65.1 nM

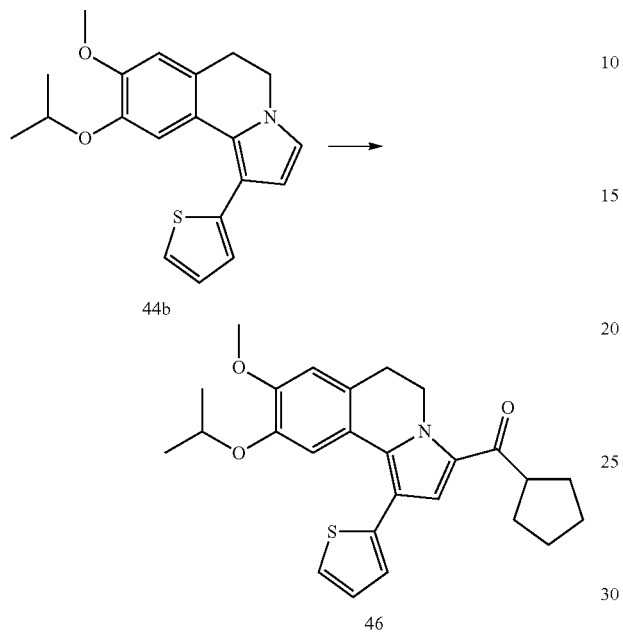

44b

46

Example 46

Cyclopentyl-(9-isopropoxy-8-methoxy-1-thiophen-2-yl-5,6,6a,10a-tetrahydro-pyrrolo[2,1-α]isoquinolin-3-yl)-methanone A mixture of the product of example 44b (100 mg), cyclopentanecarbonyl chloride (90 µl) and AlCl$_3$ (40 mg) in dioxane (4 ml) was stirred at room temperature for 18 h. The reaction mixture was poured into ice water and extracted with ethyl acetate. The organic layer was washed with water and brine. The organic layers were combined, dried (Na$_2$SO$_4$), filtered and concentrated in vacuo. The residue was purified by preparative HPLC (30→100% acetonitrile; system 1).

Yield: 29 mg. LC/MS-ESI: [M+H]$^+$=436.1; anal. HPLC: R$_t$=26.71 (Method 3); hFSHRago (CHO luc) EC$_{50}$=78.2 nM

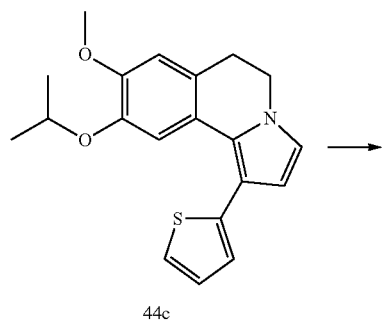

44c

-continued

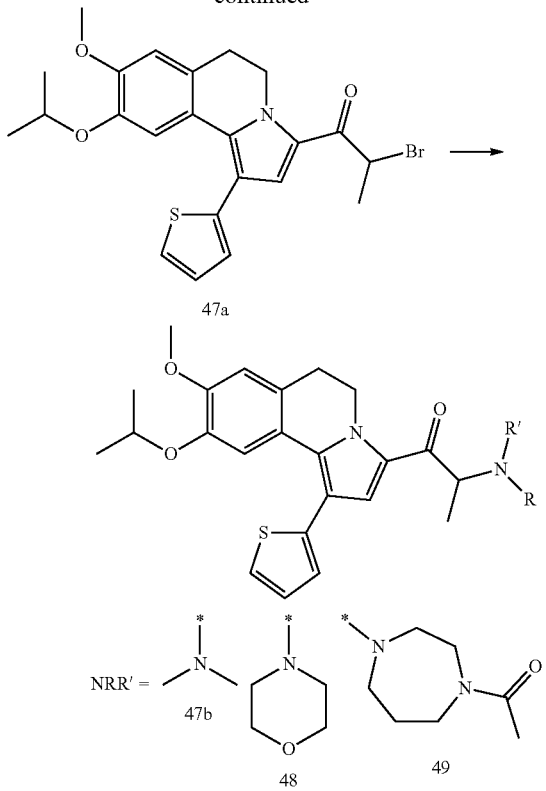

47a

NRR' = 47b, 48, 49

Example 47

2-Dimethylamino-1-(9-isopropoxy-8-methoxy-1-thiophen-2-yl-5,6-dihydro-pyrrolo[2,1-α]isoquinolin-3-yl)-propan-1-one (a). 2-Bromo-1-(9-isopropoxy-8-methoxy-1-thiophen-2-yl-5,6-dihydro-pyrrolo[2,1-α]iso-quinolin-3-yl)-propan-1-one 2-Bromopropionyl bromide (0.625 ml) was added dropwise to a solution of the product of example 44b (500 mg) in dioxane (20 ml). After stirring for 18 h at room temperature, the reaction mixture was poured into water and extracted with ethyl acetate. The organic layer was washed with brine, dried (MgSO$_4$), filtered and concentrated in vacuo.

Yield: 700 mg. LC/MS-ESI: [M+H]$^+$=474/476.

(b). 2-Dimethylamino-1-(9-isopropoxy-8-methoxy-1-thiophen-2-yl-5,6-dihydro-pyrrolo[2,1-α]isoquinolin-3-yl)-propan-1-one A mixture of the product of example 47a (50 mg) and dimethylamine (0.133 ml, 40% WT in water) was stirred for 1 h at 60° C. The reaction mixture was diluted with dichloromethane and washed with a sat. aqueous NaHCO$_3$ solution. The organic layer was dried (MgSO$_4$), filtered and concentrated in vacuo. The residue was purified by preparative HPLC (10%→90% acetonitrile, 0.1% TFA; system 1).

Yield: 20 mg. LC/MS-ESI: [M+H]$^+$=439.1; hFSHRago (CHO luc) EC$_{50}$=149.0 nM

Example 48

1-(9-Isopropoxy-8-methoxy-1-thiophen-2-yl-5,6-dihydro-pyrrolo[2,1-α]isoquinolin-3-yl)-2-morpholin-4-yl-propan-1-one Substitution of the bromine in the product of example 47a (68 mg) with morpholine (38 μl) was performed according to the method described in example 47b.

Yield: 32 mg. MS-ESI: [M+H]$^+$=481.3; anal. HPLC: $R_t$=18.64 (method 4); hFSHRago (CHO luc) $EC_{50}$=89.4 nM

Example 49

2-(4-Acetyl-[1,4]diazepan-1-yl)-1-(9-isopropoxy-8-methoxy-1-thiophen-2-yl-5,6-dihydro-pyrrolo[2,1-α]isoquinolin-3-yl)-propan-1-one Substitution of the bromine in the product of example 47a (75 mg) with 1-[1,4]diazepan-1-yl-ethanone (0.106 ml) was performed according to the method described in example 47b.

Yield: 28 mg. MS-ESI: [M+H]$^+$=536.5; anal. HPLC: $R_t$=18.37 (method 4); hFSHRago (CHO luc) $EC_{50}$=200.0 nM

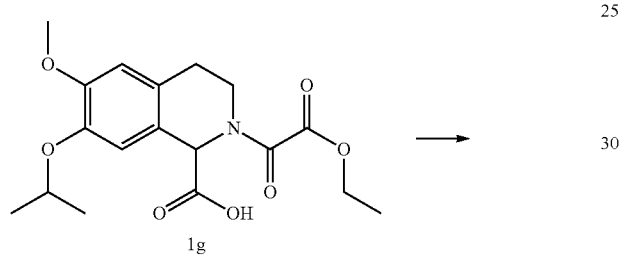

1g

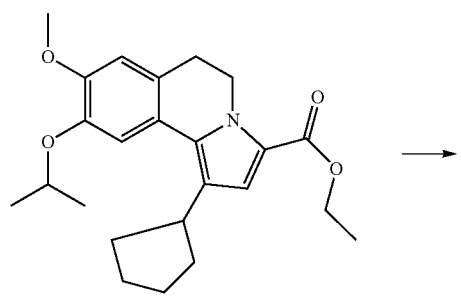

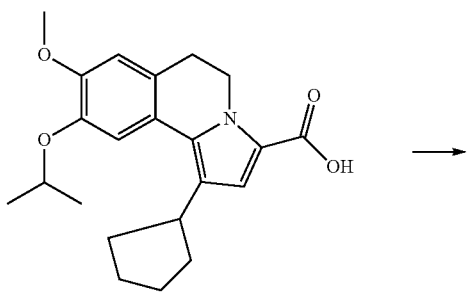

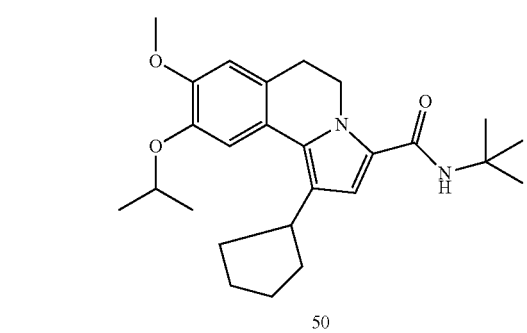

Example 50

1-Cyclopentyl-9-isopropoxy-8-methoxy-5,6-dihydro-pyrrolo[2,1-α]isoquinoline-3-tert-butylamide The product of example 1g (270 mg) and ethynyl-cyclopentane (100 mg) were subjected to similar conditions as described in example 1, to yield 1-cyclopentyl-9-isopropoxy-8-methoxy-5,6-dihydro-pyrrolo[2,1-α]isoquinoline-3-carboxylic acid. The acid (18 mg) was treated with t-butylamine under standard amide coupling conditions with HATU as described in example 1j. The residue was purified by chromatography on silica gel in heptane/ethyl acetate [0→100% isopropylamine (v/v)] as eluent.

Yield: 19 mg. LC/MS-ESI: [M+H]$^+$=425; hFSHRago (CHO luc) $EC_{50}$=220.0 nM

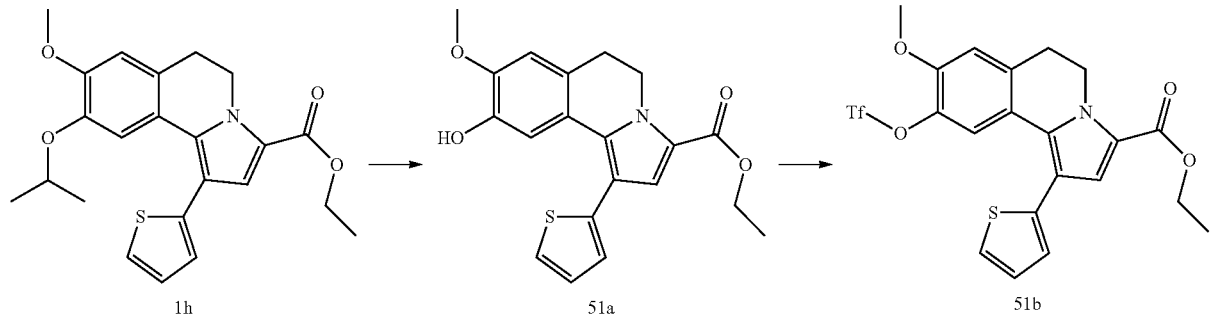

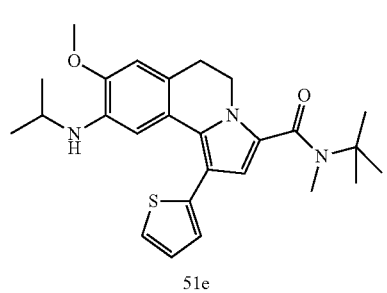

51e

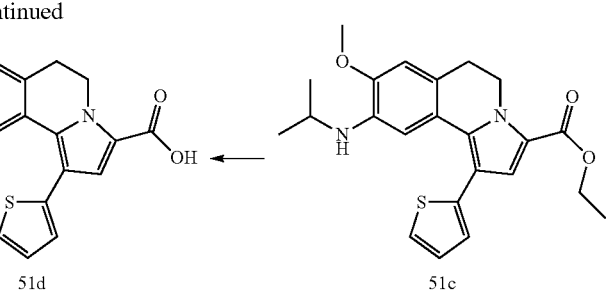

51d  51c

Example 51

9-Isopropylamino-8-methoxy-1-thiophen-2-yl-5,6-dihydro-pyrrolo[2,1-α]isoquinoline-3-carboxylic acid tert-butyl-methyl-amide (a). 9-Hydroxy-8-methoxy-1-thiophen-2-yl-5,6-dihydro-pyrrolo[2,1-α]isoquinoline-3-carboxylic acid ethyl ester Boron trichloride (100 ml) was added dropwise to a solution of the product of example 1h (51.2 g) in dichloromethane (400 ml) at 0° C. The reaction mixture was stirred at room temperature for 3 h. The reaction mixture was poured into water and extracted with dichloromethane. The organic layer was washed with brine, dried (MgSO$_4$) and concentrated in vacuo. The residue was purified by chromatography on silica gel in heptane/ethyl acetate [30→50% (v/v)] as eluent.
Yield: 44.3 g.

(b). 8-Methoxy-1-thiophen-2-yl-9-trifluoromethanesulfonyloxy-5,6-dihydro-pyrrolo[2,1-α]isoquinoline-3-carboxylic acid ethyl ester Trifluoromethane sulfonic anhydride (982 µl) was added dropwise to a solution of the product of example 51a (716 mg) in pyridine (5 ml) at 0° C. The reaction mixture was stirred at room temperature for 18 h. The reaction mixture was diluted with ethyl acetate and washed with an aqueous HCl solution (1 N). The organic layer was dried (MgSO$_4$), filtered and concentrated in vacuo. The residue was purified by chromatography on silica gel in heptane/ethyl acetate [1/1 (v/v)] as eluent.
Yield: 875 mg. LC/MS-ESI: [M+H]$^+$=502.1

(c). 9-Isopropylamino-8-methoxy-1-thiophen-2-yl-5,6-dihydro-pyrrolo[2,1-α]isoquinoline-3-carboxylic acid ethyl ester A mixture of the product of example 51b (100 mg), isopropylamine (42 µl), tris(dibenzylideneacetone)dipalladium (0) (5 mg), potassium phosphate tribasic (130 mg) and 2-(di-t-butylphosphino)biphenyl (10 mg) was stirred and heated using microwave irradiation at 150° C. for 1 h. The reaction mixture was filtered and the filtrate was concentrated in vacuo. The residue was chromographed on silica gel in heptane/ethyl acetate [1/1 (v/v)].
Yield: 73 mg. LC/MS-ESI: [M+H]$^+$=411.1

(d). 9-Isopropylamino-8-methoxy-1-thiophen-2-yl-5,6-dihydro-pyrrolo[2,1-α]isoquinoline-3-carboxylic acid A mixture of the product of example 51c (73 mg) and KOH (excess) in methanol/water [1/1 (2 ml)] was stirred at reflux for 1 h. The reaction mixture was poured into water, acidified with aq. citric acid solution (1M) and extracted with dichloromethane. The organic layer was dried (MgSO$_4$), filtered and concentrated in vacuo.
Yield: 58 mg. LC/MS-ESI: [M+H]$^+$=383.2

(e). 9-Isopropylamino-8-methoxy-1-thiophen-2-yl-5,6-dihydro-pyrrolo[2,1-α]isoquinoline-3-carboxylic acid tert-butyl-methyl-amide A mixture of the product of example 51d (58 mg), DIPEA (79 µl), HATU (86 mg) and N-methyl-N-tert-butyl-amine (187 µl) in dichloromethane (3 ml) was stirred at 40° C. for 18 h. The reaction mixture was diluted with dichloromethane and washed with water. The organic layer was dried (MgSO$_4$), filtered and concentrated in vacuo. The residue was purified by preparative HPLC (0→90% acetonitrile; system 1).
Yield: 29.7 mg. MS-ESI: [M+H]$^+$=452.3; anal HPLC: R$_t$=6.99 min (method 10); hFSHRago (CHO luc) EC$_{50}$=4.2 nM

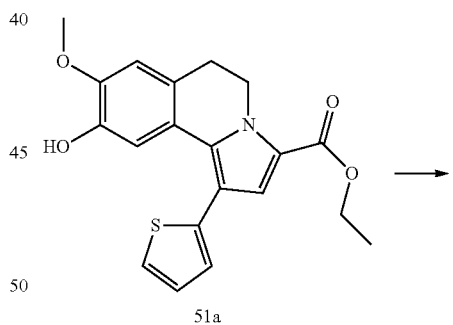

51a

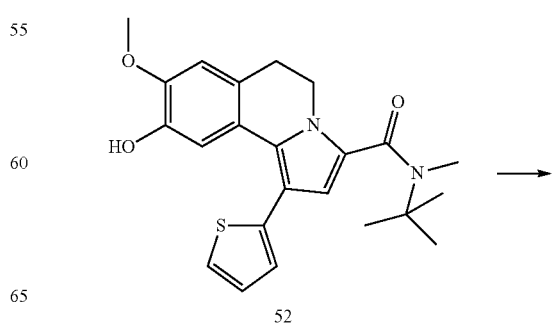

52

-continued

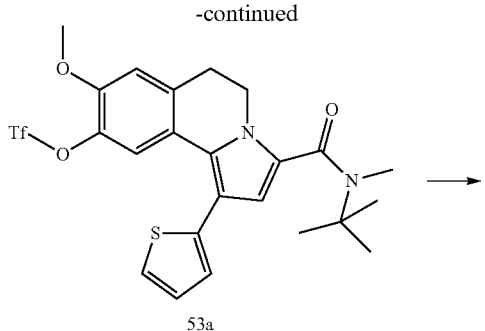

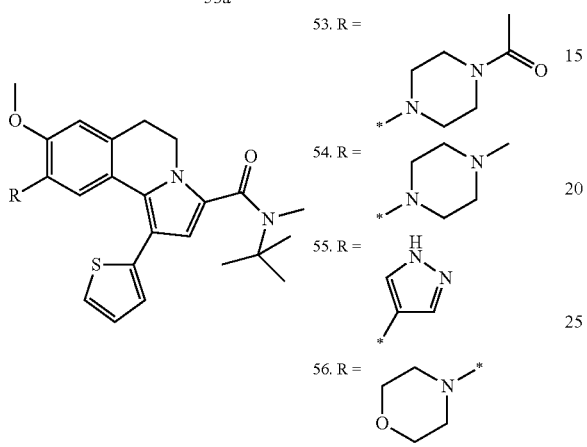

Example 52

9-Hydroxy-8-methoxy-1-thiophen-2-yl-5,6-dihydro-pyrrolo[2,1-α]isoquinoline-3-carboxylic acid tert-butyl-methyl-amide Ethyl magnesium chloride (50.8 ml 2M in THF) was added to a solution of N-methyl-N-tert-butyl-amine (13.4 ml) in dry THF (250 ml). The reaction mixture was stirred at 65° C. for 1 h. A solution of the product of example 51a (7.5 g) in dry THF (100 ml) was added dropwise to the reaction mixture. The reaction mixture was heated under reflux for 1 h. The reaction mixture was quenched with a sat. aqueous NH₄Cl solution and extracted with ethyl acetate. The organic layer was washed with water, brine, dried (MgSO₄), filtered and concentrated in vacuo. The residue was crystallized from ether.

Yield: 6.2 g. LC/MS-ESI: [M+H]⁺=411.2; hFSHRago (CHO luc) EC₅₀=356.0 nM

Example 53

9-(4-Acetyl-piperazin-1-yl)-8-methoxy-1-thiophen-2-yl-5,6-dihydro-pyrrolo[2,1-α]isoquinoline-3-carboxylic acid tert-butyl-methyl-amide (a). Trifluoro-methanesulfonic acid 3-(tert-butyl-methyl-carbamoyl)-8-methoxy-1-thiophen-2-yl-5,6-dihydro-pyrrolo[2,1-α]isoquinolin-9-yl ester The synthesis of trifluoro-methanesulfonic acid 3-(tert-butyl-methyl-carbamoyl)-8-methoxy-1-thiophen-2-yl-5,6-dihydro-pyrrolo[2,1-α]isoquinolin-9-yl ester 53a was performed according to the method described in example 51b, starting from 52 (6.2 g).

Yield: 7.45 g. LC/MS-ESI: [M+H]⁺=543.1

(b). 9-(4-Acetyl-piperazin-1-yl)-8-methoxy-1-thiophen-2-yl-5,6-dihydro-pyrrolo[2,1-α]iso-quinoline-3-carboxylic acid tert-butyl-methyl-amide Reaction of the product of example 53a (100 mg) with 1-acetylpiperazine (60 mg) was performed according the method described in example 51c.

Yield: 22 mg. MS-ESI [M+H]⁺=521.5; anal. HPLC: $R_t$=8.71 min (method 10); hFSHRago (CHO luc) EC₅₀=678.0 nM

Example 54

8-Methoxy-9-(4-methyl-piperazin-1-yl)-1-thiophen-2-yl-5,6-dihydro-pyrrolo[2,1-α]isoquinoline-3-carboxylic acid tert-butyl-methyl-amide Substitution of the triflate moiety in the product of example 53a (100 mg) with 1-methylpiperazine (46 mg) was performed according the method described in example 51c.

Yield: 38 mg. MS-ESI [M+H]⁺=493.5; anal. HPLC: $R_t$=27.45 min (method 12); hFSHRago (CHO luc) EC₅₀=455.0 nM

Example 55

8-Methoxy-9-(1H-pyrazol-4-yl)-1-thiophen-2-yl-5,6-dihydro-pyrrolo[2,1-α]isoquinoline-3-carboxylic acid tert-butyl-methyl-amide A solution of the product of example 53a (25.5 mg) in DME (2 ml) was sparged with nitrogen. Pd(PPh₃)₄ (0.5 mg) was added and the solution was sparged with nitrogen again. Then, K₂CO₃ (25.5 mg), 1H-pyrazole-4-boronic acid pinacol ester (26.8 mg) and water (200 µl) were added. The reaction mixture was stirred at 90° C. for 18 h. The reaction mixture was diluted with dichloromethane and washed with water. The organic layer was dried (MgSO₄), filtered and concentrated in vacuo. The residue was purified by preparative HPLC (0→90% acetonitrile, 0.1% TFA; system 1).

Yield: 10 mg. LC/MS-ESI: [M+H]⁺=561.2 anal. HPLC: $R_t$=36.38 min (method 12); hFSHRago (CHO luc) EC₅₀=1.1 nM

Example 56

8-Methoxy-9-morpholin-4-yl-1-thiophen-2-yl-5,6-dihydro-pyrrolo[2,1-α]isoquinoline-3-carboxylic acid tert-butyl-methyl-amide Substitution of the product of example 53a (274 mg) with morpholine (110 µl) was performed according the method described in example 51c.

Yield: 65 mg. LC/MS-ESI [M+H]⁺=480.3 anal. HPLC: $R_t$=12.89 min (method 10); hFSHRago (CHO luc) EC₅₀=15.7 nM

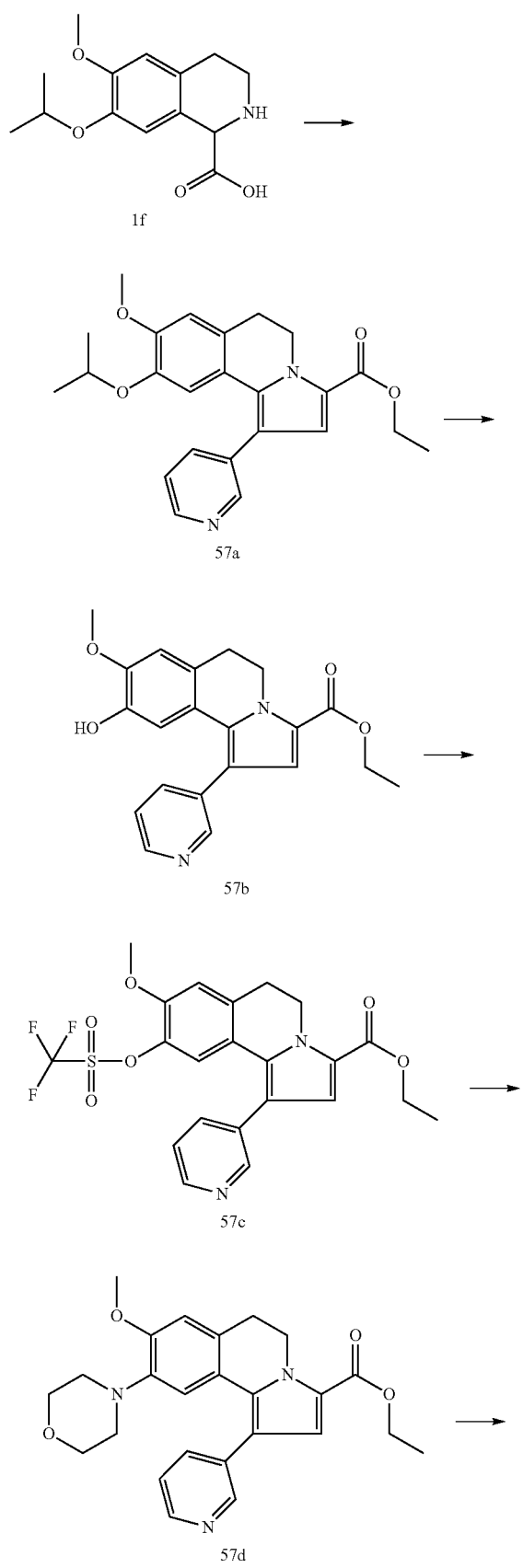

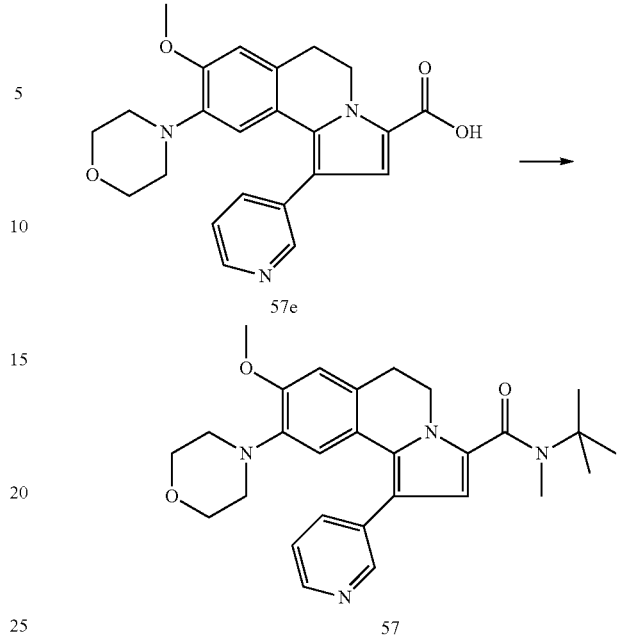

Example 57

8-Methoxy-9-morpholin-4-yl-1-pyridin-3-yl-5,6-dihydro-pyrrolo[2,1-α]isoquinoline-3-carboxylic acid tert-butyl-methyl-amide; trifluoro acetic acid (a). 9-Isopropoxy-8-methoxy-1-pyridin-3-yl-5,6-dihydro-pyrrolo[2,1-α]isoquinoline-3-carboxylic acid ethyl ester The synthesis of 9-isopropoxy-8-methoxy-1-pyridin-3-yl-5,6-dihydro-pyrrolo[2,1-α]isoquinoline-3-carboxylic acid ethyl ester (57a) was performed according to the method described for example 35a, starting from 1f (1.5 g) and 3-ethynyl-pyridine.

Yield: 2.08 g. MS-ESI: [M+H]$^+$=407.4

(b). 9-Hydroxy-8-methoxy-1-pyridin-3-yl-5,6-dihydro-pyrrolo[2,1-α]isoquinoline-3-carboxylic acid ethyl ester The synthesis of 9-hydroxy-8-methoxy-1-pyridin-3-yl-5,6-dihydro-pyrrolo[2,1-α]isoquinoline-3-carboxylic acid ethyl ester (57b) was performed according to the method described for example 51a, starting from 57a (634 mg).

Yield: 613 mg. LC/MS-ESI: [M+H]$^+$=365.2

(c). 8-Methoxy-1-pyridin-3-yl-9-trifluoromethane-sulfonyloxy-5,6-dihydro-pyrrolo[2,1-α]isoquinoline-3-carboxylic acid ethyl ester A mixture of the product of example 57b (220 mg), Cs$_2$CO$_3$ (787 mg) and 1,1,1-trifluoro-N-phenyl-N-[(trifluoromethyl)sulfonyl]methanesulfonamide (647 mg) in DMF (10 ml) was stirred at 80° C. for 2 h. At room temperature, the reaction mixture was poured into water and extracted with dichloromethane. The organic layer was washed with water, brine, dried (MgSO$_4$), filtered and concentrated in vacuo. The residue was purified by chromatography on silica gel in heptane/ethyl acetate [1:1 (v/v)] as eluent.

Yield: 140 mg. LC/MS-ESI: [M+H]$^+$=497.1

(d). 8-Methoxy-9-morpholin-4-yl-1-pyridin-3-yl-5,6-dihydro-pyrrolo[2,1-α]isoquinoline-3-carboxylic acid ethyl ester A mixture of the product of example 57c (140 mg), morpholine (61 μl), 2-(di-t-butylphosphino)biphenyl (catalytic amount), potassium phosphate tribasic (180 mg) and tris(dibenzylideneacetone) dipalladium(0) (catalytic amount) in DME (1 ml) was stirred and heated using microwave irradiation at 150° C. for 1 h. At room temperature, the reaction mixture was filtered and the residue washed with dichloromethane. The filtrate was concentrated in vacuo and purified by chromatography on silica gel in heptane/ethyl acetate [1:3→0:1 (v/v)] as eluent.

Yield: 101 mg. LC/MS-ESI: [M+H]$^+$=434.4

(e). 8-Methoxy-9-morpholin-4-yl-1-pyridin-3-yl-5,6-dihydro-pyrrolo[2,1-α]isoquinoline-3-carboxylic acid A mixture of the product of example 57d (101 mg), solid KOH in ethanol (3 ml) and water (3 ml) was stirred at 78° C. for 1 h. At room temperature, the reaction mixture was acidified with an aqueous citric acid solution (0.5 M) until pH=5-6 and extracted with dichloromethane. The organic layer was washed with brine, dried (MgSO$_4$), filtered and concentrated in vacuo.

Yield: 92 mg. LC/MS-ESI: [M+H]$^+$=406.1

(f). 8-Methoxy-9-morpholin-4-yl-1-pyridin-3-yl-5,6-dihydro-pyrrolo[2,1-α]isoquinoline-3-carboxylic acid tert-butyl-methyl-amide; trifluoro acetic acid HATU (129 mg) was added to a solution of the product of example 57e (92 mg), DIPEA (198 μl) and N-methyl-N-tert-butyl-amine (54 μl) in dichloromethane (5 ml). After stirring at room temperature for 24 h, the reaction mixture was washed with water, brine, dried (MgSO$_4$), filtered and concentrated in vacuo. The residue was purified by preparative HPLC (0→100% acetonitrile; 0.1% TFA; system 1).

Yield: 46 mg. Anal. HPLC R$_t$=17.90 min (method 12)); hFSHRago (CHO luc) EC$_{50}$=276 nM

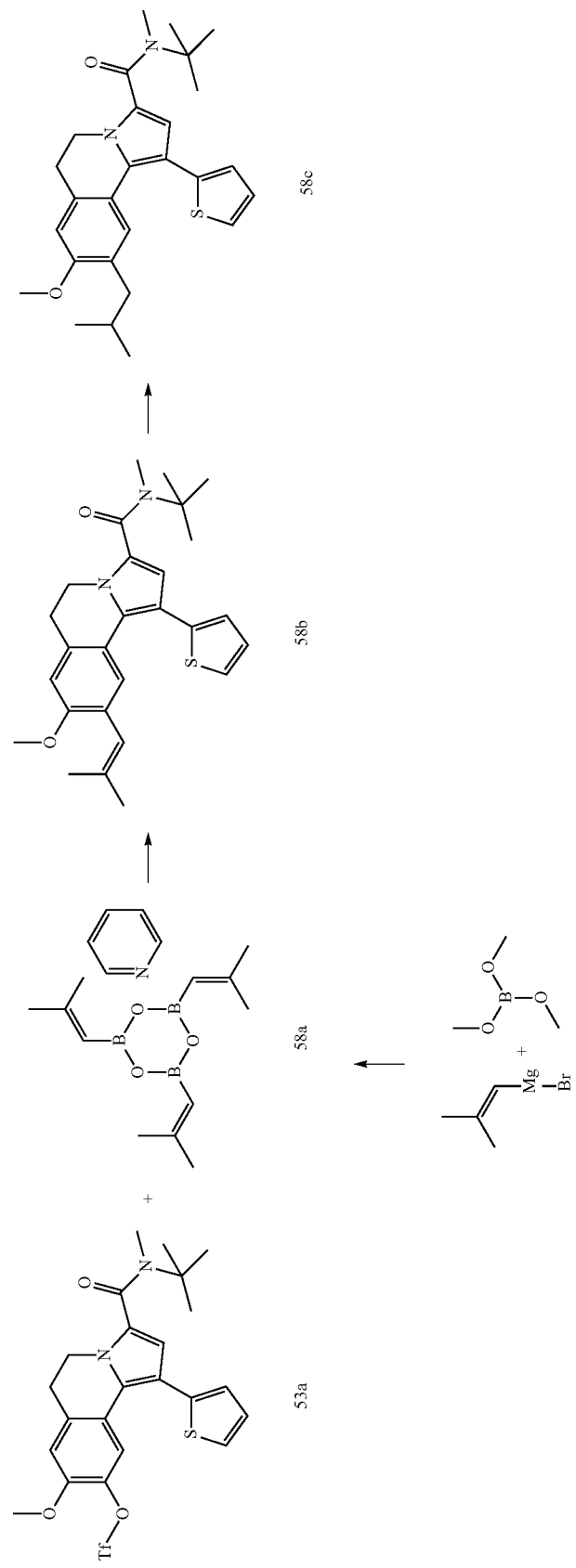

Example 58

9-Isobutyl-8-methoxy-1-thiophen-2-yl-5,6-dihydro-pyrrolo[2,1-α]isoquinoline-3-carboxylic acid tert-butyl-methyl-amide and 8-methoxy-9-(2-methyl-propenyl)-1-thiophen-2-yl-5,6-dihydro-pyrrolo[2,1-α]isoquinoline-3-carboxylic acid tert-butyl-methyl-amide

(a). 2,4,6-Tris-(2-methyl-propenyl)-cyclotriboroxane pyridine 2-methyl-1-propenylmagnesium bromide in THF (536 ml 0.5 M) was added dropwise to a solution of trimethyl borate (54 ml) in THF (320 ml) at −70° C. The reaction mixture was stirred at −70° C. for 30 min. An aqueous HCl solution (2 N) was added to the reaction mixture and the reaction mixture was stirred at room temperature for 1 h. The pH was adjusted to 4 with an aqueous HCl solution (2 N). The reaction mixture was extracted with ether and washed with brine. The organic layer was dried ($MgSO_4$), filtered and concentrated in vacuo. The residue was dissolved in pyridine (80 ml) and stirred overnight at room temperature. The reaction mixture was concentrated in vacuo and residual pyridine was removed by co-evaporation with toluene. The residue was dried at room temperature in vacuo (3 mm) for 1 h.

Yield: 27.5 g.

(b). 8-Methoxy-9-(2-methyl-propenyl)-1-thiophen-2-yl-5,6-dihydro-pyrrolo[2,1-α]isoquinoline-3-carboxylic acid tert-butyl-methyl-amide A solution of the product of example 53a (5.39 g) in DME (150 ml) was sparged with nitrogen for 2 min. $Pd(PPh_3)_4$ (585 mg) was added and the solution was sparged with nitrogen (g) again for 2 min, followed by the addition of the product of example 58a (4.98 g), $K_2CO_3$ (2 g) and water (30 ml). The reaction was stirred at 90° C. under nitrogen overnight. The reaction mixture was poured into water and extracted with ethyl acetate. The organic layer was washed with water and brine, dried ($MgSO_4$), filtered and concentrated in vacuo. The residue was purified by chromatography on silica gel in heptane/ethyl acetate [0→50% (v/v)].

Yield: 3 g. LC/MS-ESI $[M+H]^+$: 449.2; hFSHRago (CHO luc) $EC_{50}$=0.7 nM

(c). 9-Isobutyl-8-methoxy-1-thiophen-2-yl-5,6-dihydro-pyrrolo[2,1-α]isoquinoline-3-carboxylic acid tert-butyl-methyl-amide 10% palladium on carbon (20 mg) was added to a solution of the product of example 58b (40 mg) in ethyl acetate (4 ml) and methanol (4 ml). The reaction mixture was stirred under an atmosphere of hydrogen at room temperature for 8 h. The reaction mixture was filtered, washed with ethyl acetate and the filtrate was concentrated in vacuo.

Yield: 37 mg. LC/MS-ESI $[M+H]^+$: 451.2; anal. HPLC: $R_t$=31.03 min (method 10); hFSHRago (CHO luc) $EC_{50}$=4.3 nM

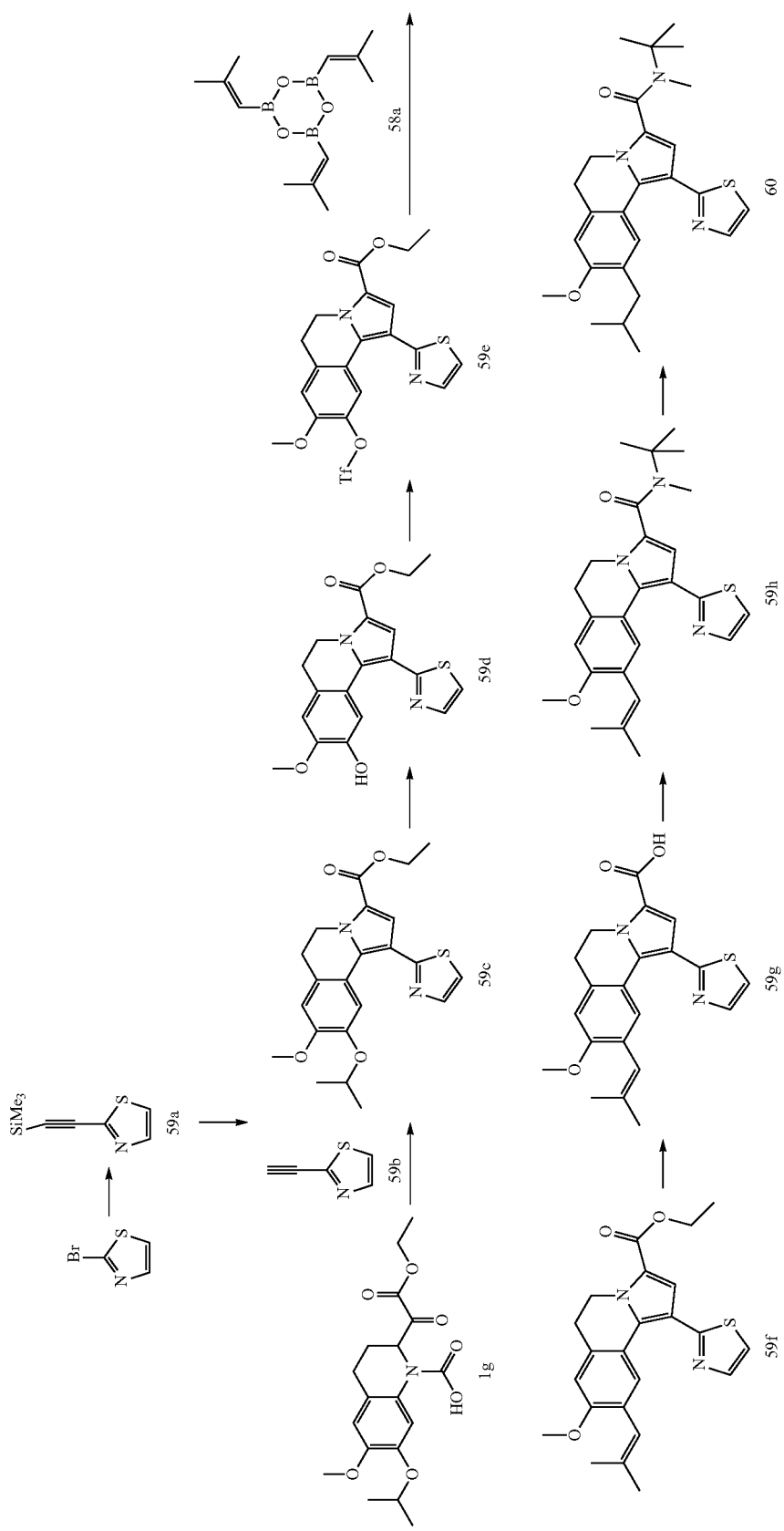

Example 59

8-Methoxy-9-(2-methyl-propenyl)-1-thiazol-2-yl-5,6-dihydro-pyrrolo[2,1-α]isoquinoline-3-carboxylic acid tert-butyl-methyl-amide

(a). 2-Trimethylsilanylethynyl-thiazole

At 50° C., 2-bromothiazole (3 ml, freshly distilled) was added to a solution of Pd(PPh$_3$)$_4$ (462 mg), Cu(OAc)$_2$ (429 mg) and ethynyl trimethylsilane (10.5 ml) in diisopropyl amine (200 ml, sparged with nitrogen). After stirring for 2 h at 50° C., the reaction mixture was filtered over decalite and washed with ethyl acetate. The filtrate was concentrated in vacuo. The residue was purified by chromatography on silica gel in toluene/ethyl acetate [9/1 (v/v)] as eluent.
Yield: 1.1 g. LC/MS-ESI: [M+H]$^+$=182.1

(b). 2-Ethynyl-thiazole

An aqueous KOH solution (0.5 ml, 0.1N) was added to a solution of the product of example 59a (1.1 g) in methanol (5 ml). After stirring for 3 h at room temperature, the reaction mixture was concentrated to a small volume. The residue was diluted with dichloromethane and washed with water. The organic layer was dried (MgSO$_4$), filtered and concentrated in vacuo.
Yield: 650 mg.

(c). 9-Isopropoxy-8-methoxy-1-thiazol-2-yl-5,6-dihydro-pyrrolo[2,1-α]isoquinoline-3-carboxylic acid ethyl ester A mixture of the product of example 59b (650 mg) and the product of example 1g (1.46 g) in acetic anhydride (10 ml) was stirred and heated using microwave irradiation for 15 min at 140° C. The reaction mixture was concentrated in vacuo. The residue was purified by chromatography on silica in heptane/ethyl acetate [9/1→7/3 (v/v)] as eluent.
Yield: 580 mg. MS-ESI: [M+H]$^+$=413.1

(d). 9-Hydroxy-8-methoxy-1-thiazol-2-yl-5,6-dihydro-pyrrolo[2,1-α]isoquinoline-3-carboxylic acid ethyl ester At 0° C., boron trichloride (2.52 ml) was added dropwise to a solution of the product of example 59c (520 mg) in dichloromethane (12 ml). After stirring for 30 min at room temperature, the reaction mixture was diluted with dichloromethane and washed with water and brine. The organic layer was dried (MgSO$_4$), filtered and concentrated in vacuo.
Yield: 478 mg. LC/MS-ESI: [M+H]$^+$=371.2

(e). 8-Methoxy-1-thiazol-2-yl-9-trifluoromethane-sulfonyloxy-5,6-dihydro-pyrrolo[2,1-α]isoquinoline-3-carboxylic acid ethyl ester A mixture of 1,1,1-trifluoro-N-phenyl-N-[(trifluoromethyl)sulfonyl]-methanesulfonamide (901 mg), Cs$_2$CO$_3$ (822 mg) and the product of example 59d (467 mg) in DMF (25 ml) was stirred for 2 h at 80° C. The reaction mixture was diluted with ethyl acetate and washed with water and brine. The organic layer was dried (MgSO$_4$), filtered and concentrated in vacuo. The residue was purified by chromatography on silica in heptane/ethyl acetate [7/3→3/2 (v/v)] as eluent.
Yield: 601 mg. LC/MS-ESI: [M+H]$^+$=503.2.

(f). 8-Methoxy-942-methyl-propenyl)-1-thiazol-2-yl-5,6-dihydro-pyrrolo[2,1-α]isoquinoline-3-carboxylic acid ethyl ester A mixture of Pd(PPh$_3$)$_4$ (11 mg), K$_2$CO$_3$ (60 mg), the product of example 58a (194 mg) and the product of example 59e (200 mg) in DME (3 ml, sparged with nitrogen) was stirred for 18 h at 90° C. The reaction mixture was diluted with ethyl acetate and washed with water and brine. The organic layer was dried (MgSO$_4$), filtered and concentrated in vacuo. The residue was purified by chromatography on silica in heptane/ethyl acetate [7/3 (v/v)] as eluent.
Yield: 127 mg. LC/MS-ESI: [M+H]$^+$=409.2

(g). 8-Methoxy-9-(2-methyl-propenyl)-1-thiazol-2-yl-5,6-dihydro-pyrrolo[2,1-α]isoquinoline-3-carboxylic acid An aqueous NaOH solution (4 ml, 1N) was added to a solution of the product of example 59f (127 mg) in ethanol (8 ml). After stirring for 2 h at 60° C., the reaction mixture was diluted with ethyl acetate and washed with an aqueous citric acid solution (2 M), water and brine. The organic layer was dried (MgSO$_4$), filtered and concentrated in vacuo.
Yield: 117 mg. LC/MS-ESI: [M+H]$^+$=381.3.

(h). 8-Methoxy-9-(2-methyl-propenyl)-1-thiazol-2-yl-5,6-dihydro-pyrrolo[2,1-α]isoquinoline-3-carboxylic acid tert-butyl-methyl-amide HATU (175 mg), N-methyl-N-tert-butyl-amine (55 µl) and DIPEA (0.286 ml) were added to a solution of the product of example 59g (117 mg) in DMF (5 ml). After stirring for 18 h at room temperature, the reaction mixture was diluted with ethyl acetate and washed with water, an aqueous HCl solution (2 N), water, a sat. aqueous NaHCO$_3$ solution and brine. The organic layer was dried (MgSO$_4$), filtered and concentrated in vacuo. The residue was purified by preparative HPLC (10%→90% acetonitrile; system 1).
Yield: 63 mg. LC/MS-ESI: [M+H]$^+$=450.3; anal. HPLC: R$_t$=20.41 min (method 10); hFSHRago (CHO luc) EC$_{50}$=2.6 nM

Example 60

9-Isobutyl-8-methoxy-1-thiazol-2-yl-5,6-dihydro-pyrrolo[2,1-α]isoquinoline-3-carboxylic acid tert-butyl-methyl-amide A mixture of the product of example 59h (55 mg) and palladium on activated carbon (6 mg) was shaken for 18 h under hydrogen atmosphere in a Parr apparatus. The reaction mixture was filtered over decalite and washed with ethyl acetate. The filtrate was concentrated in vacuo. The residue was purified by preparative HPLC (10%→90% acetonitrile; system 1).
Yield: 50 mg. LC/MS-ESI: [M+H]$^+$=452.3; anal. HPLC: R$_t$=22.92 min (method 5); hFSHRago (CHO luc) EC$_{50}$=19.0 nM

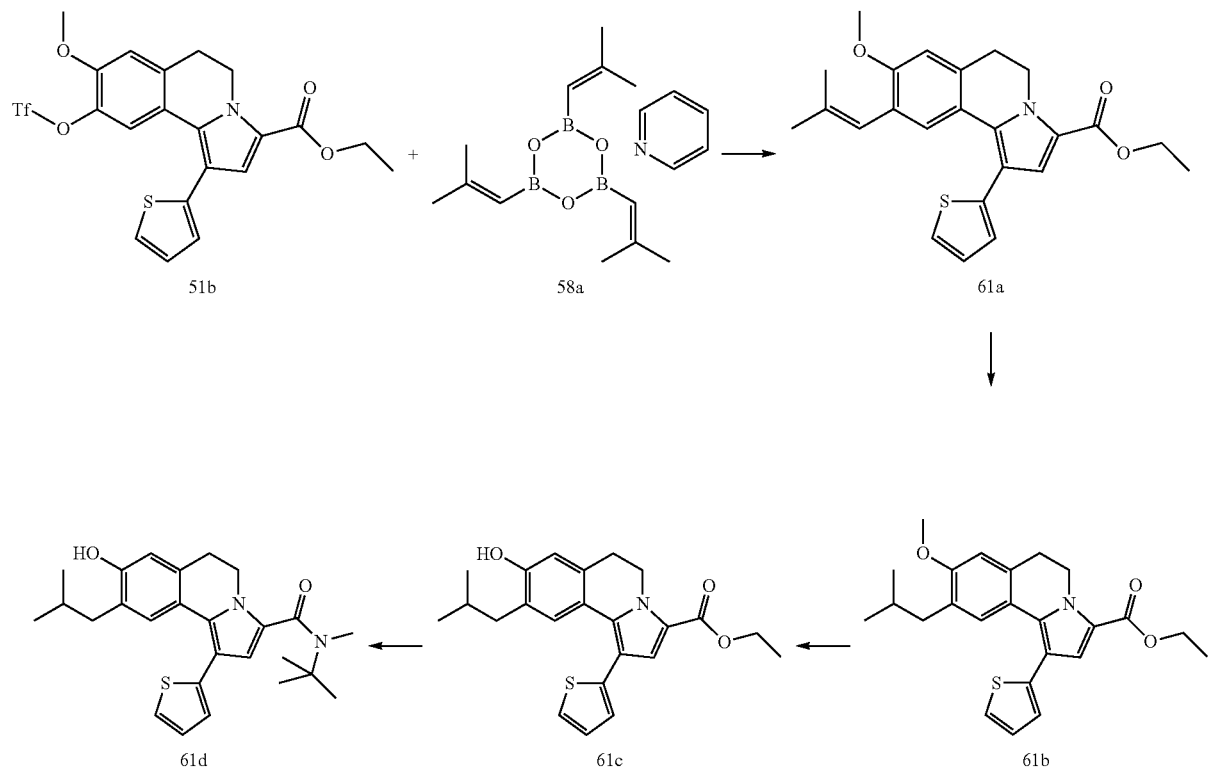

Example 61

8-Hydroxy-9-isobutyl-1-thiophen-2-yl-5,6-dihydro-pyrrolo[2,1-α]isoquinoline-3-carboxylic acid tert-butyl-methyl-amide (a). 8-Methoxy-9-(2-methyl-propenyl)-1-thiophen-2-yl-5,6-dihydro-pyrrolo[2,1-α]isoquinoline-3-carboxylic acid ethyl ester A solution of the product of example 51b (0.7 g) in DME (20 ml) was sparged with nitrogen for 5 min. Pd(PPh$_3$)$_4$ (82 mg) was added. The solution was sparged with nitrogen again for 1 min followed by the addition of the product of example 58a (0.7 g), K$_2$CO$_3$ (0.3 g) and water (4 ml). The reaction was stirred at 90° C. for 2 h. Subsequently, an additional amount of the product of example 58a (200 mg) was added. The reaction mixture was stirred for 18 h at 85° C. The reaction mixture was poured into water and extracted with ethyl acetate. The organic layer was washed with water and brine, dried (MgSO$_4$), filtered and concentrated in vacuo. The residue was purified by chromatography on silica gel in heptane/ethyl acetate [0→40% (v/v)].

Yield: 519 mg. LC/MS-ESI [M+H]$^+$=408.2

(b). 8-Methoxy-9-(2-methyl-propenyl)-1-thiophen-2-yl-5,6-dihydro-pyrrolo[2,1-α]iso-quinoline-3-carboxylic acid ethyl ester 10% Palladium on carbon (25 mg) was added to a solution of the product of example 61a (155 mg) in ethyl acetate (4 ml) and methanol (4 ml). The reaction mixture was shaken under hydrogen atmosphere (3.2 bar pressure) at room temperature for 48 h. The reaction mixture was filtered, washed with ethyl acetate and the filtrate was concentrated in vacuo. The residue was purified by chromatography on silica gel in heptane/ethyl acetate [0→40% (v/v)].

Yield: 102 mg.

(c). 8-Hydroxy-9-isobutyl-1-thiophen-2-yl-5,6-dihydro-pyrrolo[2,1-α]isoquinoline-3-carboxylic acid ethyl ester Boron tribromide (118 μl) was added at −20° C. to a solution of the product of example 61b (100 mg) in dichloromethane (3 ml). The mixture was stirred for 3 h at −20° C. The reaction mixture was warmed to room temperature, quenched with methanol and concentrated in vacuo. The residue was purified by chromatography on silica gel in heptane/ethyl acetate [0→50% (v/v)].

Yield: 48 mg.

(d). 8-Hydroxy-9-isobutyl-1-thiophen-2-yl-5,6-dihydro-pyrrolo[2,1-α]isoquinoline-3-carboxylic acid tert-butyl-methyl-amide Ethylmagnesiumchloride (419 μl, 25% wt in THF) was added slowly to a solution of N-methyl-N-tert-butyl-amine (146 μl) in THF (5 ml). After stirring for 1 h at 75° C., the product of example 61c (48 mg) dissolved in THF (2 ml) was added dropwise. After refluxing for 1 h, the cooled reaction mixture was poured in a sat. aqueous NH$_4$Cl solution and extracted with ethyl acetate. The organic layer was washed with water and brine, dried (MgSO$_4$), filtered and concentrated in vacuo. The residue was purified by preparative HPLC (20%→100% acetonitrile; system 1).

Yield: 32 mg. LC/MS-ESI: [M+H]$^+$=437.2; anal. HPLC: R$_t$=23.06 min (method 2); hFSHRago (CHO luc) EC$_{50}$=5.2 nM

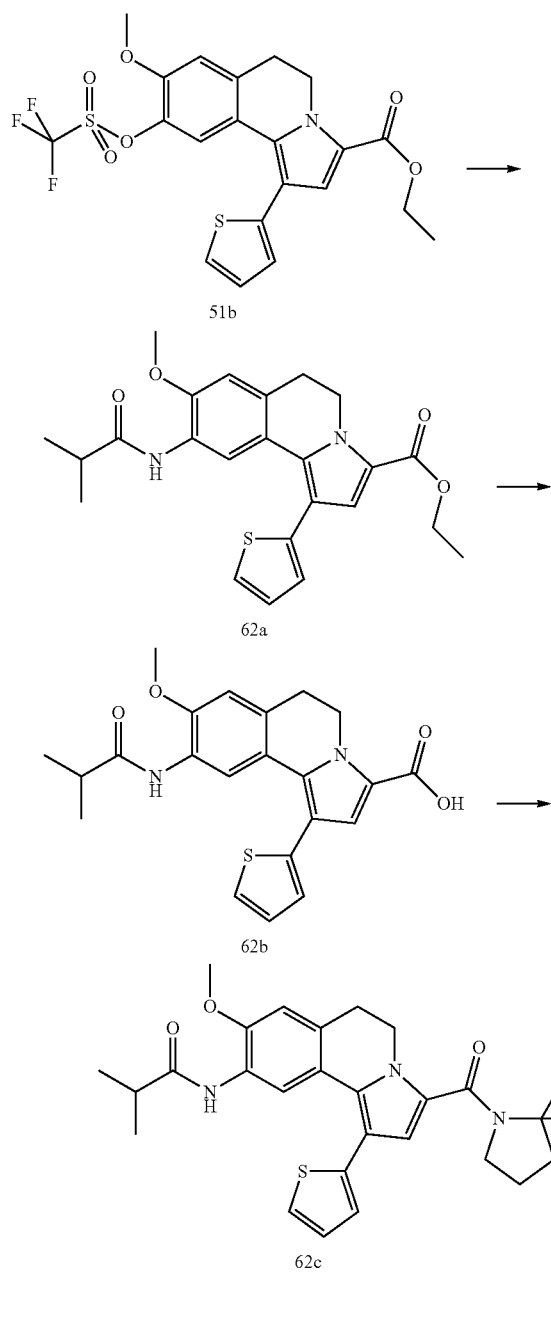

and brine. The organic layer was dried (MgSO$_4$), filtered and concentrated in vacuo. The residue was purified by chromatography on silica gel in heptane/ethyl acetate [100/0→7/3 (v/v)] as eluent.

Yield: 460 mg. LC/MS-ESI: [M+H]$^+$=439.2.

(b). 9-Isobutyrylamino-8-methoxy-1-thiophen-2-yl-5,6-dihydro-pyrrolo[2,1-α]isoquinoline-3-carboxylic acid KOH (588 mg) was added to a solution of the product of example 62a (460 mg) in ethanol/water (24 ml, 2/1 (v/v)). After stirring for 1.5 h at 80° C., the reaction mixture was diluted with ethyl acetate and washed with an aqueous citric acid solution (10%) and brine. The organic layer was dried (MgSO$_4$), filtered and concentrated in vacuo.

Yield: 462 mg.

(c). N-[3-(2,2-Dimethyl-pyrrolidine-1-carbonyl)-8-methoxy-1-thiophen-2-yl-5,6-dihydro-pyrrolo[2,1-α]isoquinolin-9-yl]-isobutyramide HATU (66 mg), 2,2-dimethylpyrrolidine (50 mg) and DIPEA (0.120 ml) were added to a solution of the product of example 62b (30 mg) in dichloromethane (3 ml). After stirring for 18 h at room temperature, the reaction mixture was diluted with ethyl acetate and washed with an aqueous citric acid solution (10%) and brine. The organic layer was dried (MgSO$_4$), filtered and concentrated in vacuo. The residue was purified by preparative HPLC (0→100% acetonitrile; system 1).

Yield: 17 mg. LC/MS-ESI: [M+H]$^+$=492.3; anal. HPLC: R$_t$=17.90 min (method 10); hFSHRago (CHO luc) EC$_{50}$=3.7 nM

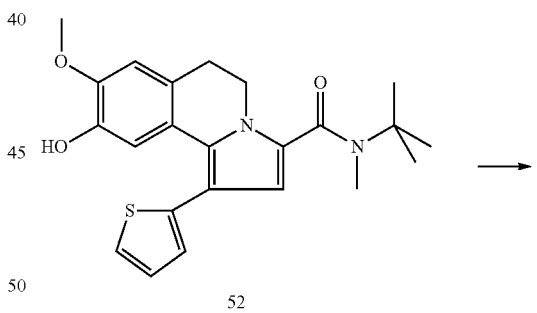

52

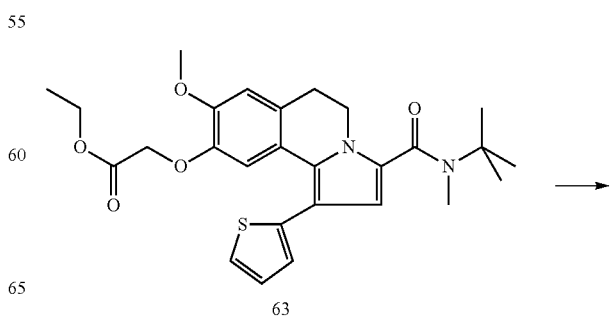

63

Example 62

N-[3-(2,2-Dimethyl-pyrrolidine-1-carbonyl)-8-methoxy-1-thiophen-2-yl-5,6-dihydro-pyrrolo[2,1-α]isoquinolin-9-yl]-isobutyramide (a). 9-Isobutyrylamino-8-methoxy-1-thiophen-2-yl-5,6-dihydro-pyrrolo[2,1-α]isoquinoline-3-carboxylic acid ethyl ester A mixture of the product of example 51b (1 g), isobutyramide (347 mg), Cs$_2$CO$_3$ (1.9 g), 4,5-bis(diphenylphosphino)-9,9-dimethylxanthene (196 mg) and Pd$_2$(dba)$_3$ (310 mg) in dioxane (15 ml, sparged with nitrogen) was stirred and heated using microwave irradiation for 1 h at 150° C. The reaction mixture was diluted with ethyl acetate and washed with water

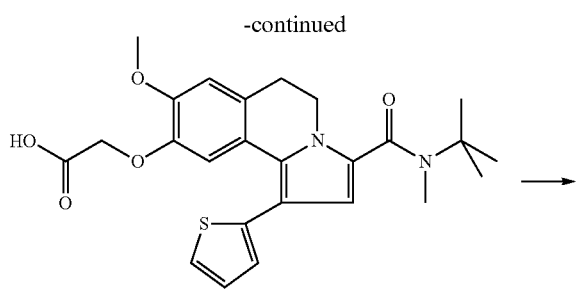

64a

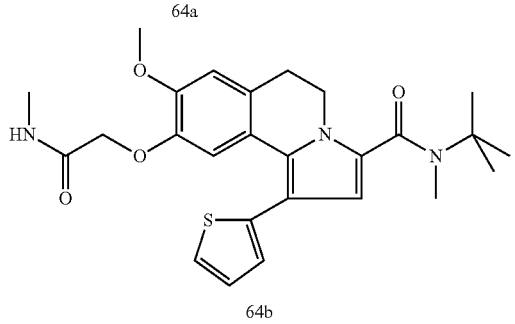

64b

Example 63

[3-(tert-Butyl-methyl-carbamoyl)-8-methoxy-1-thiophen-2-yl-5,6-dihydro-pyrrolo[2,1-a]isoquinolin-9-yloxy]-acetic acid ethyl ester A mixture of the product of example 52 (250 mg), bromoacetic acid ethyl ester (81 μl) and $Cs_2CO_3$ (595 mg) in DMF (10 ml) was stirred at 90° C. for 1 h. The reaction mixture was allowed to cool to room temperature, subsequently poured into water and extracted with dichloromethane. The organic layer was washed with an aqueous HCl solution (0.5 M), brine, dried ($MgSO_4$), filtered and concentrated in vacuo. The residue was purified by chromatography on silica gel in heptane/ethyl acetate [1/1 (v/v)] as eluent.

Yield: 270 mg. LC/MS-ESI: $[M+H]^+=497.1$; LC/MS $R_t=4.60$ min; hFSHRago (CHO luc) $EC_{50}=252.0$ nM

Example 64

8-Methoxy-9-methylcarbamoylmethoxy-1-thiophen-2-yl-5,6-dihydro-pyrrolo[2,1-α]isoquinoline-3-carboxylic acid tert-butyl-methyl-amide (a). [3-(tert-Butyl-methyl-carbamoyl)-8-methoxy-1-thiophen-2-yl-5,6-dihydro-pyrrolo[2,1-α]isoquinolin-9-yloxy]-acetic acid A mixture of the product of example 63 (150 mg) and solid KOH (51 mg) in ethanol (5 ml) and water (5 ml) was stirred at 78° C. for 1 h. At room temperature, the reaction mixture was acidified with an aqueous HCl solution (1.0 M) until pH=1-2 and extracted with dichloromethane. The organic layer was washed with brine, dried ($MgSO_4$), filtered and concentrated in vacuo.

Yield: 119 mg. LC/MS-ESI: $[M+H]^+=469.0$ (b). 8-Methoxy-9-methylcarbamoylmethoxy-1-thiophen-2-yl-5,6-dihydro-pyrrolo[2,1-α]isoquinoline-3-carboxylic acid tert-butyl-methyl-amide A mixture of the product of example 64a (50 mg), DIPEA (93 μl), HATU (61 mg) and methylamine hydrochloride (5.3 mg) in dichloromethane (3 ml) was stirred at room temperature for 18 h. The reaction mixture was diluted with dichloromethane and washed with an aqueous HCl solution (0.5 M), brine, dried ($MgSO_4$), filtered and concentrated in vacuo. The residue was purified by preparative HPLC (20→100% acetonitrile system 1).

Yield: 28 mg. MS-ESI: $[M+H]^+=482.5$; anal. HPLC: $R_t=11.73$ min (method 7); hFSHRago (CHO luc) $EC_{50}=3.1$ nM

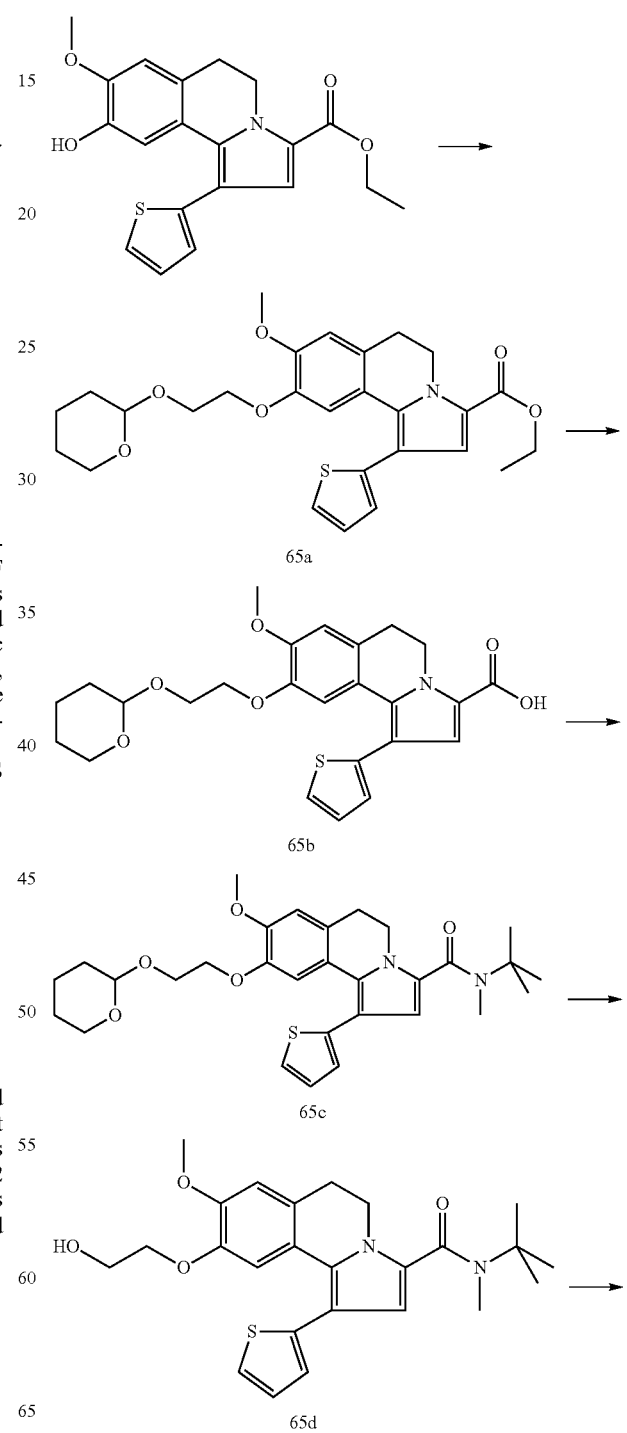

65a

65b

65c

65d

-continued

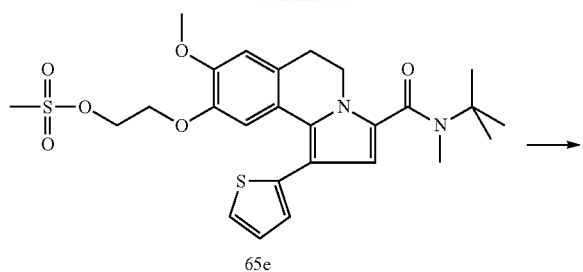

65e

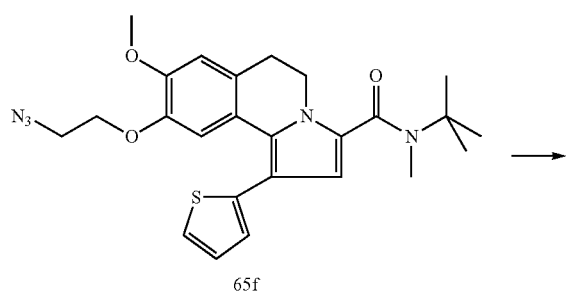

65f

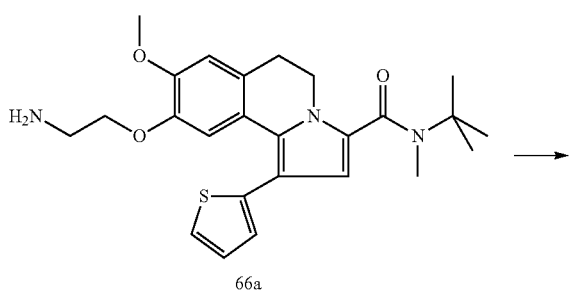

66a

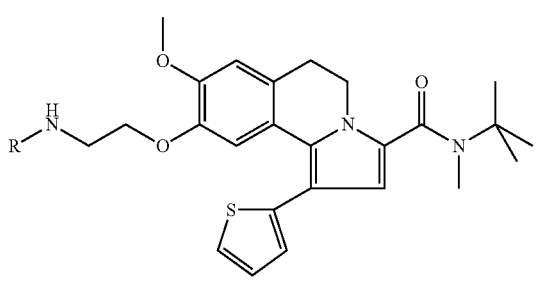

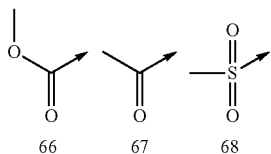

66　67　68

Example 65

9-(2-Azido-ethoxy)-8-methoxy-1-thiophen-2-yl-5,6-dihydro-pyrrolo[2,1-α]isoquinoline-3-carboxylic acid tert-butyl-methyl-amide, 8-methoxy-9-[2-(tetrahydro-pyran-2-yloxy)-ethoxy]-1-thiophen-2-yl-5,6-dihydro-pyrrolo[2,1-α]isoquinoline-3-carboxylic acid tert-butyl-methyl-amide, 9-(2-hydroxy-ethoxy)-8-methoxy-1-thiophen-2-yl-5,6-dihydro-pyrrolo[2,1-α]iso-quinoline-3-carboxylic acid tert-butyl-methyl-amide and methanesulfonic acid 2-[3-(tert-butyl-methyl-carbamoyl)-8-methoxy-1-thiophen-2-yl-5,6-dihydro-pyrrolo[2,1-α]isoquinolin-9-yloxy]-ethyl ester (a). 8-Methoxy-9-[2-(tetrahydro-pyran-2-yloxy)-ethoxy]-1-thiophen-2-yl-5,6-dihydro-pyrrolo[2,1-α]isoquinoline-3-carboxylic acid ethyl ester A mixture of the product of example 51a (600 mg), $Cs_2CO_3$ (1.32 g) and 2-(2-bromo-ethoxy)-tetrahydropyran (294 μl) in DMF (15 ml) was stirred at 100° C. for 4 h. At room temperature the reaction mixture was poured into water and extracted with dichloromethane. The organic layer was washed with water, brine, dried ($MgSO_4$) filtered and concentrated in vacuo. The residue was purified by chromatography on silica gel in heptane/ethyl acetate [1:1 (v/v)] as eluent.
Yield: 731 mg. MS-ESI: $[M+H]^+=498.3$ (b). 8-Methoxy-9-[2-(tetrahydro-pyran-2-yloxy)-ethoxy]-1-thiophen-2-yl-5,6-dihydro-pyrrolo[2,1-α]isoquinoline-3-carboxylic acid A mixture of the product of example 65a (731 mg) and solid KOH (250 mg) in ethanol (10 ml) and water (10 ml) was stirred at 78° C. for 2 h. At room temperature, the reaction mixture was acidified with an aqueous citric acid solution (2 M) until pH=5-6 and extracted with dichloromethane. The organic layer was washed with brine, dried ($MgSO_4$), filtered and concentrated in vacuo.
Yield: 682 mg. MS-ESI: $[M+H]^+=468.1$ (c). 8-Methoxy-9-[2-(tetrahydro-pyran-2-yloxy)-ethoxy]-1-thiophen-2-yl-5,6-dihydro-pyrrolo[2,1-α]isoquinoline-3-carboxylic acid tert-butyl-methyl-amide A mixture of the product of example 65b (682 mg), DIPEA (1.27 ml), N-methyl-N-tert-butyl-amine (348 μl) and HATU (827 mg) in dichloromethane (10 ml) was stirred at room temperature for 18 h. The reaction mixture was washed with a sat. aqueous $NaHCO_3$ solution, brine, dried ($MgSO_4$), filtered and concentrated in vacuo. The residue was purified by chromatography on silica gel in heptane/ethyl acetate [1:1 (v/v)] as eluent.
Yield: 726 mg. MS-ESI: $[M+H]^+=539.5$; hFSHRago (CHO luc) $EC_{50}=102.0$ nM (d). 9-(2-Hydroxy-ethoxy)-8-methoxy-1-thiophen-2-yl-5,6-dihydro-pyrrolo[2,1-α]iso-quinoline-3-carboxylic acid tert-butyl-methyl-amide An aqueous HCl solution (2 ml 5 M) was added dropwise to a mixture of the product of example 65c (716 mg) in methanol (50 ml). After stirring at room temperature for 1 h, the reaction mixture was poured into a sat. aqueous $NaHCO_3$ solution and extracted with dichloromethane. The organic layer was washed with water, brine, dried (MgSO$_4$), filtered and concentrated in vacuo. The residue was purified by chromatography on silica gel in heptane/ethyl acetate [1:2 (v/v)] as eluent.

Yield: 414 mg. LC/MS-ESI: [M+H]$^+$=455.0; hFSHRago (CHO luc) EC$_{50}$=1.3 nM (e). Methanesulfonic acid 2-[3-(tert-butyl-methyl-carbamoyl)-8-methoxy-1-thiophen-2-yl-5,6-dihydro-pyrrolo[2,1-α]isoquinolin-9-yloxy]-ethyl ester Methanesulfonyl chloride (85 μl) was added dropwise to a mixture of the product of example 65d (414 mg) and triethylamine (380 μl) in dichloromethane (25 ml). After stirring at room temperature for 1 h, the reaction mixture was washed with a sat. aqueous NaHCO$_3$ solution, brine, dried (MgSO$_4$), filtered and concentrated in vacuo. The residue was purified by chromatography on silica gel in heptane/ethyl acetate [1:2 (v/v)] as eluent.

Yield: 465 mg. LC/MS-ESI: [M+H]$^+$=533.0; hFSHRago (CHO luc) EC$_{50}$=15 nM (f). 9-(2-Azido-ethoxy)-8-methoxy-1-thiophen-2-yl-5,6-dihydro-pyrrolo[2,1-α]isoquinoline-3-carboxylic acid tert-butyl-methyl-amide A mixture of the product of example 65e (250 mg) and sodium azide (92 mg) in DMF (15 ml) was stirred at 90° C. for 1 h. At room temperature, the reaction mixture was poured into water and extracted twice with dichloromethane. The organic layer was washed twice with water, brine, dried (MgSO$_4$), filtered and concentrated in vacuo. The residue was purified by chromatography on silica gel in heptane/ethyl acetate [1:1 (v/v)] as eluent.

Yield: 210 mg. LC/MS-ESI: [M+H]$^+$=480.0; anal. HPLC: R$_t$=24.73 min (method 2); hFSHRago (CHO luc) EC$_{50}$=7.1 nM Example 66

{2-[3-(tert-Butyl-methyl-carbamoyl)-8-methoxy-1-thiophen-2-yl-5,6-dihydro-pyrrolo[2,1-α]isoquinolin-9-yloxy]-ethyl}-carbamic acid methyl ester (a). 9-(2-Amino-ethoxy)-8-methoxy-1-thiophen-2-yl-5,6-dihydro-pyrrolo[2,1-α]isoquinoline-3-carboxylic acid tert-butyl-methyl-amide A mixture of the product of example 65f (210 mg), triphenylphosphine polymer bound (290 mg; loading 3 mmol/g resin), water (1 ml) in THF (5 ml) and dichloromethane (5 ml) was heated under reflux for 18 h. The reaction mixture was filtered and the residue was washed with dichloromethane and methanol. The filtrate was concentrated in vacuo, dissolved in dichloromethane and washed with brine, dried (MgSO$_4$), filtered and concentrated in vacuo.

Yield: 197 mg. LC/MS-ESI: [M+H]$^+$=454.1

(b). {2-[3-(tert-Butyl-methyl-carbamoyl)-8-methoxy-1-thiophen-2-yl-5,6-dihydro-pyrrolo[2,1-α]isoquinolin-9-yloxy]-ethyl}-carbamic acid methyl ester Methylchloroformate (15 μl) was added dropwise to a mixture of the product of example 66a (66 mg) and DIPEA (76 μl) in dichloromethane (5 ml). After stirring at room temperature for 18 h, the reaction mixture was diluted with dichloromethane, washed with an aqueous HCl solution (0.5 M), brine, dried (MgSO$_4$), filtered and concentrated in vacuo. The residue was purified by preparative HPLC (20→100% acetonitrile; system 1).

Yield: 42 mg. MS-ESI: [M+H]$^+$=512.5; anal. HPLC: R$_t$=15.50 min (method 7); hFSHRago (CHO luc) EC$_{50}$=31.3 nM Example 67

9-(2-Acetylamino-ethoxy)-8-methoxy-1-thiophen-2-yl-5,6-dihydro-pyrrolo[2,1-α]isoquinoline-3-carboxylic acid tert-butyl-methyl-amide Acetyl chloride (13 μl) was added dropwise to a mixture of the product of example 66a (66 mg) and DIPEA (76 μl) in dichloromethane (5 ml). After stirring at room temperature for 18 h, the reaction mixture was diluted with dichloromethane, washed with an aqueous HCl solution (0.5 M), brine, dried (MgSO$_4$), filtered and concentrated in vacuo. The residue was purified by preparative HPLC (20→100% acetonitrile; system 1).

Yield: 49 mg. MS-ESI: [M+H]$^+$=496.3; anal. HPLC: R$_t$=10.67 min (method 7); hFSHRago (CHO luc) EC$_{50}$=36.5 nM Example 68

9-(2-Methanesulfonylamino-ethoxy)-8-methoxy-1-thiophen-2-yl-5,6-dihydro-pyrrolo[2,1-α]isoquinoline-3-carboxylic acid tert-butyl-methyl-amide Methanesulphonyl chloride (15 μl) was added dropwise to a mixture of the product of example 66a (66 mg) and DIPEA (76 μl) in dichloromethane (5 ml). After stirring at room temperature for 18 h, the reaction mixture was diluted with dichloromethane, washed with an aqueous HCl solution (0.5 M) and brine, dried (MgSO$_4$), filtered and concentrated in vacuo. The residue was purified by preparative HPLC (20→100% acetonitrile; system 1).

Yield: 49 mg. MS-ESI: [M+H]$^+$=532.5; anal. HPLC: R$_t$=13.94 min (method 7); hFSHRago (CHO luc) EC$_{50}$=16.0 nM

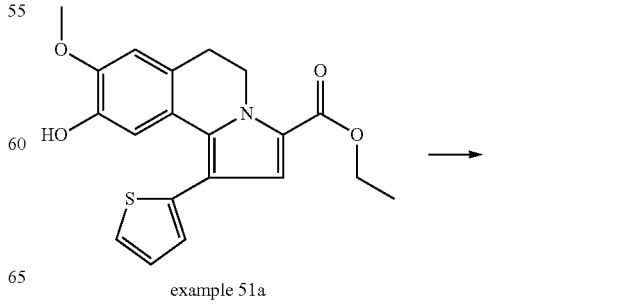

example 51a

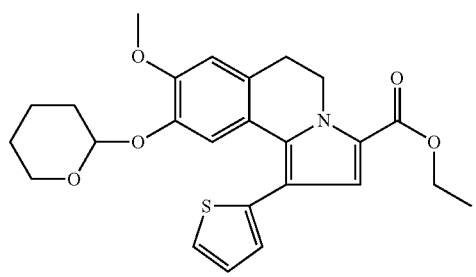

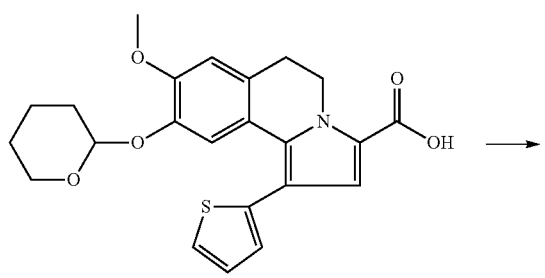

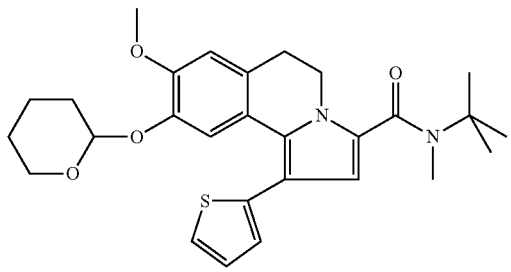

69

Example 69

8-Methoxy-9-(tetrahydro-pyran-2-yloxy)-1-thiophen-2-yl-5,6-dihydro-pyrrolo[2,1-α]isoquinoline-3-carboxylic acid tert-butyl-methyl-amide (a). 8-Methoxy-9-(tetrahydro-pyran-2-yloxy)-1-thiophen-2-yl-5,6-dihydro-pyrrolo[2,1-α]isoquinoline-3-carboxylic acid ethyl ester At 0° C., 2,3-dihydropyran (50 µl) and pyridinium p-toluenesulfonate (catalytic amount) were added to a solution of the product of example 51a (100 mg) in dichloromethane (5 ml) and the reaction mixture was stirred at 40° C. for 18 h. The reaction mixture was diluted with dichloromethane and washed with a sat. aqueous $NaHCO_3$ solution and brine, dried ($MgSO_4$), filtered and concentrated in vacuo. The residue was purified by chromatography on silica gel in heptane/ethyl acetate [1:1 (v/v)] as eluent.

Yield: 100 mg. LC/MS-ESI: $[M+H]^+$=454.0

(b). 8-Methoxy-9-(tetrahydro-pyran-2-yloxy)-1-thiophen-2-yl-5,6-dihydro-pyrrolo[2,1-α]isoquinoline-3-carboxylic acid A mixture of the product of example 69a (100 mg) and solid KOH (37 mg) in ethanol (4 ml) and water (4 ml) was stirred at 78° C. for 2 h. At room temperature, the reaction mixture was acidified to pH=5 and extracted with dichloromethane. The organic layer was washed with brine, dried ($MgSO_4$), filtered and concentrated in vacuo. Yield: 100 mg. MS-ESI: $[M+H]^+$=426.3

(c). 8-Methoxy-9-(tetrahydro-pyran-2-yloxy)-1-thiophen-2-yl-5,6-dihydro-pyrrolo[2,1-α]isoquinoline-3-carboxylic acid tert-butyl-methyl-amide A mixture of the product of example 69b (100 mg), DIPEA (205 µl), N-methyl-N-tert-butyl-amine (56 µl) and HATU (134 mg) in dichloromethane (5 ml) was stirred at room temperature for 18 h. The reaction mixture was washed with a sat. aqueous $NaHCO_3$ solution, brine, dried ($MgSO_4$), filtered and concentrated in vacuo. The residue was purified by chromatography on silica gel in heptane/ethyl acetate [1:1 (v/v)] as eluent.

Yield: 85 mg. MS-ESI: $[M+H]^+$=495.5; anal. HPLC Rt: 23.59 min (method 7); hFSHRago (CHO luc) $EC_{50}$=6.9 nM

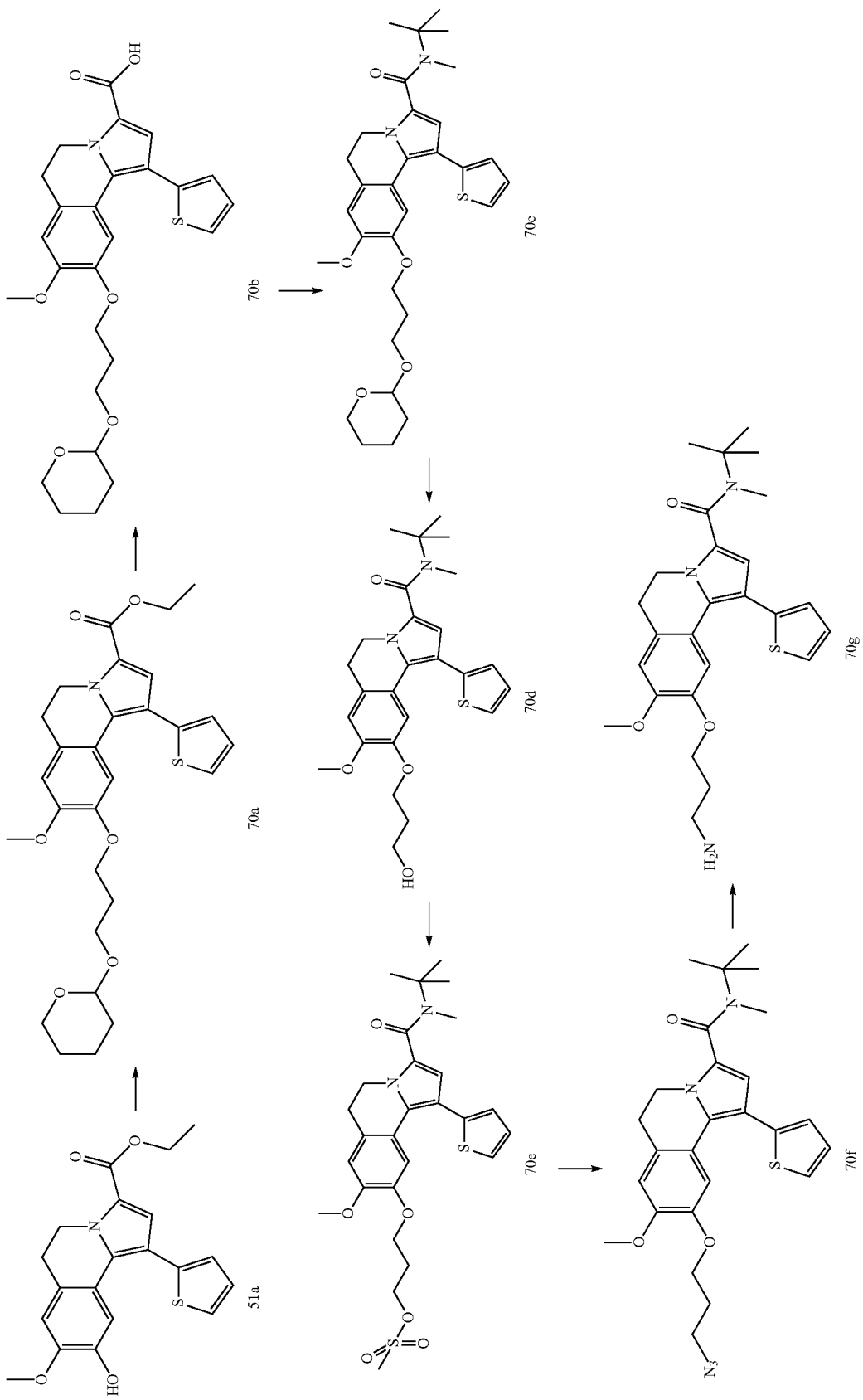

Example 70

9-(3-Amino-propoxy)-8-methoxy-1-thiophen-2-yl-5,6-dihydro-pyrrolo[2,1-α]isoquinoline-3-carboxylic acid tert-butyl-methyl-amide, 8-methoxy-9-[3-(tetrahydro-pyran-2-yloxy)-propoxy]-1-thiophen-2-yl-5,6-dihydro-pyrrolo[2,1-α]isoquinoline-3-carboxylic acid tert-butyl-methyl-amide, 9-(3-hydroxy-propoxy)-8-methoxy-1-thiophen-2-yl-5,6-dihydro-pyrrolo[2,1-α]iso-quinoline-3-carboxylic acid tert-butyl-methyl-amide, methanesulfonic acid 3-[3-tert-butyl-methyl-carbamoyl-8-methoxy-1-thiophen-2-yl-5,6-dihydro-pyrrolo[2,1-α]isoquinolin-9-yloxy]-propyl ester and 9-(3-azido-propoxy)-8-methoxy-1-thiophen-2-yl-5,6-dihydro-pyrrolo[2,1-α]isoquinoline-3-carboxylic acid tert-butyl-methyl-amide

(a) 8-Methoxy-9-[3-(tetrahydro-pyran-2-yloxy)-propoxy]-1-thiophen-2-yl-5,6-dihydro-pyrrolo[2,1-α]isoquinoline-3-carboxylic acid ethyl ester A mixture of the product of example 51a (1.31 g), $K_2CO_3$ (12.3 g) and 2-(1-bromo-3-propoxy)-tetrahydropyran (1.21 ml) in DMF (45 ml) was stirred for 2 h at 60° C. and 18 h at room temperature. The reaction mixture was poured into water and extracted with ethyl acetate. The organic layer was washed with water and brine, dried ($MgSO_4$), filtered and concentrated in vacuo.

Yield: 1.83 g. LC/MS-ESI: $[M+H]^+=512.1$.

(b). 8-Methoxy-9-[3-(tetrahydro-pyran-2-yloxy)-propoxy]-1-thiophen-2-yl-5,6-dihydro-pyrrolo[2,1-α]isoquinoline-3-carboxylic acid KOH (1 g) was added to a solution of the product of example 70a (1.83 g) in ethanol/water (60 ml, 1/1 (v/v)). After stirring for 1 h at 80° C., the reaction mixture was diluted with ethyl acetate and washed with an aqueous citric acid solution (10%) and brine. The organic layer was dried ($MgSO_4$), filtered and concentrated in vacuo.

Yield: 1.63 g.

(c). 8-Methoxy-9-[3-(tetrahydro-pyran-2-yloxy)-propoxy]-1-thiophen-2-yl-5,6-dihydro-pyrrolo[2,1-α]isoquinoline-3-carboxylic acid tert-butyl-methyl-amide HATU (1.93 g), N-methyl-N-tert-butylamine (2.02 ml) and DIPEA (2.79 ml) were added to a solution of the product of example 70b (1.63 g) in DMF (20 ml). After stirring for 2 h at 50° C., the reaction mixture was diluted with ethyl acetate and washed with water and brine. The organic layer was separated, dried ($MgSO_4$), filtered and concentrated in vacuo. The residue was purified by chromatography on silica gel in heptane/ethyl acetate [1/0→6/4 (v/v)] as eluent.

Yield: 1.9 g. MS-ESI: $[M+H]^+=553.1$; hFSHRago (CHO luc) $EC_{50}=155.0$ nM

(d). 9-(3-Hydroxy-propoxy)-8-methoxy-1-thiophen-2-yl-5,6-dihydro-pyrrolo[2,1-α]iso-quinoline-3-carboxylic acid tert-butyl-methyl-amide A mixture of the product of example 70c (1.83 g) and p-toluenesulfonic acid monohydrate (942 mg) in methanol (30 ml) was stirred for 1 h at room temperature. The reaction mixture was diluted with ethyl acetate and washed with a sat. aqueous $NaHCO_3$ solution and brine. The organic layer was dried ($MgSO_4$), filtered and concentrated in vacuo. The residue was purified by chromatography on silica gel in heptane/ethyl acetate [100/0→0/100 (v/v)] as eluent.

Yield: 1.28 g. MS-ESI: $[M+H]^+=469.2$; hFSHRago (CHO luc) $EC_{50}=1.3$ nM

(e). Methanesulfonic acid 3-[3-(tert-butyl-methyl-carbamoyl)-8-methoxy-1-thiophen-2-yl-5,6-dihydro-pyrrolo[2,1-α]isoquinolin-9-yloxy]-propyl ester Mesyl chloride (0.99 ml) and triethylamine (0.443 ml) were added to a solution of the product of example 70d (500 mg) in dichloromethane (25 ml). After stirring for 1 h at room temperature, the reaction mixture was diluted with dichloromethane and washed with water and brine. The organic layer was dried ($MgSO_4$), filtered and concentrated in vacuo. The residue was purified by chromatography on silica gel in heptane/ethyl acetate [100/0→1/1 (v/v)] as eluent.

Yield: 503 mg. MS-ESI: $[M+H]^+=547.1$

(f). 9-(3-Azido-propoxy)-8-methoxy-1-thiophen-2-yl-5,6-dihydro-pyrrolo[2,1-α]isoquinoline-3-carboxylic acid tert-butyl-methyl-amide Sodium azide (179 mg) was added to a solution of the product of example 70e (503 mg) in DMF (25 ml). After stirring for 2 h at 90° C., the reaction mixture was diluted with dichloromethane and washed with water and brine. The organic layer was dried ($MgSO_4$), filtered and concentrated in vacuo.

Yield: 452 mg. MS-ESI: $[M+H]^+=494.1$; hFSHRago (CHO luc) $EC_{50}=10.9$ nM

(g). 9-(3-Amino-propoxy)-8-methoxy-1-thiophen-2-yl-5,6-dihydro-pyrrolo[2,1-α]iso-quinoline-3-carboxylic acid tert-butyl-methyl-amide Water (3 ml) and triphenylphosphine polymer bound (613 mg; loading 3 mmol/g resin) were added to a solution of the product of example 70f (454 mg) in THF/dichloromethane (30 ml, 1/1 (v/v)). After stirring for 18 h at 40° C., the reaction mixture was filtered. The filtrate was concentrated in vacuo.

Yield: 442 mg. MS-ESI: $[M+H]^+=468.2$; hFSHRago (CHO luc) $EC_{50}=111.0$ nM

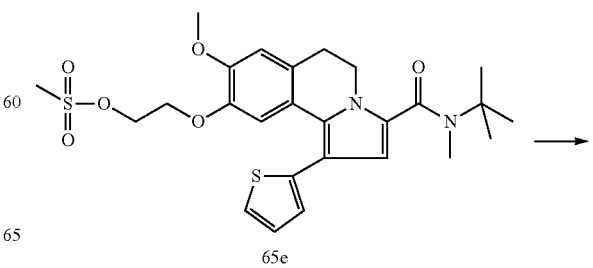

65e

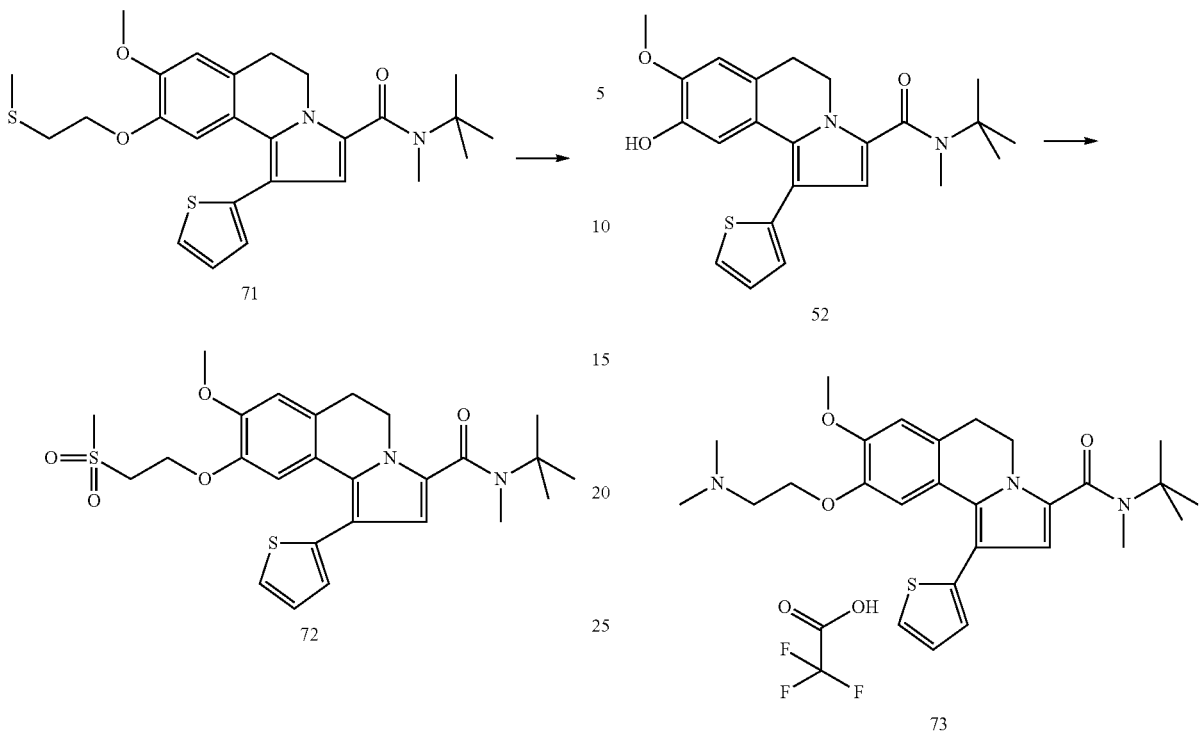

Example 71

8-Methoxy-9-(2-methylsulfanyl-ethoxy)-1-thiophen-2-yl-5,6-dihydro-pyrrolo[2,1-α]isoquinoline-3-carboxylic acid tert-butyl-methyl-amide A mixture of the product of example 65e (124 mg) and sodium methyl sulfide (32 mg) in DMF (5 ml) was stirred at 50° C. for 1 h. The reaction mixture was poured into water and extracted twice with dichloromethane. The organic layer was washed with water, brine, dried (MgSO$_4$), filtered and concentrated in vacuo. The residue was purified by chromatography on silica gel in heptane/ethyl acetate [1:2 (v/v)] as eluent.

Yield: 97 mg. LC/MS-ESI: [M+H]$^+$=485.2; anal. HPLC R$_t$=22.30 min (method 7); hFSHRago (CHO luc) EC$_{50}$=26.3 nM

Example 72

9-(2-Methanesulfonyl-ethoxy)-8-methoxy-1-thiophen-2-yl-5,6-dihydro-pyrrolo[2,1-α]isoquinoline-3-carboxylic acid tert-butyl-methyl-amide A mixture of the product of example 71 (30 mg) and 3-chloroperbenzoic acid (45.8 mg) in dichloromethane (3 ml) was stirred at room temperature for 1 h. The reaction mixture was diluted with dichloromethane and washed with water and brine. The organic layer was dried (MgSO$_4$), filtered and concentrated in vacuo. The residue was purified by preparative HPLC (20→100% acetonitrile; system 1).

Yield: 12 mg. MS-ESI: [M+H]$^+$=517.5; anal. HPLC R$_t$=15.23 min (method 7); hFSHRago (CHO luc) EC$_{50}$=16.9 nM

Example 73

9-(2-Dimethylamino-ethoxy)-8-methoxy-1-thiophen-2-yl-5,6-dihydro-pyrrolo[2,1-α]isoquinoline-3-carboxylic acid tert-butyl-methyl-amide; trifluoro acetic acid A mixture of the product of example 52 (50 mg), Cs$_2$CO$_3$ (120 mg) and (2-chloro-ethyl)-dimethyl-amine (20 mg) in DMF (5 ml) was stirred at 100° C. for 2 h. The reaction mixture was allowed to reach room temperature and was diluted with dichloromethane. The organic layer was washed with water, brine, dried (MgSO$_4$), filtered and concentrated in vacuo. The residue was purified by preparative HPLC (0→100% acetonitrile; 0.1% TFA; system 1).

Yield: 42 mg. MS-ESI: [M+H]$^+$=482.5; anal. HPLC: Rt=11.98 min (method 2); hFSHRago (CHO luc) EC$_{50}$=118 nM

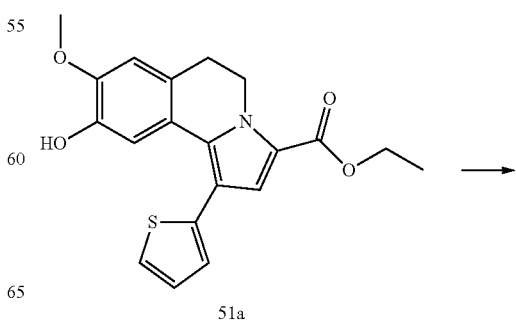

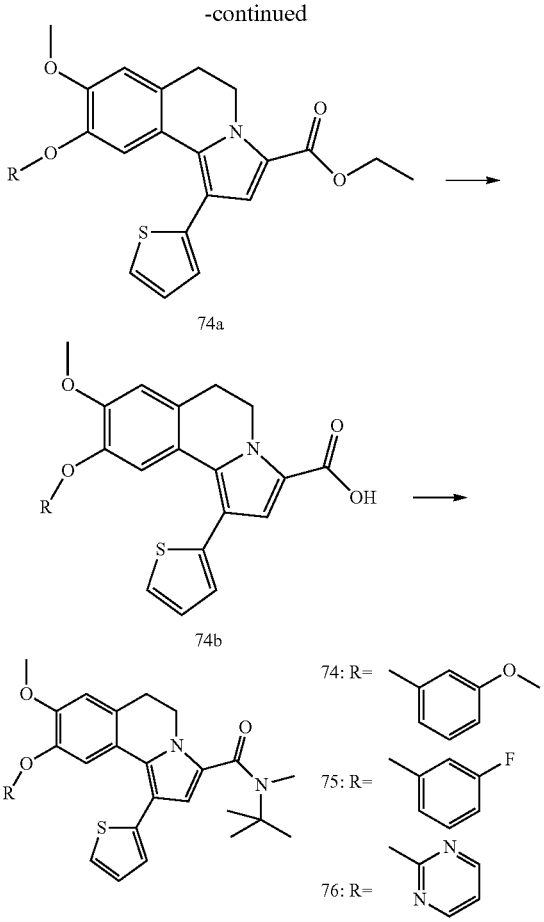

74a

74b

74: R= (3-methoxyphenyl)

75: R= (3-fluorophenyl)

76: R= (2-methylpyrimidinyl)

Example 74

N-tert-butyl-8-methoxy-9-(3-methoxyphenoxy)-N-methyl-1-(thiophen-2-yl)-5,6-dihydropyrrolo[2,1-α]isoquinoline-3-carboxamide (a). Ethyl 8-methoxy-9-(3-methoxyphenoxy)-1-(thiophen-2-yl)-5,6-dihydropyrrolo[2,1-α]iso-quinoline-3-carboxylate A mixture of the product of example 51a (150 mg), 3-methoxyphenyl boronic acid (140 mg), dichloromethane (2.5 ml), $Cu(OAc)_2$ (80 mg), pyridine (250 μl) 4 Å mol sieves (2 g) was stirred at room temperature for 24 h. The reaction mixture was diluted with water, a sat. aqueous $NH_4Cl$ solution and ethyl acetate. The reaction mixture was stirred for 10 min, filtered through Hyflo and extracted with ethyl acetate. The organic solution was concentrated in vacuo. The residue was filtered through a short silica column using heptane/ethyl acetate as eluent.

Yield: 160 mg. TLC $R_f$=0.55 (heptane/ethyl acetate 1/1); $^1$H NMR (DMSO-d6) 3.70 (s, 3, OC$H_3$), 3.78 (s, 3, OC$H_3$), 3.10 (t, 2, C(6)$H_2$), 4.55 (t, 2, C(5)$H_2$), 6.85 (s, 1, H(3); LC/MS-ESI: [M+H]$^+$=476.

(b). 8-Methoxy-9-(3-methoxyphenoxy)-1-(thiophen-2-yl)-5,6-dihydropyrrolo[2,1-α]iso-quinoline-3-carboxylic acid A mixture of the product of example 74a (160 mg), dioxane (2 ml), water (2 ml) and 100 mg of KOH (100 mg) was heated at 100° C. for 90 min. The reaction mixture was concentrated to a small volume in vacuo and acidified with aq. citric acid (1 M) to pH 3-4. The product that precipitated as white crystalline material, was dried in vacuo (50° C.).

Yield: 120 mg. Mp: 172-174° C. (decomp); TLC $R_f$=0.15 (heptane/ethyl acetate 1/1); LC/MS-ESI: [M+H]$^+$=448.

(c). N-tert-butyl-8-methoxy-9-(3-methoxyphenoxy)-N-methyl-1-(thiophen-2-yl)-5,6-dihydropyrrolo[2,1-α]isoquinoline-3-carboxamide A mixture of the product of example 74b (120 mg), N-ethylmorpholine (120 μl), 120 μl of N-methyl-N-tert-butylamine (120 μl), 1 ml of DMF (1 ml), HOBt (20 mg) and TBTU (160 mg) was stirred at room temperature for 18 h. A sat. aqueous $NH_4Cl$ solution was added. The reaction mixture was stirred for 10 min and extracted with ethyl acetate. The combined organic layers were washed with water, dried (MgSO$_4$), filtered and concentrated in vacuo. The residue was purified by chromatography on silica gel in heptane/ethyl acetate as eluent.

Yield: 75 mg. Mp: 176-177° C.; TLC $R_f$=0.53 (heptane/acetone 1/1); LC/MS-ESI: [M+H]$^+$=517; hFSHRago (CHO luc) $EC_{50}$=203.0 nM

Example 75

9-(3-Fluoro-phenoxy)-8-methoxy-1-thiophen-2-yl-5,6-dihydro-pyrrolo[2,1-α]isoquinoline-3-carboxylic acid tert-butyl-methyl-amide (a) Ethyl 9-(3-fluorophenoxy)-8-methoxy-1-(thiophen-2-yl)-5,6-dihydropyrrolo[2,1-α]iso-quinoline-3-carboxylate This product was prepared in a similar manner as described for example 74a, starting from the product from example 51a.

Mp: 139-140° C.; TLC $R_f$=0.60 (hept/ethyl acetate 1/1); LC/MS-ESI: [M+H]$^+$=446.

(b) 9-(3-Fluorophenoxy)-8-methoxy-1-(thiophen-2-yl)-5,6-dihydropyrrolo[2,1-α]iso-quinoline-3-carboxylic acid This product was prepared from the product of example 75a (130 mg) in a similar manner as described for example 74b.

Yield: 100 mg. Mp: 179-183° C. (decarb); TLC $R_f$=0.15 (heptane/ethyl acetate 1/1); LC/MS-ESI: [M+H]$^+$=436.

(c). 9-(3-Fluoro-phenoxy)-8-methoxy-1-thiophen-2-yl-5,6-dihydro-pyrrolo[2,1-α]isoquinoline-3-carboxylic acid tert-butyl-methyl-amide This product was prepared from the product of example 75b (200 mg) in a similar manner as described for example 74c.

Yield: 120 mg. Mp: 158-159° C.; $^1$H NMR (DMSO-d6) δ 6.38 (s, 1H, H2), 6.96 (s, 1H, H7), 7.18 (s, 1H, H10), 7.38 (dd, 1H, thiophene), 6.98 (dd, 1H, thiophene), 6.92 (m, 1H, thiophene), 7.30, 6.85, 6.62 (m, 4H, 4F-Phe), 3.75 (s, 3H, OCH3), 4.18 (t, 2H, H6), 3.05 (m, 5H, H6+NMe), 1.41 (s, 9H, tert-butyl); LC/MS-ESI: [M+H]$^+$=505.5; hFSHRago (CHO luc) $EC_{50}$=16.3 nM

Example 76

N-tert-butyl-8-methoxy-N-methyl-9-(pyrimidin-2-yloxy)-1-(thiophen-2-yl)-5,6-dihydro-pyrrolo[2,1-α]isoquinoline-3-carboxamide

(a). Ethyl 8-methoxy-9-(pyrimidin-2-yloxy)-1-(thiophen-2-yl)-5,6-dihydropyrrolo[2,1-α]isoquinoline-3-carboxylate A mixture of the product of example 51a (100 mg), 2-bromopyrimidine (50 mg), $Cs_2CO_3$ (300 mg), Cu powder (9 mg) in DMF (2 ml) was heated using microwave irradiation at 140° C. for 25 min. The reaction mixture was diluted with a sat. aqueous $NH_4Cl$ solution and extracted with ethyl acetate. The combined organic layers were washed with water, dried ($MgSO_4$), filtered and concentrated in vacuo. The residue was passed through a short silica pad (dichloromethane/ethyl acetate) and was triturated with diisopropyl ether to provide white crystals.

Yield: 145 mg. TLC $R_f$=0.20 (heptane/ethyl acetate 1/1) TLC $R_f$ starting material=0.40; Mp: 163-164° C.; LC/MS-ESI: $[M+H]^+$=448.

(b). 8-Methoxy-9-(pyrimidin-2-yloxy)-1-(thiophen-2-yl)-5,6-dihydropyrrolo[2,1-α]iso-quinoline-3-carboxylic acid This product was prepared from the product of example 76a (140 mg) in a similar manner as described for example 74b.

Yield: 95 mg. TLC $R_f$=0.30 (dichloromethane/acetone 1/1 v/v); Mp: 227° C.

(c). N-tert-butyl-8-methoxy-N-methyl-9-(pyrimidin-2-yloxy)-1-(thiophen-2-yl)-5,6-dihydro-pyrrolo[2,1-α]isoquinoline-3-carboxamide This product was prepared from the product of example 76b (90 mg) in a similar manner as described for example 74c.

Yield: 65 mg. Mp: 164-165° C.; TLC $R_f$=0.45 (heptane/acetone 1/1); LC/MS-ESI: $[M+H]^+$=489.3; hFSHRago (CHO luc) $EC_{50}$=18.9 nM

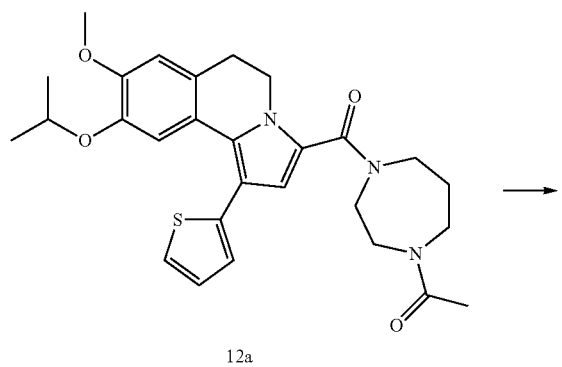

12a

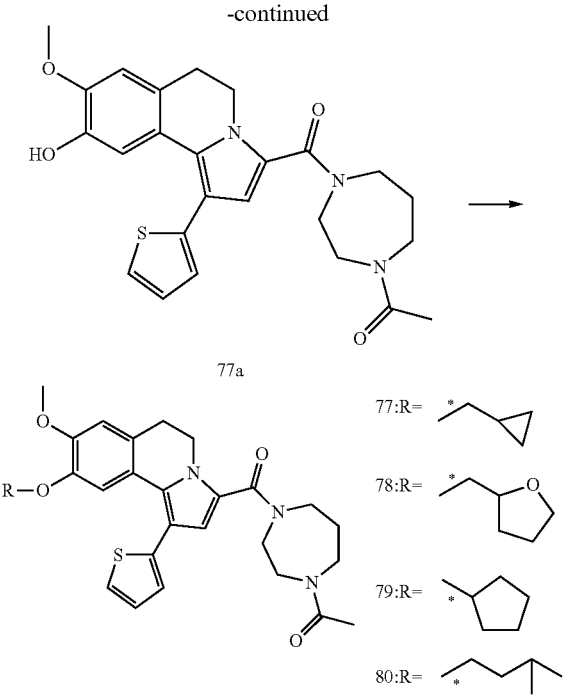

77a

77:R= * cyclopropyl
78:R= * tetrahydrofuran
79:R= * cyclopentyl
80:R= * isobutyl

Example 77

1-[4-(9-Cyclopropylmethoxy-8-methoxy-1-thiophen-2-yl-5,6-dihydro-pyrrolo[2,1-α]iso-quinoline-3-carbonyl)-perhydro-1,4-diazepin-1-yl]-ethanone

(a) 1-[4-(9-Hydroxy-8-methoxy-1-thiophen-2-yl-5,6-dihydro-pyrrolo[2,1-α]isoquinoline-3-carbonyl)-perhydro-1,4-diazepin-1-yl]-ethanone To a solution of the product of example 12a (315 mg) in dichloromethane (20 ml) was added at −10° C. a solution of boron trichloride (5 ml 1M in dichloromethane). The reaction was complete after 15 min and quenched by addition of water. The organic layer was separated, dried ($MgSO_4$), filtered and concentrated in vacuo. The residue was triturated with acetone/ether.

Yield: 284 mg. LC/MS-ESI: $[M+H]^+$=366.

(b). 1-[4-(9-Cyclopropylmethoxy-8-methoxy-1-thiophen-2-yl-5,6-dihydro-pyrrolo[2,1-α]iso-quinoline-3-carbonyl)-perhydro-1,4-diazepin-1-yl]-ethanone A mixture of the product of example 77a (36 mg), $K_2CO_3$ (70 mg) and cyclopropylmethyl bromide (30 mg) in DMF (1 ml) were stirred and heated using microwave irradiation reactor for 5 min at 220° C. The reaction mixture was cooled, diluted with water and extracted with ethyl acetate. The combined organic layers were washed with water, dried ($MgSO_4$), filtered and concentrated in vacuo. The residue was purified by preparative HPLC (20→100% acetonitrile; system 1).

Yield: 15 mg. LC/MS-ESI: $[M+H]^+$=520; hFSHRago (CHO luc) $EC_{50}$=57.6 nM

Example 78

1-{4-[8-Methoxy-9-(tetrahydro-furan-2-ylmethoxy)-1-thiophen-2-yl-5,6-dihydro-pyrrolo[2,1-α]isoquinoline-3-carbonyl]-perhydro-1,4-diazepin-1-yl}-ethanone This product was prepared from the product of example 77a (15 mg) in a similar manner as described for example 77b.

Yield: 2.2 mg. LC/MS-ESI: [M+H]$^+$=550; hFSHRago (CHO luc) EC$_{50}$=96.2 nM

Example 79

1-[4-(9-Cyclopentyloxy-8-methoxy-1-thiophen-2-yl-5,6-dihydro-pyrrolo[2,1-α]isoquinoline-3-carbonyl)-perhydro-1,4-diazepin-1-yl]-ethanone This product was prepared from the product of example 77a (15 mg) in a similar manner as described for example 77b.

Yield: 4.4 mg. LC/MS-ESI: [M+H]$^+$=534; hFSHRago (CHO luc) EC$_{50}$=14.2 nM

Example 80

1-{4-[8-Methoxy-9-(3-methyl-butoxy)-1-thiophen-2-yl-5,6-dihydro-pyrrolo[2,1-α]isoquinoline-3-carbonyl]-perhydro-1,4-diazepin-1-yl}-ethanone This product was prepared from the product of example 77a (215 mg) in a similar manner as described for example 77b.

Yield: 60 mg. LC/MS-ESI: [M+H]$^+$=536; hFSHRago (CHO luc) EC$_{50}$=101.0 nM

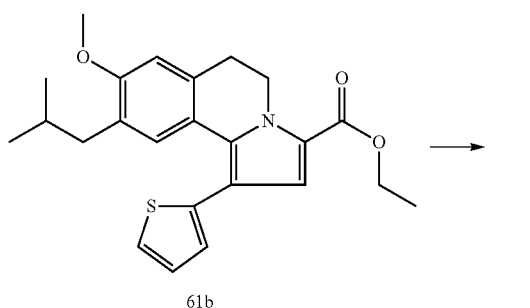

61b

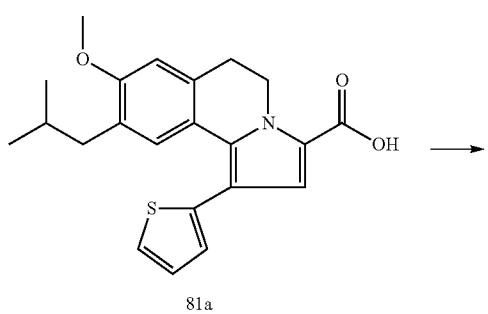

81a

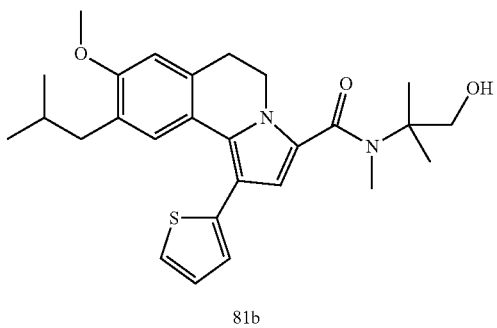

81b

Example 81

9-Isobutyl-8-methoxy-1-thiophen-2-yl-5,6-dihydro-pyrrolo[2,1-α]isoquinoline-3-carboxylic acid (2-hydroxy-1,1-dimethyl-ethyl)-methyl-amide (a). 9-Isobutyl-8-methoxy-1-thiophen-2-yl-5,6-dihydro-pyrrolo[2,1-α]isoquinoline-3-carboxylic acid This product was prepared in a similar manner as described for example 1i starting from the product of example 61b (3.19 g).

Yield: 3.2 g. LC/MS-ESI: [M+H]$^+$=382.2

(k). 9-Isobutyl-8-methoxy-1-thiophen-2-yl-5,6-dihydro-pyrrolo[2,1-α]isoquinoline-3-carboxylic acid (2-hydroxy-1,1-dimethyl-ethyl)-methyl-amide A slurry of the product of example 81a (215 mg) in dichloromethane (2 ml) was treated with oxalylchloride solution (400 µl 2M in dichloromethane). A drop of DMF was added. The mixture was stirred at room temperature for 1 h. The reaction mixture was concentrated in vacuo, and redissolved in dichloromethane (2 ml). This solution was treated with 2-methyl-2-methylamino-propan-1-ol (175 mg; prepared in a similar manner as described by S. G. Kuznetsov, A. V. Eltsov, *J. Gen. Chem. USSR*, 32, 502 (1962)) and stirred for 1 h at room temperature. The reaction mixture was poured into an aqueous NaHCO$_3$ solution (5%) and was extracted with ethyl acetate. The organic layer was dried (MgSO$_4$), filtered and concentrated in vacuo. The residue was triturated with heptane/ethyl acetate to provide crystalline material.

Yield: 80 mg. Mp 114-116° C.; LC/MS-ESI: [M+H]$^+$=476.5; hFSHRago (CHO luc) EC$_{50}$=6.0 nM

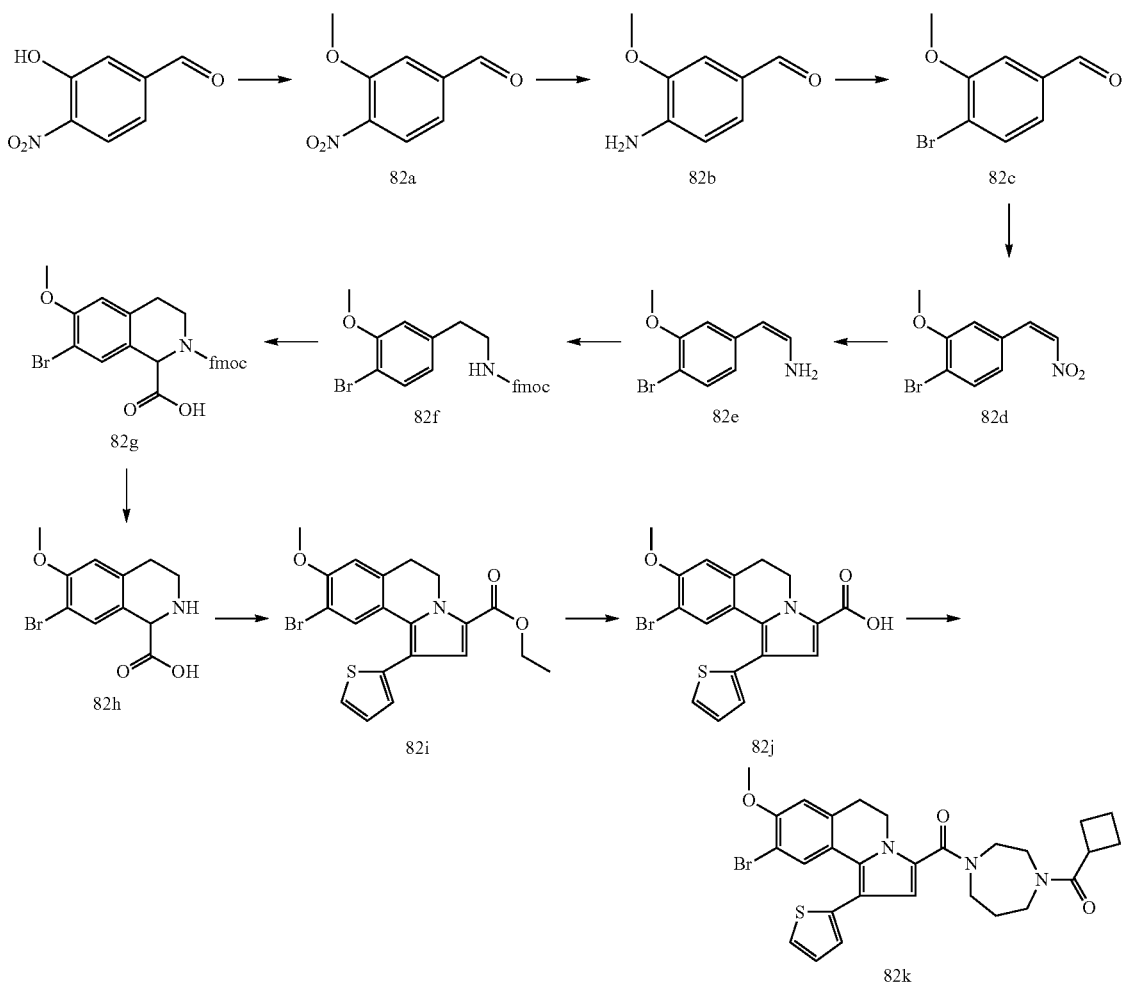

Example 82

(9-Bromo-8-methoxy-1-thiophen-2-yl-5,6,6a,10a-tetrahydro-pyrrolo[2,1--α]isoquinolin-3-yl)-(4-cyclobutanecarbonyl-[1,4]diazepan-1-yl)-methanone (a). 3-Methoxy-4-nitro-benzaldehyde A mixture of 3-hydroxy-4-nitrobenzaldehyde (51.3 g), iodomethane (38.3 ml) and K$_2$CO$_3$ (85 g) in DMF (250 ml) was stirred at 60° C. for 1 h. The reaction mixture was cooled to room temperature and poured into water (600 ml). The solids were collected by filtration and dried in vacuo (50° C.).
Yield: 49.7 g.

(b). 4-Amino-3-methoxy-benzaldyde

Iron (112 g) was added to a mixture of the product of example 82a (49.7 g) and ammonium chloride (103 g) in ethanol (500 ml) and water (500 ml). After stirring with a mechanical stirrer at 78° C. for 2 h, the reaction mixture was cooled to room temperature and extracted with diethyl ether (3×500 ml). The combined organic layers were concentrated in vacuo and water (400 ml) was added to the residue. The solids were collected by filtration and dried in vacuo (50° C.).
Yield: 38.3 g.

(c). 4-Bromo-3-methoxy-benzaldehyde

A solution of the product of example 82b (38.3 g) in acetonitrile (600 ml) was added dropwise to a mixture of n-butyl nitrite (43.1 ml) and copper(I) bromide (63.6 g) in acetonitrile (1300 ml). After stirring for 18 h at room temperature, the reaction mixture was diluted with ethyl acetate and washed with an aqueous HCl solution (1 N). The organic layer was separated and washed with brine, dried (MgSO$_4$), filtered and concentrated in vacuo. The residue was purified by chromatography on silica gel in heptane/ethyl acetate [1:1 (v/v)].
Yield: 27.4 g. LC/MS-ESI: [M+H]$^+$=215.1/217.0.

(d). 1-Bromo-2-methoxy-4-((E)-2-nitro-vinyl)-benzene

A mixture of the product of example 82c (27.4 g), ammonium acetate (10.8 g) and nitromethane (35 ml) in acetic acid (125 ml) was stirred at 80° C. for 18 h. The reaction mixture was cooled to room temperature and poured into water (1 l). The solids were collected by filtration and dissolved in dichloromethane (2 l). The organic layer was washed with brine, dried (MgSO$_4$), filtered and concentrated in vacuo.
Yield: 29.8 g.

(e). 2-(4-Bromo-3-methoxy-phenyl)-ethylamine

At 0° C. and under a nitrogen atmosphere a solution of borane-THF complex (262 ml 1M) was added dropwise to a solution of the product of example 82d (15 g) in THF (250 ml). After the addition, the icebath was removed. Sodium borohydride (0.11 g) was added (a slight exothermic reaction took place). After stirring for 18 h at 65° C. under a nitrogen atmosphere, the reaction mixture was cooled to room temperature and poured into an aqueous HCl solution (250 ml 2 M). After stirring for 1.5 h at 70° C., the reaction mixture was cooled to room temperature and extracted twice with diethyl ether. The aqueous layer was made basic with solid NaOH until pH=10 and extracted three times with ethyl acetate. The combined organic layers were washed with brine, dried (MgSO$_4$), filtered and concentrated in vacuo.

Yield: 13.5 g. LC/MS-ESI: [M+H]$^+$=230.1/232.1

(f). [2-(4-Bromo-3-methoxy-phenyl)-ethyl]-carbamic acid 9H-fluoren-9-ylmethyl ester A solution of 9-fluorenylmethyl chloroformate (29.2 g) in dichloromethane (100 ml) was added dropwise to a solution of the product of example 82e (22.4 g) and DIPEA (51 ml) in dichloromethane (300 ml). After stirring for 18 h at room temperature, the reaction mixture was washed with an aqueous HCl solution (1 M), water, dried (MgSO$_4$), filtered and concentrated in vacuo. The residue was taken up in diethyl ether and the solids were collected by filtration and dried in vacuo (50° C.).

Yield: 35.1 g. LC/MS-ESI: [M+H]$^+$=454.1

(g). 7-Bromo-6-methoxy-3,4-dihydro-1H-isoquinoline-1,2-dicarboxylic acid 2-(9H-fluoren-9-ylmethyl) ester At 0° C., concentrated sulfuric acid (140 ml) was added dropwise to a solution of the product of example 82f (35.1 g) and glyoxylic acid hydrate (8.57 g) in acetic acid (700 ml). After stirring for 1 h at room temperature, the reaction mixture was poured out on crushed ice and extracted twice with ethyl acetate. The organic layer was washed with an aqueous HCl solution (0.2 M), brine, dried (MgSO$_4$), filtered and concentrated in vacuo. Residual solvents were removed by co-evaporation (twice) with toluene.

Yield: 39.8 g. LC/MS-ESI: [M+H]$^+$=508.1/510.1

(h). 7-Bromo-6-methoxy-1,2,3,4-tetrahydro-isoquinoline-1-carboxylic acid

A mixture of the product of example 82g (37.8 g) and piperidine (36.7 ml) in DMF (350 ml) was stirred at room temperature for 15 min. The reaction mixture was concentrated in vacuo and the residue was taken up in THF (200 ml) and diethyl ether (200 ml). The solids were collected by filtration and dried in vacuo (50° C.).

Yield: 18.5 g (i). 9-Bromo-8-methoxy-1-thiophen-2-yl-5,6,6a,10a-tetrahydro-pyrrolo[2,1-α]isoquinoline-3-carboxylic acid ethyl ester A mixture of the product of example 82h (3 g) and ethyl oxalyl chloride (1.4 ml) in THF (25 ml) was stirred at 65° C. for 30 min and the reaction mixture was concentrated in vacuo. A mixture of the residue and 2-ethynyl-thiophene (1.24 ml) in acetic anhydride (10 ml) was heated using microwave irradiation at 140° C. for 15 min. The reaction mixture was diluted with dichloromethane and washed with water, sat. aqueous NaHCO$_3$ solution, brine, dried (MgSO$_4$), filtered and concentrated in vacuo. The residue was purified by chromatography on silica gel in heptane/ethyl acetate [2/1 (v/v)] as eluent.

Yield: 3.82 g. LC/MS-ESI: [M+H]$^+$=432.0/434.0

(j). 9-Bromo-8-methoxy-1-thiophen-2-yl-5,6,6a,10a-tetrahydro-pyrrolo[2,1-α]isoquinoline-3-carboxylic acid A mixture of the product of example 82i (200 mg) and solid KOH (100 mg) in ethanol (4 ml) and water (1 ml) was stirred at 80° C. for 1 h. At room temperature, the reaction mixture was acidified with an aqueous HCl solution (6 M). The aqueous layer was extracted with ethyl acetate. The organic layer was washed with brine, dried (MgSO$_4$), filtered and concentrated in vacuo.

Yield: 180 mg.

(k). (9-Bromo-8-methoxy-1-thiophen-2-yl-5,6,6a,10a-tetrahydro-pyrrolo[2,1-α]isoquinolin-3-yl)-(4-cyclobutanecarbonyl-[1,4]diazepan-1-yl)-methanone A mixture of the product of example 82j (50 mg), DIPEA (150 µl), BOP (137 mg) and cyclobutyl-[1,4]diazepan-1-yl-methanone (55 mg) was stirred at room temperature for 18 h. The reaction mixture was extracted with water, brine, dried (MgSO$_4$), filtered and concentrated in vacuo. The residue was purified by preparative HPLC (30→90% acetonitrile; system 1).

Yield: 42 mg. LC/MS-ESI: [M+H]$^+$=568.1/570.1; anal. HPLC R$_t$=23.89 min; hFSHRago (CHO luc) EC$_{50}$=5. nM

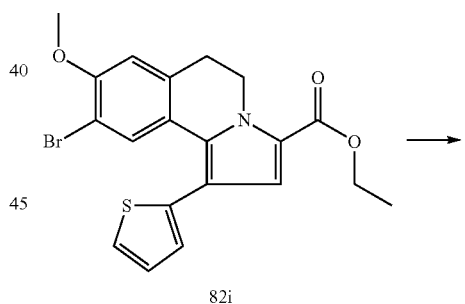

82i

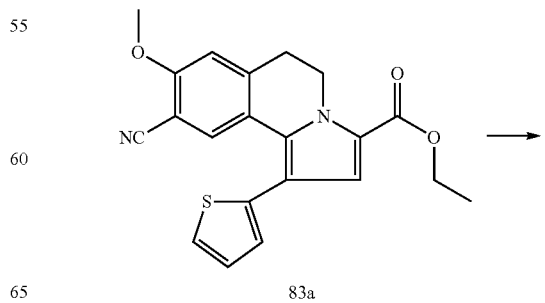

83a

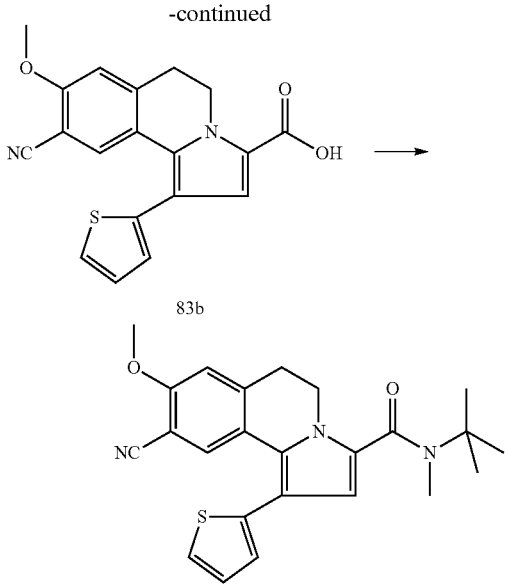

83b

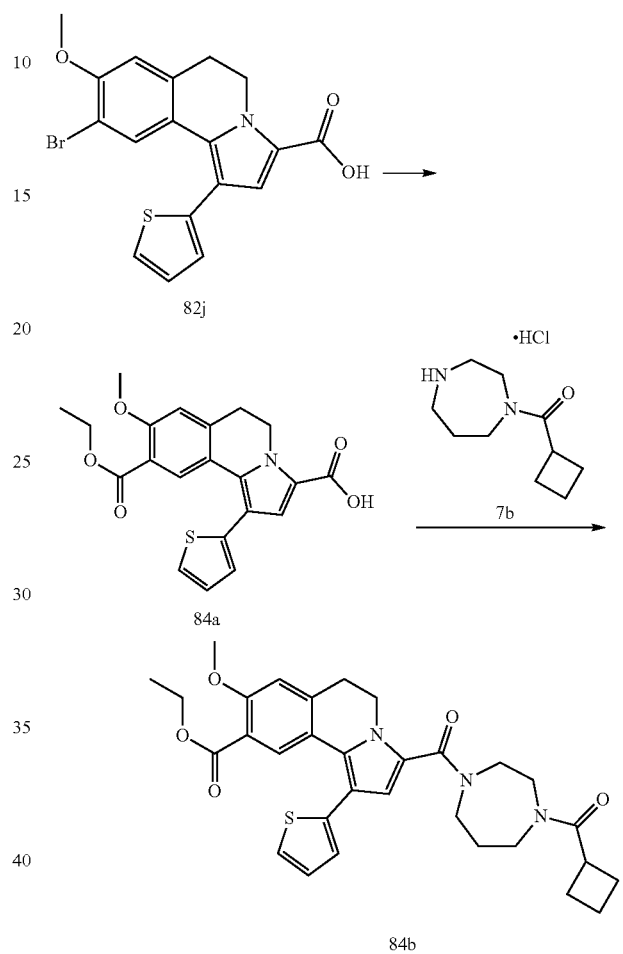

in vacuo. The residue was purified by chromatography on silica gel in heptane/ethyl acetate [1:1 (v/v)] as eluent.

Yield: 26 mg. LC/MS-ESI: [M+H]$^+$=420.2; anal. HPLC: R$_t$=19.52 min (method 7); hFSHRago (CHO luc) EC$_{50}$=4.3 nM

Example 83

9-Cyano-8-methoxy-1-thiophen-2-yl-5,6-dihydro-pyrrolo[2,1--α]isoquinoline-3-carboxylic acid tert-butyl-methyl-amide (a). 9-Cyano-8-methoxy-1-thiophen-2-yl-5,6-dihydro-pyrrolo[2,1-α]isoquinoline-3-carboxylic acid ethyl ester A mixture of the product of example 80i (48 mg), copper (I)cyanide (20 mg) and copper(I)iodide (2.1 mg) in NMP (1 ml) was heated using microwave irradiation at 180° C. for 15 min. The reaction mixture was concentrated in vacuo. The residue was purified by chromatography on silica gel in heptane/ethyl acetate [1:1 (v/v)] as eluent.

Yield: 41 mg. MS-ESI: [M+H]$^+$=379.3

(b). 9-Cyano-8-methoxy-1-thiophen-2-yl-5,6-dihydro-pyrrolo[2,1--α]isoquinoline-3-carboxylic acid A mixture of the product of example 83a (41 mg) and solid KOH (18 mg) in ethanol (2 ml) and water (2 ml) was stirred at 80° C. for 4 h. At room temperature, the reaction mixture was acidified with an aqueous citric acid solution (2 M) and extracted with dichloromethane. The organic layer was washed with brine, dried (MgSO$_4$), filtered and concentrated in vacuo.

Yield: 43 mg. LC/MS-ESI: [M+H]$^+$=351.1

(c). 9-Cyano-8-methoxy-1-thiophen-2-yl-5,6-dihydro-pyrrolo[2,1--α]isoquinoline-3-carboxylic acid tert-butyl-methyl-amide HATU (70 mg) was added to a solution of the product of example 83b (43 mg), DIPEA (107 µl) and N-methyl-N-tert-butyl-amine (29 µl) in dichloromethane (5 ml). After stirring at room temperature for 18 h, the reaction mixture was diluted with dichloromethane and washed with an aqueous HCl solution (0.5 M), brine, dried (MgSO$_4$), filtered and concentrated

Example 84

3-(4-Cyclobutanecarbonyl-[1,4]diazepane-1-carbonyl)-8-methoxy-1-thiophen-2-yl-5,6-dihydro-pyrrolo[2,1--α]isoquinoline-9-carboxylic acid ethyl ester (a). 8-Methoxy-1-thiophen-2-yl-5,6-dihydro-pyrrolo[2,1--α]isoquinoline-3,9-dicarboxylic acid 9-ethyl ester At −70° C., n-butyllithium (1.26 ml, 1.6 M in heptane) was added dropwise to a solution of the product of example 80j (370 mg) in THF (15 ml). After stirring for 30 min at −70° C., the reaction mixture was treated with ethyl chloroformate (0.4 ml). At room temperature, the reaction mixture was diluted with ethyl acetate and washed with water. The organic layer was dried (MgSO$_4$), filtered and concentrated in vacuo.

Yield: 100 mg.

(b). 3-(4-Cyclobutanecarbonyl-[1,4]diazepane-1-carbonyl)-8-methoxy-1-thiophen-2-yl-5,6-dihydro-pyrrolo[2,1--α]isoquinoline-9-carboxylic acid ethyl ester Amide formation of the product of example 7b (50 mg) and the product of example 84a (50 mg) was performed according to the method described for example 13.

Yield: 52 mg. LC/MS-ESI: [M+H]$^+$=548.2; anal. HPLC: R$_t$=17.3 min (method 2); hFSHRago (CHO luc) EC$_{50}$=2.9 nM

Example 85

8-Methoxy-9-prop-1-ynyl-1-thiophen-2-yl-5,6-dihydro-pyrrolo[2,1--α]isoquinoline-3-carboxylic acid tert-butyl-methyl-amide and 9-bromo-8-methoxy-1-thiophen-2-yl-5,6-dihydro-pyrrolo[2,1--α]isoquinoline-3-carboxylic acid tert-butyl-methyl-amide

(a). 9-Bromo-8-methoxy-1-thiophen-2-yl-5,6-dihydro-pyrrolo[2,1--α]isoquinoline-3-carboxylic acid tert-butyl-methyl-amide Ethylmagnesium chloride (6.6 ml, 25% WT in THF) dissolved in THF (6 ml) was added slowly to a solution of N-methyl-N-tert-butyl-amine (2.3 ml) in THF (6 ml). After stirring for 1 h at 75° C., the product of example 82i (1.1 g) dissolved in THF (3 ml) was added dropwise. After stirring for an additional 1 h at 75° C., the reaction mixture was poured in a sat. aqueous NH$_4$Cl solution and extracted with ethyl acetate. The organic layer was washed with water and brine, dried (MgSO$_4$), filtered and concentrated in vacuo. The residue was dissolved in a minimum amount of ethanol followed by addition of a small amount of water. After cooling in an ice bath, the precipitate was filtered.

Yield: 667 mg. LC/MS-ESI: [M+H]$^+$=473/475; hFSHRago (CHO luc) EC$_{50}$=11.3 nM

(b). 8-Methoxy-9-prop-1-ynyl-1-thiophen-2-yl-5,6-dihydro-pyrrolo[2,1--α]isoquinoline-3-carboxylic acid tert-butyl-methyl-amide A mixture of the product of example 85a (50 mg), Pd(PPh$_3$)$_4$ (12.2 mg) and tributyl(1-propynyl)tin (104 mg) in toluene (1 ml, sparged with nitrogen) was stirred and heated using microwave irradiation for 20 min at 150° C. The reaction mixture was filtered and concentrated in vacuo. The residue was purified by preparative HPLC (10→90% acetonitrile; system 1).

Yield: 10 mg. LC/MS-ESI: [M+H]$^+$=433.2; anal. HPLC: R$_t$=24.47 min (method 5); hFSHRago (CHO luc) EC$_{50}$=2.7 nM

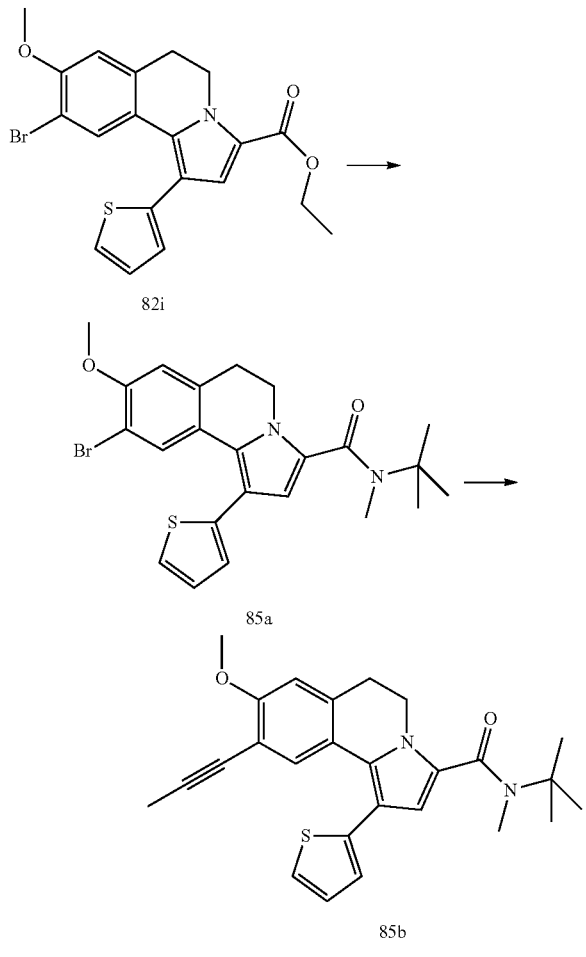

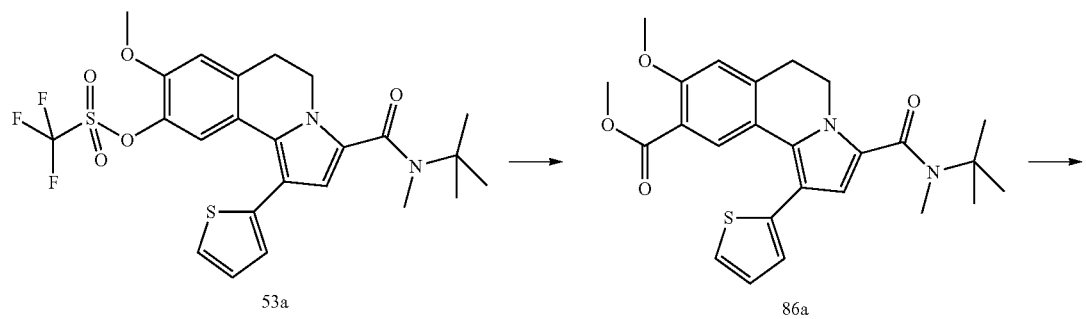

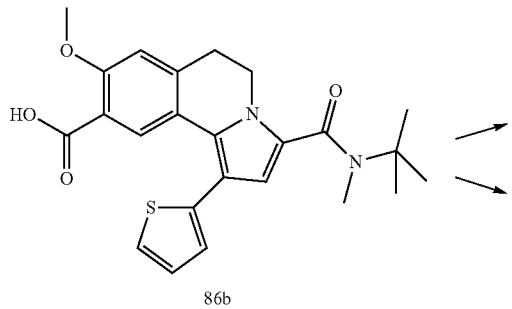

86b

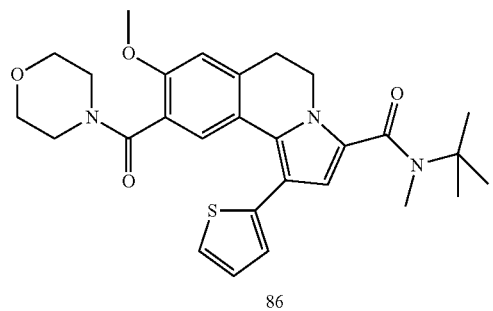

86

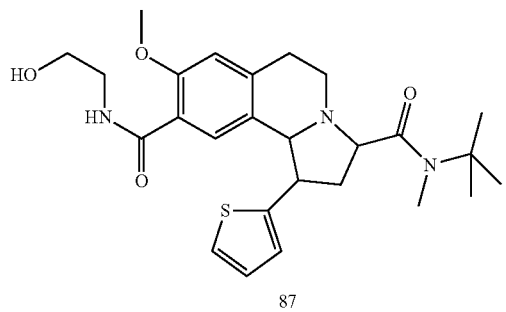

87

Example 86

8-Methoxy-9-(morpholine-4-carbonyl)-1-thiophen-2-yl-5,6,6 a,10a-tetrahydro-pyrrolo[2,1--α]isoquinoline-3-carboxylic acid tert-butyl-methyl-amide (a). 3-(tert-Butyl-methyl-carbamoyl)-8-methoxy-1-thiophen-2-yl-5,6-dihydro-pyrrolo[2,1--α]isoquinoline-9-carboxylic acid methyl ester A mixture of the product of example 53a (1 g), triethylamine (0.771 ml) and 1,3-di(phenylphosphino)propane (184 mg) in 10 ml DMF and 10 ml methanol was flushed with CO (g) for 10 min. Then, palladium(II) acetate (103 mg) was added. The reaction mixture was stirred at 70° C. under a CO (g) atmosphere for 72 h. The reaction mixture was diluted with ethyl acetate and washed with brine. The organic layer was dried (MgSO$_4$), filtered and concentrated in vacuo. The residue was purified by chromatography on silica gel in heptane/ethyl acetate [0→50% ethyl acetate].
Yield: 476 mg. LC-MS-ESI: [M+H]$^+$=453.2

(b). 3-(tert-Butyl-methyl-carbamoyl)-8-methoxy-1-thiophen-2-yl-5,6,6 a,10a-tetrahydro-pyrrolo[2,1--α]isoquinoline-9-carboxylic acid The product of example 86a (500 mg) was suspended in methanol (10 ml) and water (10 ml). KOH (620 mg) was added and the reaction mixture was heated under reflux for 2 h. The reaction mixture was diluted with dichloromethane and washed with an aqueous citric acid solution (2 N). The organic layer was dried (MgSO$_4$), filtered and concentrated in vacuo.
Yield: 485 mg LC-MS-ESI: [M+H]$^+$=439.2

(c). 8-Methoxy-9-(morpholine-4-carbonyl)-1-thiophen-2-yl-5,6,6 a,10a-tetrahydro-pyrrolo[2,1--α]-isoquinoline-3-carboxylic acid tert-butyl-methyl-amide A mixture of the product of example 86b (60 mg), HATU (86 mg), DIPEA (70 μl) and morpholine (36 μl) in dichloromethane (5 ml) was stirred at room temperature for 2 h. The reaction mixture was washed with water and brine. The organic layer was dried (MgSO$_4$), filtered and concentrated in vacuo. The residue was purified by preparative HPLC (20→100% acetonitrile; system 1).
Yield: 41 mg. LC/MS-ESI: [M+H]$^+$=508.2; anal. HPLC: R$_t$=1.95 min (method 13); hFSHRago (CHO luc) EC$_{50}$=69.4 nM

Example 87

8-Methoxy-1-thiophen-2-yl-5,6,6a,10a-tetrahydro-pyrrolo[2,1-α]isoquinoline-3,9-dicarboxylic acid 3-(tert-butyl-methyl-amide) 9-[(2-hydroxy-ethyl)-amide]

A mixture of the product of example 86b (60 mg), HATU (186 mg), DIPEA (70 μl) and ethanolamine (25 μl) in dichloromethane (5 ml) was stirred at room temperature for 2 h. The reaction mixture was washed with water and brine. The organic layer was dried (MgSO$_4$), filtered and concentrated in vacuo. The residue was purified by preparative HPLC (20→100% acetonitrile; system 1).
Yield: 30 mg. LC/MS-ESI: [M+H]$^+$=482.2; anal. HPLC: R$_t$=1.55 (method 13); hFSHRago (CHO luc) EC$_{50}$=23.9 nM

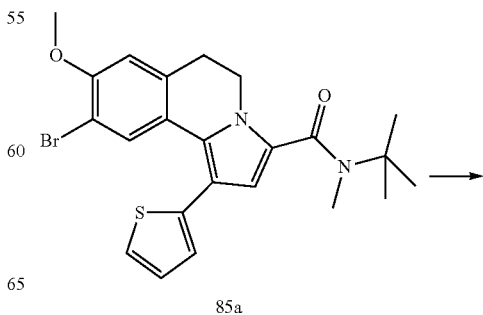

85a

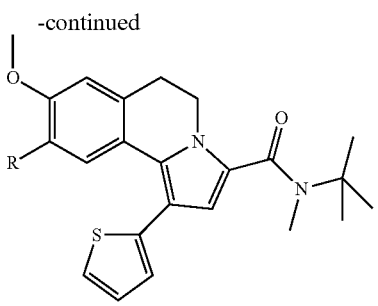

88: R = 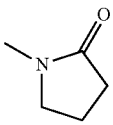

89: R = 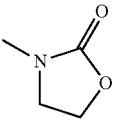

90: R = 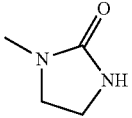

Example 88

9-(2-Oxo-pyrrolidin-1-yl)-1-thiophen-2-yl-5,6-dihydro-pyrrolo[2,1-α]isoquinoline-3-carboxylic acid tert-butyl-methyl-amide A mixture of the product of example 85a (25 mg), 9,9-dimethyl-4,5,-bis(diphenylphospino)-xanthene (6 mg), tris(dibenzylideneacetone)dipalladium(0) (5 mg), $Cs_2CO_3$ (20 mg) and 2-pyrrolidinone (24 mg) in dioxane/NMP [0.5 ml 9/1 (v/17)] was stirred and heated using microwave irradiation at 150° C. for 5 min. The reaction mixture was diluted with ethyl acetate and washed with water and brine. The organic layer was dried ($MgSO_4$), filtered and concentrated in vacuo. The residue was purified by chromatography on silica gel in heptane/ethyl acetate [2/8→7/3 (v/v)] as eluent.

Yield: 1 mg. LC/MS-ESI: $[M+H]^+$=448; hFSHRago (CHO luc) $EC_{50}$=310.0 nM

Example 89

9-(2-Oxo-oxazolidin-3-yl)-1-thiophen-2-yl-5,6-dihydro-pyrrolo[2,1-α]isoquinoline-3-carboxylic acid tert-butyl-methyl-amide This product was prepared in a similar manner as described for example 88 starting from the product of example 85a (25 mg).

Yield: 5 mg. LC/MS-ESI: $[M+H]^+$=450; hFSHRago (CHO luc) $EC_{50}$=245.0 nM

Example 90

9-(2-Oxo-imidazolidin-1-yl)-1-thiophen-2-yl-5,6-dihydro-pyrrolo[2,1-α]isoquinoline-3-carboxylic acid tert-butyl-methyl-amide This product was prepared in a similar manner as described for example 88, starting from the product of example 85a (25 mg).

Yield: 5 mg. LC/MS-ESI: $[M+H]^+$=449; hFSHRago (CHO luc) $EC_{50}$=218.0 nM

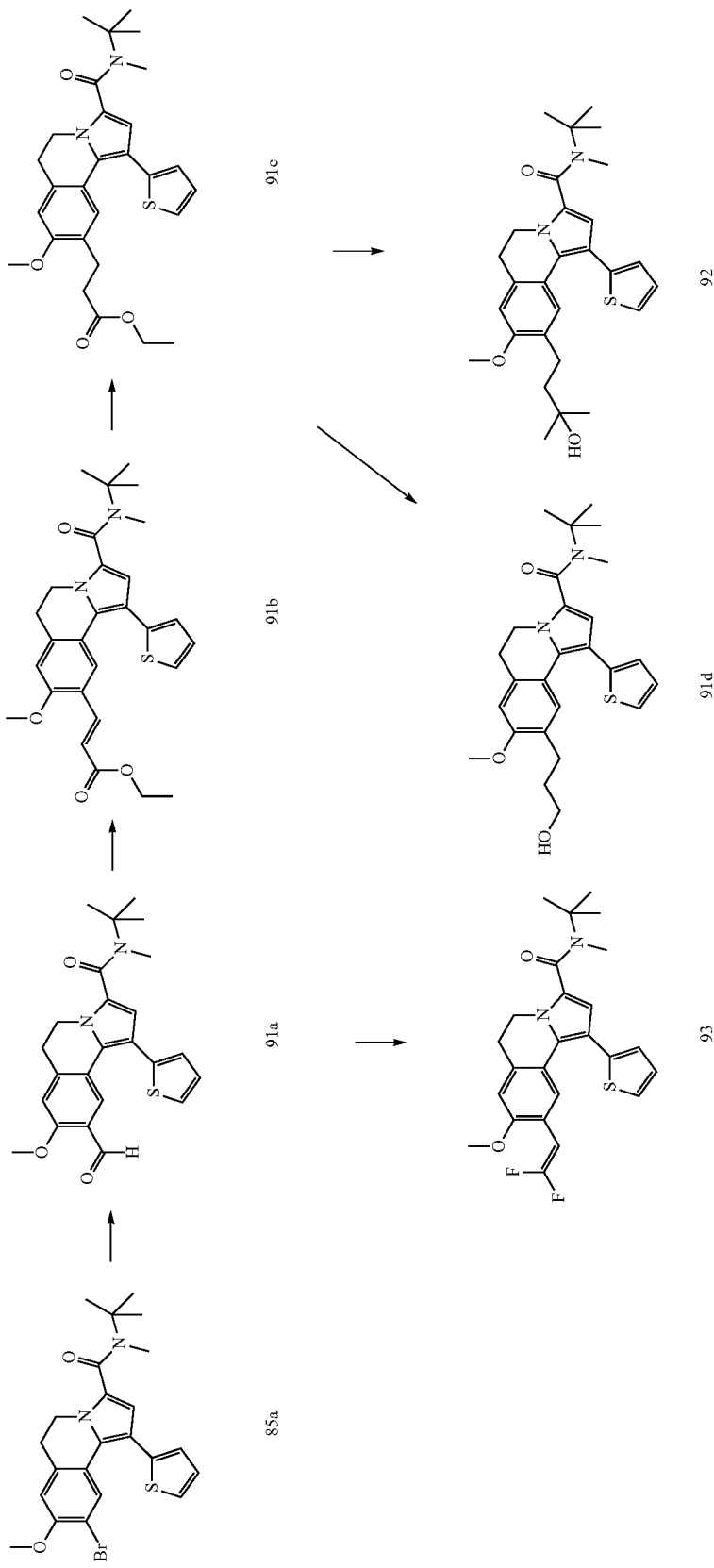

Example 91

9-(3-Hydroxy-propyl)-8-methoxy-1-thiophen-2-yl-5,6-dihydro-pyrrolo[2,1-α]isoquinoline-3-carboxylic acid tert-butyl-methyl-amide and 9-formyl-8-methoxy-1-thiophen-2-yl-5,6-dihydro-pyrrolo[2,1-α]isoquinoline-3-carboxylic acid tert-butyl-methyl-amide

(a). 9-Formyl-8-methoxy-1-thiophen-2-yl-5,6-dihydro-pyrrolo[2,1-α]isoquinoline-3-carboxylic acid tert-butyl-methyl-amide To a suspension of the product of example 85a (1.27 g) in a mixture of diethyl ether (12 ml) and THF (3 ml) was added at −60° C. a solution of n-butyllithium (2 ml 1.6 M in heptane). The mixture was stirred for 30 min at −60° C. and then treated with DMF (300 µl). The cooling equipment was removed and stirring was continued for 30 min at ambient temperature. The reaction was quenched by addition of water, and extracted with ethyl acetate. The organic layers were combined, dried (MgSO$_4$), filtered and concentrated in vacuo. The residue was purified by chromatography through a short silica column (heptane/ethyl acetate as eluent). The product was triturated with heptane/diisopropylether.

Yield: 650 mg. Mp 193-194° C.; TLC R$_f$=0.35 (heptane/ethyl acetate 1/1); LC/MS-ESI: [M+H]$^+$=423.3; hFSHRago (CHO luc) EC$_{50}$=6 nM.

(b). (E)-3-[3-(tert-butyl-methyl-carbamoyl)-8-methoxy-1-thiophen-2-yl-5,6-dihydro-pyrrolo[2,1-α]isoquinolin-9-yl]-acrylic acid ethyl ter A solution of triethylphosphonoacetate (200 µl) in THF (2 ml) was treated with sodium hydride (60 mg, 60% dispersion in oil). After stirring for 20 min, the product of example 91a (400 mg) was added in small portions. The reaction was complete after 30 min. The reaction mixture was diluted with water and extracted with ethyl acetate. The organic layers were combined, dried (MgSO$_4$), filtered and concentrated in vacuo. The residue was purified by chromatography through a short silica column and triturated with heptane to give white crystalline material.

Yield: 350 mg. Mp 163-164° C.; TLC R$_f$=0.28 (heptane/ethyl acetate 1/1); LC/MS-ESI: [M+H]$^+$=493.5

(c). 3-[3-(tert-butyl-methyl-carbamoyl)-8-methoxy-1-thiophen-2-yl-5,6-dihydro-pyrrolo[2,1-α]isoquinolin-9-yl]-propionic acid ethyl ester A solution of the product of example 91b (350 mg) in ethanol and ethyl acetate [20 ml 1/2 (v/v)] was hydrogenated at 2 bar pressure in the presence of 10% Pd/C (200 mg). After 48 h the sluggish hydrogenation was almost completed. The reaction product was purified by chromatography through a short silica column and triturated with heptane, to provide white crystalline material.

Yield: 170 mg. Mp 127-128° C. TLC R$_f$=0.50 (heptane/ethyl acetate 1/1); LC/MS-ESI: [M+H]$^+$=495.5

(d). 9-(3-hydroxy-propyl)-8-methoxy-1-thiophen-2-yl-5,6-dihydro-pyrrolo[2,1-α]iso-quinoline-3-carboxylic acid tert-butyl-methyl-amide A solution of the product of example 91c (60 mg) in THF (2 ml) was treated with LiAlH$_4$ (6 mg). After stirring for 60 min reduction was complete. The reaction was diluted with a sat. aqueous Na$_2$SO$_4$ solution and extracted with ethyl acetate. The organic layers were combined, dried (MgSO$_4$), filtered and concentrated in vacuo. The residue was purified by chromatography (heptane/ethyl acetate 1/1) through a silica column, followed by treatment with ethyl acetate/diethyl ether to yield a white solid.

Yield: 45 mg. Mp 163-164° C. TLC R$_f$=0.30 (heptane/ethyl acetate 1/1); LC/MS-ESI: [M+H]$^+$=453.5; hFSHRago (CHO luc) EC$_{50}$=0.4 nM

Example 92

9-(3-Hydroxy-3-methyl-butyl)-8-methoxy-1-thiophen-2-yl-5,6-dihydro-pyrrolo[2,1-α]isoquinoline-3-carboxylic acid tert-butyl-methyl-amide A solution of the product of example 91c (85 mg) in THF (2 ml) was treated with methyl magnesium chloride (200 µl 2M solution in THF) at room temperature. After stirring for 1 h, the reaction was completed. A solution of sat. aqueous NH$_4$Cl solution was added and the mixture was extracted with ethyl acetate. The organic layers were combined, dried (MgSO$_4$), filtered and concentrated in vacuo. The residue was purified by chromatography through a short silica column, followed by crystallization from ether to afford a white solid.

Yield: 70 mg. Mp 153-154° C. TLC R$_f$=0.24 (heptane/ethyl acetate 1/1); LC/MS-ESI: [M+H]$^+$=481.5; hFSHRago (CHO luc) EC$_{50}$=6.0 nM

Example 93

(9-(2,2-Difluoro-vinyl)-8-methoxy-1-thiophen-2-yl-5,6-dihydro-pyrrolo[2,1-α]isoquinoline-3-carboxylic acid tert-butyl-methyl-amide To a solution of LDA, prepared from diisopropylamine (50 µl) and n-butyllithium (200 µl 1.6 M in heptane) in dry THF (2 ml) was added at −70° C., a solution of difluoromethyl-diphenylphosphine oxide (75 mg; prepared from dibromodifluoromethane and triphenylphosphine) in THF (0.5 ml). The mixture was stirred at −70° C. for 20 min and then a solution of the product of example 91a (125 mg) in 0.5 ml dry THF was added. The reaction mixture was stirred at ambient temperature for 10 min and heated at 80° C. for 30 min. Water was added and the mixture was extracted with ethyl acetate. The organic layers were combined, dried (MgSO$_4$), filtered and concentrated in vacuo. The residue was purified by chromatography on silica (heptane/ethyl acetate 2/1). The product isolated was triturated with cold heptane.

Yield: 55 mg. Mp 111-112° C. TLC R$_f$=0.47 (heptane/ethyl acetate 1/1), TLC R$_f$ starting material=0.30; hFSHRago (CHO luc) EC$_{50}$=3.0 nM

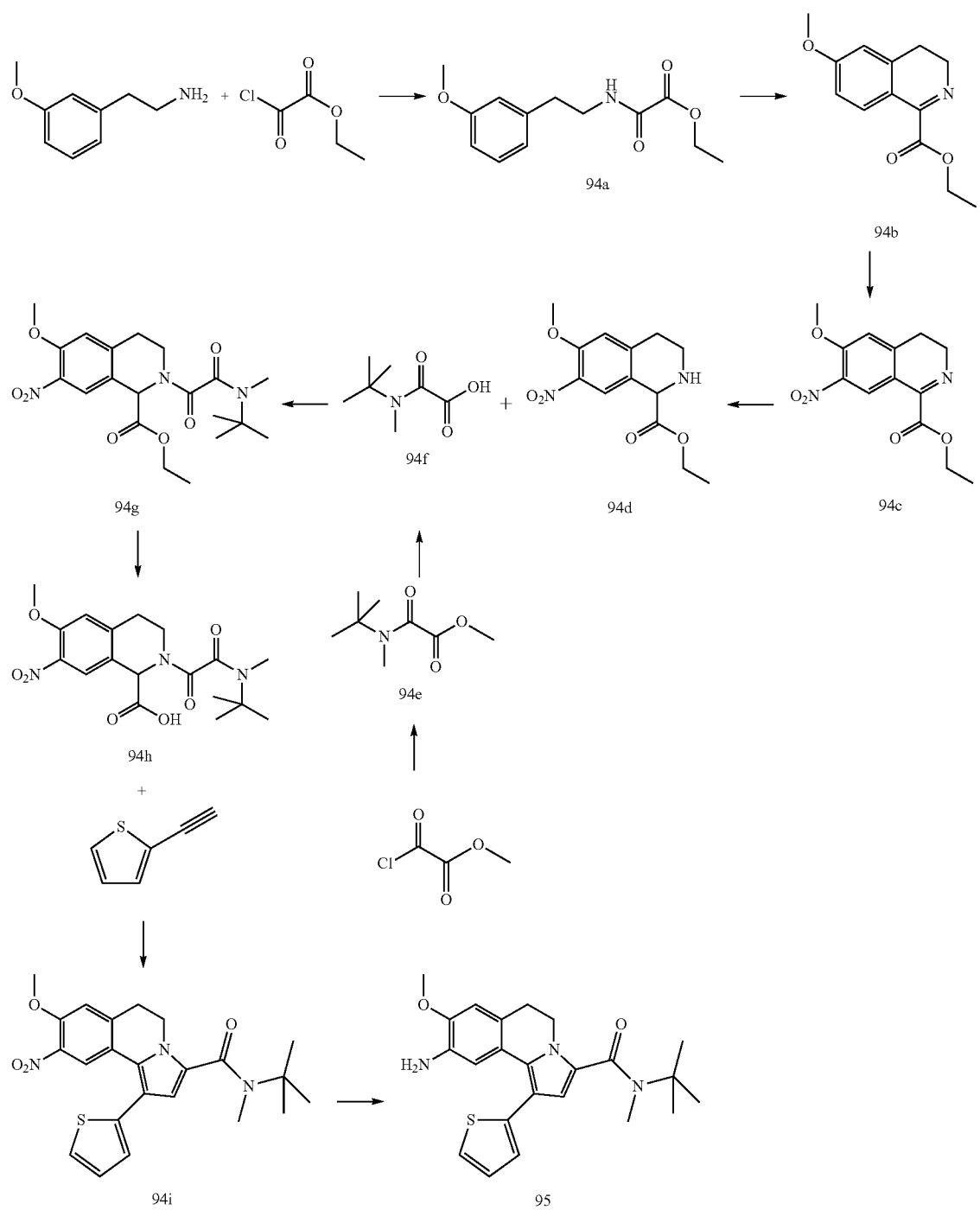

Example 94

8-Methoxy-9-nitro-1-thiophen-2-yl-5,6-dihydro-pyrrolo[2,1-α]isoquinoline-3-carboxylic acid tert-butyl-methyl-amide (a). N-[2-(3-Methoxy-phenyl)-ethyl]-oxalamic acid ethyl ester A solution of ethyl oxalyl chloride (1.5 ml) in dichloromethane (5 ml) was added dropwise to a solution of 3-methoxyphenetylamine (2.0 ml) and DIPEA (4.8 ml) in dichloromethane (40 ml) at 0° C. The reaction mixture was stirred for 1 h, washed with an aqueous citric acid solution (2 M), water and brine. The organic layer was dried (MgSO$_4$), filtered and concentrated in vacuo. The residue was purified by chromatography on silica gel in heptane/ethyl acetate [6/4 (v/v)] as eluent.

Yield: 2.76 g. LC/MS-ESI: [M+H]$^+$=252.2

(b). 6-Methoxy-3,4-dihydro-isoquinoline-1-carboxylic acid ethyl ester

The product of example 94a (10 g) dissolved in dichloromethane (20 ml) was added to a solution of phosphorus pentoxide (10 g) in methanesulfonic acid (40 ml) at 80° C. After stirring for 2 h at 80° C., the reaction mixture was poured onto solid NaHCO$_3$, diluted with ice water and extracted with ethyl acetate. The organic layer was washed with water and brine, dried (MgSO$_4$), filtered and concentrated in vacuo.

Yield: 9.3 g. LC/MS-ESI: [M+H]$^+$=234.2

(c). 6-Methoxy-7-nitro-3,4-dihydro-isoquinoline-1-carboxylic acid ethyl ester Potassium nitrate (3.59 g) was added to a stirred solution of the product of example 94b (9.2 g) in sulfuric acid (50 ml) at 0° C. After stirring for 2 h at room temperature the reaction mixture was poured into ice water, neutralized with NaHCO$_3$ and extracted with ethyl acetate. The organic layer was washed with water and brine, dried (MgSO$_4$) filtered and concentrated in vacuo. The residue was purified by chromatography on silica gel in heptane/ethyl acetate [2/8 (v/v)] as eluent.

Yield: 6.04 g. LC/MS-ESI: [M+H]$^+$=279.1

(d). 6-Methoxy-7-nitro-1,2,3,4-tetrahydro-isoquinoline-1-carboxylic acid ethyl ester Sodium cyanoborohydride (10.64 g) was added portionwise to a stirred solution of the product of example 94c (6.04 g) in acetic acid (100 ml) over a period of 15 min. After stirring for 1 h, the reaction mixture was poured into ice water, made basic with Na$_2$CO$_3$, extracted with ethyl acetate and concentrated in vacuo. Residue was purified by chromatography on silica gel in heptane/ethyl acetate [2/8 (v/v)] as eluent.

Yield: 3.6 g. LC/MS-ESI: [M+H]$^+$=281.1

(e). N-tert-butyl-N-methyl-oxalamic acid ethyl ester

Methyl tert-butylamine (13.2 ml) was added dropwise to a solution of methyl oxalyl chloride (9.2 ml) and pyridine (10.5 ml) in dichloromethane (140 ml) at 0° C. After stirring for 1 h, the reaction mixture was washed with an aqueous HCl solution (2 M) and brine, dried (MgSO$_4$), filtered and concentrated in vacuo.

Yield: 17.3 g.

(f). N-tert-butyl-N-methyl-oxalamic acid

Potassium hydroxide (6.2 g) dissolved in methanol (100 ml) was added dropwise to a solution of the product of example 94e (17.3 g) in methanol (120 ml) at 0° C. The reaction mixture was warmed to room temperature and concentrated in vacuo. The residue was dissolved in water (50 ml), acidified with sulfuric acid solution (10%) to pH=4, filtered and dried under vacuum.

Yield: 7 g.

(g). 2-(tert-butyl-methyl-aminooxalyl)-6-methoxy-7-nitro-1,2,3,4-tetrahydro-iso-quinoline-1-carboxylic acid ethyl ester A mixture of the product of example 94d (3.2 g), the product of example 94f (2.0 g), TBTU (5.5 g) and DIPEA (9.94 ml) in dichloromethane (150 ml) was stirred at room temperature for 1 h. The reaction mixture was washed with water and brine, dried (MgSO$_4$), filtered and concentrated in vacuo. The residue was purified by chromatography on silica gel in heptane/ethyl acetate [3/7 (v/v)] as eluent.

Yield: 3.79 g. LC/MS-ESI: [M+H]$^+$=422.2

(h). 2-(tert-butyl-methyl-aminooxalyl)-6-methoxy-7-nitro-1,2,3,4-tetrahydro-isoquinoline-1-carboxylic acid A mixture of the product of example 94g (3.78 g) and potassium hydroxide (1.0 g) in tetrahydrofuran (100 ml) and water (50 ml) was stirred at room temperature for 1 h. The reaction mixture was acidified with an aqueous HCl solution (10%) and extracted with ethyl acetate. The organic layer was washed with water and brine, dried (MgSO$_4$), filtered and concentrated in vacuo.

Yield: 3.11 g. LC/MS-ESI: [M+H]$^+$=394.2

(i). 8-Methoxy-9-nitro-1-thiophen-2-yl-5,6-dihydro-pyrrolo[2,1-α]isoquinoline-3-carboxylic acid tert-butyl-methyl-amide A mixture of the product of example 94h (2.62 g) and 2-ethynylthiophene (0.779 ml) in acetic anhydride (15 ml) was heated using microwave irradiation to 140° C. for 15 min. The reaction mixture was poured into ice water, basified with NaHCO$_3$ and extracted with ethyl acetate. The organic layer was dried (MgSO$_4$), filtered and concentrated in vacuo. The residue was purified by chromatography on silica gel in heptane/ethyl acetate [2/8 (v/v)] as eluent.

Yield: 2.51 g. LC/MS-ESI: [M+H]$^+$=440.1; anal. HPLC: R$_t$=19.67 (Method 12); hFSHRago (CHO luc) EC$_{50}$=3.0 nM

Example 95

9-Amino-8-methoxy-1-thiophen-2-yl-5,6-dihydro-pyrrolo[2,1-α]isoquinoline-3-carboxylic acid tert-butyl-methyl-amide Acetic acid (0.39 ml) was added portionwise to a solution of the product of example 94 (300 mg) in THF (10 ml) at 0° C., followed by the portionwise addition of zinc (893 mg). After stirring for 2 h at room temperature, the reaction mixture was filtered over decalite. The filtrate was concentrated in vacuo and dissolved in ethyl acetate. The organic layer was washed with saturated NaHCO$_3$ solution and brine. The organic layer was dried (MgSO$_4$), filtered and concentrated in vacuo. Residue was purified by preparative HPLC (0→100% acetonitrile; system 1).

Yield: 159 mg. LC/MS-ESI: [M+H]$^+$=410.2; anal. HPLC: R$_t$=26.18 min (Method 12); hFSHRago (CHO luc) EC$_{50}$=44.8 nM

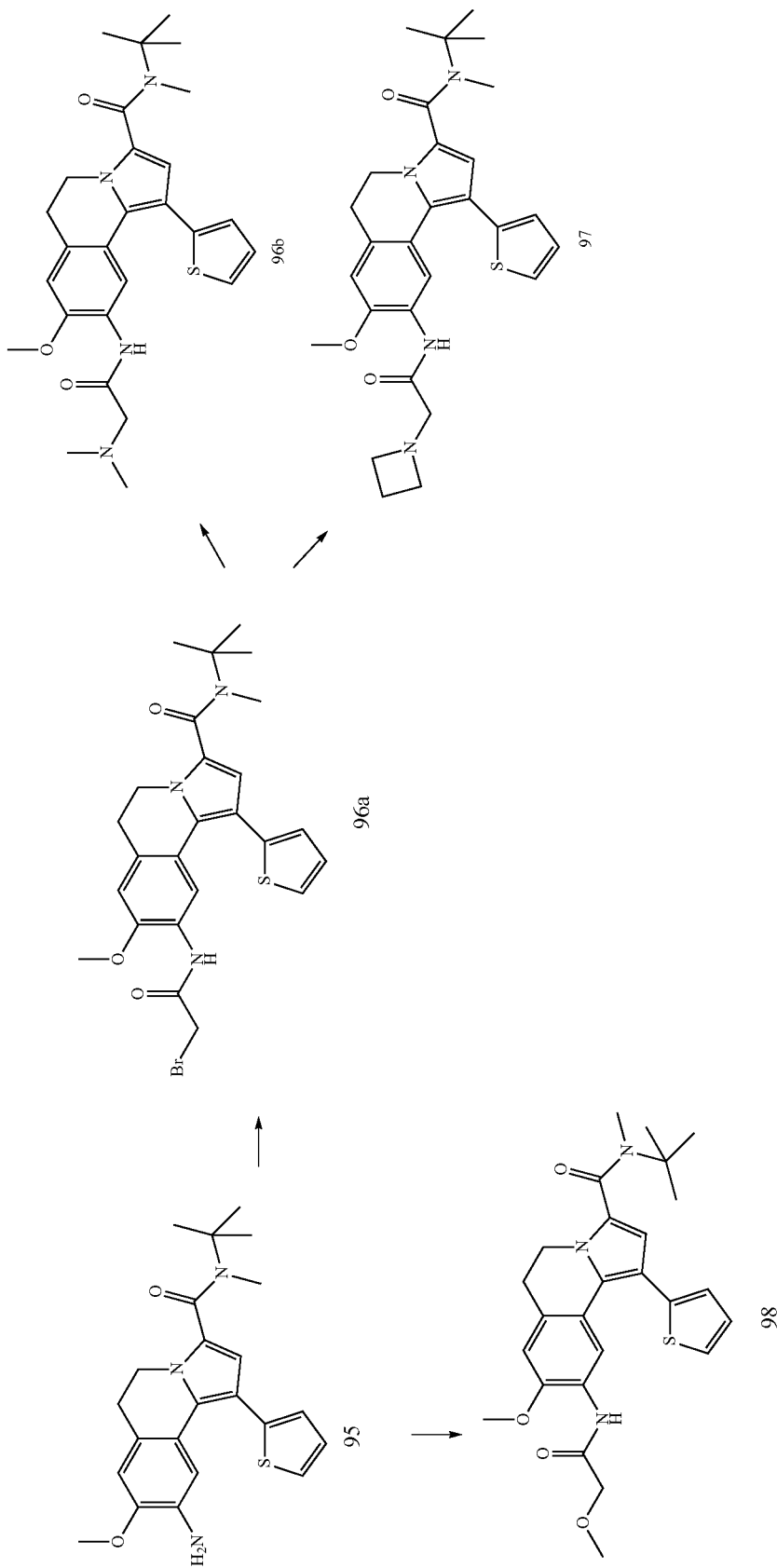

Example 96

9-(2-Dimethylamino-acetylamino)-8-methoxy-1-thiophen-2-yl-5,6,6 a,10a-tetrahydro-pyrrolo[2,1-α]isoquinoline-3-carboxylic acid tert-butyl-methyl-amide

(a). 9-(2-Bromo-acetylamino)-8-methoxy-1-thiophen-2-yl-5,6,6a,10a-tetrahydro-pyrrolo[2,1-α]isoquinoline-3-carboxylic acid tert-butyl-methyl-amide Bromoacetyl bromide (0.137 ml) was added to a stirred solution of the product of example 95 (500 mg) and DIPEA (0.425 ml) in dichloromethane (20 ml) over a period of 6 h. The reaction mixture was concentrated in vacuo.
Yield: 648 mg. LC/MS-ESI: $[M+H]^+=530.1/532.1$

(b). 9-(2-Dimethylamino-acetylamino)-8-methoxy-1-thiophen-2-yl-5,6,6 a,10a-tetrahydro-pyrrolo[2,1-α]isoquinoline-3-carboxylic acid tert-butyl-methyl-amide A mixture of the product of example 96a (100 mg), DIPEA (0.165 ml) and N,N-dimethylamine hydrochloric acid (66 mg) in THF (4 ml) was stirred at room temperature for 18 h. Reaction mixture was washed with water and brine, The organic layer was dried (MgSO$_4$), filtered and concentrated in vacuo. The residue was purified by preparative HPLC (0→80% acetonitrile, 0.1% TFA; system 1).
Yield: 33 mg (as TFA-salt). LC/MS-ESI: $[M+H]^+=495.2$; anal. HPLC: $R_t=24.61$ (Method 12); hFSHRago (CHO luc) $EC_{50}=2.8$ nM

Example 97

9-(2-Azetidin-1-yl-acetylamino)-8-methoxy-1-thiophen-2-yl-5,6-dihydro-pyrrolo[2,1-α]isoquinoline-3-carboxylic acid tert-butyl-methyl-amide A mixture of the product of example 96a (100 mg), DIPEA (0.165 ml) and azetidine (37 mg) in THF (4 ml) was stirred at room temperature for 18 h. Reaction mixture was washed with water and brine. The organic layer was dried (MgSO$_4$), filtered and concentrated in vacuo. Residue was purified by preparative HPLC (0→80% acetonitrile, 0.1% TFA; system 1).
Yield: 11 mg. LC/MS-ESI: $[M+H]^+=507.3$; anal. HPLC: $R_t=25.06$ (Method 12); hFSHRago (CHO luc) $EC_{50}=4.0$ nM

Example 98

8-Methoxy-9-(2-methoxy-acetylamino)-1-thiophen-2-yl-5,6-dihydro-pyrrolo[2,1-α]isoquinoline-3-carboxylic acid tert-butyl-methyl-amide A mixture of the product of example 95 (30 mg), triethylamine (10.2 µl) and methoxyacetyl chloride (6.7 µl) was stirred at room temperature for 3 h. The reaction mixture was diluted with dichloromethane and washed with water. The organic layer was dried (MgSO$_4$), filtered and concentrated in vacuo. The residue was purified by preparative HPLC (0→90% acetonitrile; system 1).
Yield: 16 mg. MS-ESI $[M+H]^+=482.5$; anal. HPLC: $R_t=35.92$ min (method 12); hFSHRago (CHO luc) $EC_{50}=1.4$ nM

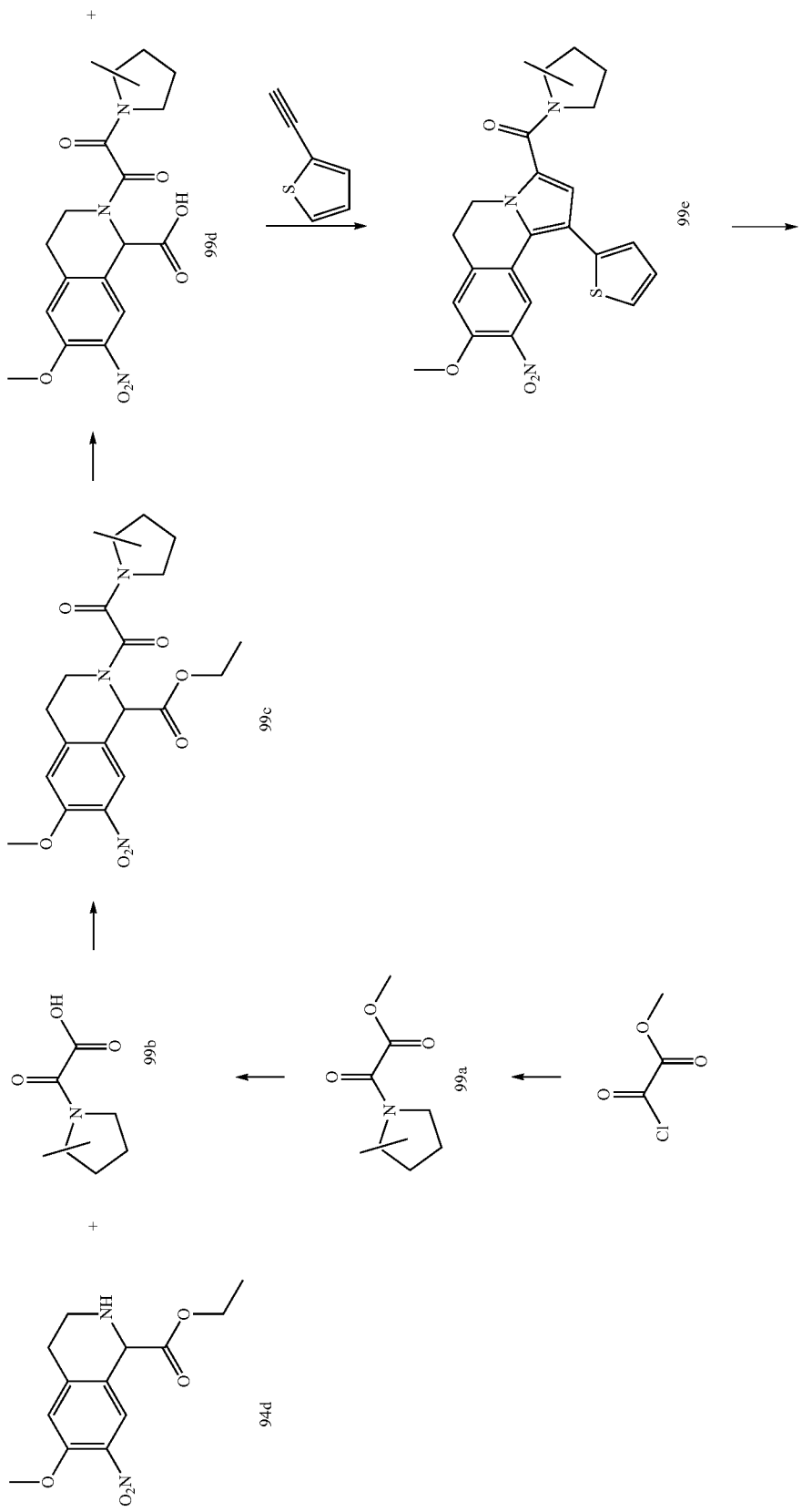

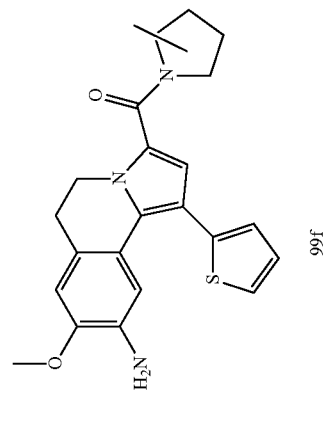
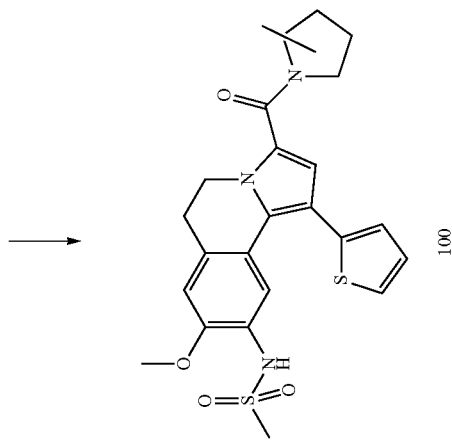
-continued
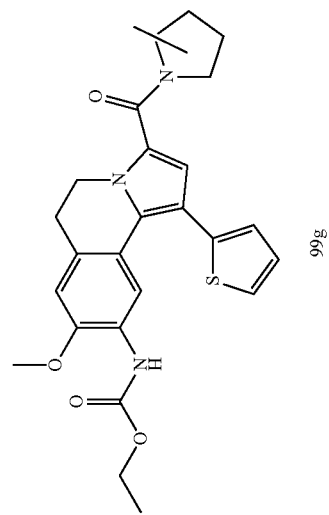

Example 99

[3-(2,2-Dimethyl-pyrrolidine-1-carbonyl)-8-methoxy-1-thiophen-2-yl-5,6-dihydro-pyrrolo[2,1-α]isoquinolin-9-yl]-carbamic acid ethyl ester

(a). (2,2-Dimethyl-pyrrolidin-1-yl)-oxo-acetic acid ethyl ester

Methyl oxalyl chloride (5 ml) was added dropwise to a solution of 2,2-dimethylpyrrolidine (8.11 g) and pyridine (5.7 ml) in dichloromethane (50 ml) at 0° C. After stirring for 1 h the reaction mixture was washed with an aqueous HCl solution (2 N) and brine. The organic layer was dried (MgSO$_4$), filtered and concentrated in vacuo.
Yield: 6.62 g.

(b). (2,2-Dimethyl-pyrrolidin-1-yl)-oxo-acetic acid

KOH (2.20 g) dissolved in methanol (100 ml) was added dropwise to a solution of the product of example 99a (6.62 g) in methanol (120 ml) at 0° C. The reaction mixture was warmed to room temperature and concentrated in vacuo. The residue was dissolved in water (30 ml), acidified with an aqueous H$_2$SO$_4$ solution (10%) to pH=4, filtered and dried under vacuum.
Yield: 3.35 g.

(c). 2-[2-(2,2-Dimethyl-pyrrolidin-1-yl)-2-oxo-acetyl]-6-methoxy-7-nitro-1,2,3,4-tetrahydro-isoquinoline-1-carboxylic acid ethyl ester A mixture of the product of example 94d (3.0 g), the product of example 99b (2.2 g), TBTU (5.16 g) and DIPEA (9.3 ml) in dichloromethane (150 ml) was stirred at room temperature for 1 h. The reaction mixture was washed with water and brine. The organic layer was dried (MgSO$_4$), filtered and concentrated in vacuo. The residue was purified by chromatography on silica gel in heptane/ethyl acetate [10/0→0/10 (v/v)] as eluent.
Yield: 4.37 g. LC/MS-ESI: [M+H]$^+$=434.2

(d). 2-[2-(2,2-Dimethyl-pyrrolidin-1-yl)-2-oxo-acetyl]-6-methoxy-7-nitro-1,2,3,4-tetrahydro-isoquinoline-1-carboxylic acid A mixture of the product of example 99c (4.37 g) and potassium hydroxide (1.13 g) in THF (100 ml) and water (50 ml) was stirred at room temperature for 1 h. The reaction mixture was acidified with an aqueous HCl solution (2 N) and extracted with ethyl acetate. The organic layer was washed with water and brine, dried (MgSO$_4$), filtered and concentrated in vacuo.
Yield: 3.18 g. LC/MS-ESI: [M+H]$^+$=406.2

(e). (2,2-Dimethyl-pyrrolidin-1-yl)-(8-methoxy-9-nitro-1-thiophen-2-yl-5,6-dihydro-pyrrolo[2,1-α]isoquinolin-3-yl)-methanone A mixture of the product of example 99d (3.18 g) and 2-ethynylthiophene (1.82 ml) in acetic anhydride (15 ml) was heated using microwave irradiation at 140° C. for 15 min. The reaction mixture was poured into ice water, neutralized with NaHCO$_3$ and extracted with ethyl acetate. The organic layer was washed with water and brine, dried (MgSO$_4$), filtered and concentrated in vacuo. The residue was crystallized from diethyl ether.
Yield: 2.28 g. LC/MS-ESI: [M+H]$^+$=452.2

(f). (9-Amino-8-methoxy-1-thiophen-2-yl-5,6-dihydro-pyrrolo[2,1-α]isoquinolin-3-yl)-(2,2-dimethyl-pyrrolidin-1-yl)-methanone Zinc (29.0 g) was added portionwise to a solution of the product of example 99e (10.0 g) in THF (500 ml) and acetic acid (12.7 ml) at 0° C. After stirring for 18 h at room temperature the reaction mixture was filtered over decalite. The filtrate was washed with saturated aqueous NaHCO$_3$ solution and brine. The organic layer was washed with water and brine, dried (MgSO$_4$), filtered and concentrated in vacuo.
Yield: 10.36 g: LC/MS-ESI: [M+H]$^+$=422.18

(g). [3-(2,2-Dimethyl-pyrrolidine-1-carbonyl)-8-methoxy-1-thiophen-2-yl-5,6-dihydro-pyrrolo[2,1-α]isoquinolin-9-yl]-carbamic acid ethyl ester A solution of the product of example 99f (50 mg), DIPEA (0.041 ml) and ethylchloroformate (0.011 ml) in dichloromethane (2 ml) was stirred at 20° C. for 2 h. The reaction mixture was washed with water and brine and concentrated in vacuo. The residue was purified by preparative HPLC (10→100% acetonitrile; system 1).
Yield: 38 mg. LC/MS-ESI: [M+H]$^+$=494.1; anal. HPLC: $R_t$=15.28 (Method 10); hFSHRago (CHO luc) $EC_{50}$=22 nM

Example 100

N-[3-(2,2-Dimethyl-pyrrolidine-1-carbonyl)-8-methoxy-1-thiophen-2-yl-5,6-dihydro-pyrrolo[2,1-α]isoquinolin-9-yl]-methanesulfonamide A solution of the product of example 99f (50 mg), DIPEA (0.041 ml) and methanesulphonyl chloride (0.011 ml) in dichloromethane (2 ml) was stirred at 20° C. for 2 h. The reaction mixture was washed with water and brine and concentrated in vacuo. The residue was purified by preparative HPLC (0→80% acetonitrile; system 1).
Yield: 25 mg. LC/MS-ESI: [M+H]$^+$=500.1; anal. HPLC: $R_t$=21.15 min (Method 10); hFSHRago (CHO luc) $EC_{50}$=1.0 nM

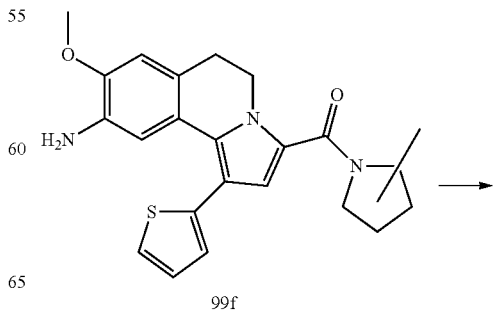

99f

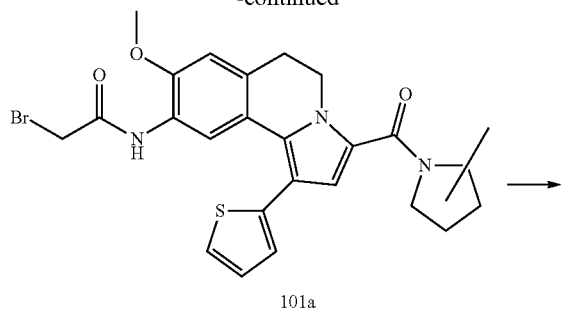

101a

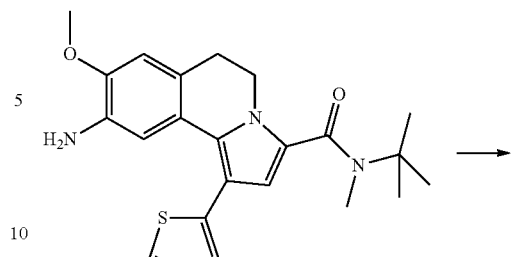

95

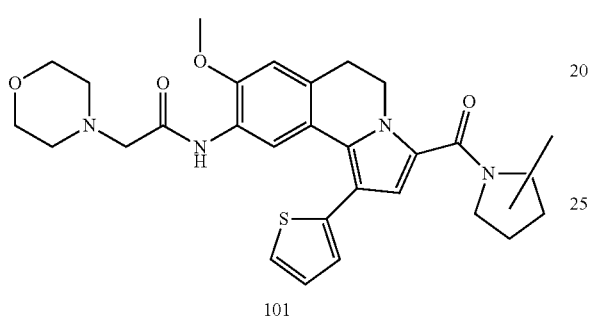

101

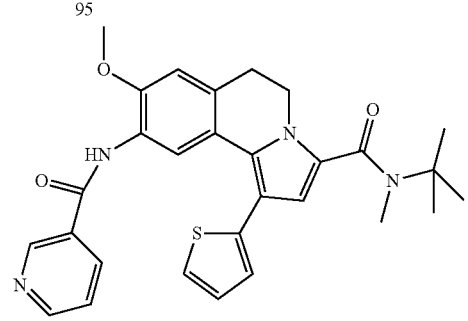

102

Example 101

N-[3-(2,2-Dimethyl-pyrrolidine-1-carbonyl)-8-methoxy-1-thiophen-2-yl-5,6-dihydro-pyrrolo[2,1-α]isoquinolin-9-yl]-2-morpholin-4-yl-acetamide (a). 2-Bromo-N-[3-(2,2-dimethyl-pyrrolidine-1-carbonyl)-8-methoxy-1-thiophen-2-yl-5,6-dihydro-pyrrolo[2,1-α]isoquinolin-9-yl]-acetamide Bromoacetyl bromide (0.155 ml) was added to a stirred solution of the product of example 99f (500 mg) and DIPEA (0.413 ml) in dichloromethane (20 ml) over a period of 6 h. The reaction mixture was concentrated in vacuo.

Yield: 643 mg. LC/MS-ESI: [M+H]$^+$=542.0/544.0

(b). N-[3-(2,2-Dimethyl-pyrrolidine-1-carbonyl)-8-methoxy-1-thiophen-2-yl-5,6-dihydro-pyrrolo[2,1-α]isoquinolin-9-yl]-2-morpholin-4-yl-acetamide A mixture of the product of example 101a (100 mg), DIPEA (0.165 ml) and morpholine (62 mg) in THF (4 ml) was stirred at room temperature for 18 h. The reaction mixture was washed with water and brine, dried (MgSO$_4$), filtered and concentrated in vacuo. The residue was purified by preparative HPLC (0→80% ACN, 0.1% TFA; system 1).

Yield: 95 mg (as TFA salt). LC/MS-ESI: [M+H]$^+$=549.2; anal. HPLC: R$_t$=27.19 min (Method 12); hFSHRago (CHO luc) EC$_{50}$=2.0 nM

Example 102

8-Methoxy-9-[(pyridine-3-carbonyl)-amino]-1-thiophen-2-yl-5,6-dihydro-pyrrolo[2,1-α]isoquinoline-3-carboxylic acid tert-butyl-methyl-amide A mixture of the product of example 95 (50 mg), pyridine-3-carboxylic acid (30 mg), TBTU (150 mg), DIPEA (300 μl) and HOBt (20 mg) in pyridine (1 ml) was stirred for 1 h at room temperature. The mixture was diluted with water and extracted with ethyl acetate. The organic layer was dried (MgSO$_4$), filtered and concentrated in vacuo. The crude material was purified by chromatography (heptane/acetone 1/1 v/v) and triturated using diethyl ether.

Yield: 30 mg. Mp 223-224° C., TLC R$_f$=0.25 (heptane/acetone 1/1); LC/MS-ESI: [M+H]$^+$=515.3; hFSHRago (CHO luc) EC$_{50}$=13.0 nM

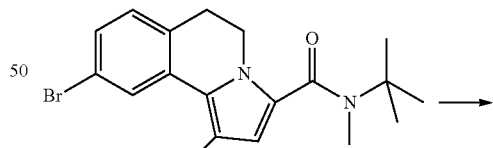

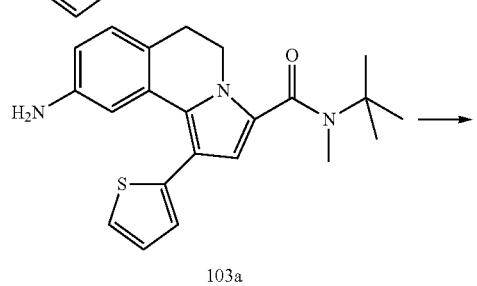

103a

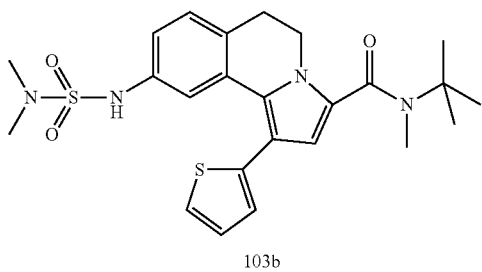

103b

Example 103

9-Dimethylaminosulfonylamino-1-thiophen-2-yl-5,6-dihydro-pyrrolo[2,1-α]isoquinoline-3-carboxylic acid tert-butyl-methyl-amide

(a). 9-Amino-1-thiophen-2-yl-5,6-dihydro-pyrrolo[2,1-α]isoquinoline-3-carboxylic acid tert-butyl-methyl-amide A solution of 9-bromo-1-thiophen-2-yl-5,6-dihydro-pyrrolo[2,1-α]isoquinoline-3-carboxylic acid tert-butyl-methyl-amide (500 mg), LiHMDS (1.25 ml 20% solution in THF), (tertBu)$_3$P (3 mg), Pd$_2$(dba)$_3$ (10 mg) in toluene (20 ml) was flushed with nitrogen and then heated at 100° C. for 16 hr. The reaction mixture was cooled and washed with NaOH solution (10 ml 2N) and water. The organic layer was dried (MgSO$_4$), filtered and concentrated in vacuo. The residue was purified by chromatography on silica (heptane/ethyl acetate).

Yield: 153 mg. LC/MS-ESI: [M+H]$^+$=380.

(b). 9-Dimethylaminosulfonylamino-1-thiophen-2-yl-5,6-dihydro-pyrrolo[2,1-α]isoquinoline-3-carboxylic acid tert-butyl-methyl-amide A solution of the product of example 103a (36 mg), triethylamine (20 mg), and dimethylsulphamoyl chloride (15 mg) in dichloromethane (1 ml) was stirred and heated using microwave irradiation at 140° C. for 5 min. The reaction was diluted with dichloromethane, washed with an aqueous HCl solution (2 N) and an aqueous NaHCO$_3$ solution (10%). The organic layer was dried (MgSO$_4$), filtered and concentrated in vacuo. The residue was purified by passing through a short silica column using toluene/EtOAc (2/1 v/v) as an eluent.

Yield: 13 mg. LC/MS-ESI: [M+H]$^+$=487; hFSHRago (CHO luc) EC$_{50}$=756.0 nM

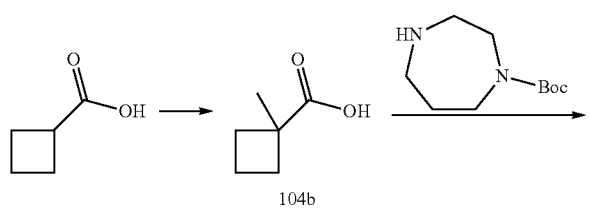

104b

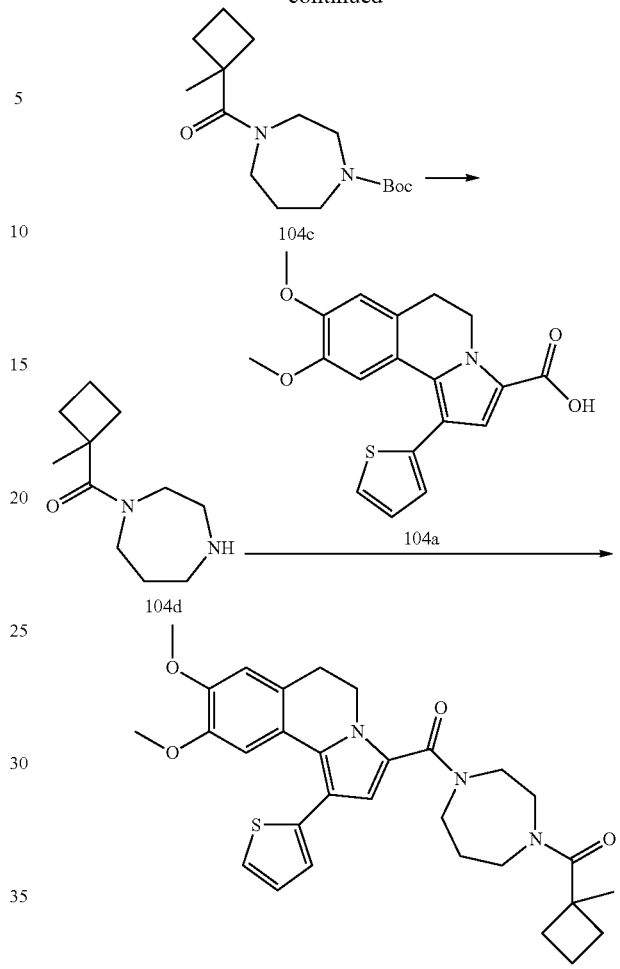

Example 104

(8,9-Dimethoxy-1-thiophen-2-yl-5,6-dihydro-pyrrolo[2,1-α]isoquinolin-3-yl)-[4-(1 methyl-cyclobutanecarbonyl)-[1,4]diazepan-1-yl]-methanone

(a). 8,9-Dimethoxy-1-thiophen-2-yl-5,6-dihydro-pyrrolo[2,1-α]isoquinoline-3-carboxylic acid The synthesis of 8,9-dimethoxy-1-thiophen-2-yl-5,6-dihydro-pyrrolo[2,1-α]iso-quinoline-3-carboxylic acid, starting from 2-(3,4-dimethoxy-phenyl)-ethylamine, was performed according to the method described for example 1i.

Yield: 3.16 g. MS-ESI: [M+H]$^+$=356.0

(b). 1-Methyl-cyclobutanecarboxylic acid

At 0° C., n-butyllithium (13.75 ml, 1.6M in heptane) was added dropwise to a solution of diisopropylamine (3.08 ml) in THF (30 ml). After stirring for 30 min at 0° C., the reaction mixture was cooled to −20° C. followed by dropwise addition of cyclobutanecarboxylic acid (0.956 ml) dissolved in THF (10 ml, dry) to yield an anion solution of approximately 0.25 M. At 0° C., methyl iodide (1.0 ml) was added dropwise to the freshly prepared anion solution (20 ml, 0.25M). After stirring for 18 h at room temperature, the reaction mixture was quenched with a sat. aqueous NH$_4$Cl solution and concentrated in vacuo to a small volume. The residue was dissolved in an aqueous NaOH solution (5%) and extracted with diethyl ether. The aqueous layer was acidified and extracted with dichloromethane. The organic layer was dried (MgSO$_4$), filtered and concentrated in vacuo.

Yield: 470 mg.

(c). 4-(1-Methyl-cyclobutanecarbonyl)-[1,4]diazepane-1-carboxylic acid tert-butyl ester HATU (1.71 g), [1,4]diazepane-1-carboxylic acid tert-butyl ester (0.813 ml) and DIPEA (3.58 ml) were added to a solution of the product of example 104b (470 mg) in dichloromethane (20 ml). After stirring for 2 h at room temperature, the reaction mixture was poured in an aqueous citric acid solution (10%) and extracted with ethyl acetate. The organic layer was washed with a sat. aqueous NaHCO$_3$ solution, dried (MgSO$_4$), filtered and concentrated in vacuo. The residue was purified by chromatography on silica in toluene/acetone [100/0→3/1 (v/v)] as eluent.

Yield: 591 mg. LC/MS-ESI: [M+H]$^+$=297.4

(d). [1,4]Diazepan-1-yl-(1-methyl-cyclobutyl)-methanone, hydrochloride

An HCl solution (4 ml, 4 N in dioxane) was added to a solution of the product of example 104c (580 mg) in dichloromethane (25 ml). After stirring for 4 h at room temperature, the reaction mixture was concentrated in vacuo.

Yield: 473 mg (as HCl-salt).

(e). (8,9-Dimethoxy-1-thiophen-2-yl-5,6-dihydro-pyrrolo[2,1-α]isoquinolin-3-yl)-[4-(1-methyl-cyclobutanecarbonyl)-[1,4]diazepan-1-yl]-methanone Amide formation of the product of example 104d (85 mg) with the product of example 104a (64 mg) was performed according to the method described for example 104c. The residue was purified by preparative HPLC (20%→100% acetonitrile; system 1).

Yield: 60.4 mg. LC/MS-ESI: [M+H]$^+$=534.3; anal. HPLC: R$_t$=18.67 min (method 2); hFSHRago (CHO luc) EC$_{50}$=3.0 nM

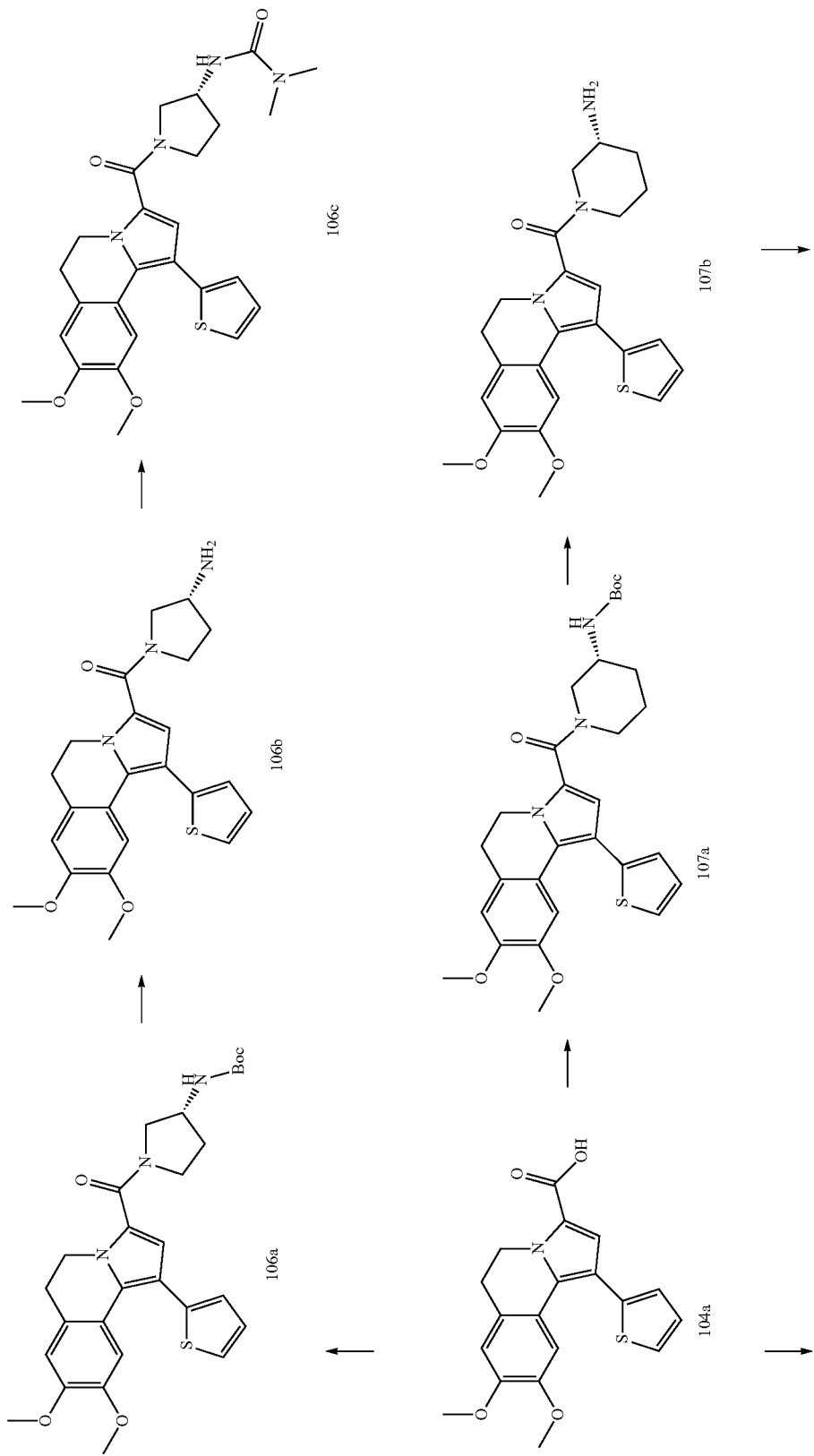

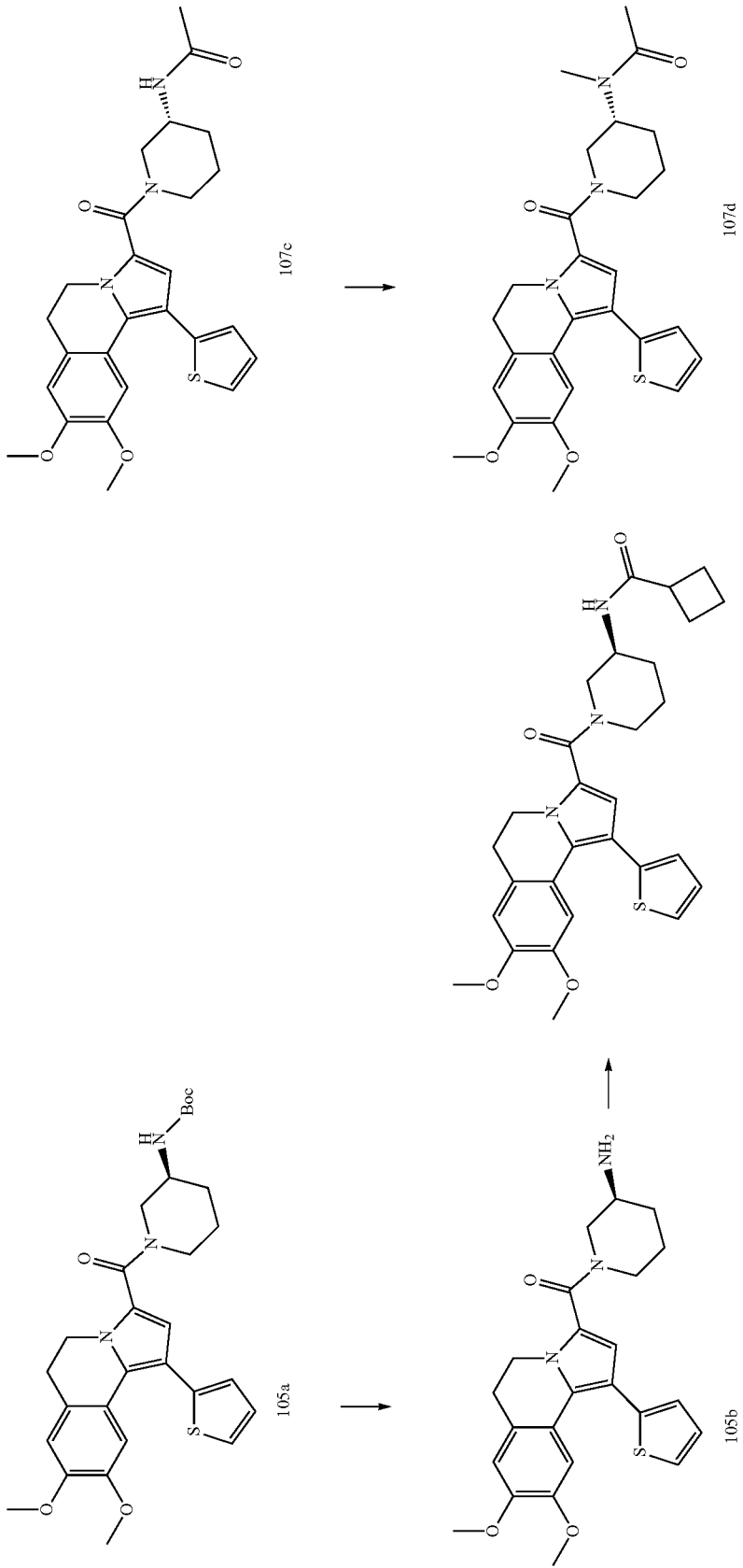

Example 105

Cyclobutanecarboxylic acid [(S)-1-(8,9-dimethoxy-1-thiophen-2-yl-5,6-dihydro-pyrrolo[2,1-α]isoquinoline-3-carbonyl)-piperidin-3-yl]-amide (a). [(S)-1-(8,9-Dimethoxy-1-thiophen-2-yl-5,6-dihydro-pyrrolo[2,1-α]isoquinoline-3-carbonyl)-piperidin-3-yl]-carbamic acid tert-butyl ester Amide formation of (S)-piperidin-3-yl-carbamic acid tert-butyl ester (168 mg) with the product of example 104a (200 mg) was performed according to the method described for example 104c. The residue was purified by chromatography on silica in heptane/ethyl acetate [1/1→0/100 (v/v)] as eluent.
Yield: 345 mg. MS-ESI: $[M+H]^+=538.4$ (b). ((S)-3-Amino-piperidin-1-yl)-(8,9-dimethoxy-1-thiophen-2-yl-5,6-dihydro-pyrrolo[2,1-α]isoquinolin-3-yl)-methanone Deprotection of the product of example 105a (302 mg) was performed according to the method described in example 104d.
Yield: 245 mg (as HCl-salt). LC/MS-ESI: $[M+H]^+=438.2$ (c). Cyclobutanecarboxylic acid [(S)-1-(8,9-dimethoxy-1-thiophen-2-yl-5,6-dihydro-pyrrolo[2,1-α]isoquinoline-3-carbonyl)-piperidin-3-yl]-amide A mixture of BOP (280 mg), DIPEA (0.276 ml), cyclobutanecarboxylic acid (45.7 µl) and the product of example 105b (150 mg) in dichloromethane (2 ml) was stirred for 5 h at room temperature. The reaction mixture was diluted with dichloromethane and washed with water and brine. The organic layer was dried ($MgSO_4$), filtered and concentrated in vacuo. The residue was purified by preparative HPLC (10→90% acetonitrile; system 1).
Yield: 89 mg. MS-ESI: $[M+H]^+=520.4$; anal. HPLC: $R_t=20.88$ min (method 2); hFSHRago (CHO luc) $EC_{50}=1730.0$ nM

Example 106

3-[(R)-1-(8,9-Dimethoxy-1-thiophen-2-yl-5,6-dihydro-pyrrolo[2,1-α]isoquinoline-3-carbonyl)-pyrrolidin-3-yl]-1,1-dimethyl-urea (a). [(R)-1-(8,9-Dimethoxy-1-thiophen-2-yl-5,6-dihydro-pyrrolo[2,1-α]isoquinoline-3-carbonyl)-pyrrolidin-3-yl]-carbamic acid tert-butyl ester Amide formation of (R)-pyrrolidin-3-yl-carbamic acid tert-butyl ester (428 mg) with the product of example 104a (400 mg) was performed according to the method described for example 104c.
Yield: 720 mg.

(b). ((R)-3-Amino-pyrrolidin-1-yl)-(8,9-dimethoxy-1-thiophen-2-yl-5,6-dihydro-pyrrolo[2,1-α]isoquinolin-3-yl)-methanone Deprotection of the product of example 106a (715 mg) was performed according to the method described in example 104d.
Yield: 494 mg (as HCl-salt). LC/MS-ESI: $[M+H]^+=424.2$ (c). 3-[(R)-1-(8,9-Dimethoxy-1-thiophen-2-yl-5,6-dihydro-pyrrolo[2,1-α]isoquinoline-3-carbonyl)-pyrrolidin-3-yl]-1,1-dimethyl-urea Acylation of the product of example 106b (50 mg) with N,N-dimethylcarbamoyl chloride (48 mg) was performed according to the method described in example 107c. The residue was purified by chromatography on silica in dichloromethane/methanol [100/0→95/5 (v/v)] as eluent.
Yield: 37.4 mg. LC/MS-ESI: $[M+H]^+=495.2$; anal. HPLC: $R_t=12.25$ min (method 2); hFSHRago (CHO luc) $EC_{50}=755.0$ nM

Example 107

N-[(R)-1-(8,9-Dimethoxy-1-thiophen-2-yl-5,6-dihydro-pyrrolo[2,1-α]isoquinoline-3-carbonyl)-piperidin-3-yl]-N-methyl-acetamide (a). [(R)-1-(8,9-Dimethoxy-1-thiophen-2-yl-5,6-dihydro-pyrrolo[2,1-α]isoquinoline-3-carbonyl)-piperidin-3-yl]-carbamic acid tert-butyl ester Amide formation of (R)-piperidin-3-yl-carbamic acid tert-butyl ester (168 mg) with the product of example 104a (200 mg) was performed according to the method described for example 104c. The residue was purified by chromatography on silica in heptane/(ethyl acetate/methanol 95/5) [1/1→0/1 (v/v)] as eluent.
Yield: 303 mg. MS-ESI: $[M+H]^+=538.4$ (b). ((R)-3-Amino-piperidin-1-yl)-(8,9-dimethoxy-1-thiophen-2-yl-5,6-dihydro-pyrrolo[2,1-α]isoquinolin-3-yl)-methanone Deprotection of the product of example 107a (300 mg) was performed according to the method described in example 104d.
Yield: 265 mg (as HCl-salt). LC/MS-ESI: $[M+H]^+=438.2$ (c). N-[(R)-1-(8,9-Dimethoxy-1-thiophen-2-yl-5,6-dihydro-pyrrolo[2,1-α]isoquinoline-3-carbonyl)-piperidin-3-yl]-acetamide Acetyl chloride (29.9 µl) and triethylamine (116 µl) were added to a solution of the product of example 107b (132 mg) in dichloromethane (2 ml). After stirring for 18 h at room temperature, the reaction mixture was diluted with dichloromethane and washed with water and brine. The organic layer was dried ($MgSO_4$), filtered and concentrated in vacuo. The residue was purified by preparative HPLC (10%→90% acetonitrile; system 1).
Yield: 92 mg. MS-ESI: $[M+H]^+=480.4$; anal. HPLC: $R_t=16.18$ min (method 2).

(d). N-[(R)-1-(8,9-Dimethoxy-1-thiophen-2-yl-5,6-dihydro-pyrrolo[2,1-α]isoquinoline-3-carbonyl)-piperidin-3-yl]-N-methyl-acetamide Methyl iodide (62.3 µl) and sodium hydride (7.3 mg, 60% dispersion on oil) were added to a solution of the product of example 107c (35 mg) in DMF (1 ml). After stirring for 3 h at 50° C., a few drops of water were added and the reaction mixture was concentrated in vacuo. The residue was dissolved in ethyl acetate and washed with water and brine. The organic layer was dried ($MgSO_4$), filtered and concentrated in vacuo. The residue was purified by preparative HPLC (10→90% acetonitrile; system 1).
Yield: 25.6 mg. MS-ESI: $[M+H]^+=494.4$; anal. HPLC: $R_t=18.51$ min (method 2); hFSHRago (CHO luc) $EC_{50}=30.9$ nM

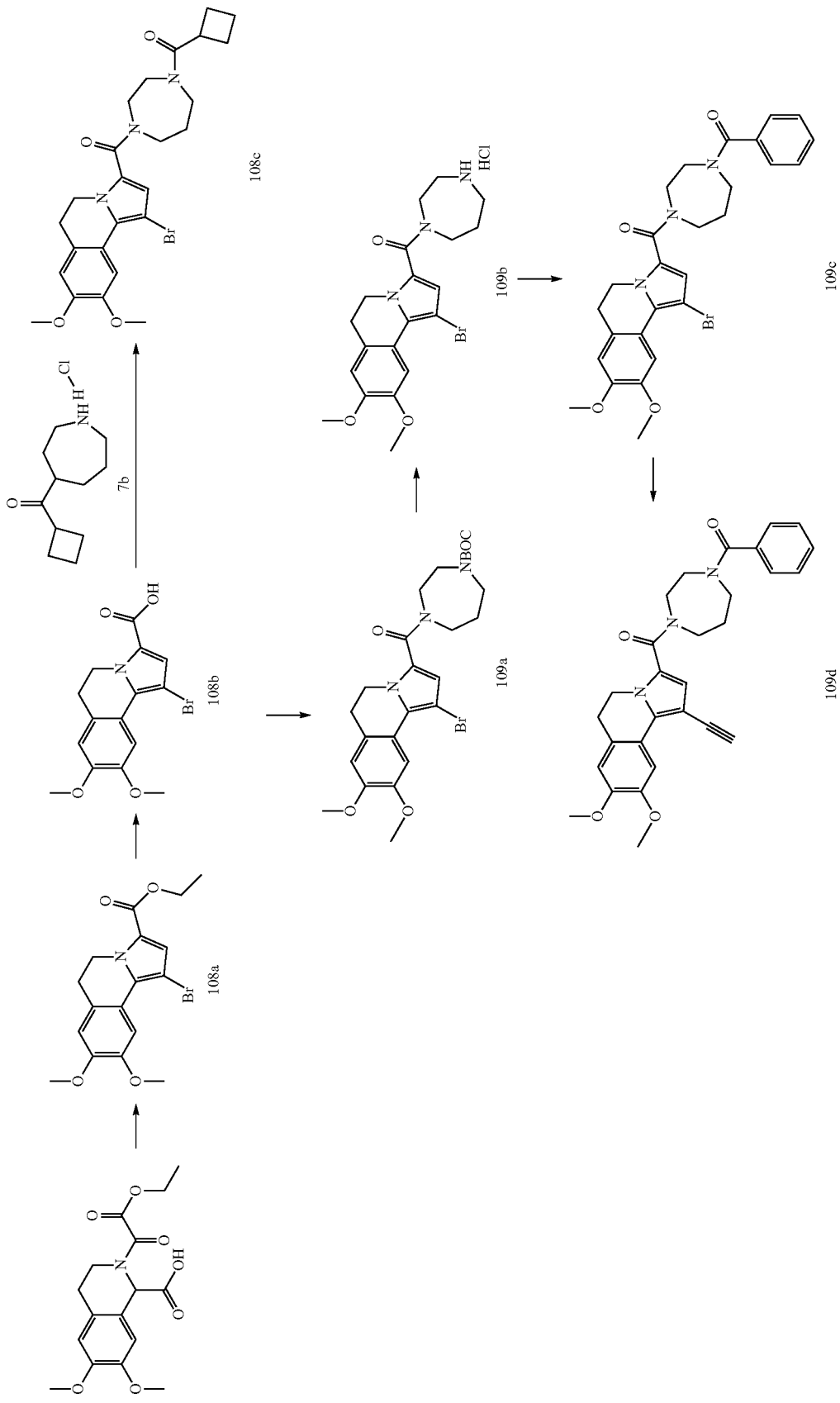

Example 108

(1-Bromo-8,9-dimethoxy-5,6-dihydro-pyrrolo[2,1-α] isoquinolin-3-yl)-(4-cyclobutane-carbonyl-[1,4]diazepan-1-yl)-methanone and (1-bromo-8,9-dimethoxy-5,6-dihydro-pyrrolo[2,1-α]isoquinolin-3-yl)-(4-cyclobutane-carbonyl-[1,4]diazepan-1-yl)-methanone

(a). 1-Bromo-8,9-dimethoxy-5,6-dihydro-pyrrolo[2,1-α]isoquinoline-3-carboxylic acid ethyl ester 2-Ethoxyoxalyl-6,7-dimethoxy-1,2,3,4-tetrahydro-isoquinoline-1-carboxylic acid was prepared in analogy with example 1g. A mixture of 2-ethoxyoxalyl-6,7-dimethoxy-1,2,3,4-tetrahydro-isoquinoline-1-carboxylic acid (3.4 g), trimethylsilyacetylene (2 g) and acetic anhydride (10 ml) in THF (10 ml) was stirred and heated using microwave irradiation at 150° C. for 5 min. The reaction mixture was poured into water and neutralized with sodium carbonate. The mixture was extracted with ethyl acetate and washed with water and brine. The organic layer was dried ($MgSO_4$), filtered and concentrated in vacuo. The residue was purified by chromatography on silica gel in heptane/ethyl acetate [10/0→6/4 (v/v)] as eluent.

To a mixture of the isolated product in DMF (20 ml) was added NBS (1.9 g). The reaction mixture was stirred at room temperature for 5 min. The reaction mixture was diluted with ethyl acetate and an aqueous HCl solution (0.2 M), and washed with water and brine. The organic layer was dried ($MgSO_4$), filtered and concentrated in vacuo. The residue was recrystallized from methanol.

Yield: 2.6 g. MS-ESI: $[M+H]^+$=380/382. anal. HPLC $R_t$=2.47 (method 10)

(b). (1-Bromo-8,9-dimethoxy-5,6-dihydro-pyrrolo[2,1-α]isoquinolin-3-yl)-(4-cyclobutane-carbonyl-[1,4]diazepan-1-yl)-methanone A mixture of the product of example 108a (2.6 g) and aqueous lithium hydroxide solution (3M)/dioxane [2:1 (v/v) 15 ml] was stirred and heated using microwave irradiation at 150° C. for 5 min. The reaction mixture was acidified to pH=5 with an aqueous HCl solution (6 M). The product was filtered and isolated.

Yield: 2.3 g; hFSHRago (CHO luc) $EC_{50}$=99.2 nM

(c). 2-Acetyl-9-ethoxy-8-methoxy-1-thiophen-2-yl-5,6-dihydro-pyrrolo[2,1-α]isoquinoline-3-carboxylic acid ethyl-isopropyl-amide A mixture of the product of example 108b (1.06 g), DIPEA (2.6 ml) and HATU (1.37 g) in dichloromethane (10 ml) was stirred at room temperature for 30 min. The product of example 7b was added and the reaction mixture was stirred at ambient temperature for 2 h. The reaction mixture was diluted with ethyl acetate and washed with an aqueous HCl solution (0.2 M), water and brine. The organic layer was dried ($MgSO_4$), filtered and concentrated in vacuo. The residue was purified by chromatography on silica gel in ethyl acetate [0→10% isopropylamine (v/v)] as eluent.

Yield: 1.4 g. LCMS-ESI: $[M+H]^+$=517/519. anal. HPLC $R_t$=2.92 min (method 10); hFSHRago (CHO luc) $EC_{50}$=100 nM

Example 109

(4-Benzoyl-[1,4]diazepan-1-yl)-(1-ethynyl-8,9-dimethoxy-5,6-dihydro-pyrrolo[2,1-α]isoquinolin-3-yl)-methanone

(a). 4-(1-Bromo-8,9-dimethoxy-5,6-dihydro-pyrrolo[2,1-α]isoquinoline-3-carbonyl)-[1,4]diazepane-1-carboxylic acid tert-butyl ester A mixture of the product of example 108b (1.0 g), HATU (1.61 g), triethylamine (0.8 ml) and tert-butyl 1,4-diazepane-1-carboxylate (1.1 ml) in dichloromethane (30 ml) was stirred at room temperature for 30 min. The reaction mixture was washed with aqueous citric acid solution (3%). The organic layer was washed with water, dried ($Na_2SO_4$), filtered and concentrated in vacuo. The residue was purified by chromatography on silica gel in dichloromethane/methanol [0→10% (v/v)] as eluent.

Yield: 1.39 g. LC/MS-ESI: $[M+H]^+$=536.0

(b). (1-Bromo-8,9-dimethoxy-5,6-dihydro-pyrrolo[2,1-α]isoquinolin-3-yl)-[1,4]diazepan-1-yl-methanone, hydrochloride HCl (6.3 ml, 4 N in dioxane) was added to a solution of the product of example 109a (1.34 g) in dioxane (50 ml). The reaction mixture was stirred at room temperature for 18 h. The reaction mixture was diluted with diethyl ether and the solids were collected by filtration.

Yield: 972 mg.

(c). (4-Benzoyl-[1,4]diazepan-1-yl)-(1-bromo-8,9-dimethoxy-5,6-dihydro-pyrrolo[2,1-α]isoquinolin-3-yl)-methanone A mixture of the product of example 109b (972 mg), DIPEA (740 μl) and benzoyl chloride (338 μl) in dichloromethane (50 ml) was stirred for 1 h at room temperature. The reaction mixture was subsequently washed with an aqueous HCl solution (2 N), water and brine. The organic layer was dried ($Na_2SO_4$) and concentrated in vacuo. The residue was purified by chromatography on silica gel in dichloromethane/methanol [0→5% (v/v)] as eluent.

Yield: 1.08 g. LC/MS-ESI: $[M+H]^+$=536.0

(d). (4-Benzoyl-[1,4]diazepan-1-yl)-(1-ethynyl-8,9-dimethoxy-5,6-dihydro-pyrrolo[2,1-α]isoquinolin-3-yl)-methanone To a solution of the product of example 109c (61 mg) in toluene (3 ml) was added tributylethynyl stannane (67 μl). The reaction mixture was sparged with nitrogen for 5 min, $Pd(PPh_3)_4$ (9 mg) was added and the solution was stirred for 30 min at 100° C. The reaction mixture was concentrated in vacuo. The residue was purified by chromatography on silica gel in dichloromethane/methanol [0→5% (v/v)] as eluent. The purest fractions were collected, concentrated and purified further by preparative HPLC (20%→70% acetonitrile; system 1).

Yield: 15 mg. LC/MS-ESI: $[M+H]^+$=484.3; anal. HPLC: $R_t$=14.36 min (method 2); hFSHRago (CHO luc) $EC_{50}$=76.2 nM

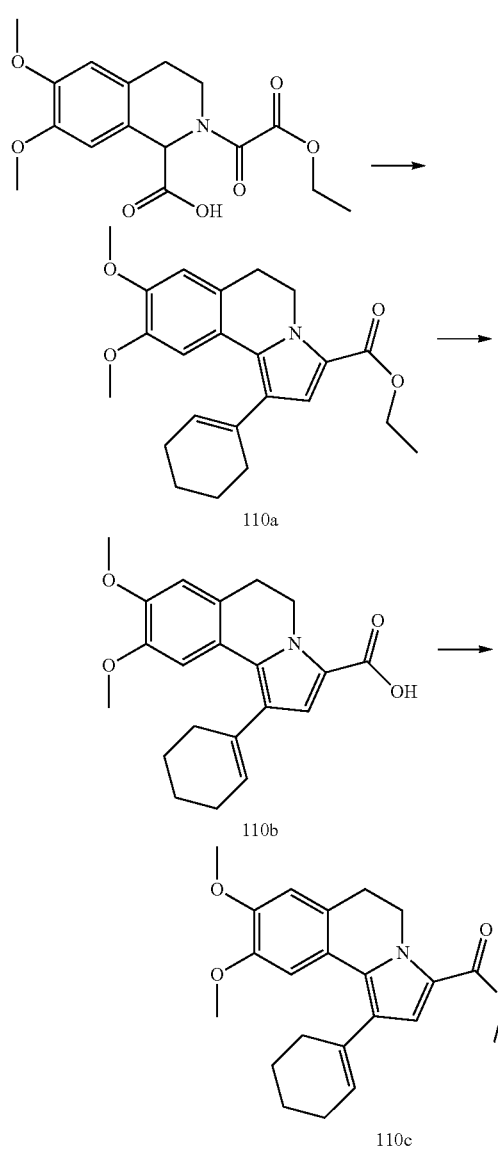

Example 110

1-Cyclohex-1-enyl-8,9-dimethoxy-5,6-dihydro-pyrrolo[2,1-α]isoquinoline-3-carboxylic acid tert-butyl-methyl-amide (a). 1-Cyclohex-1-enyl-8,9-dimethoxy-5,6-dihydro-pyrrolo[2,1-α]isoquinoline-3-carboxylic acid ethyl ester A mixture of 2-ethoxyoxalyl-6,7-dimethoxy-1,2,3,4-tetrahydro-isoquinoline-1-carboxylic acid (5 g), prepared in analogy with example 1g, 1-ethynyl-cyclohexene (14 mmol) and acetic anhydride (5 ml) in THF (15 ml) was stirred and heated using microwave irradiation at 120° C. for 15 min. The reaction mixture was diluted with ethyl acetate and aqueous sodium hydroxide solution (1 N), and washed with water and brine. The organic layer was dried (MgSO$_4$), filtered and concentrated in vacuo. The residue was purified by chromatography on silica gel in heptane/ethyl acetate [1/9→6/4 (v/v)] as eluent. The compound was isolated as a white solid.
Yield: 1.8 g. MS-ESI: [M+H]$^+$=440

(b). 1-Cyclohex-1-enyl-8,9-dimethoxy-5,6-dihydro-pyrrolo[2,1-α]isoquinoline-3-carboxylic acid A mixture of the product of example 110a (935 mg) in aqueous LiOH solution (2 M)/dioxane [1:1 (v/v) 40 ml] was heated at reflux for 1 h. The reaction mixture was cooled to room temperature and acidified to pH=5. The product was filtered and isolated as a brown solid.
Yield: 680 mg.

(c). 1-Cyclohex-1-enyl-8,9-dimethoxy-5,6-dihydro-pyrrolo[2,1-α]isoquinoline-3-carboxylic acid tert-butyl-methyl-amide A mixture of the product of example 110b (25 mg), N-methyl-N-tert-butyl-amine, HATU (40 mg) and DIPEA (61 μl) in dichloromethane (1 ml) was stirred and heated using microwave irradiation at 100° C. for 5 min. The reaction mixture was diluted with ethyl acetate and washed with water and an aqueous citric acid solution (3%). The organic layer was dried (MgSO$_4$), filtered and concentrated in vacuo. The residue was purified by chromatography on silica gel in heptane/ethyl acetate [0→6/4 (v/v)] as eluent.
Yield: 9 mg. MS-ESI: [M+H]$^+$=423; hFSHRago (CHO luc) EC$_{50}$=76.5 nM

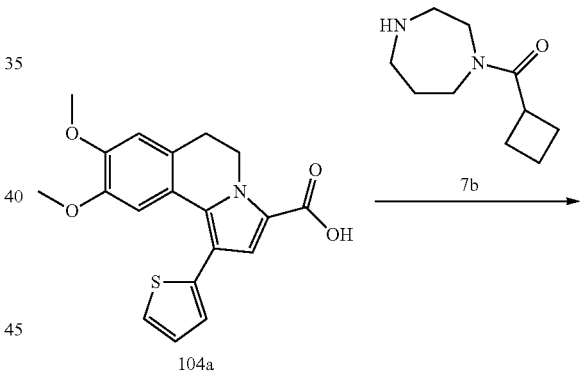

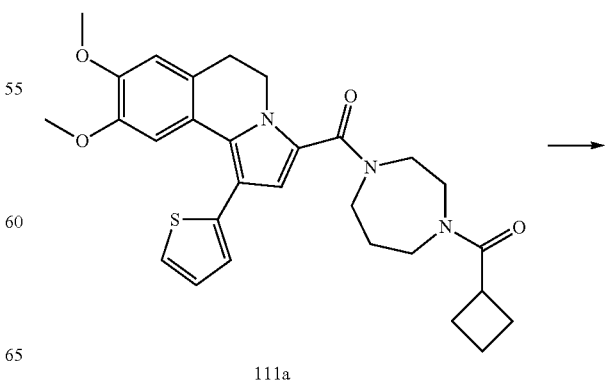

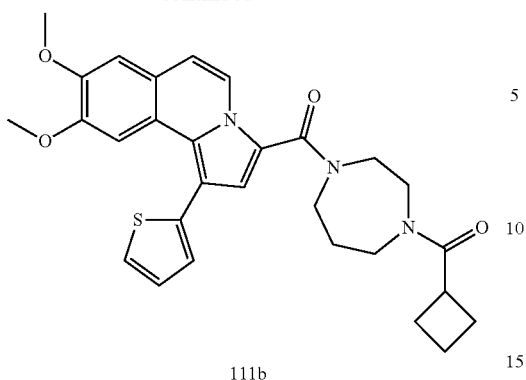

111b

Example 111

(4-Cyclobutanecarbonyl-[1,4]diazepan-1-yl)-(8,9-dimethoxy-1-thiophen-2-yl-pyrrolo[2,1-α]isoquinolin-3-yl)-methanone and (4-cyclobutanecarbonyl-[1,4]diazepan-1-yl)-(8,9-dimethoxy-1-thiophen-2-yl-5,6-dihydro-pyrrolo[2,1-α]isoquinolin-3-yl)-methanone (a). (4-Cyclobutanecarbonyl-[1,4]diazepan-1-yl)-(8,9-dimethoxy-1-thiophen-2-yl-5,6-dihydro-pyrrolo[2,1-α]isoquinolin-3-yl)-methanone Amide formation of the product of example 7b (30 mg) with the product of example 104a (70 mg) was performed according to the method described for example 7c. The residue was purified by preparative HPLC (10→90% acetonitrile; system 1).

Yield: 40 mg. MS-ESI: [M+H]$^+$=520.4; anal. HPLC: R$_t$=20.15 min (method 2); hFSHRago (CHO luc) EC$_{50}$=2.9 nM (b). (4-Cyclobutanecarbonyl-[1,4]diazepan-1-yl)-(8,9-dimethoxy-1-thiophen-2-yl-pyrrolo[2,1-α]isoquinolin-3-yl)-methanone Oxidation of the product of example 111a (15 mg) was performed according to the method described for example 36. The residue was purified by chromatography on silica in ethyl acetate as eluent.

Yield: 12.7 mg. LC/MS-ESI: [M+H]$^+$=518.2; anal. HPLC: R$_t$=2.64 min (method 2); hFSHRago (CHO luc) EC$_{50}$=4.9 nM

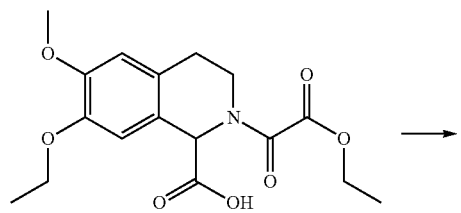

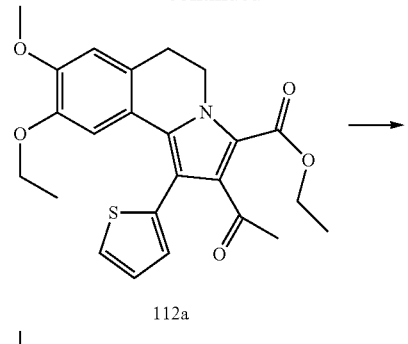

112a

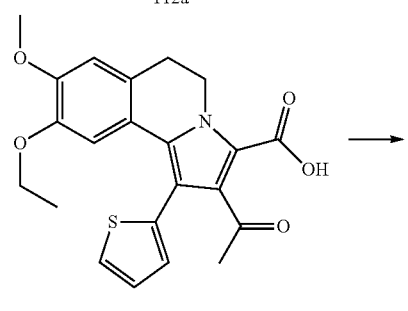

112b

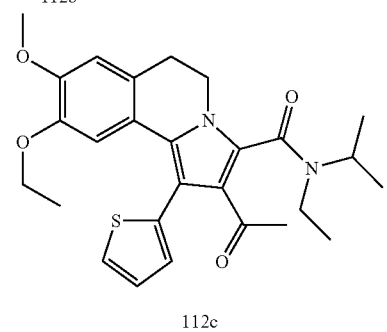

112c

Example 112

2-Acetyl-9-ethoxy-8-methoxy-1-thiophen-2-yl-5,6-dihydro-pyrrolo[2,1-α]isoquinoline-3-carboxylic acid ethyl-isopropyl-amide (a). 2-Acetyl-9-ethoxy-8-methoxy-1-thiophen-2-yl-5,6-dihydro-pyrrolo[2,1-α]isoquinoline-3-carboxylic acid ethyl ester 7-Ethoxy-2-ethoxyoxalyl-6-methoxy-1,2,3,4-tetrahydro-isoquinoline-1-carboxylic acid was prepared in analogy with example 1g. A mixture of 7-ethoxy-2-ethoxyoxalyl-6-methoxy-1,2,3,4-tetrahydro-isoquinoline-1-carboxylic acid (5 g), 4-thiophen-2-yl-but-3-yn-2-one (14 mmol) and acetic anhydride (5 ml) in THF (15 ml) was stirred and heated using microwave irradiation at 120° C. for 15 min. The reaction mixture was diluted with ethyl acetate and aqueous NaOH solution (1 N), and washed with water and brine. The organic layer was dried (MgSO$_4$), filtered and concentrated in vacuo. The residue was purified by chromatography on silica gel in heptane/ethyl acetate [1/9 →6/4 (v/v)] as eluent to yield a white solid.

Yield: 1.8 g. MS-ESI: [M+H]$^+$=440

(b). 2-Acetyl-9-ethoxy-8-methoxy-1-thiophen-2-yl-5,6-dihydro-pyrrolo[2,1-α]isoquinoline-3-carboxylic acid A mixture of the product of example 112a (840 mg) and an aqueous LiOH solution (2M)/dioxane [1:1 (v/v) 4 ml] was stirred and heated using microwave irradiation at 150° C. for 5 min. The reaction mixture was acidified to pH=5. The product was filtered and isolated as a white solid.
Yield: 776 mg. MS-ESI: $[M+H]^+=354$ (c). 2-Acetyl-9-ethoxy-8-methoxy-1-thiophen-2-yl-5,6-dihydro-pyrrolo[2,1-α]isoquinoline-3-carboxylic acid ethyl-isopropyl-amide A mixture of the product of example 112b (20 mg), N-ethyl-isopropylamine (12 µl), CIP (20 mg) and DIPEA (42 µl) in dichloromethane (1 ml) was stirred and heated using microwave irradiation at 100° C. for 5 min. The reaction mixture was concentrated in vacuo. The residue was purified by preparative HPLC (0→90% acetonitrile; system 1). TFA was removed by washing the product with an aqueous sodium bicarbonate solution.
Yield: 9 mg. MS-ESI: $[M+H]^+=481$; HPLC: $R_t=3.36$ min (method 1); hFSHRago (CHO luc) $EC_{50}=200.0$ nM Example 113

9-Difluoromethoxy-8-methoxy-1-thiazol-2-yl-5,6-dihydro-pyrrolo[2,1-α]isoquinoline-3-carboxylic acid tert-butyl-methyl-amide (a). 4-Difluoromethoxy-3-methoxy-benzaldehyde A mixture of 4-hydroxy-3-methoxybenzaldehyde (6 g), $Cs_2CO_3$ (25.7 g) and methyl 2-chloro-2,2-difluoroacetate (5 ml) in DMF (50 ml) was stirred at 90° C. for 1 h. At room temperature, the reaction mixture was poured into water and extracted with ethyl acetate. The organic layer was washed twice with water, brine, dried ($MgSO_4$), filtered and concentrated in vacuo. The residue was purified by chromatography on silica gel in heptane/ethyl acetate [1:1 (v/v)] as eluent.
Yield: 2.1 g. LC/MS-ESI: $[M+H]^+=203.1$ (b). 1-Difluoromethoxy-2-methoxy-4-((E)-2-nitro-vinyl)-benzene A mixture of the product of example 113a (2.1 g) and ammonium acetate (0.76 g) in nitromethane (15 ml) was stirred at 100° C. for 1 h. The reaction mixture was concentrated in vacuo and the residue was dissolved in dichlo-

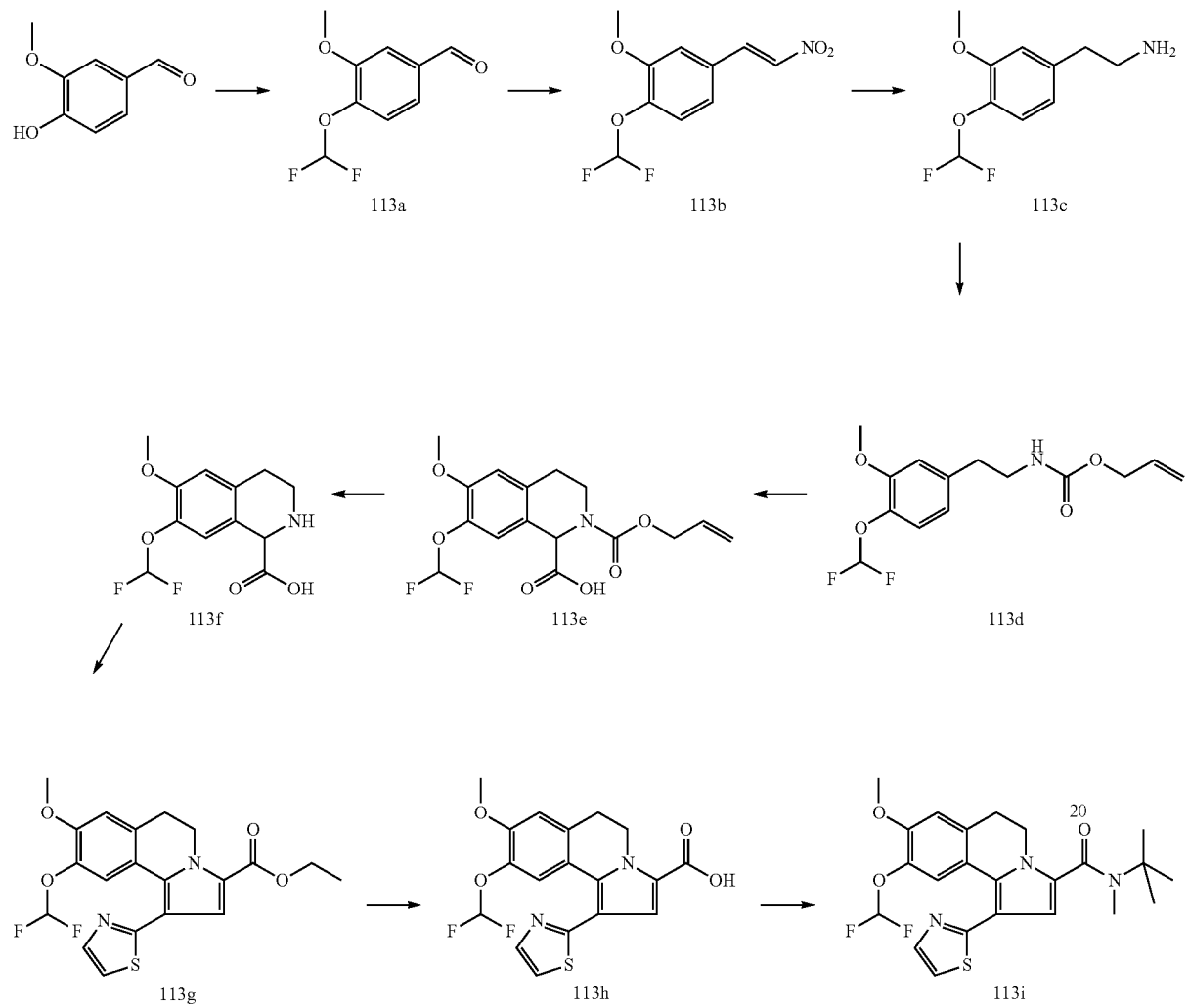

romethane. The organic layer was washed with water, brine, dried (MgSO$_4$), filtered and concentrated in vacuo. The residue was purified by chromatography on silica gel in heptane/ethyl acetate [2:1 (v/v)] as eluent.

Yield: 1.36 g. LC/MS-ESI: [M+H]$^+$=246.0

(c). 2-(4-Difluoromethoxy-3-methoxy-phenyl)-ethylamine

At 0° C., a solution of the product of example 113b (1.36 g) in dry THF (5 ml) was added dropwise to a mixture of lithium aluminum hydride in dry THF (10 ml) and diethyl ether (10 ml). After stirring at 65° C. for 2 h, the reaction mixture was allowed to reach room temperature and quenched with 5 ml water in THF (12 ml). An aqueous NaOH solution (2.5 ml 2 M) and water (1.3 ml) were added. The mixture was filtered over decalite. The filtrate was concentrated in vacuo and dissolved in ethyl acetate. The organic layer was washed twice with an aqueous HCl solution (1 M). The aqueous layer was basified with an aqueous NaOH solution (2 M) until pH=10 and extracted with ethyl acetate. The organic layer was washed with brine, dried (MgSO$_4$), filtered and concentrated in vacuo.

Yield: 760 mg. MS-ESI: [M+H]$^+$=218.3

(d). [2-(4-Difluoromethoxy-3-methoxy-phenyl)-ethyl]-carbamic acid allyl ester At 0° C., a solution of allyl chloroformate (450 µl) in dichloromethane (5 ml) was added dropwise to a solution of the product of example 113c (760 mg) and DIPEA (0.9 ml) in dichloromethane (25 ml). After stirring at room temperature for 2 h, the reaction mixture was washed with an aqueous HCl solution (1 M), a sat. aqueous NaHCO$_3$ solution, brine, dried (MgSO$_4$), filtered and concentrated in vacuo. The residue was purified by chromatography on silica gel in heptane/ethyl acetate [2:1 (v/v)] as eluent.

Yield: 669 mg. MS-ESI: [M+H]$^+$=302.3

(e). 7-Difluoromethoxy-6-methoxy-3,4-dihydro-1H-isoquinoline-1,2-dicarboxylic acid 2-allyl ester At 0° C., concentrated sulfuric acid (2.5 ml) was added dropwise to a mixture of the product of example 113d (670 mg) and glyoxylic acid monohydrate (307 mg) in acetic acid (8 ml). After stirring at room temperature for 1 h, the reaction mixture was poured onto ice-water and extracted with dichloromethane. The organic layer was washed with water, brine, dried (MgSO$_4$), filtered and concentrated in vacuo. The residue was purified by chromatography on silica gel in heptane/ethyl acetate [1:4 (v/v)] as eluent.

Yield: 613 mg.

(f). 7-Difluoromethoxy-6-methoxy-1,2,3,4-tetrahydro-isoquinoline-1-carboxylic acid A mixture of the product of example 113e (610 mg), dimedone (359 mg) and Pd(PPh$_3$)$_4$ (1.97 g) in THF (5 ml) and water (0.5 ml) was stirred at 65° C. for 1 h. The reaction mixture became cloudy. At room temperature, diethyl ether (5 ml) was added and the mixture was cooled in an ice-bath. The solids were collected by filtration and dried in vacuo (50° C.) for 18 h.

Yield: 350 mg

(g). 9-Difluoromethoxy-8-methoxy-1-thiazol-2-yl-5,6-dihydro-pyrrolo[2,1-α]isoquinoline-3-carboxylic acid ethyl ester A mixture of the product of example 113f (85 mg) and ethyl oxalyl chloride (38 µl) in THF (2 ml) was stirred and heated using microwave irradiation at 100° C. for 5 min. The reaction mixture was concentrated in vacuo. A mixture of the residue and 2-ethynyl-thiazole (102 mg) in acetic anhydride (3 ml) was heated using microwave irradiation at 140° C. for 15 min. The reaction mixture was diluted with dichloromethane and washed with a sat. aqueous NaHCO$_3$ solution, brine, dried (MgSO$_4$), filtered and concentrated in vacuo. The residue was purified by chromatography on silica gel in heptane/ethyl acetate [2:1 (v/v)] as eluent.

Yield: 48 mg. MS-ESI: [M+H]$^+$=421.1

(h). 9-Difluoromethoxy-8-methoxy-1-thiazol-2-yl-5,6-dihydro-pyrrolo[2,1-α]isoquinoline-3-carboxylic acid A mixture of the product of example 113g (48 mg) and solid KOH (19 mg) in ethanol (2 ml) and water (2 ml) was stirred at 80° C. for 1 h. At room temperature, the reaction mixture was acidified with an aqueous citric acid solution (1.0 M). The aqueous layer was extracted with dichloromethane and the organic layer washed with brine, dried (MgSO$_4$), filtered and concentrated in vacuo.

Yield: 37 mg. MS-ESI: [M+H]$^+$=392.9

(i). 9-Difluoromethoxy-8-methoxy-1-thiazol-2-yl-5,6-dihydro-pyrrolo[2,1-α]isoquinoline-3-carboxylic acid tert-butyl-methyl-amide A mixture of the product of example 113h (37 mg), DIPEA (82 µl), tert-butyl-methyl-amine (23 µl) and HATU (54 mg) in dichloromethane (3 ml) was stirred at room temperature for 18 h. The reaction mixture was washed with an aqueous HCl solution (0.1 N) and brine. The organic layer was dried (MgSO$_4$), filtered and concentrated in vacuo. The residue was purified by preparative HPLC (20→100% acetonitrile; system 1).

Yield: 28 mg. MS-ESI: [M+H]$^+$=462.3; anal. HPLC: R$_t$=17.31 min (method 7); hFSHRago (CHO luc) EC$_{50}$=39.6 nM

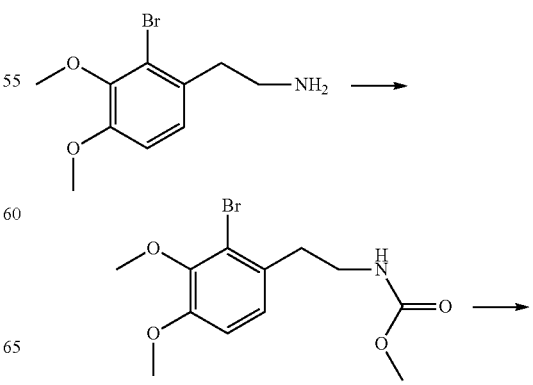

171

-continued

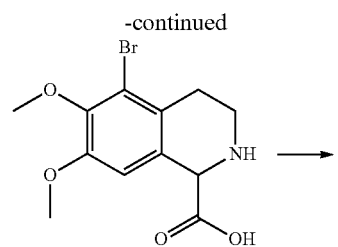

↓

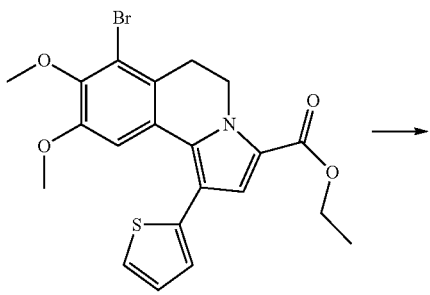

↓

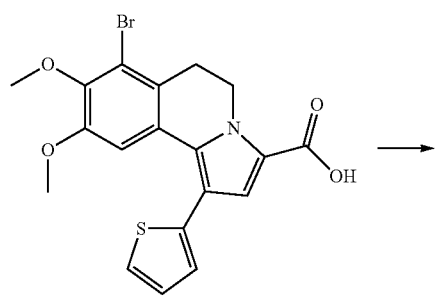

↓

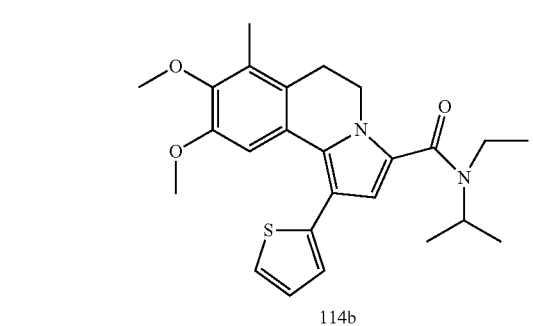
114a

↓

[structure 114b]

172

Example 114

8,9-Dimethoxy-7-methyl-1-thiophen-2-yl-5,6-dihydro-pyrrolo[2,1-α]isoquinoline-3-carboxylic acid ethyl-isopropyl-amide

(a). 7-Bromo-8,9-dimethoxy-1-thiophen-2-yl-5,6-dihydro-pyrrolo[2,1-α]isoquinoline-3-carboxylic acid ethyl-isopropyl-amide 7-Bromo-8,9-dimethoxy-1-thiophen-2-yl-5,6-dihydro-pyrrolo[2,1-α]isoquinoline-3-carboxylic acid ethyl-isopropyl-amide was prepared similar to example 1 from 2-(2-bromo-3,4-dimethoxy-phenyl)-ethylamine. The preparation of 2-(2-bromo-3,4-dimethoxy-phenyl)-ethylamin can be found in literature: J. Weinstock, et al., J. Med. Chem., 29, 2315 (1986); J. E. Toth, P. R. Hamann and P. L. Fuchs, J. Org. Chem., 53, 4694 (1988).

$^1$H NMR (CDCl$_3$) 1.28 (9H, 3×CH$_3$), 3.15 (t, 2H, H-6), 4.20 (t, 2H, H-5), 4.65 (m, 1H, CH-isopropyl), 6.40 (s, 1H, H2-pyrrole), 6.97 (s, 1H, H9), 3.48 (s, 3H, OCH$_3$), 3.84 (s, 3H, OCH$_3$); LC/MS-ESI: [M+H]$^+$=504.

(b). 8,9-Dimethoxy-7-methyl-1-thiophen-2-yl-5,6-dihydro-pyrrolo[2,1-α]isoquinoline-3-carboxylic acid ethyl-isopropyl-amide To a solution of the product of example 114a (50 mg) in dry THF (2 ml) was added at −70° C., n-butyllithium solution (70 μl of 1.6 M in heptane). The mixture was stirred for 30 min. Methyl iodide (100 μl) was added. The mixture was stirred for 30 min at −70° C. and for 1 h at ambient temperature. The mixture was poured into water and extracted with ethyl acetate. The organic layer was dried (MgSO$_4$), filtered and concentrated in vacuo. The residue was purified by passing through a short silica column, employing heptane/ethyl acetate (1/1 v/v) as eluent.

Yield: 25 mg. LC/MS-ESI: [M+H]$^+$=439; hFSHRago (CHO luc) EC$_{50}$=321.0 nM

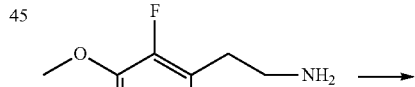

↓

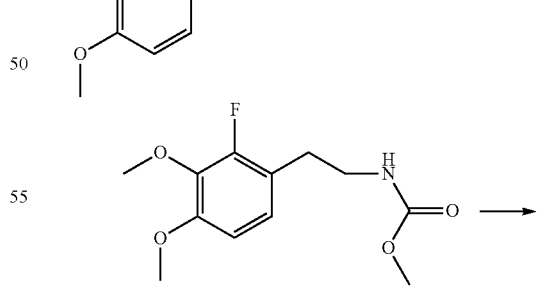

↓

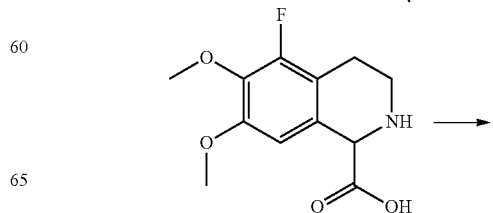

↓

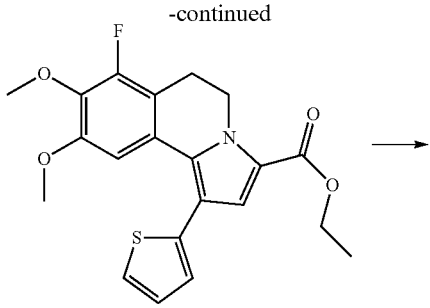

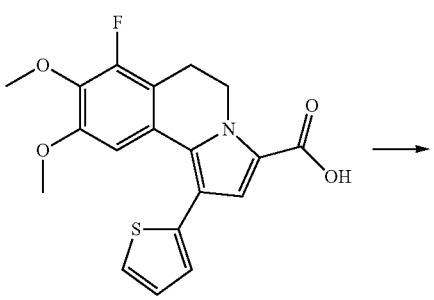

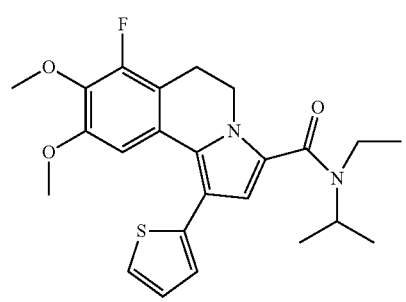

115

Example 115

7-Fluoro-8,9-dimethoxy-1-thiophen-2-yl-5,6-dihydro-pyrrolo[2,1-a]isoquinoline-3-carboxylic acid ethyl-isopropyl-amide This product was prepared in a similar fashion as earlier described in example 1 starting from 2-(2-fluoro-3,4-dimethoxy-phenyl)-ethylamine (D. L. Ladd and J. Weinstock, *J. Org. Chem.*, 46, 203 (1981).

LC/MS-ESI: [M+H]$^+$=442; hFSHRago (CHO luc) EC$_{50}$=937.0 nM

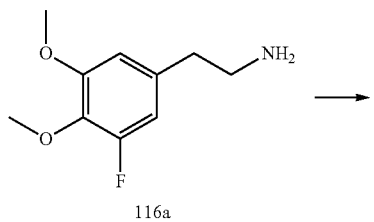

116a

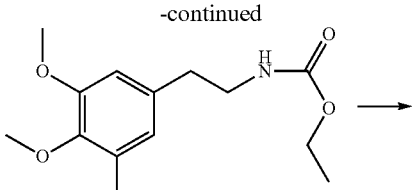

116b

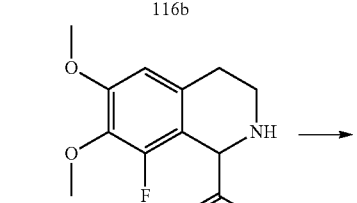

116c

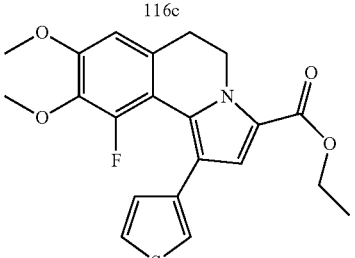

116d

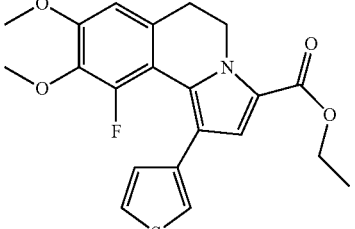

116e

Example 116

10-Fluoro-8,9-dimethoxy-1-thiophen-3-yl-5,6-dihydro-pyrrolo[2,1-a]isoquinoline-3-carboxylic acid ethyl-isopropyl-amide (a). 2-(3-Fluoro-4,5-dimethoxy-phenyl)-ethylamine This product can be prepared from commercially available 3-fluoro-5-hydroxy-4-methoxy-benzaldehyde according to routine procedures: K. L. Kirk, D. Cantacuzene, B. Collins, G. T. Chen, Y. Nimit, C. R. Creveling, *J. Med. Chem.*, 25, 680, (1982); J. Dixon, F. Ince, A. C. Tinker, Eur. Pat. App. 0.142.283 (1984). Alternatively, from 2-allyloxy-1-fluoro-3-methoxy-benzene as described by M. T. Clark, D. D. Miller, *Tetrahedron Lett.*, 26, 4299 (1985).

(b). [2-(3-Fluoro-4,5-dimethoxy-phenyl)-ethyl]-carbamic acid ethyl ester

To a solution of 2-(3-fluoro-4,5-dimethoxy-phenyl)-ethylamine (576 mg) and triethylamine (0.8 ml) in dichloromethane (20 ml) was added dropwise at 0° C. ethylchloroformate (300 μl). The mixture was stirred for 1 h, poured into ice water, neutralized with NaHCO₃ and extracted with dichloromethane. The organic layers were separated, dried (MgSO₄), filtered and concentrated in vacuo. The residue was passed through a short silica column (heptane/ethyl acetate as eluent).

Yield: 210 mg. $^1$H NMR (CDCl₃): δ 6.54 (2, m, ArH's), 4.65 (s, 1, NH), 4.1 and 2.75 (t, 2, —CH₂—), 3.4 (m, 2, —CH₂—), 1.2 (t, 3, ethyl), 4.1 (q, 2, ethyl), 3.86, and 3.90 (2xs, 6, OCH₃).

(c). 8-Fluoro-6,7-dimethoxy-1,2,3,4-tetrahydro-isoquinoline-1-carboxylic acid To the product of example 116b (210 mg) in acetic acid (3 ml) was added glyoxylic acid monohydrate (80 mg). At 0° C., sulphuric acid (1 ml) was added dropwise. After stirring for 30 min, the mixture was diluted with water and extracted with dichloromethane. The combined organic layers were dried (MgSO₄), filtered and concentrated in vacuo. The residue was treated with an aqueous LiOH solution (3 ml 3 M) using microwave irradiation at 190° C. for 5 min in order to hydrolyze the carbamate. The pH of the reaction was adjusted to 5.5 and the mixture was freeze-dried.

Yield: 520 mg.

(d). 10-Fluoro-8,9-dimethoxy-1-thiophen-3-yl-5,6-dihydro-pyrrolo[2,1-α]isoquinoline-3-carboxylic acid ethyl ester A mixture of the product of example 116c (500 mg) and ethyloxalyl chloride (250 mg) in THF (3 ml) was stirred using microwave irradiation at 100° C. for 5 min to form the N-oxalate. Then, acetic anhydride (1 ml) and 3-ethynyl-thiophene (220 mg) were added. The mixture was heated at 140° C. using microwave irradiation for 5 min. The mixture was poured into water, stirred for 15 min, extracted with ethyl acetate and washed until neutral with NaHCO₃ solution. The combined organic layers were dried (MgSO₄), filtered and concentrated in vacuo. The residue was purified by silica gel chromatography (heptane/ethyl acetate).

Yield: 60 mg.

(e). 10-Fluoro-8,9-dimethoxy-1-thiophen-3-yl-5,6-dihydro-pyrrolo[2,1-α]isoquinoline-3-carboxylic acid ethyl-isopropyl-amide The product of example 116d was saponified with LiOH in dioxane-water (1:1 v/v) and coupled with ethyldiisopropyl amine using the method described in example 105c.

Yield: 9 mg. $^1$H NMR (CDCl₃) δ 6.43 (s, 1H, pyrrole H), 6.65 (br s, 1H, H7-Ar), 3.78 (s, 3H, OC H₃), 3.90 (s, 3H, OC H₃), 2.98 (t, 2H, H-6), 4.20 (t, 2H, H5), 1.25 (9H, isopropyl and ethyl CH₃), 4.70 (m, 1H, isopropyl CH), 3.45 (m, 2H, NCH₂); LC/MS-ESI: [M+H]⁺=442; hFSHRago (CHO luc) EC₅₀=318.0 nM

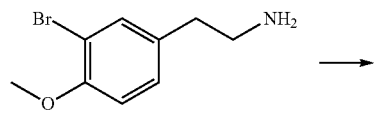

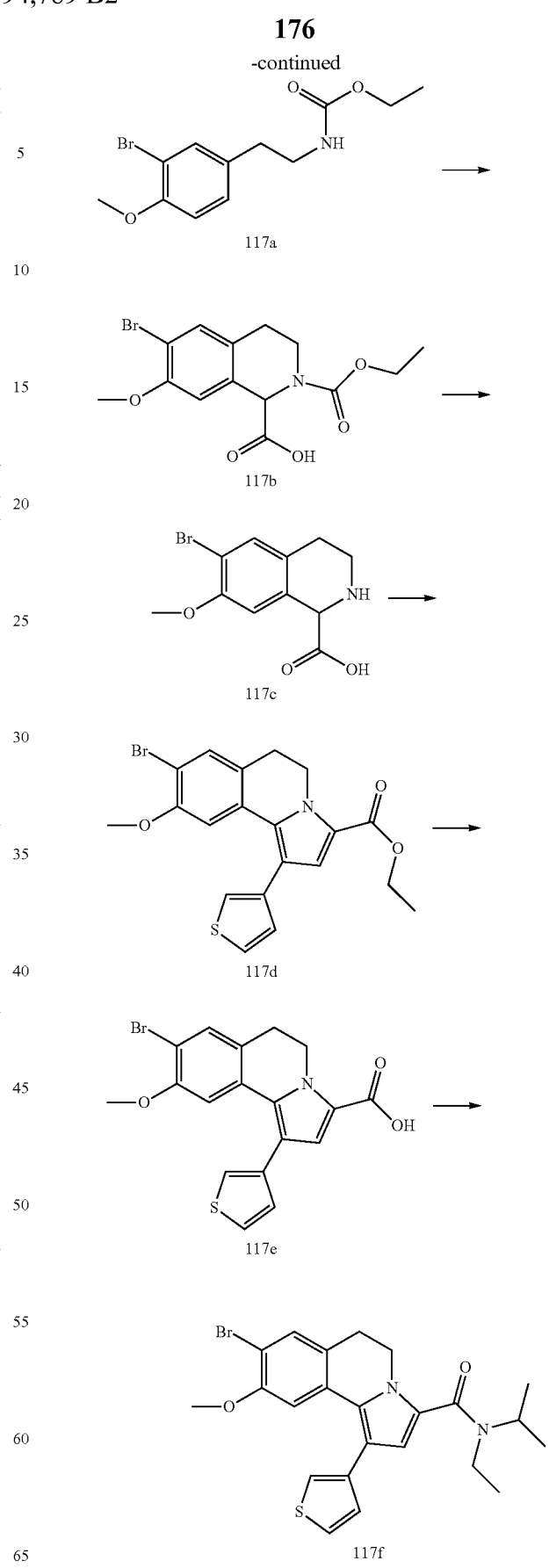

Example 117

8-Bromo-9-methoxy-1-thiophen-3-yl-5,6-dihydropyrrolo[2,1-α]isoquinoline-3-carboxylic acid ethylisopropyl-amide

(a). [2-(3-Bromo-4-methoxy-phenyl)-ethyl]-carbamic acid ethyl ester

To a solution of 3-methoxy-4-bromophenethylamine (2.3 g) and triethylamine (2.7 ml) in dichloromethane (20 ml) was added dropwise at 0° C. ethylchloroformate (1.5 ml). After stirring for 3 h, the reaction mixture was washed with water and 10% $NaHCO_3$. The organic layer was dried ($MgSO_4$), filtered and concentrated in vacuo. The residue was purified by chromatography on silica gel using heptane/ethyl acetate (1/1 v/v) as eluent.

Yield: 2.9 g. TLC $R_f$=0.35 (heptane/ethyl acetate 1/1); LC/MS-ESI: $[M+H]^+$=302/304.

(b). 6-Bromo-7-methoxy-3,4-dihydro-1H-isoquinoline-1,2-dicarboxylic acid 2-ethyl ester A solution of the product of example 117a (2.7 g) and glyoxylic acid (1.1 g) in acetic acid (12 ml) was treated with sulphuric acid (4 ml) at 5-10° C. The mixture was stirred at room temperature for 16 h and poured into ice water. The mixture was extracted with dichloromethane. The combined organic layers were dried ($MgSO_4$), filtered and concentrated in vacuo. The residue was purified by chromatography on silica gel (dichloromethane/methanol as eluent).

Yield: 2.9 g. TLC $R_f$=0.31 (dichloromethane/methanol 9/1); LC/MS-ESI: $[M+H]^+$=358/360.

(c). 6-Bromo-7-methoxy-1,2,3,4-tetrahydro-isoquinoline-1-carboxylic acid

A mixture of the product of example 117b (2.9 g) in water (12 ml) was treated with LiOH (1.2 g) and heated for 5 min using microwave irradiation at 200° C. The mixture was cooled and acidified to pH 5. The product was filtered and the remaining solids were dried in vacuo.

Yield: 1.29 g. LC/MS-ESI: $[M+H]^+$=286/288

(d). 8-Bromo-9-methoxy-1-thiophen-3-yl-5,6-dihydro-pyrrolo[2,1-α]isoquinoline-3-carboxylic acid ethyl ester To a suspension of the product of example 117c (645 mg) in THF (4 ml) was added dropwise ethyloxalyl chloride (250 μl). The mixture was then heated at 100° C. using microwave irradiation for 5 min. The mixture was cooled. Acetic anhydride (2 ml) and 3-thienyl acetylene (220 μl) were added. The mixture was stirred and heated again using microwave irradiation for 5 min at 140° C. The reaction mixture was cooled, diluted with 40 ml of dichloromethane and washed successively with NaOH solution (2 M) and water. The organic layer was dried ($MgSO_4$), filtered and concentrated in vacuo. The residue was purified by chromatography over silica gel (heptane/ethyl acetate as eluent).

Yield: 900 mg.

(e). 8-Bromo-9-methoxy-1-thiophen-3-yl-5,6-dihydro-pyrrolo[2,1-α]isoquinoline-3-carboxylic acid A suspension of the product of example 117e (900 mg) in dioxane (5 ml) was treated with LiOH solution (2 ml 3 M) and heated using microwave irradiation for 5 min at 180° C. The mixture was cooled and acidified to pH 4 with 2N HCl. The precipitate was dried.

Yield: 850 mg.

(f). 8-Bromo-9-methoxy-1-thiophen-3-yl-5,6-dihydro-pyrrolo[2,1-α]isoquinoline-3-carboxylic acid ethyl-isopropyl-amide To a suspension of the product of example 117c (850 mg) in dichloromethane (8 ml) were added 2-chloro-1,3-dimethylimidazoline hexafluorophosphate (877 mg), N-ethyl-N-isopropyl-amine (1.5 ml) and DIPEA (0.5 ml). The mixture was heated using microwave irradiation at 100° C. for 5 min. The mixture was then concentrated and purified by chromatography over silica gel (heptane/ethyl acetate as eluent)

Yield: 375 mg. $^1$H NMR ($CDCl_3$): δ 7.13, 7.27, 7.38 (3 m. thienyl-H), 7.35 (s, C7-H), 6.87 (s, C10-), 6.36 (s, C2-H), 4.65 (m, 1, isopropyl), 4.21 (t, 2, H5), 2.98 (t, 2, H6), 3.44 (q, 2, ethyl), 3.51 (s, 3, methoxy), 0.88 (t, 3, ethyl), 1.26 (m, 6, isopropyl); hFSHRago (CHO luc) $EC_{50}$=1100 nM

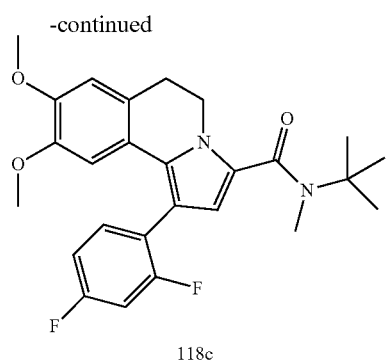

118c

Example 118

1-(2,4-Difluoro-phenyl)-8,9-dimethoxy-5,6-dihydro-pyrrolo[2,1-α]isoquinoline-3-carboxylic acid tert-butyl-methyl-amide (a). 1-(2,4-Difluoro-phenyl)-8,9-dimethoxy-5,6-dihydro-pyrrolo[2,1-α]isoquinoline-3-carboxylic acid ethyl ester A mixture of 2-ethoxyoxalyl-6,7-dimethoxy-1,2,3,4-tetrahydro-isoquinoline-1-carboxylic acid (1 g), 1-ethynyl-2,4-difluoro-benzene (450 mg) and acetic anhydride (1 ml) in THF (3 ml) was stirred and heated using microwave irradiation at 120° C. for 15 min. The reaction mixture was diluted with ethyl acetate and an aqueous sodium hydroxide solution (1 N), washed with water and brine. The organic layer was dried (MgSO$_4$), filtered and concentrated in vacuo. The residue was purified by chromatography on silica gel in heptane/ethyl acetate [1/0→6/4 (v/v)] as eluent. The compound was isolated as a white solid.

Yield: 980 mg. MS-ESI: [M+H]$^+$=414

(b). 1-(2,4-Difluoro-phenyl)-8,9-dimethoxy-5,6-dihydro-pyrrolo[2,1-α]isoquinoline-3-carboxylic acid A mixture of the product of example 118a (980 mg) and an aqueous LiOH solution (3 M)/dioxane [1:1 (v/v) 6 ml] was stirred and heated using microwave irradiation at 150° C. for 5 min. The reaction mixture was cooled to room temperature. An aqueous ammonium chloride solution (10 ml 4N) was added. The precipitate was filtered and washed with water. The product was isolated as a white solid.

Yield: 881 mg. MS-ESI: [M+H]$^+$=386

(c). 1-(2,4-Difluoro-phenyl)-8,9-dimethoxy-5,6-dihydro-pyrrolo[2,1-α]isoquinoline-3-carboxylic acid tert-butyl-methyl-amide A mixture of the product of example 118b (25 mg), N-methyl-N-tert-butyl-amine, HATU (37 mg) and DIPEA (57 μL) in dichloromethane (1 ml) was stirred and heated using microwave irradiation at 110° C. for 5 min. The reaction mixture was diluted with ethyl acetate and washed with water and an aqueous citric acid solution (3%). The organic layer was dried (MgSO$_4$), filtered and concentrated in vacuo. The residue was purified by chromatography on silica gel in heptane/ethyl acetate [0→6/4 (v/v)] as eluent.

Yield: 14 mg. MS-ESI: [M+H]$^+$=455; Anal HPLC: R$_t$=2.56 min (method 1); hFSHRago (CHO luc) EC$_{50}$=48.3 nM

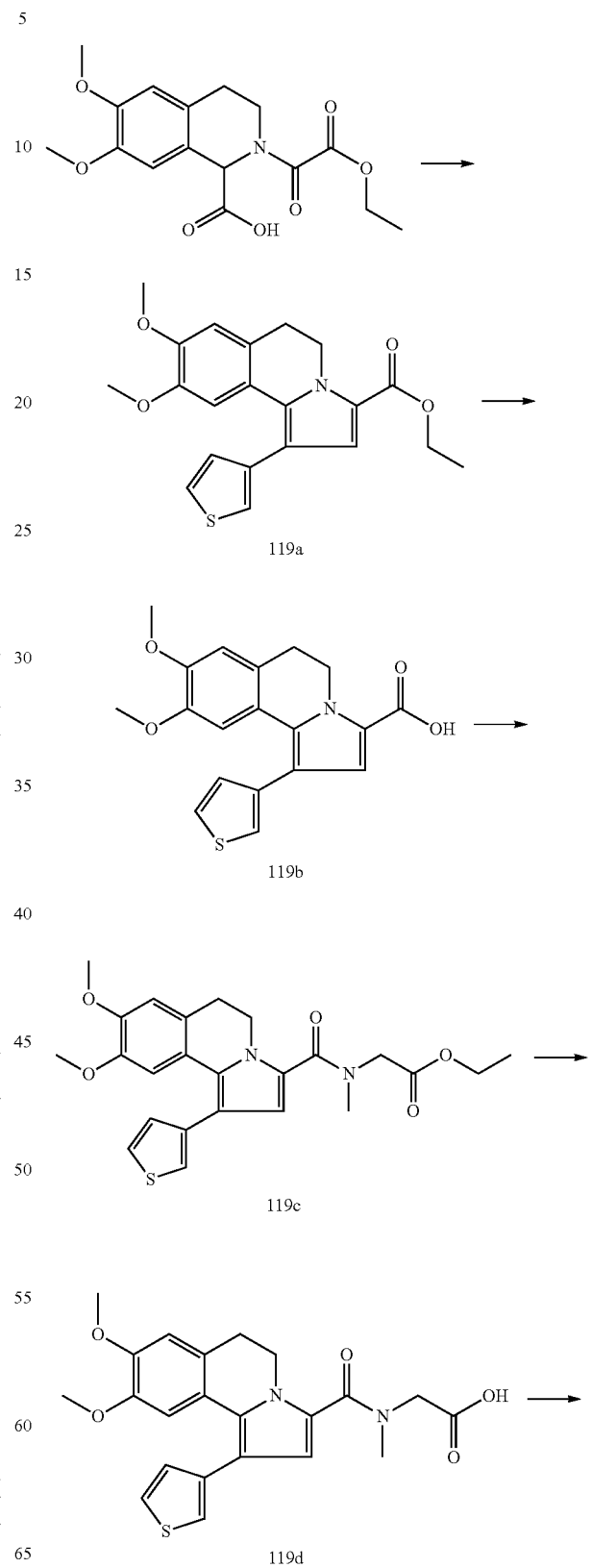

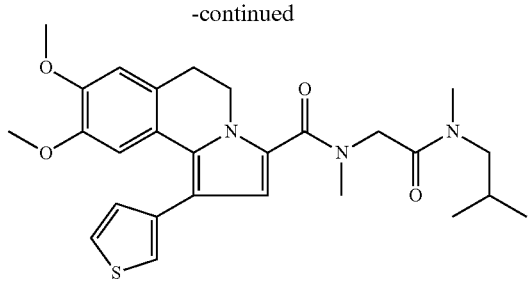

119e

Example 119

8,9-Dimethoxy-1-thiophen-3-yl-5,6-dihydro-pyrrolo[2,1-α]isoquinoline-3-carboxylic acid [(isobutyl-methyl-carbamoyl)-methyl]-methyl-amide and [(8,9-dimethoxy-1-thiophen-3-yl-5,6-dihydro-pyrrolo[2,1-α]isoquinoline-3-carbonyl)-methyl-amino]-acetic acid ethyl ester (a). 8,9-Dimethoxy-1-thiophen-3-yl-5,6-dihydro-pyrrolo[2,1-α]isoquinoline-3-carboxylic acid ethyl ester The synthesis of 8,9-dimethoxy-1-thiophen-3-yl-5,6-dihydro-pyrrolo[2,1-α]isoquinoline-3-carboxylic acid ethyl ester (119a) was performed according to the method described for example 1h, starting from 2-ethoxyoxalyl-6,7-dimethoxy-1,2,3,4-tetrahydro-isoquinoline-1-carboxylic acid.
Yield: 14.95 g. LC/MS-ESI: $[M+H]^+=384.0$ (b). 8,9-Dimethoxy-1-thiophen-3-yl-5,6-dihydro-pyrrolo[2,1-α]isoquinoline-3-carboxylic acid A mixture of the product of example 119a (4.45 g) and a LiOH solution in dioxane (88 ml 2 M) was heated under reflux for 2 h. The reaction mixture was cooled to room temperature and acidified with an aqueous HCl solution (2 N) until pH=6. The solids were collected by filtration and dried in vacuo.
Yield: 4 g. LC/MS-ESI: $[M+H]^+=356.1$ (c). [(8,9-Dimethoxy-1-thiophen-3-yl-5,6-dihydro-pyrrolo[2,1-α]isoquinoline-3-carbonyl)-methyl-amino]-acetic acid ethyl ester A mixture of the product of example 119b (500 mg), triethylamine (1.98 ml), CIP (1.96 g) and sarcosine ethyl ester hydrochloride (866 mg) in dichloromethane (100 ml) was stirred at room temperature for 18 h. The reaction mixture was concentrated in vacuo and the residue was purified by chromatography on silica gel in dichloromethane/methanol [98/2 (v/v)] as eluent.
Yield: 430 mg. LC/MS-ESI: $[M+H]^+=455.1$; hFSHRago (CHO luc) $EC_{50}=42$ nM (d). [(8,9-dimethoxy-1-thiophen-3-yl-5,6-dihydro-pyrrolo[2,1-α]isoquinoline-3-carbonyl)-methyl-amino]-acetic acid A mixture of the product of example 119c (430 mg) and an aqueous LiOH solution (4.8 ml 2 M) in dioxane (4.8 ml) was stirred at room temperature for 2 h. The reaction mixture was acidified with an aqueous HCl solution (2 N) until pH=6 and extracted with ethyl acetate. The organic layer was washed with water, brine, dried (MgSO₄), filtered and concentrated in vacuo.
Yield: 360 mg. LC/MS-ESI: $[M+H]^+=427.1$ (e). 8,9-dimethoxy-1-thiophen-3-yl-5,6-dihydro-pyrrolo[2,1-α]isoquinoline-3-carboxylic acid [(isobutyl-methyl-carbamoyl)-methyl]-methyl-amide A mixture of the product of example 119d (15 mg), HATU (15 mg), DIPEA (12 μl) and N-methyl-N-isobutyl-amine (4 mg) in dichloromethane (1 ml) was stirred for 48 h and concentrated in vacuo. The residue was dissolved in ethyl acetate and washed with water, brine, dried (MgSO₄), filtered and concentrated in vacuo. The residue was purified by chromatography on silica gel in heptane/ethyl acetate [40→100% ethyl acetate] as eluent.
Yield: 7.6 mg. LC/MS-ESI: $[M+H]^+=496.1$; hFSHRago (CHO luc) $EC_{50}=1080$ nM

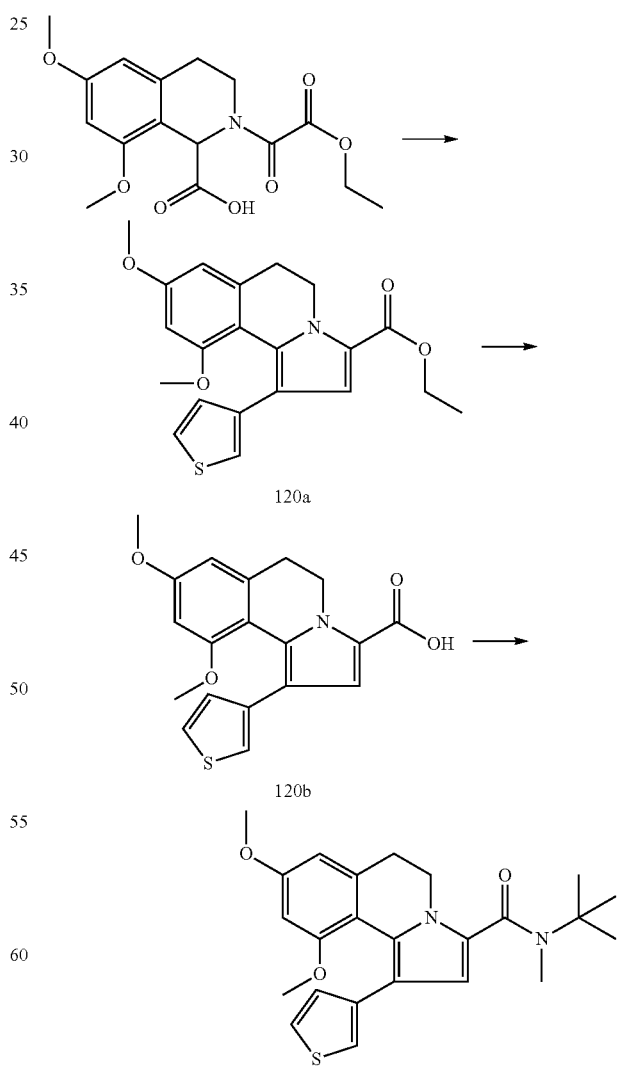

Example 120

8,10-Dimethoxy-1-thiophen-3-yl-5,6-dihydro-pyrrolo[2,1-α]isoquinoline-3-carboxylic acid tert-butyl-methyl-amide This product was prepared as earlier described in example 1a-1g, starting from 3,5-dimethoxyphenethylamine.

TLC $R_f$=0.34 (CH$_2$Cl$_2$-acetone 8/2); $^1$H NMR (CDCl$_3$) δ 3.83, 3.22 (2xs, 6H, OCH$_3$), 6.4 (d, 1H, 2H-pyrrole), 6.28, 6.44 (2xbd, 2H, H7 and H9), 6.84, 7.02, 7.20 (3xm, 3H, H3,H4,H5-thiophene), 2.98 (m, 2H, H6), 4.20 (m, 2H, H5); hFSHRago (CHO luc) EC$_{50}$=699.0 nM

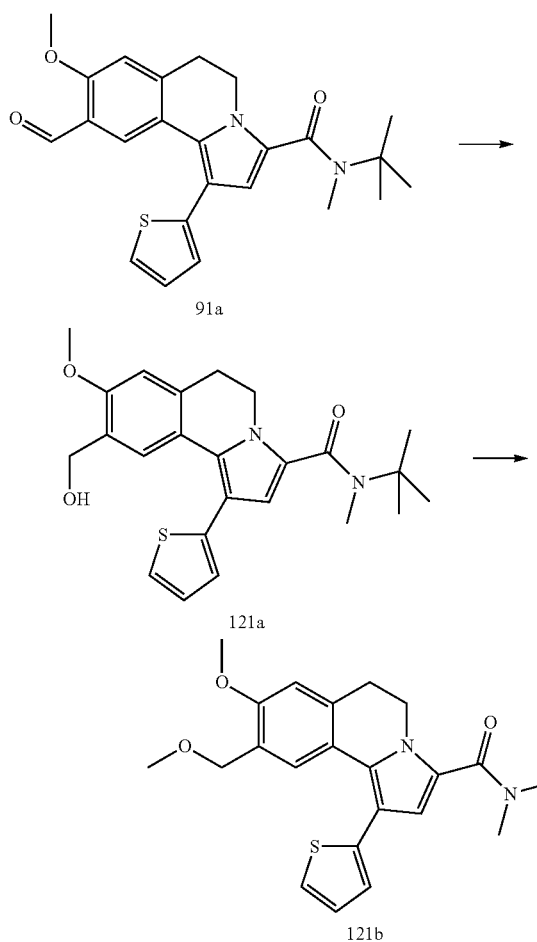

Example 121

8-Methoxy-9-methoxymethyl-1-thiophen-2-yl-5,6-dihydro-pyrrolo[2,1-α]isoquinoline-3-carboxylic acid tert-butyl-methyl-amide and 9-hydroxymethyl-8-methoxy-1-thiophen-2-yl-5,6-dihydro-pyrrolo[2,1-α]isoquinoline-3-carboxylic acid tert-butyl-methyl-amide (a). 9-Hydroxymethyl-8-methoxy-1-thiophen-2-yl-5,6-dihydro-pyrrolo[2,1-α]isoquinoline-3-carboxylic acid tert-butyl-methyl-amide To a solution of the product of example 91a (450 mg) in a mixture of THF and methanol [10 ml 1/1 (v/v)] was added NaBH$_4$ (80 mg) in portions. After stirring for 1 h, the mixture was diluted with water and extracted with dichloromethane. The organic layer was washed with water, brine, dried (MgSO$_4$), filtered and concentrated in vacuo. The residue was triturated with diisopropylether, to provide a white crystalline material.

Yield: 290 mg. Mp 146-150° C. TLC $R_f$=0.30 (heptane/ethyl acetate 1/1). LC/MS-ESI: [M+H]$^+$=425.2. $^1$H NMR (CDCl$_3$) δ 4.47 (s, 2H, CH$_2$OH), 7.33 and 6.45 (2xs, 2H, H7 and H10), 6.75 (s, 1H, H2 pyrrole); hFSHRago (CHO luc) EC$_{50}$=10 nM (b). 8-Methoxy-9-methoxymethyl-1-thiophen-2-yl-5,6-dihydro-pyrrolo[2,1-α]isoquinoline-3-carboxylic acid tert-butyl-methyl-amide To a solution of the product of example 121a (156 mg) in DMF (3 ml) was added NaH (50 mg; 60% dispersion in oil). The mixture was stirred for 15 min, followed by addition of methyl iodide (200 µl). The reaction was stirred for an additional 2 h and poured into water. The mixture was extracted with ethyl acetate. The organic layer was washed with water, brine, dried (MgSO$_4$), filtered and concentrated in vacuo. The residue was purified on silica gel in heptane/ethyl acetate as eluent. The product was crystallized from diethyl ether/heptane.

Yield: 75 mg. Mp 128-130° C. LC/MS-ESI: [M+H]$^+$=439.2. $^1$H NMR (CDCl$_3$) δ 3.22 and 3.85 (2xs, 6H, 2x OCH$_3$), 3.17 (s, 3H, NCH$_3$), 6.73 (s, 1H, H2 pyrrole), 6.45 and 7.40 (2xs, 2H, H7 and H10); hFSHRago (CHO luc) EC$_{50}$=1.6 nM

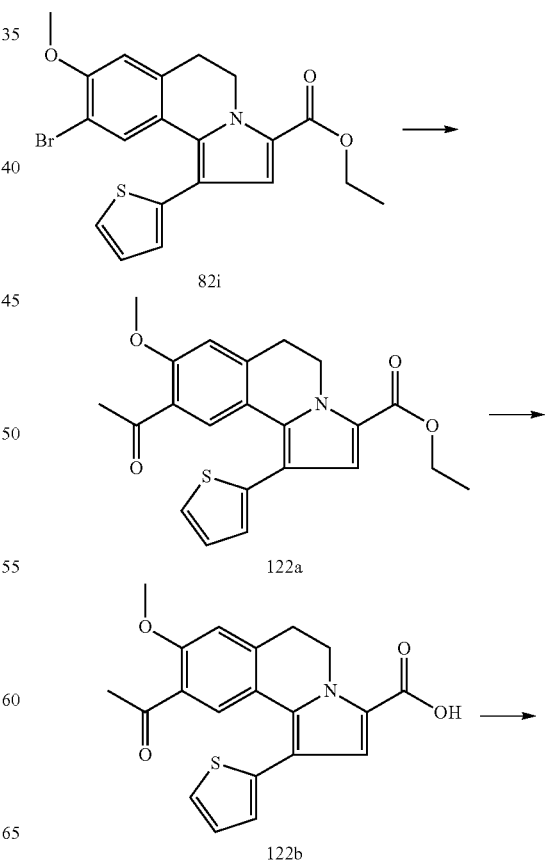

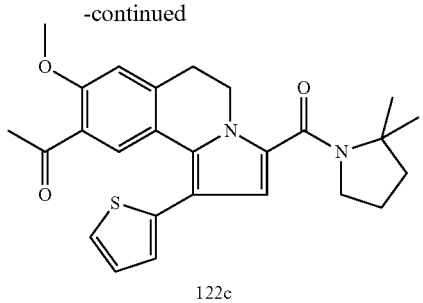

122c

Example 122

1-[3-(2,2-Dimethyl-pyrrolidine-1-carbonyl)-8-methoxy-1-thiophen-2-yl-5,6-dihydro-pyrrolo[2,1-α]isoquinolin-9-yl]-ethanone (a). 9-Acetyl-8-methoxy-1-thiophen-2-yl-5,6-dihydro-pyrrolo[2,1-α]isoquinoline-3-carboxylic acid ethyl ester A mixture of the product of example 82i (115 mg) and 1-ethoxyvinyltri-n-butyltin (288 mg) in toluene (4 ml) was deoxygenated by passing through nitrogen gas for 2 min. Bis(triphenylphosphine)palladium(II) chloride (7.5 mg) was added, the suspension was deoxygenated again and stirred for 6 h at 110° C. Ethyl acetate (4 ml) and an aqueous HCl solution (1 N) were added. The mixture was stirred vigorously for 5 min. The layers were separated. The organic layer was washed with brine, dried (MgSO$_4$), filtered and concentrated in vacuo. The residue was purified by chromatography on silica gel in heptane/ethyl acetate [9/1→6/4 (v/v)] as eluent.

Yield: 95 mg. LC/MS-ESI: [M+H]$^+$=396.1.

(b). 9-Acetyl-8-methoxy-1-thiophen-2-yl-5,6-dihydro-pyrrolo[2,1-α]isoquinoline-3-carboxylic acid An aqueous NaOH solution (1 ml, 2N) was added to a solution of the product of example 122a (90 mg) in ethanol (10 ml). After stirring for 6 h at 60° C., the reaction mixture was poured into an aqueous citric acid solution (10%) and extracted with ethyl acetate. The organic layer was washed with brine, dried (MgSO$_4$), filtered and concentrated in vacuo.

Yield: 84 mg. LC/MS-ESI: [M+H]$^+$=368.2.

(c). 1-[3-(2,2-Dimethyl-pyrrolidine-1-carbonyl)-8-methoxy-1-thiophen-2-yl-5,6-dihydro-pyrrolo[2,1-α]isoquinolin-9-yl]-ethanone TBTU (110 mg) was added to a solution of the product of example 122b (84 mg), DIPEA (200 µl) and 2,2-dimethylpyrrolidine hydrochloride (62 µl) in NMP (5 ml). After stirring at room temperature for 2 h, the reaction mixture was poured into a sat. aqueous NH$_4$Cl solution and extracted with ethyl acetate. The organic layer was washed with brine, dried (MgSO$_4$), filtered and concentrated in vacuo. The residue was purified by chromatography on silica gel in heptane/ethyl acetate [1/0→6/4 (v/v)] as eluent.

Yield: 76 mg. LC/MS-ESI: [M+H]$^+$=449.2; anal. HPLC: R$_t$=20.08 min (method 7); hFSHRago (CHO luc) EC$_{50}$=2.0 nM

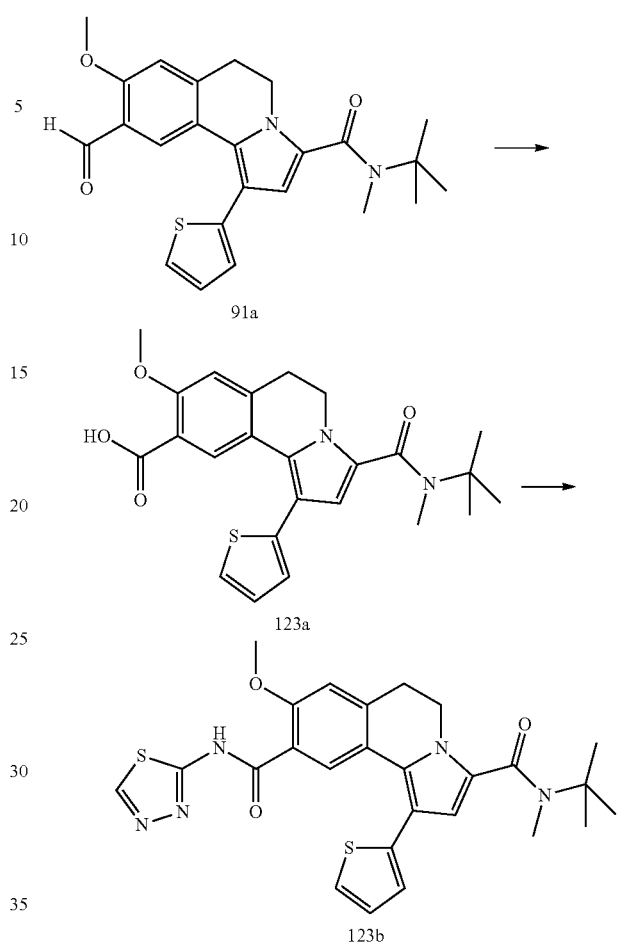

91a

123a

123b

Example 123

8-Methoxy-1-thiophen-2-yl-5,6-dihydro-pyrrolo[2,1-α]isoquinoline-3,9-dicarboxylic acid 3-(tert-butyl-methyl-amide) 9-[1,3,4]thiadiazol-2-ylamide (a). 3-(tert-Butyl-methyl-carbamoyl)-8-methoxy-1-thiophen-2-yl-5,6-dihydro-pyrrolo[2,1-α]isoquinoline-9-carboxylic acid A solution of the product of example 91a (220 mg) in a mixture of t-butanol (15 ml), dioxane (2 ml) and 2-methyl-2-butene (0.5 ml) was treated with a solution of NaClO$_2$ (200 mg) and NaH$_2$PO$_4$ (350 mg) in water (2 ml). After stirring for 1 h, the reaction was complete. Water (30 ml) was added, followed by sat. sodiumthiosulfate (2 ml) and NaH$_2$PO$_4$ (0.5 g). The product was extracted with ethylacetate. The combined organic layers were washed, dried and concentrated in vacuo. The residue was treated with diisopropylether to yield a light orange solid.

Yield: 200 mg. Mp: 215-217° C. (ethyl acetate); Rf 0.42 (toluene/acetone 1/1); NMR (DMSO-d$_6$) δ 12.4 (bs, 1, COOH), 7.78 (s, 1, H10), 7.12 (s, 1, H7), 6.4 (s, 1, pyrrole H3), 3.83 (s, 3, OCH$_3$), 3.04 (s, 3, NCH$_3$); MS-ESI: [M+1]$^+$ 439.1

(b). 8-Methoxy-1-thiophen-2-yl-5,6-dihydro-pyrrolo[2,1-α]isoquinoline-3,9-dicarboxylic acid 3-(tert-butyl-methyl-amide) 9-1,3,4-thiadiazol-2-ylamide A mixture of the product of example 123a (45 mg), 2-aminothiadiazole (25 mg), N-ethylmorpholine (40μ), TBTU (40 mg) and DMF (1 ml) was stirred at RT for 16 h. The mixture was poured onto 5% aqueous NH₄Cl solution and extracted with ethyl acetate. The combined organic layers were washed with water, dried and concentrated in vacuo. The residue was purified by chromatography on silica gel in toluene\acetone as eluent. The residue was triturated with ether, to provide white crystals.

Yield: 26 mg. Mp: 149-152° C.; MS-ESI: [M+H]⁺ 522.14; NMR (DMSO-d6) δ 12.1 (s, 1, NH), 9.20 (s, 1, thiadiazole), 7.83 (s, 1, H10), 7.25 (s, 1, H7), 6.42 (s, 1, H3-pyrrole), 3.97 (s, 3, OCH₃), 3.07 (s, 3, NCH₃); R$_f$(toluene/acetone 1/1) 0.34; hFSHRago (CHO luc) EC$_{50}$=1 nM.

Example 124

Agonistic Activity of Compounds at the Human FSH Receptor Expressed in CHO Cells Agonistic activity of the compounds at the human FSH receptor was determined in Chinese Hamster Ovary (CHO) cells stably transfected with the human FSH receptor and cotransfected with a cAMP responsive element (CRE)/promoter directing the expression of a firefly luciferase reporter gene. Binding of the compounds to the Gs protein-coupled FSH receptor will result in an increase of cAMP, which in turn will induce an increased transactivation of the luciferase reporter. Cells (7,500 cells/well of a 384 well plate) were incubated in Dulbecco' minimal essential F12 modified medium (Invitrogen), supplemented with 1 μg/ml bovine insulin, 5 μg/ml human apo-transferrin, 80 U/ml penicillin G and 80 μg/ml streptomycin with the test compounds (concentration between 0.0316 nM and 10.0 μM) in duplicate in a humidified atmosphere (95%) at 5-7% CO2 and 37° C. The final concentration of DMSO was 1%. After 4 hours of incubation, plates were allowed to adjust to room temperature for 1 hour. Then, Luclite (PerkinElmer) solution was added to the wells and cells were allowed to lyse for at least 1 hour at room temperature. Subsequently, luciferase activity was measured in a luminescence counter. The signal is expressed as counts per second (cps). The EC50 (concentration of the test compound that elicits half-maximal (50%) luciferase stimulation compared to the compound's maximally attainable effect) and efficacy values (maximal effect of the test compound as percentage of the maximal effect of recombinant human FSH) of the compounds were determined using the software program MathIQ (version 2.0, ID Business Solutions Limited). EC$_{50}$ data are indicated at the synthesis examples.

The invention claimed is:

1. A compound according to formula I

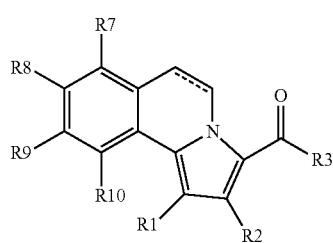

Formula I or a pharmaceutically acceptable salt thereof, wherein the C5-C6 bond can either be saturated or unsaturated, R¹ is halogen, cyano, (1-6C)alkyl, (2-6C)alkenyl, (2-6C)alkynyl, (3-6C)cycloalkyl, (5-6C)cycloalkenyl, or phenyl or heteroaryl containing 1-5 carbon atoms and 1-4 heteroatoms selected from N, O, and S, each of said phenyl and heteroaryl moieties being independently optionally substituted with one or more substituents selected from R¹³;

R² is H, cyano, halogen, (1-4C)alkyl, (1-4C)alkoxy(1-4C)alkyl, hydroxy(1-4C)alkyl, formyl, (1-4C)alkylcarbonyl or C=N—OH, C=N—OCH₃;

R³ is (R¹⁵)(R¹⁶)N— or

R³ is (1-6C)alkyl, (3-6C)cycloalkyl, ((1-4C)alkyl)$_{1-2}$N(1-4C)alkyl, or

R³ is a saturated heterocycle-(1-4C)alkyl-, wherein the heterocycle contains 2-6 carbon atoms and 1-3 heteroatoms selected from N, O and S, the heterocycle moiety of which optionally may be substituted with (1-4C)alkylcarbonyl or (3-6C)cycloalkylcarbonyl, or R³ is a group selected from

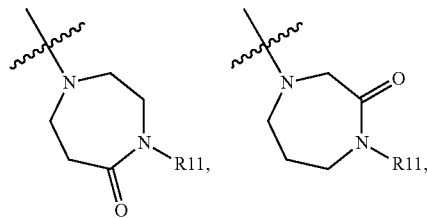

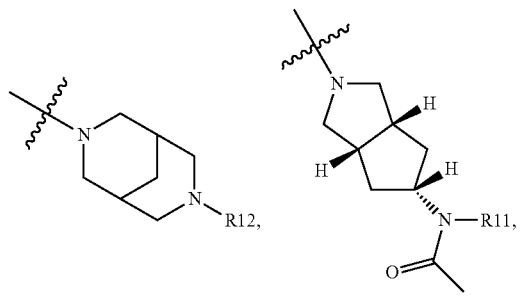

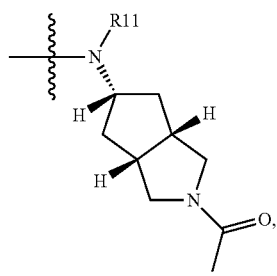

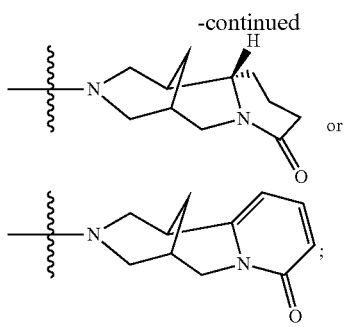

R⁷ is H, halogen, or methyl;

R⁸ is H, halogen, (1-4C)alkyl, (1-4C)alkoxy, (1-4C)alkoxy (1-4C)alkyl or hydroxy;

R⁹ is H, formyl, halogen, hydroxy, amino, cyano, nitro, (2-6C)alkynyl, (3-6C)cycloalkoxy, saturated heterocyle-O—, wherein the heterocycle group contains 2-5 carbon atoms and 1-3 heteroatoms selected from N, O and S, heteroaryl-O—, wherein the heteroaryl group contains 2-5 carbon atoms and 1-4 heteroatoms selected from N, O and S, ((1-4C)alkyl)₁₋₂NCOO—, (1-6C)alkylcarbonyl, (1-4C)alkoxycarbonyl, ((1-4C)alkyl)₁₋₂NCO—, saturated heterocycle-CO—, wherein the heterocycle group contains 2-6 carbon atoms and 1-3 heteroatoms selected from N, O and S, ((1-4C)alkyl)₁₋₂N—, saturated heterocycle-CONH—, wherein the heterocycle group contains 2-6 carbon atoms and 1-3 heteroatoms selected from N, O, and S, ((1-4C)alkyl)₁₋₂NCONH—, (1-4C)alkoxycarbonylamino, ((1-4C)alkyl)₁₋₂NS(O)₂NH—, (1-4C)alkylsulfonylamino, 1-imidazolidinyl-2-one, 3-oxazolidinyl-2-one, 1-pyrrolidinyl-2-one, or R⁹ is (1-6C)alkyl, (1-6C)alkoxy, (2-6C)alkenyl, (1-6C)alkylcarbonylamino or saturated heterocycle containing 2-6 carbon atoms and 1-3 heteroatoms selected from N, O and S, heteroaryl-NHCO—, wherein the heteroaryl group contains 2-5 carbon atoms and 1-4 heteroatoms selected from N, O and S, each of said alkyl, alkoxy, alkenyl, heterocycle and heteroaryl being independently optionally substituted with one or more substituents selected from R¹⁴, or R⁹ is heteroaryl containing 1-5 carbon atoms and 1-3 heteroatoms selected from N, O and S, phenyl or phenoxy, all independently optionally substituted with one or more substituents selected from R¹³;

R¹⁰ is H, methoxy, halogen or methyl;

R¹¹ is H, (1-6C)alkyl or (3-4C)alkenyl;

R¹² is (1-4C)alkylcarbonyl or (3-6C)cycloalkylcarbonyl, both optionally substituted with one or more substituents selected from R¹³, R¹³ is hydroxy, amino, halogen, nitro, trifluoromethyl, cyano, (1-4C)alkyl, (1-4C)alkoxy, (1-4C)alkylthio or ((1-4C)alkyl)₁₋₂N—;

R¹⁴ is hydroxy, amino, halogen, azide, cyano, (1-4C)alkyl, (1-4C)alkoxy, (1-4C)alkylthio, ((1-4C)alkyl)₁₋₂N—, (3-6C)cycloalkyl, saturated heterocycle containing 2-6 carbon atoms and 1-3 heteroatoms selected from N, O and S, (1-4C)alkylcarbonylamino, ((1-4C)alkyl)₁₋₂NCONH—, (1-4C)alkylsulfonylamino, (1-4C)alkoxycarbonylamino, (1-4C)alkylcarbonyl, (1-4C)alkoxycarbonyl, (1-4C)alkylsulfoxy, saturated heterocycle-O—, wherein the heterocycle group contains 2-6 carbon atoms and 1-3 heteroatoms selected from N, O and S, ((1-4C)alkyl)₁₋₂NCO—, (1-4C)alkylsulfonyl, (3-6C)cycloalkylcarbonylamino and [(1-4C)alkyl][(1-4C)alkylcarbonyl]amino;

R¹⁵ and R¹⁶ in (R¹⁵)(R¹⁶)N— are independently selected from H, or (1-6C)alkyl, (3-6C)cycloalkyl, saturated heterocycle containing 2-6 carbon atoms and 1-3 heteroatoms selected from N, O and S or ((1-4C)alkyl)₁₋₂N—, all optionally substituted with hydroxy, (1 -4C)alkyl, (1 -4C)alkoxy, (1-4C)alkylcarbonyl, (1 -4C)alkoxycarbonyl, (3-6C)cycloalkylcarbonyl, ((1-4C)alkyl)₁₋₂N—, ((1-4C)alkyl )₁₋₂NCO or ((1-4C)alkoxy(1-4)alkyl)₁₋₂N—; or (R¹⁵)(R¹⁶)N— are joint in a saturated heterocycle containing 3-8 carbon atoms and 2-3 heteroatoms selected from N, O and S ring, optionally substituted with R¹⁸ or (R¹⁵)(R¹⁶)N— are joint in a saturated heterocycle containing 4-8 carbon atoms and 1 N atom or a unsaturated nonaromatic heterocycle containing containing 4-6 carbon atoms and 1-3 heteroatoms selected from N, O and S, which both contain one nitrogen and which are optionally substituted with one or more substituents selected from R¹⁷;

R¹⁷ is hydroxy, amino, halogen, (1-4C)alkyl, (1-4C)alkoxy, ((1-4C)alkyl)₁₋₂N—, (1-4C)alkylcarbonylamino, ((1-4C)alkyl)₁₋₂NCONH—, (1-4C)alkylsulfonylamino, (1-4C)alkoxycarbonylamino, (1-4C)alkylsulfoxy, (3-6C)cycloalkylcarbonylamino, [(1-4C)alkyl][(1-4C)alkylcarbonyl]amino, or R¹⁷ is phenyl and heteroaryl containing 2-5 carbon atoms and 1-4 heteroatoms selected from N, O and S, both optionally substituted with one or more substituents selected from R¹³; and R¹⁸ is (1-4C)alkyl, (3-6C)cycloalkyl, (4-6C)cycloalkenylcarbonyl, ((1-4C)alkyl)₁₋₂NCO (1-4C)alkylsulfonyl, ((1-4C)alkyl)₁₋₂NSO₂-, saturated heterocycle-SO₂-, wherein the heterocycle group contains 2-6 carbon atoms and 1-3 heteroatoms selected from N, O and S, heteroaryl containing 2-5 carbon atoms 1-4 heteroatoms selected from N, O and S, phenylcarbonyl, (1-4C)alkylcarbonyl, (3-6C) cycloalkylcarbonyl, heteroaryl-CO—, wherein the heteroaryl group contains 2-5 carbon atoms and 1-4 heteroatoms selected from N, O and S, phenyl, phenylsulfonyl, heteroaryl containing 2-5 carbon atoms and 1-4 heteroatoms selected from N, O and S and saturated heterocycle-CO—, wherein the heterocycle group contains 2-6 carbon atoms and 1-3 heteroatoms selected from N, S and O, the (cyclo)alkyl and (hetero)aryl moieties of which can be substituted with one or more substituents selected from R¹³, with the proviso that the compound is not 3-acetyl-pyrrolo[2,1-a]isoquinoline-1-carbonitrile.

2. The compound according to claim 1 wherein the C5-C6 bond is saturated.

3. The compound according to claim 1 wherein R¹ is heteroaryl containing 1-5 carbon atoms and 1-3 heteroatoms selected from N, O and S, optionally substituted with one or more substituents selected from R¹³.

4. The compound according to claim 1 wherein R² is H, cyano, halogen, (1-4C)alkoxy(1-4C)alkyl or hydroxy(1-4C)alkyl.

5. The compound according to claim 1 wherein $R^3$ is $(R^{15})(R^{16})N$— or

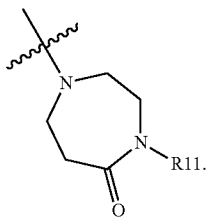

6. The compound of claim 1 wherein $R^7$ is H.

7. The compound of claim 1 wherein $R^8$ is (1-4C)alkoxy or hydroxy.

8. The compound according to claim 1 wherein $R^9$ is halogen, cyano, nitro, (2-6C)alkynyl, (3-6C)cycloalkoxy, heterocycle-O—, wherein the heterocycle contains 2-5 carbon atoms and 1-3 heteroatoms selected from N, O and S, heteroaryl-O—, wherein the heteroaryl group contains 2-5 carbon atoms and 1-4 heteroatoms selected from N, O and S, $((1-4C)alkyl)_{1-2}NCO$—, heterocycle-CO—, wherein the heterocycle group contains 2-6 carbon atoms and 1-3 heteroatoms selected from N, O and S or $((1-4C)alkyl)_{1-2}N$—, or $R^9$ is (1-6C)alkyl, (1-6C)alkoxy, (2-6C)alkenyl, (1-6C)alkylcarbonylamino or heteroaryl-NHCO—, wherein the heteroaryl group contains 2-5 carbon atoms and 1-4 heteroatoms selected from N, O and S, each of said alkyl, alkoxy, alkenyl or heteroaryl groups independently optionally substituted with one or more substituents selected from $R^{14}$, or $R^9$ is heteroaryl containing 1-5 carbon atoms and 1-4 heteroatoms selected from N, O and S or phenoxy, both indpendently optionally substituted with one or more substituents selected from $R^{13}$.

9. The compound according to claim 8 wherein $R^9$ is halogen, cyano, nitro, (2-6C)alkynyl or $((1-4C)alkyl)_{1-2}N$—, or $R^9$ is (1-6C)alkyl, (1-6C)alkoxy, (2-6C)alkenyl or (1-6C)alkylcarbonylamino, said alkyl, alkoxy or alkenyl groups independently optionally substituted with one or more substituents selected from $R^{14}$, or $R^9$ is heteroaryl containing 1-5 carbon atoms and 1-4 heteroatoms selected from N, O and S, optionally substituted with one or more substituents selected from $R^{13}$.

10. The compound according to claim 9 wherein $R^9$ is (2-6C)alkynyl, or $R^9$ is (1-6C)alkyl, (1-6C)alkoxy, (2-6C)alkenyl, or (1-6C)alkylcarbonylamino, said alkyl, alkoxy or alkenyl groups independently optionally substituted with one or more substituents selected from $R^{14}$, or $R^9$ is heteroaryl containing 1-5 carbon atoms and 1-4 heteroatoms selected from N, O and S optionally substituted with one or more substituents selected from $R^{13}$.

11. The compound according to claim 1 wherein $R^{10}$ is H.

12. The compound according to claim 8 wherein $R^1$ is heteroaryl containing 1-5 carbon atoms and 1-4 heteroatoms selected from N, O and S, optionally substituted with one or more substituents selected from $R^{13}$, $R^2$ is H, $R^3$ is $(R^{15})(R^{16})N$—, $R^7$ is H, $R^8$ is (1-4C)alkoxy and $R^{10}$ is H.

13. The compound according to claim 6 wherein $R^{14}$ is a saturated heterocycle containing 2-6 carbon atoms and 1-3 heteroatom selected from N, O and S, hydroxy, (1-4C)alkoxy or $((1-4C)alkyl)_{1-2}N$—.

14. The compound according to claim 6 wherein $R^{15}$ and $R^{16}$ may be independently selected from (1-6C)alkyl.

15. The compound according to claims 1 wherein $R^3$ is 1,4 diazacycloheptan-1-yl, optionally substituted with (1-4C)alkylcarbonyl or (3-6C)cycloalkylcarbonyl.

16. The compound according to claim 1 wherein $R^3$ is 2,2-dimethylpyrrolidin-1-yl.

17. The compound according to claim 1 selected from:
(9-Isopropoxy-8-methoxy-1-thiophen-2-yl-5,6-dihydro-pyrrolo[2,1-α] isoquinolin-3-yl)-[4-(tetrahydro-furan-2-carbonyl)-[1,4]diazepan-1-yl]-methanone;
1-[4-(9-Isopropoxy-8-methoxy--thiophen-2-yl-5,6-dihydro-pyrrolo[2,1-α] isoquinoline-3-carbonyl)-[1,4]diazepan-1-yl]-2-methylsulfanyl-ethanone;
(9-Isopropoxy-8-methoxy-1-thiophen-2-yl-5,6-dihydro-pyrrolo[2,1-α] isoquinolin-3-yl)-[4-(thiophene-2-sulfonyl)-[1,4]diazepan-1-yl]-methanone;
3,3,3-Trifluoro-2-hydroxy-1-[4-(9-isopropoxy-8-methoxy-1-thiophen-2-yl-5,6-dihydro-pyrrolo[2,1-α]isoquinoline-3-carbonyl)1,4]diazepan-1-yl]-propan-1-one;
(4-Cyclobutanecarbonyl-[1,4]diazepan-1-yl)-(9-isopropoxy-8-methoxy-1-thiophen-2-yl-5,6-dihydro-pyrrolo[2,1-α] isoquinolin-3-yl)-methanone;
3-(4-Cyclobutanecarbonyl-[1,4]diazepane-1-carbonyl)-9-isopropoxy-8-methoxy-1-thiophen-2-yl-5,6-dihydro-pyrrolo[2,1-α] isoquinoline-2-carbonitrile;
[4-(1-Bromo-cyclobutanecarbonyl)-[1,4]diazepan-1-yl]-(9-isopropoxy-8-methoxy-1-thiophen-2-yl-5,6-dihydro-pyrrolo[2,1-α] isoquinolin-3-yl)-methanone;
[4-(1-Hydroxy-cyclobutanecarbonyl)-[1,4]diazepan-1-yl]-(9-isopropoxy-8-methoxy-1-thiophen-2-yl-5,6-dihydro-pyrrolo[2,1-α] isoquinolin-3-yl)-methanone;
(9-Isopropoxy-8-methoxy-1-thiophen-2-yl-5,6-dihydro-pyrrolo[2,1-α] isoquinolin-3-yl)-[4-(1-methoxy-cyclobutanecarbonyl)1,4]diazepan-1-yl]-methanone;
2-Acetyl-9-ethoxy-8-methoxy-l-thiophen-2-yl-5,6-dihydro-pyrrolo[2,1 -α] isoquinoline-3-carboxylic acid ethyl ester;
1-[4-(2-Chloro-9-isopropoxy-8-methoxy-1-thiophen-2-yl-5,6-dihydro-pyrrolo[2,1-α] isoquinoline-3-carbonyl)-[1,4]diazepan-1-ethanone;
4-Butyl-1-(9-isopropoxy-8-methoxy-1-thiophen-2-yl-5,6-dihydro-pyrrolo[2,1-α]iso-quinoline-3-carbonyl)-[1,4]diazepan-5-one;
4-Butyl-1-[9-(2-hydroxy-2-methyl-propoxy)-8-methoxy-1-thiophen-2-yl-5,6-dihydro-pyrrolo[2,1-]isoquinoline-3-carbonyl]-[1,4]diazepan-5-one;
1-[5-(9-Isopropoxy-8-methoxy-l-thiophen-2-yl-5,6-dihydro-pyrrolo[2,1-α] isoquinoline-3-carbonyl)-[1,5]diazocan-1-yl]-ethanone;
7-(9-Isopropoxy-8-methoxy-1-thiophen-2-yl-5,6-dihydro-pyrrolo[2,1-α] iso-quinoline-3-carbonyl)-3,7-diaza-bicyclo[3.3.1]nonane-3-carboxylic acid tert-butyl ester;
1-[7-(9-Isopropoxy-8-methoxy-1-thiophen-2-yl-5,6-dihydro-pyrrolo[2,1-α] isoquinoline-3-carbonyl)-3,7-diaza-bicyclo[3.3.1]non-3-yl]-2-methylsulfanyl-ethanone;
9-(2-Hydroxy-ethoxy)-8-methoxy-1-thiophen-2-yl-pyrrolo[2,1 -α] isoquinoline-3-carboxylic acid tert-butyl-methyl-amide;
2-Formyl-9-isopropoxy-8-methoxy-1-thiophen-2-yl-5,6-dihydro-pyrrolo[2,1-α] isoquinoline-3-carboxylic acid tert-butyl-methyl-amide;
2-Hydroxymethyl-9-isopropoxy-8-methoxy-1-thiophen-2-yl-5,6-dihydro-pyrrolo[2,1-α] isoquinoline-3-carboxylic acid tert-butyl-methyl-amide;

9-Isopropoxy-8-methoxy-2-methoxymethyl-l-thiophen-2-yl-5,6-dihydro-pyrrolo[2,1-α] isoquinoline-3-carboxylic acid tert-butyl-methyl-amide:

2-(Hydroxyimino-methyl)-9-isopropoxy-8-methoxy-1-thiophen-2-yl-5,6-dihydro-pyrrolo[2,1-α]isoquinoline-3-carboxylic acid tert-butyl-methyl-amide;

9-Isopropoxy-8-methoxy-2-(methoxyimino-methyl)-1-thiophen-2-yl-5,6-dihydro-pyrrolo[2,1-α]isoquinoline-3-carboxylic acid tert-butyl-methyl-amide;

9-Isopropylamino-8-methoxy-1-thiophen-2-yl-5,6-dihydro-pyrrolo[2,1-α] isoquinoline-3-carboxylic acid tert-butyl-methyl-amide;

8-Methoxy-9-(1H-pyrazol-4-yl)-1-thiophen-2-yl-5,6-dihydro-pyrrolo[2,1-α] isoquinoline-3-carboxylic acid tert-butyl-methyl-amide;;

8-Methoxy-9-(2-methyl-propenyl)-1-thiophen-2-yl-5,6-dihydro-pyrrolo[2,1-α] isoquinoline-3-carboxylic acid tert-butyl-methyl-amide;

9-Isobutyl-8-methoxy-1-thiophen-2-yl-5,6-dihydro-pyrrolo[2,1 -α] isoquinoline-3-carboxylic acid tert-butyl-methyl-amide;

8-Methoxy-9-(2-methyl-propenyl)-1-thiazol-2-yl-5,6-dihydro-pyrrolo[2,1-α] isoquinoline-3-carboxylic acid tert-butyl-methyl-amide;

8-Hydroxy-9-isobutyl-1-thiophen-2-yl-5,6-dihydro-pyrrolo[2,1 -α] isoquinoline-3-carboxylic acid tert-butyl-methyl-amide;

N—[3-(2,2-Dimethyl-pyrrolidine-1-carbonyl)-8-methoxy-1-thiophen-2-yl-5,6-dihydro-pyrrolo[2,1-α]isoquinolin-9-yl]-isobutyramide;

8-Methoxy-9-methylcarbamoylmethoxy-1-thiophen-2-yl-5,6-dihydro-pyrrolo[2,1 -α] isoquinoline-3-carboxylic acid tert-butyl-methyl-amide;

9-(2-Hydroxy-ethoxy)-8-methoxy-l-thiophen-2-yl-5,6-dihydro-pyrrolo[2,1-α] iso-quinoline-3-carboxylic acid tert-butyl-methyl-amide;

9-(2-Azido-ethoxy)-8-methoxy-l-thiophen-2-yl-5,6-dihydro-pyrrolo[2,1-α] isoquinoline-3-carboxylic acid tert-butyl-methyl-amide;

8-Methoxy-9-(tetrahydro-pyran-2-yloxy)-1-thiophen-2-yl-5,6-dihydro-pyrrolo[2,1-α] isoquinoline-3-carboxylic acid tert-butyl-methyl-amide;

9-(3-Hydroxy-propoxy)-8-methoxy-1-thiophen-2-yl-5,6-dihydro-pyrrolo[2,1-α]iso-quinoline-3-carboxylic acid tert-butyl-methyl-amide;

9-Isobutyl-8-methoxy-1-thiophen-2-yl-5,6-dihydro-pyrrolo[2,1-α] isoquinoline-3-carboxylic acid (2-hydroxy-1,1-dimethyl-ethyl)-methyl-amide;

(9-Bromo-8-methoxy-1-thiophen-2-yl-5,6,6a, 10a-tetrahydro-pyrrolo[2,1-α]isoquinolin-3-yl)-(4-cyclobutanecarbonyl-[1,4]diazepan-1-yl)-methanone;

9-Cyano-8-methoxy-1-thiophen-2-yl-5,6-dihydro-pyrrolo[2,1-α]isoquinoline-3-carboxylic acid tert-butyl-methyl-amide;

3-(4-Cyclobutanecarbonyl-[1,4]diazepane-1-carbonyl)-8-methoxy-1-thiophen-2-yl-5,6-dihydro-pyrrolo[2,1-α] isoquinoline-9-carboxylic acid ethyl ester;

8-Methoxy-9-prop-1-ynyl-1-thiophen-2-yl-5,6-dihydro-pyrrolo[2,1-α] isoquinoline-3-carboxylic acid tert-butyl-methyl-amide;

9-Formyl-8-methoxy-1-thiophen-2-yl-5,6-dihydro-pyrrolo[2,1-α] isoquinoline-3-carboxylic acid tert-butyl-methyl-amide;

9-(3-hydroxy-propyl)-8-methoxy-1-thiophen-2-yl-5,6-dihydro-pyrrolo[2,1-α] iso-quinoline-3-carboxylic acid tert-butyl-methyl-amide;

9-(3-Hydroxy-3-methyl-butyl)-8-methoxy-l-thiophen-2-yl-5,6-dihydro-pyrrolo[2,1-α] isoquinoline-3-carboxylic acid tert-butyl-methyl-amide;

(9-(2,2-Difluoro-vinyl)-8-methoxy-1-thiophen-2-yl-5,6-dihydro-pyrrolo[2,1-α] isoquinoline-3-carboxylic acid tert-butyl-methyl-amide.;

8-Methoxy-9-nitro-1-thiophen-2-yl-5,6-dihydro-pyrrolo[2,1-α] isoquinoline-3-carboxylic acid tert-butyl-methyl-amide;

9-(2-Dimethylamino-acetylamino)-8-methoxy-1-thiophen-2-yl-5,6,6a,10a-tetrahydro-pyrrolo[2,1-α]isoquinoline-3-carboxylic acid tert-butyl-methyl-amide;

9-(2-Azetidin-1-yl-acetylamino)-8-methoxy-l-thiophen-2-yl-5,6-dihydro-pyrrolo[2,1-α] isoquinoline-3-carboxylic acid tert-butyl-methyl-amide;

8-Methoxy-9-(2-methoxy-acetylamino)-1-thiophen-2-yl-5,6-dihydro-pyrrolo[2,1-α] isoquinoline-3-carboxylic acid tert-butyl-methyl-amide;

N—[3-(2,2-Dimethyl-pyrrolidine-1-carbonyl)-8-methoxy-1-thiophen-2-yl-5,6-dihydro-pyrrolo[2,1-α]isoquinolin-9-yl]-methanesulfonamide;

N—[3-(2,2-Dimethyl-pyrrolidine-1-carbonyl)-8-methoxy-1-thiophen-2-yl-5,6-dihydro-pyrrolo[2,1-α]isoquinolin-9-yl]-2-morpholin-4-yl-acetamide;

(8,9-Dimethoxy-1-thiophen-2-yl-5,6-dihydro-pyrrolo[2,1-α] isoquinolin-3-yl)-[4-(1-methyl-cyclobutanecarbonyl)-[1,4] diazepan-1-yl] -methanone;

(4-Cyclobutanecarbonyl-[1,4]diazepan-1-yl)-(8,9-dimethoxy-1-thiophen-2-yl-5,6-dihydro-pyrrolo[2,1-α]isoquinolin-3-yl)-methanone;

(4-Cyclobutanecarbonyl-[1,4]diazepan-1-yl)-(8,9-dimethoxy-1-thiophen-2-yl-pyrrolo[2,1 -α] isoquinolin-3-yl)-methanone;

9-Hydroxymethyl-8-methoxy-1-thiophen-2-yl-5,6-dihydro-pyrrolo[2,1-α] isoquinoline-3-carboxylic acid tert-butyl-methyl-amide;

8-Methoxy-9-methoxymethyl-l-thiophen-2-yl-5,6-dihydro-pyrrolo[2,1-α] isoquinoline-3-carboxylic acid tert-butyl-methyl-amide;

1-[3-(2,2-Dimethyl-pyrrolidine-1-carbonyl)-8-methoxy-1-thiophen-2-yl-5,6-dihydro-pyrrolo[2,1-α]isoquinolin-9-yl]-ethanone; and 8-Methoxy-1-thiophen-2-yl-5,6-dihydro-pyrrolo[2,1-α] isoquinoline-3,9-dicarboxylic acid 3-(tert-butyl-methyl-amide) 9-[1,3,4]thiadiazol-2-yl-amide.

18. A pharmaceutical composition which comprises a compound according to claim 1, or a pharmaceutically acceptable salt thereof, and one or more pharmaceutically acceptable excipients.

19. A method of ovarian stimulation comprising administering a pharmaceutical composition according to claim 18.

20. A method of treating a fertility disorder comprising administering a pharmaceutical composition according to claim 18.

* * * * *

UNITED STATES PATENT AND TRADEMARK OFFICE
CERTIFICATE OF CORRECTION

PATENT NO. : 8,394,789 B2  Page 1 of 1
APPLICATION NO. : 12/866468
DATED : March 12, 2013
INVENTOR(S) : van Rijn et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 212 days.

Signed and Sealed this
First Day of September, 2015

Michelle K. Lee
*Director of the United States Patent and Trademark Office*